United States Patent
Marcucci et al.

(10) Patent No.: US 11,801,266 B2
(45) Date of Patent: *Oct. 31, 2023

(54) METHODS OF USING ANTI-MIR126 COMPOUNDS

(71) Applicant: CITY OF HOPE, Duarte, CA (US)

(72) Inventors: Guido Marcucci, Duarte, CA (US); Bin Zhang, Duarte, CA (US); Ya-Huei Kuo, Duarte, CA (US); Marcin Tomasz Kortylewski, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 428 days.

This patent is subject to a terminal disclaimer.

(21) Appl. No.: 16/810,739

(22) Filed: Mar. 5, 2020

(65) Prior Publication Data
US 2020/0281982 A1    Sep. 10, 2020

Related U.S. Application Data

(60) Provisional application No. 62/814,204, filed on Mar. 5, 2019.

(51) Int. Cl.
*A61K 35/28*  (2015.01)
*A61P 35/00*  (2006.01)
*A61K 45/06*  (2006.01)
*C12N 15/113* (2010.01)

(52) U.S. Cl.
CPC .............. *A61K 35/28* (2013.01); *A61K 45/06* (2013.01); *A61P 35/00* (2018.01); *C12N 15/113* (2013.01)

(58) Field of Classification Search
CPC ........ A61K 45/06; A61K 35/28; A61K 38/00; A61P 7/06; A61P 35/00; C12N 15/113; C12N 2310/318; C12N 2310/113; C12N 2310/315; C12N 2310/321; C12N 2310/3521; C07K 16/289; C07K 16/18
See application file for complete search history.

(56) References Cited

U.S. PATENT DOCUMENTS 10,801,026 B2 * 10/2020 Kortylewski ......... C12N 15/111
2003/0050442 A1 * 3/2003 Ruben .................... C07K 14/47
435/325

FOREIGN PATENT DOCUMENTS

WO    WO-2017066639 A1 *  4/2017 ........... A61K 31/506

OTHER PUBLICATIONS

Dorrance, A.M. et al. (Nov. 2015, e-published Jun. 9, 2015,). "Targeting leukemia stem cells in vivo with antagomiR-126 nanoparticles in acute myeloid leukemia," *Leukemia* 29(11):2143-2153.

Lechman, E.R. et al. (Apr. 11, 2016). "miR-126 Regulates Distinct Self-Renewal Outcomes in Normal and Malignant Hematopoietic Stem Cells," *Cancer Cell* 29(4):602-606.

Li, Z. et al. (Oct. 22, 2015, e-published Sep. 11, 2015). "Overexpression and knockout of miR-126 both promote leukemogenesis," *Blood* 126(17):2005-2015.

Wang, S. et al. (Aug. 2008). "The endothelial-specific microRNA miR-126 governs vascular integrity and angiogenesis," *Developmental Cell* 15(2):261-271.

* cited by examiner

*Primary Examiner* — Blessing M Fubara
(74) *Attorney, Agent, or Firm* — MINTZ LEVIN COHN FERRIS GLOVSKY AND POPEO, P.C.

(57) ABSTRACT

Provided herein are, inter alia, methods of treating red blood cell disorders and cancer using anti-miR126 compounds. The methods include administering phosphorothioated CpG oligodeoxynucleotides conjugated to an anti-miR126 nucleic acid sequence to treat red blood cell disorders. Other methods provided herein include administering phosphorothioated CpG oligodeoxynucleotides conjugated to an anti-miR126 nucleic acid sequence and a tyrosine kinase inhibitor to treat cancer.

14 Claims, 103 Drawing Sheets

Specification includes a Sequence Listing.

FIG. 6Q

| Cell dose/mouse | Leukemia developed/tested | | | |
|---|---|---|---|---|
| | scrRNA | Inhibitor | scrRNA+NIL | Inhibitor +NIL |
| 4 million | 6/6 | 2/6 | 3/6 | 0/6 |
| 2 million | 2/6 | 1/6 | 3/6 | 0/6 |
| 1 million | 2/6 | 0/6 | 2/6 | 0/6 |
| 0.5 million | 1/6 | 0/6 | 0/6 | 0/6 |
| Frequency of LICs | 4.20E-07 | 7.54E-08 | 2.36E-07 | 0 |

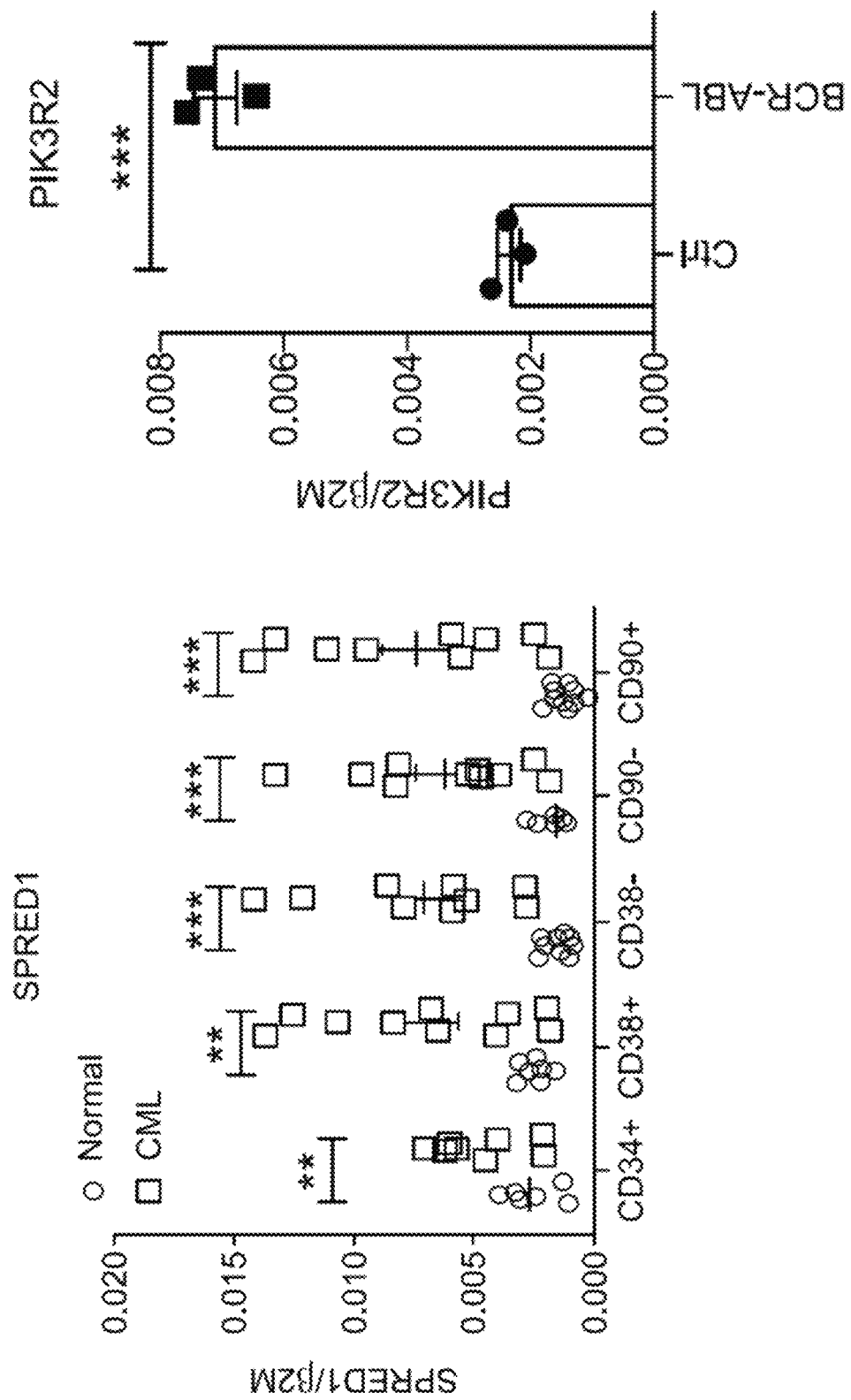

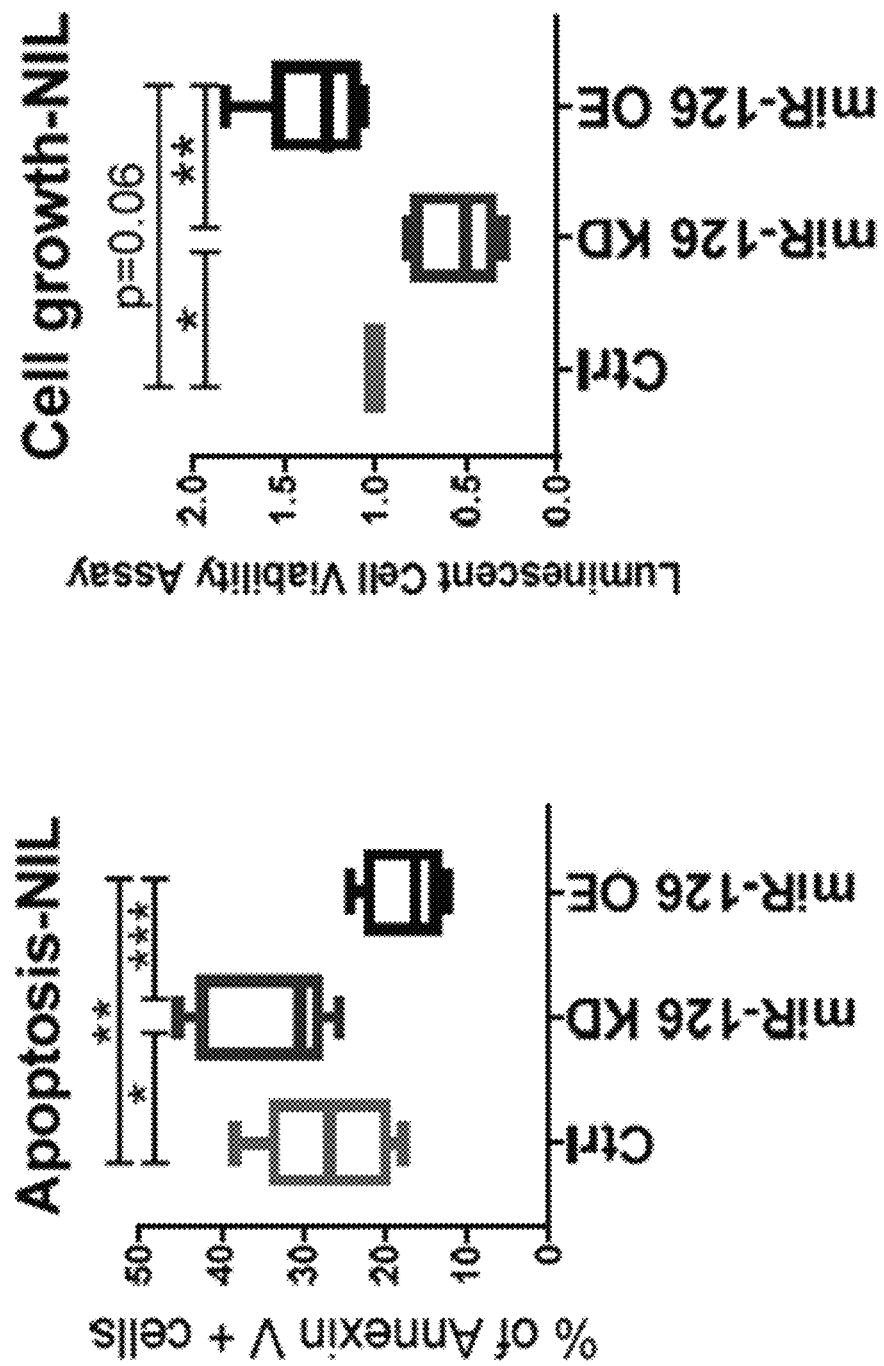

Gels for FIG. 3D

Gels for FIG. 3E

Gels for FIG. 3G

Gels for FIG. 3H and 3N

Gels for FIG. 3J

SEQUENCE LISTING

```
<160> NUMBER OF SEQ ID NOS: 7

<210> SEQ ID NO 1
<211> LENGTH: 29
<212> TYPE: DNA
<213> ORGANISM: Artificial sequence
<220> FEATURE:
<223> OTHER INFORMATION: Synthetic polynucleotide

<400> SEQUENCE: 1
tctggaattc tcgggtgcca aggaactcc                                  29

<210> SEQ ID NO 2
<211> LENGTH: 27
<212> TYPE: DNA
<213> ORGANISM: Artificial sequence
<220> FEATURE:
<223> OTHER INFORMATION: Synthetic polynucleotide

<400> SEQUENCE: 2
ggagttcctt ggcacccgag aattcca                                    27

<210> SEQ ID NO 3
<211> LENGTH: 29
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (27)..(29)
<223> OTHER INFORMATION: N is any nucleotide

<400> SEQUENCE: 3
guucagaguu cuacaguccg acgaucnnn                                  29

<210> SEQ ID NO 4
```

```
<211> LENGTH: 63
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (25)..(30)
<223> OTHER INFORMATION: N is any nucleotide

<400> SEQUENCE: 4
caagcagaag acggcatacg agatnnnnnn gtgactggag ttcagacgtg tgctcttccg      60
atc                                                                   63

<210> SEQ ID NO 5
<211> LENGTH: 50
<212> TYPE: DNA
<213> ORGANISM: Artificial sequence
<220> FEATURE:
<223> OTHER INFORMATION: Synthetic polynucleotide

<400> SEQUENCE: 5
aatgatacgg cgaccaccga gatctacacg ttcagagttc tacagtccga                 50

<210> SEQ ID NO 6
<211> LENGTH: 42
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (2)..(3)
<223> OTHER INFORMATION: phosphorothioation
<220> FEATURE:
<221> NAME/KEY: misc_feature
<222> LOCATION: (16)..(17)
<223> OTHER INFORMATION: phosphorothioation
<220> FEATURE:
<221> NAME/KEY: misc_feature
<222> LOCATION: (17)..(18)
<223> OTHER INFORMATION: phosphorothioation
<220> FEATURE:
<221> NAME/KEY: misc_feature
<222> LOCATION: (18)..(19)
<223> OTHER INFORMATION: phosphorothioation
<220> FEATURE:
<221> NAME/KEY: misc_feature
<222> LOCATION: (19)..(20)
<223> OTHER INFORMATION: phosphorothioation
<220> FEATURE:
<221> NAME/KEY: misc_feature
<222> LOCATION: (20)..(21)
<223> OTHER INFORMATION: Five C3 carbon chain linkers, ((CH2)3)5
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (23)..(23)
<223> OTHER INFORMATION: cm
<220> FEATURE:
<221> NAME/KEY: modified_base
<222> LOCATION: (24)..(24)
<223> OTHER INFORMATION: 2'-O-Methyladenosine
```

```
<220> FEATURE:
<221> NAME/KEY: modified_base
<222> LOCATION: (25)..(26)
<223> OTHER INFORMATION: um
<220> FEATURE:
<221> NAME/KEY: modified_base
<222> LOCATION: (27)..(27)
<223> OTHER INFORMATION: 2'-O-Methyladenosine
<220> FEATURE:
<221> NAME/KEY: modified_base
<222> LOCATION: (28)..(29)
<223> OTHER INFORMATION: um
<220> FEATURE:
<221> NAME/KEY: modified_base
<222> LOCATION: (30)..(30)
<223> OTHER INFORMATION: 2'-O-Methyladenosine
<220> FEATURE:
<221> NAME/KEY: modified_base
<222> LOCATION: (31)..(31)
<223> OTHER INFORMATION: cm
<220> FEATURE:
<221> NAME/KEY: modified_base
<222> LOCATION: (32)..(32)
<223> OTHER INFORMATION: um
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (34)..(34)
<223> OTHER INFORMATION: 2'-O-Methyladenosine
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (36)..(37)
<223> OTHER INFORMATION: gm
<220> FEATURE:
<221> NAME/KEY: modified_base
<222> LOCATION: (38)..(38)
<223> OTHER INFORMATION: um
<220> FEATURE:
<221> NAME/KEY: modified_base
<222> LOCATION: (39)..(39)
<223> OTHER INFORMATION: 2'-O-Methyladenosine
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (41)..(41)
<223> OTHER INFORMATION: gm
<220> FEATURE:
<221> NAME/KEY: modified_base
<222> LOCATION: (42)..(42)
<223> OTHER INFORMATION: 2'-O-Methyladenosine

<400> SEQUENCE: 6
ggtgcatcga tgcagggggg cgcauuauua cucacgguac ga                          42

<210> SEQ ID NO 7
<211> LENGTH: 42
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioation
<220> FEATURE:
<221> NAME/KEY: misc_feature
<222> LOCATION: (2)..(3)
```

```
<223> OTHER INFORMATION: phosphorothioation
<220> FEATURE:
<221> NAME/KEY: misc_feature
<222> LOCATION: (16)..(17)
<223> OTHER INFORMATION: phosphorothioation
<220> FEATURE:
<221> NAME/KEY: misc_feature
<222> LOCATION: (17)..(18)
<223> OTHER INFORMATION: phosphorothioation
<220> FEATURE:
<221> NAME/KEY: misc_feature
<222> LOCATION: (18)..(19)
<223> OTHER INFORMATION: phosphorothioation
<220> FEATURE:
<221> NAME/KEY: misc_feature
<222> LOCATION: (19)..(20)
<223> OTHER INFORMATION: phosphorothioation
<220> FEATURE:
<221> NAME/KEY: misc_feature
<222> LOCATION: (20)..(21)
<223> OTHER INFORMATION: ((CH2)3)5
<220> FEATURE:
<221> NAME/KEY: misc_feature
<222> LOCATION: (20)..(21)
<223> OTHER INFORMATION: Five C3 carbon chain linkers, ((CH2)3)5
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: um
<220> FEATURE:
<221> NAME/KEY: modified_base
<222> LOCATION: (23)..(23)
<223> OTHER INFORMATION: 2'-O-Methyladenosine
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(26)
<223> OTHER INFORMATION: 2'-O-Methyladenosine
<220> FEATURE:
<221> NAME/KEY: modified_base
<222> LOCATION: (27)..(28)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: um
<220> FEATURE:
<221> NAME/KEY: modified_base
<222> LOCATION: (31)..(31)
<223> OTHER INFORMATION: 2'-O-Methyladenosine
<220> FEATURE:
<221> NAME/KEY: modified_base
<222> LOCATION: (32)..(32)
<223> OTHER INFORMATION: cm
<220> FEATURE:
<221> NAME/KEY: modified_base
<222> LOCATION: (33)..(33)
<223> OTHER INFORMATION: um
<220> FEATURE:
<221> NAME/KEY: modified_base
<222> LOCATION: (34)..(34)
<223> OTHER INFORMATION: cm
<220> FEATURE:
<221> NAME/KEY: modified_base
<222> LOCATION: (35)..(35)
<223> OTHER INFORMATION: gm
<220> FEATURE:
<221> NAME/KEY: modified_base
```

```
<222> LOCATION: (36)..(36)
<223> OTHER INFORMATION: um
<220> FEATURE:
<221> NAME/KEY: modified_base
<222> LOCATION: (37)..(37)
<223> OTHER INFORMATION: cm
<220> FEATURE:
<221> NAME/KEY: modified_base
<222> LOCATION: (38)..(38)
<223> OTHER INFORMATION: 2'-O-Methyladenosine
<220> FEATURE:
<221> NAME/KEY: modified_base
<222> LOCATION: (39)..(39)
<223> OTHER INFORMATION: cm
<220> FEATURE:
<221> NAME/KEY: modified_base
<222> LOCATION: (40)..(41)
<223> OTHER INFORMATION: um
<220> FEATURE:
<221> NAME/KEY: modified_base
<222> LOCATION: (42)..(42)
<223> OTHER INFORMATION: 2'-O-Methyladenosine

<400> SEQUENCE: 7
ggtgcatcga tgcagggggg guagaaccgu acucgucacu ua                42
```

METHODS OF USING ANTI-MIR126 COMPOUNDS

CROSS-REFERENCES TO RELATED APPLICATIONS

This application claims the benefit of U.S. Provisional Application No. 62/814,204, filed Mar. 5, 2019, which is incorporated herein by reference in entirety and for all purposes

STATEMENT AS TO RIGHTS TO INVENTIONS MADE UNDER FEDERALLY SPONSORED RESEARCH AND DEVELOPMENT

This invention was made with government support under grant nos. CA205247, CA102031, CA213131, CA180861, CA158350, and CA184411 awarded by the National Cancer Institute, and grant no. P30CA33572 awarded by the National Cancer Institute of the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-689001US_SequenceListing_ST25.TXT, created Mar. 4, 2020, 5,613 bytes, machine format IBM-PC, MS Windows operating system, is hereby incorporated by reference.

BACKGROUND

Chronic myelogenous leukemia (CML) is a clonal myeloproliferative disorder characterized at the cytogenetic level by the translocation of chromosomes 9q34 and 22q11[1]. This translocation creates a fusion gene, BCR-ABL, which encodes a constitutively activated tyrosine kinase responsible for transforming normal hematopoietic stem cells (HSCs) into leukemia stem cells (LSCs). LSCs are characterized by growth factor-independent proliferation and enhanced survival, resulting in uncontrolled myeloproliferation that eventually evolves into fatal blast crisis if left untreated. CML LSCs are at the apex of malignant clonal hematopoiesis and initiate and maintain leukemia growth. In CML, LSC activity is restricted to the LT-HSC-enriched Lin-CD34+CD38–CD90+ cell population in humans, and the Lin-Sca-1+c-Kit+Flt3-CD150+CD48– cell population in mice. CIVIL LSCs are thought to reside in a leukemia niche that may be anatomically and functionally different from that of normal HSCs.

Currently, oral tyrosine kinase inhibitors (TKI) are used as the first-line treatment to induce long-term disease remission in CML patients. Although most patients treated with TKI monotherapy achieve major clinical and molecular responses, cells from the original BCR-ABL clone frequently persist, likely due to the failure of these agents to eliminate CML LSC[3], and treatment discontinuation frequently results in disease relapse. Thus, the identification of mechanisms that support CML LSC persistence is clinically relevant as it may enable the design of new targeting strategies aimed at complete disease elimination, allowing for discontinuation of life-long TKI therapy.

miR-126-3p (miR-126) is a microRNA (miRNA) that is highly expressed in normal HSCs and hematopoietic progenitor cells (HPCs) and restrains cell-cycle progression during hematopoiesis[4]. Our group and others have shown that increased miR-126 levels are associated with an increased frequency of quiescent LSCs and a worse outcome in acute myeloid leukemia (AML)[5-8]. Here we show that miR-126 biogenesis in CIVIL LSCs is down-regulated through a BCR-ABL-dependent mechanism, a finding which is seemingly inconsistent with a pro-leukemic role for miR-126. However, miR-126 is also highly expressed in endothelial cells (ECs)[9]. Anatomical and functional connections between the endothelium and normal HSCs regulate normal hematopoiesis[10]. We hypothesized that miR-126 may mediate a functional interplay between ECs and LSCs in the leukemia BM niche that regulates CML progression. Consistent with this hypothesis, we found that ECs supply miR-126 to CML LSCs to modulate their quiescence and self-renewal.

BRIEF SUMMARY OF THE INVENTION

In an aspect is provided a method of treating anemia in a subject in need thereof, the method including administering to the subject an effective amount of an anti-microRNA126 (miR126) compound.

In another aspect is provided a method of treating or preventing anemia in a subject in need thereof, the method including: (i) isolating a hematopoietic stem cell (HSC) from a subject, thereby forming an isolated HSC; (ii) contacting the isolated HSC with an anti-microRNA126 (miR126) compound thereby forming a contacted HSC; and administering the contacted HSC to the subject, thereby treating or preventing anemia in the subject.

In an aspect a method of forming a red blood cell is provided, the method including: (i) contacting a hematopoietic stem cell (HSC) with an anti-microRNA126 (miR126) compound, thereby forming a contacted HSC; and allowing the contacted HSC to divide, thereby forming a red blood cell.

In an aspect is provided a method of treating cancer in a subject in need thereof, the method including administering to the subject a therapeutically effective amount of a tyrosine kinase inhibitor and a therapeutically effective amount of an anti-microRNA126 (miR126) compound.

In another aspect, is provided a method of treating cancer in a subject in need thereof, the method including administering to the subject a therapeutically effective amount of an anti-microRNA126 (miR126) compound, wherein the subject has been treated with a tyrosine kinase inhibitor prior to the administering a therapeutically effective amount of an anti-microRNA126 (miR126) compound.

In another aspect, is provided a method of treating cancer in a subject undergoing cancer treatment, the method including administering to the subject a therapeutically effective amount of an anti-microRNA126 (miR126) compound.

In another aspect, is provided a method of treating a chemoresistant cancer in a subject in need thereof, the method including administering to the subject a therapeutically effective amount of an anti-microRNA126 (miR126) compound.

In an aspect, a pharmaceutical composition including a pharmaceutically acceptable excipient, an anti-microRNA126 (miR126) compound and a tyrosine kinase inhibitor is provided.

BRIEF DESCRIPTION OF THE DRAWINGS

FIG. 1A and FIG. 1B show miR-126 expression, as assessed by QPCR, in HPCs [Lin-CD34+ (CD34+) and Lin-CD34+CD38+(CD38+)], HSCs [Lin-CD34+CD38− (CD38−) and Lin-CD34+CD38−CD90− (CD90−)] and LT-HSCs [Lin-CD34+CD38−CD90+ (CD90+)] from blood and BM samples from normal donors (n=12 biologically independent samples) (FIG. 1A) and newly diagnosed CP CIVIL patients (n=12 biologically independent samples) (FIG. 1B). FIG. 1O and FIG. 1P show White blood cell (WBC) counts (FIG. 1O) and donor CML cell engraftment in PB (FIG. 1P) of mice transplanted with G0 or G1/S/G2/M LT-HSCs from CML mice (n=10). Comparison between groups was performed by two-tailed, paired Student's t-test. P values <0.05 were considered significant. Results shown represent mean±SEM. *p<0.05, p<0.01, *p<0.001, ****p<0.0001.

FIG. 2A and FIG. 2B show miR-126 expression in normal and CML cell populations from human samples, as assessed by QPCR (n=10 biologically independent samples) wherein for each group of two data points, the data point on the left represents data for normal cells and the data point on the right represents data for CML cells (FIG. 2A) and miRNA staining (FIG. 2B) using 3 independent samples with similar results. FIG. 2O shows cell cycle analysis of human CML Lin-CD34+CD38− cells treated with DMSO (Ctrl) or 5 µM NIL (n=4), wherein for each group of two data points, the data point on the left represents data for Ctrl cells and the data point on the right represents data for cells treated with NIL. Comparison between groups was performed by two-tailed, unpaired Student's t-test. P values <0.05 were considered significant. Results shown represent mean±SEM. *p<0.05, p<0.01, *p<0.001, ****p<0.0001.

FIG. 3A and FIG. 3B show pri-miR-126 (n=8 biologically independent samples) (FIG. 3A) and pre-miR-126 (n=8 biologically independent samples) (FIG. 3B) expression levels, as assessed by QPCR, in the indicated human normal and CML cell populations. For each group of two data sets, the group on the left represents data for normal cell populations and the group on the right represents data for CML cell populations. FIGS. 3Q-3S show mature (left two bars), pri- (middle two bars) and pre-miR-126 (right two bars) expression, as assessed by QPCR (n=3 independent experiments) (FIG. 3Q) and miR-126 staining (FIG. 3R) in K562 cells without (siSCR) or with RAN KD (siRAN), as assessed by D3 with anti-RNA and anti-actin antibodies (FIG. 3S). All of the above IF, IP, D3 and miRNA staining experiments including FIGS. 3C-H, FIG. 3J, FIGS. 3L-N, FIG. 3P, FIG. 3R, and FIG. 3S, were repeated at least twice using independent samples, with similar results. Full-length gels and blots with molecular weight standards for FIG. 3D, FIG. 3E, FIG. 3G, FIG. 3H, FIG. 3J, FIG. 3M, FIG. 3N, and FIG. 3Q are provided in FIGS. 14-16. Comparison between groups was performed by two-tailed, unpaired Student's t-test. P values <0.05 were considered significant. Results shown represent mean±SEM. *p<0.05, p<0.01, *p<0.001, ****p<0.0001.

FIG. 4A shows gating strategy for the isolation of ECs (CD45–Ter119-CD31+), osteoblasts (OBs, CD45–Ter119-CD31–CD166+Sca-1-) and mesenchymal stem cells (MSCs, CD45–Ter119-CD31–CD166–Sca-1+). These experiments were repeated 5 times independently with similar results. FIGS. 4Q-4S show representative flow cytometry plots of Ki-67 and DAPI staining of endosteal or central LT-HSCs from normal and CML mice (FIG. 4Q), cell cycle analysis of endosteal or central LT-HSCs from normal (n=3) (FIG. 4R) or CML (n=3) (FIG. 4S) mice, where the legend from top to bottom represents each set of two data points from left to right. Comparison between groups was performed by two-tailed, paired Student's t-test. P values <0.05 were considered significant. Results shown represent mean±SEM. *p<0.05, p<0.01, *p<0.001, ****p<0.0001.

FIG. 5A and FIG. 5B show frequency of BM mononuclear cell subpopulations (n=5 independent samples), where the legend from top to bottom represents each set of two data points from left to right (FIG. 5A) and LT-HSCs (n=5) (FIG. 5B) in miR-126flox/flox/Mx1-cre+ (Mx1+) and miR-126flox/flox/Mx1-cre– (Mx1–) mice at 16 weeks after pIpC injection.

(n=14), miR-126flox/wt(het)/Tie2+(n=10) and miR-126flox/flox(hom)/Tie2+ recipient mice (n=8). FIG. 5Q and FIG. 5R show WBC counts, where the legend from top to bottom represents each group of two data sets from left to right (FIG. 5Q) and survival, where the line with a higher value at 150 days represents data for Mx1+ to Tie2+ mice and the line with a lower value at 150 days represents data for Mx1+ to Tie2− mice(FIG. 5R) of the recipient mice from p. Comparison between groups was performed by two-tailed, unpaired Student's t-test. The log-rank test was used to assess significant differences between survival curves. P values <0.05 were considered significant. Results shown represent mean±SEM. *p<0.05, p<0.01, *p<0.001, ****p<0.0001.

FIGS. 6A-6Q. The figures show miR-126 knockdown by lentiviruses or CpG-miR-126 inhibitor in combination with nilotinib enhances the in vivo targeting of CML LSCs. FIG. 6A and FIG. 6B show engraftment of human CD45+GFP+ cells in PB at 4 weeks (n=8 independent samples) (FIG. 6A) and in BM at 16 weeks (n=10 independent samples) (FIG. 6B) in NSG-SGM3 mice transplanted with human CML Lin-CD34+CD38− cells ($5\times10^5$ cells/mouse, n=8-10 in each group), which were transduced with miR-126 KD or control lentiviruses and treated with NIL (5 µM) for 4 days. FIGS. 6I-6O show percentage of donor CML cells in PB (FIG. 6I), spleen (FIG. 6J) and BM (FIG. 6K), numbers of donor CML LSK in spleen (FIG. 6L) and BM (FIG. 6M), and numbers of donor CML LT-HSC in spleen (FIG. 6N) and BM (FIG. 6O) of recipient mice transplanted with CML BM cells and then treated with scrRNA (n=9), inhibitor (n=7), scrRNA+NIL (n=8), or inhibitor+NIL (n=10) for 3 weeks (total 34 mice). FIG. 6Q shows frequency of leukemia initiating cells (LICs) in BM cells from treated leukemic mice, as assessed by leukemia development rate in secondary recipient mice transplanted with $4\times10^6$, $2\times10^6$, $1\times10^6$, and $5\times10^5$ BM cells/mouse from the treated mice (n=6 mice/dose/condition×4 doses×4 conditions=96 mice) by L-Calc software. Comparison between groups was performed by two-tailed, unpaired Student's t-test. P values <0.05 were considered significant. Results shown represent mean±SEM. *p<0.05, p<0.01, *p<0.001, ****p<0.0001.

FIGS. 7A-7K. The figure shows that BCR-ABL downregulates miR-126 expression in CML cells. FIG. 7A shows representative flow cytometry plots of the populations sorted from the BM of normal and CML mice including Lin-Sca-1-c-Kit-(L-S-K-), Lin-Sca-1-c-Kit+(L-S-K+), Lin-Sca-1+c-Kit+(LSK) and LSK Flt3-CD150+CD48− (LT-HSCs). FIG. 7B shows PIK3R2 and FIG. 7C shows SPRED1 expression in human normal and CML CD34+ subpopulations as assessed by QPCR (n=8 independent samples), where the legend from top to bottom represents each group of two data sets from left to right. FIG. 7D shows PIK3R2 (n=3) and FIG. 7E shows SPRED1 (n=4) levels in mouse normal LSK cells transduced with BCR-ABL retroviral or control construct as assessed by QPCR (n=3 independent experiments). FIG. 7F shows PIK3R2 and FIG. 7G shows SPRED1 expression in human CML Lin-CD34+CD38− cells treated with NIL (n=3 biologically independent samples) and FIG. 7H shows miR-126 expression in human normal Lin-CD34+CD38−cells treated with NIL (n=3 biologically independent samples). For FIG. 7G and FIG. 7H, the legends from top to bottom represent each group of three data sets from left to right. FIG. 7I shows miR-126 staining in K562 cells treated with and without 5 µM NIL. The experiments were repeated 3 times with similar results. FIG. 7J shows schematic model of BCR-ABL regulated miR-126 biogenesis through SPRED1 and RAN/Exp-5/RCC1 complex in the absence (left panel) or presence of NIL (right panel). FIG. 7K shows a heatmap of differentially expressed miRNAs measured by miRNA-sequencing. Comparison between groups was performed by two-tailed, unpaired Student's t-test. P values ≤0.05 were considered significant. Results shown represent mean±SEM. *p≤0.05, p<0.01, *p<0.001.

FIG. 8A shows miR-126 levels in HUVECs (n=6 independent experiments) and human CML CD34+ subpopulations (n=12 biologically independent samples in each group) as assessed by QPCR. FIG. 8B and FIG. 8C shows miR-126 expression as assessed by QPCR (n=4) (FIG. 8B) and by miRNA staining in HUVECs transduced with miR-126 KD or control lentiviruses (n=3 independent experiments) (FIG. 8C). FIG. 8D and FIG. 8E show miR-126 expression as assessed by miRNA staining (n=3 independent experiments with similar results) (FIG. 8D) and QPCR (n=4 independent samples) (FIG. 8E) in CML Lin-CD34+CD38− cells co-cultured with ctrl or KD HUVECs or none. FIGS. 8F-8H show accumulated results where the legend from top to bottom represents each group of three data sets from left to right (FIG. 8F) and representative plots of cell cycling (n=3 independent samples), and representative plots (FIG. 8G) and accumulated results of apoptosis (n=4 independent samples) (FIG. 8H) in CML Lin-CD34+CD38− cells co-cultured with ctrl or KD HUVECs or none for 72 h. FIG. 8I shows the percentage of CD34+ cells from f-h was assessed by flow cytometry at 96 h (n=4). FIGS. 8J-8L show human CD45+ cells in PB at 6 weeks (n=8) (FIG. 8J) and in BM at 16 weeks (n=8) (FIG. 8K), and Bcr-Abl expression in BM at 16 weeks (n=8) (FIG. 8L) assessed by QPCR (n=8), from NSG-SGM3 mice transplanted with CML CD34+ cells after co-culture with ctrl or KD HUVECs or none for 96 h. Comparison between groups was performed by two-tailed, unpaired Student's t-test. P values ≤0.05 were considered significant. Results shown represent mean±SEM. *p≤0.05, p<0.01, *p<0.001.

FIG. 9A shows that EVs isolated from control and miR-126 KD HUVECs were visualized by electron microscopy. The experiments were repeated twice with similar results. FIGS. 9Q-9T show miR-126 expression in donor CML LT-HSCs (n=3) (FIG. 9Q), WBC counts where the legend from top to bottom represents each group of two data sets from left to right (FIG. 9R) and donor CML cell engraftment in PB, where the legend from top to bottom represents each group of two data sets from left to right (FIG. 9S) and survival where the line with a higher value at day 60 represents data for cells cultured with KD HUVEC-derived EVs and the line with a lower value represents data for cells cultured with ctrl (FIG. 9T) of the CD45.1 recipient mice transplanted with CD45.2 CML LT-HSCs co-cultured with ctrl (n=10) or KD (n=9) HUVEC-derived EVs for 96 h. Comparison between groups was performed by two-tailed, unpaired Student's t-test. P values ≤0.05 were considered significant. Results shown represent mean±SEM. *p≤0.05, p<0.01, *p<0.001.

FIGS. 10A-10K. The figure shows miR-126 knockdown enhanced TKI-mediated targeting of CML LSCs. FIGS. 10A-10F show miR-126 expression (FIG. 10A), cell cycling, where the legend from top to bottom represents each group of two data sets from left to right (FIG. 10B), apoptosis (FIG. 10C), cell growth (FIG. 10D), CFC (FIG. 10E), and CFC replating efficiency (FIG. 10F) in human CML Lin-CD34+CD38− cells transduced with miR-126 KD or miR-126 OE or control lentiviruses, with or without NIL (5 μM) for 72 h (n=4 independent experiments for all assays). FIGS. 10G-10K show miR-126 expression (FIG. 10G), cell cycling, where the legend from top to bottom represents each group of two data sets from left to right (FIG. 10H), apoptosis (FIG. 10I), cell growth (FIG. 10J) and CFC (FIG. 10K) (n=4 independent experiments for all) in mouse CML LT-HSCs transduced with miR-126 KD or miR-126 OE or control lentiviruses, with or without NIL (5 μM) for 72 h. Comparison between groups was performed by two-tailed, unpaired Student's t-test. P values ≤0.05 were considered significant. Results shown represent mean±SEM. *p≤0.05, p<0.01, *p<0.001.

FIG. 11A and FIG. 11B show representative plots of human CD45+ cell engraftment (FIG. 11A) and BCR-ABL expression by QPCR (n=7 independent samples) (FIG. 11B) in BM cells from NSG-SGM3 mice transplanted with human CML HSCs with or without miR-126 KD by lentiviruses transduction and treated with or without NIL (5 μM) for 4 days. (FIG. 11K) SPRED1, p-ERK, BCL-2 and β-actin in miR-126 KD cells from FIG. 11H, as assessed by western blot. The experiments were repeated twice using independent samples with similar results. FIG. 11L and FIG. 11M show SPRED1 mRNA by QPCR (n=4 independent experiments) (FIG. 11L) and SPRED1, p-ERK, BCL-2 and β-actin expression by western blot (FIG. 11M) in CML Lin-CD34+ cells with SPRED1 KD by siRNA transduction. The experiments were repeated twice using independent samples with similar results. FIG. 11R and FIG. 11S show BCL-2 by QPCR (FIG. 11R) and apoptosis by flow cytometry(FIG. 11S) in CML Lin-CD34+ cells with BCL-2 KD by siRNA transduction and treated with and without NIL (2 μM) for 48 h (n=4 independent experiments for both). Full-length gels and blots with molecular weight standards for FIGS. 11H, 11K, 11M, 11P were provided in FIG. 16. Comparison between groups was performed by two-tailed, unpaired Student's t-test. P values ≤0.05 were considered significant. Results shown represent mean±SEM. *p≤0.05, p<0.01, *p<0.001.

FIGS. 12A-12C show uptake of Cy3 as assessed by flow cytometry at 4 h (FIG. 12A) and 24 h (FIG. 12B) and miR-126 expression as assessed by QPCR at 24 h (FIG. 12C) in K562 cells after addition of CpG-miR-126 inhibitor-Cy3 (200 nM), Ab-NPs or TF-NPs containing miR-126 inhibitor-Cy3 (200 nM), or naked miR-126 inhibitor-Cy3 (200 nM, control) (n=3 independent experiments with similar results). For FIG. 12A and FIG. 12B, the legends from top to bottom represent the curves from left to right. FIG. 12P and FIG. 12Q show miR-126 expression in BM, LT-HSCs and ECs, as assessed by QPCR, from normal (FIG. 12P) and CML mice (FIG. 12Q) treated with CpG-miR-126 inhibitor (5 mg/kg/day, iv, daily) for 3 days (n=4 mice in each group), where the legend from top to bottom represents each group of two data sets from left to right Comparison between groups was performed by two-tailed, unpaired Student's t-test. P values ≤0.05 were considered significant. Results shown represent mean±SEM. *p≤0.05, p<0.01, *p<0.001.

FIGS. 13A-13F show red blood cell (RBC) (FIG. 13A), WBC (FIG. 13B) and platelet (PLT) (FIG. 13C) counts in PB and mononuclear cell (FIG. 13D), LT-HSC (FIG. 13E) and EC (FIG. 13F) counts in BM from WT B6 mice treated with CpG-scrRNA (scrRNA) or CpG-miR-126 inhibitor (inhibitor, 5 mg/kg/day i.v. 4 times a week) for 3 weeks (n=8 mice for each group). FIGS. 13K-13N show BCR-ABL levels in BM cells by QPCR (n=6 independent samples) (FIG. 13K), miR-126 expression in BM ECs (n=4 independent samples) (FIG. 13L) and in selected Sca-1+ and Sca-1-BM ECs (n=4 independent samples), where the legend from top to bottom represents each group of two data sets from left to right (FIG. 13M) from a cohort of CML mice treated as above with scrRNA, inhibitor, scrRNA+NIL, or inhibitor+NIL respectively, for 3 weeks. FIG. 13N shows schematic model of the role of miR-126 in modulating quiescence and self-renewal of CML LSCs through a well-orchestrated interplay between the hematopoietic compartment and the microenvironment in the BM niche. Comparison between groups was performed by two-tailed, unpaired Student's t-test. P values ≤0.05 were considered significant. Results shown represent mean±SEM. *p≤0.05, p<0.01, *p<0.001.

DETAILED DESCRIPTION

Figure 1A:
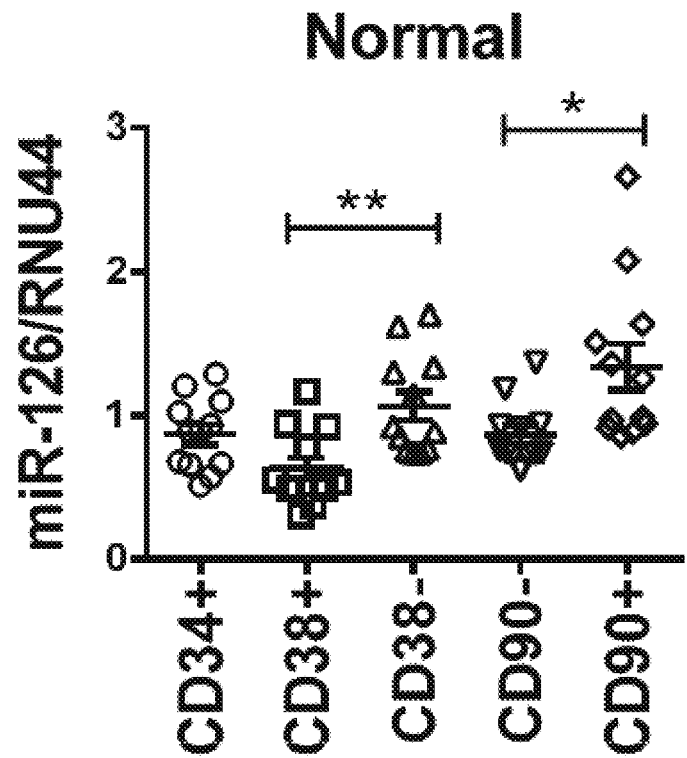
FIGS. 1A-1P. The figure shows that human and mouse CML LSCs express the highest levels of miR-126 among CML subpopulations.

Provided herein, inter alia, a compound including a phosphorothioated CpG oligodeoxynucleotide (CpG-ODN), conjugated to an anti-microRNA (anti-miR) or to a microRNA (miRNA)-mimic nucleic acid sequence (miRNA-mimic) or a compound including an anti-microRNA (anti-miR) sequence, where the anti-miR sequence contains one or more phosphorothioate linkages and one or more chemically modified nucleotides.

Definitions

"Disease" or "condition" refer to a state of being or health status of a patient or subject capable of being treated using the methods provided herein. In embodiments, the disease is a disease related to (e.g. caused by) miR126 or aberrant miR126 activity (e.g. anemia, leukemia, myeloid disease). Examples of diseases, disorders, or conditions include hematological diseases such as red blood cell diseases (e.g., anemia).

The term "red blood cell disease" refers to a disease affecting a red blood cell. Non-limiting examples of red blood cell diseases include anemia, sickle cell disease, acute lymphoblastic leukemia, hemolytic anemia, aplastic anemia, polycythemia, myelodysplastic syndrome, polycythemia vera, iron-deficiency anemia, autoimmune hemolytic anemia, sphercytosis, hereditary spherocytosis, megaloblastic anemia, glucose-6-phosphate dehydrogenase deficiency, normocytic anemia, paroxysmal nocturnal hemoglobinuria, hypochromic anemia, macrocytic anemia, pyruvate kinase deficiency, hereditary stomatocytosis, microcytosis, microcytic anemia, macrocytosis and hereditary elliptocytosis.

In some instances, "disease" or "condition" refer to "hematological disease" or "cancer." A hematological disease refers to a disease affecting a hematologic cell. In some instances, the hematological disease is a non-cancerous (i.e. non-malignant) hematological disease. Non-cancerous hematological diseases as provided herein include any disease, disorder or condition related to hematologic cells that is not cancer. Examples of non-cancerous hematological diseases, disorders, or conditions include, but are not limited to hemoglobinopathies including sickle-cell disease, thalassemia, methemoglobinemia; anemias including iron deficiency anemia, folate deficiency, hemolytic anemias, megaloblastic anemia, vitamin B12 deficiency, pernicious anemia, immune mediated hemolytic anemia, drug-induced immune mediated hemolytic anemia (e.g. due to high dose of penicillin, methyldopa), hemoglobinopathies, paroxysmal nocturnal hemoglobinuria, and microangiopathic hemolytic anemia; disease characterized by decreased numbers of blood cells (e.g. erythrocytes, lymphocytes, myeloid cells) including myelodysplastic syndrome, myelofibrosis, neutropenia, agranulocytosis, Glanzmann's thrombasthenia, thrombocytopenia, idiopathic thrombocytopenic purpura, thrombotic thrombocytopenic purpura, and heparin-induced thrombocytopenia; myeloproliferative disorders including polycythemia vera, erythrocytosis, leukocytosis, and thrombocytosis; coagulopathies including thrombocytosis, recurrent thrombosis, disseminated intravascular coagulation, hemophilia, Von Willebrand disease, disseminated intravascular coagulation, protein S deficiency, and antiphospholipid syndrome.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, aleukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

By "Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

The terms "Control" or "control experiment" are used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

A "multi-kinase inhibitor" is a small molecule inhibitor of at least one protein kinase, including tyrosine protein kinases and serine/threonine kinases. A multi-kinase inhibitor may include a single kinase inhibitor. Multi-kinase inhibitors may block phosphorylation. Multi-kinases inhibitors may act as covalent modifiers of protein kinases. Multi-kinase inhibitors may bind to the kinase active site or to a secondary or tertiary site inhibiting protein kinase activity. A multi-kinase inhibitor may be an anti-cancer multi-kinase inhibitor. Exemplary anti-cancer multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. Exemplary anti-cancer agents include antibodies, small molecules, large molecules, and combinations thereof. In embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all transretinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole;

etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or $rIL_2$), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, Inanocine (i.e. NSC-698666), Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

"Selective" or "selectivity" or the like of a compound refers to the compound's ability to discriminate between molecular targets.

"Specific", "specifically", "specificity", or the like of a compound refers to the compound's ability to cause a particular action, such as inhibition, to a particular molecular target with minimal or no action to other proteins in the cell.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

A polynucleotide is typically composed of a specific sequence of four nucleotide bases: adenine (A); cytosine (C); guanine (G); and thymin (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of an enzyme with a compound as described herein may reduce the level of a product of the enzyme catalyzed reaction or the level of a downstream derivative of the product or binding may reduce the interactions between the enzyme or a reaction product and downstream effectors or signaling pathway components, resulting in changes in cell growth, proliferation, or survival.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division. The term does not imply that all cells in the culture survive or grow or divide, as some may naturally senesce, etc. Cells are typically cultured in media, which can be changed during the course of the culture.

The terms "media" and "culture solution" refer to the cell culture milieu. Media is typically an isotonic solution, and can be liquid, gelatinous, or semi-solid, e.g., to provide a matrix for cell adhesion or support. Media, as used herein, can include the components for nutritional, chemical, and structural support necessary for culturing a cell.

As used herein, "conditions to allow growth" in culture and the like refers to conditions of temperature (typically at about 37° C. for mammalian cells), humidity, $CO_2$ (typically around 5%), in appropriate media (including salts, buffer, serum), such that the cells are able to undergo cell division or at least maintain viability for at least 24 hours, preferably longer (e.g., for days, weeks or months).

Suitable culture conditions are described herein, and can include standard tissue culture conditions. For example, HSCs, iPSCs, ES cells, or somatic cells can be cultured in a buffered media that includes amino acids, nutrients, growth factors, etc., as will be understood in the art. In some aspects, the culture of ES cells or iPSCs includes feeder cells (e.g., fibroblasts), while in others, the culture is devoid of feeder cells. Cell culture conditions are described in more detail, e.g., in Picot, Human Cell Culture Protocols (Methods in Molecular Medicine) 2010 ed. and Davis, Basic Cell Culture 2002 ed.

Culture conditions that support differentiation of HSCs to red blood cells, lymphoid or myeloid cells are well known in the art and described in more detail in Kevin D. Bunting (Ed) Hematopoietic Stem Cell Protocols in series Methods in Molecular Biology (John M. Walker, Series Ed.) ISBN 978-1-58829-868-3 and Dravid, G. et al. Molecular Therapy, 2011, 19: 768-781. Growth factors can also be included in the culture to promote HSC differentiation in to red blood cells, lymphoid cell or myeloid cells. Non-limiting examples of growth factors known in the art to support in vitro myeloid differentiation include stem cell factor (SCF), Flt3 ligand, thrombopoietin, interleukin-3 (IL-3) and erythropoietin. Non-limiting examples of growth factors known in the art to support in vitro lymphoid differentiation include SCF, Flt3 ligand, thrombopoietin, plus IL-7 (for B and T cells) or IL-15 (for NK cells). Further, Notch receptor ligand Delta-like 1 may be used to enhance T cell differentiation.

The term "derived from," when referring to cells or a biological sample, indicates that the cell or sample was obtained from the stated source at some point in time. For example, a cell derived from an individual can represent a primary cell obtained directly from the individual (i.e., unmodified), or can be modified, e.g., by introduction of a recombinant vector, by culturing under particular conditions, or immortalization. In some cases, a cell derived from a given source will undergo cell division and/or differentiation such that the original cell is no longer exists, but the continuing cells will be understood to derive from the same source.

A "somatic cell" is a cell forming the body of an organism. Somatic cells include cells making up organs, skin, blood, bones and connective tissue in an organism, but not germ line cells or stem cells.

A "hematologic cell" is a cell forming the blood, bone marrow and lymph nodes of an organism. Hematologic cells include platelets, neutrophils, monocytes, macrophages, basophils, lymphocytes, erythrocytes and eosinophils. Hematologic cells are derived from a common hematopoietic stem cell (HSC). A "hematopoietic stem cell" as provided herein refers to a somatic stem cell that is able to give rise to all blood cells. A hematopoietic stem cell has the capacity to differentiate into cells of the myeloid lineage (i.e. erythrocytes, mast cells, basophils, neutrophils, eosinophils, monocytes and macrophages) and the lymphoid lineage (i.e. natural killer cells, T cells and B cells).

A "stem cell" is a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

Where appropriate the expanding transfected derived stem cell may be subjected to a process of selection. A process of selection may include a selection marker introduced into an induced pluripotent stem cell upon transfection. A selection marker may be a gene encoding for a polypeptide with enzymatic activity. The enzymatic activity includes, but is not limited to, the activity of an acetyltransferase and a phosphotransferase. In some embodiments, the enzymatic activity of the selection marker is the activity of a phosphotransferase. The enzymatic activity of a selection marker may confer to a transfected induced pluripotent stem cell the ability to expand in the presence of a toxin. Such a toxin typically inhibits cell expansion and/or causes cell death. Examples of such toxins include, but are not limited to, hygromycin, neomycin, puromycin and gentamycin. In some embodiments, the toxin is hygromycin. Through the enzymatic activity of a selection marker, a toxin may be converted to a non-toxin, which no longer inhibits expansion and causes cell death of a transfected induced pluripotent stem cell. Upon exposure to a toxin, a cell lacking a selection marker may be eliminated and thereby precluded from expansion.

Identification of the induced pluripotent stem cell may include, but is not limited to the evaluation of afore mentioned pluripotent stem cell characteristics. Such pluripotent stem cell characteristics include without further limitation, the expression or non-expression of certain combinations of molecular markers. Further, cell morphologies associated with pluripotent stem cells are also pluripotent stem cell characteristics.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a DNA nucleic acid sequence (e.g., a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual,* 18.1-18.88). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and animals are those that express a heterologous gene or coding sequence, typically as a result of recombinant methods.

The term "exogenous" refers to a molecule or substance (e.g., a compound, nucleic acid or protein) that originates from outside a given cell or organism. Conversely, the term "endogenous" refers to a molecule or substance that is native to, or originates within, a given cell or organism.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

Unless indicated otherwise, the following annotations are used in the nucleic acid sequences disclosed herein: *=phosphorothioate linkage; xxxxx=any linker described herein and in embodiments xxxxx may be=—$(CH_2)_n$—$PO_4$—[$(CH_2)_n$—$PO_4$]$_z$—$(CH_2)_n$) bonded to phosphate groups at both ends except at the termini where terminal phosphates are optionally added and 5'x has an OH terminus and 3' x has a —$C^6$—$NH_2$ bonded to the final phosphate group, other linkages are phosphodiester; mN indicates a 2'OMe modified nucleotide; fN indicates a 2'fluoro modified nucleotide; and rN indicates a ribonucleotide.

As used herein, the term "anti-microRNA (anti-miR)" or "anti-microRNA (anti-miR) nucleic acid sequence" is used according to its plain and ordinary meaning and refers to RNA that is capable of suppressing or reducing expression and/or activity of a target microRNA. In embodiments, the anti-miR oligomer may be a single stranded oligomer of 20-30 bases. In embodiments, the anti-miR oligomer may be a double stranded oligomer of 20-30 bases. In embodiments, the anti-miR oligomer may be partially double stranded, with single stranded overhangs. In embodiments, the oligomer may have a 2' chemical modification. In embodiments, the oligomer may have serum stability-enhancing chemical modification, e.g., a phosphothioate internucleotide linkage, a 2'-O-methyl ribonucleotide, a 2'-deoxy-2'fluoro ribonucleotide, a 2'-deoxy ribonucleotide, a universal base nucleotide, a 5-C methyl nucleotide, an inverted deoxybasic residue incorporation, or a locked nucleic acid. In embodiments, an anti-miR sequence hybridizes to the corresponding miR sequence. Full complementarity is not necessarily required, provided there is sufficient complementarity to cause hybridization. In some embodiments, the degree of complementarity between an anti-miR sequence and its corresponding miR sequence, when optimally aligned using a suitable alignment algorithm, is about or more than about 50%, 60%, 75%, 80%, 85%, 90%, 91%, 92%, 93%, 94%, 95%, 96%, 97%, 98%, 99%, or 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In embodiments, the anti-miR sequence has at least 80%, 85%, 90%, 95%, 96%, 97%, 98%, 99% or 100% sequence identity with the perfectly complementary sequence of the target miR sequence.

A "microRNA," "microRNA nucleic acid sequence," "miR," "miRNA" as used herein, refers to a nucleic acid that functions in RNA silencing and post-transcriptional regulation of gene expression. The term includes all forms of a miRNA, such as the pri-, pre-, and mature forms of the miRNA. In embodiments, microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA. In embodiments, a miRNA nucleic acid sequence described herein is about 10 to 80 nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 nucleotides) in length. In embodiments, a miRNA nucleic acid sequence described herein is about 15 to 50 nucleotides (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides) in length. In embodiments, a miRNA nucleic acid sequence described herein is about 18 to 25 nucleotides (e.g., 18, 19, 20, 21, 22, 23, 24, 25 nucleotides) in length.

As used herein, the term "miR126" or "miR142 nucleic acid sequence" includes all forms of miR126 including the pri-, pre-, and mature forms of miR126, as well as variants, homologues, modifications, and derivatives thereof (e.g., within at least 50%, 80%, 90%, 95%, 96%, 97%, 98%, 99% or 100% activity compared to the native miR126). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR126 is the miRNA as identified by NCBI Reference Sequence: NR 029695.1 or sequence:

```
  1 cgctggcgac gggacattat tacttttggt acgcgctgtg
    acacttcaaa ctcgtaccgt
 61 gagtaataat gcgccgtcca cggca.
```

The term "anti-miR126" or "anti-miR126 nucleic acid sequence" refers to a sequence that is at least 80%, 85%, 90%, 95%, 96%, 97%, 98%, 99% or 100% sequence identity with the perfectly complementary sequence to the target miR126 nucleic acid as defined above.

As used herein, the term "microRNA-mimic (miRNA-mimic)" or "miRNA-mimic nucleic acid sequence" is used according to its plain and ordinary meaning and refers to single, double or triple stranded oligonucleotide that is capable of effecting a biological function similar to a microRNA. In embodiments, miRNA-mimic may be non-natural double-stranded miR-like RNA fragments. Such an RNA fragment may be designed to have its 5'-end bearing a partially complementary motif to the selected sequence in the 3'UTR unique to the target gene. Once introduced into cells, this RNA fragment, may mimic an endogenous miRNA, bind specifically to its target gene and produce posttranscriptional repression, more specifically translational inhibition, of the gene. Unlike endogenous miRNAs, miRNA-mimics may act in a gene-specific fashion. In embodiments, the miRNA-mimic may be a double stranded oligomer of 20-30 bases (e.g., 20, 21, 22, 23, 24, 25, 26, 27, 28, 29, 30 bases). In embodiments, the miRNA-mimic may be a triple stranded oligomer of 20-30 bases (e.g., 20, 21, 22, 23, 24, 25, 26, 27, 28, 29, 30 bases). In embodiments, the miRNA-mimic may have a 2' chemical modification. In embodiments, the miRNA-mimic may have serum stability-enhancing chemical modification, e.g., a phosphothioate internucleotide linkage, a 2'-O-methyl ribonucleotide, a 2'-deoxy-2'fluoro ribonucleotide, a 2'-deoxy ribonucleotide, a universal base nucleotide, a 5-C methyl nucleotide, an inverted deoxybasic residue incorporation, or a locked nucleic acid.

As used herein, the term "miR126-mimic" or "miR26-mimic nucleic acid sequence" refers to an oligonucleotide that is structurally substantially similar to miR126 and is capable of effecting a biological function similar to miR126. In embodiments, the miR126-mimic has at least 50%, 80%, 90%, 95%, 96%, 97%, 98%, 99% or 100% activity compared to the native miR126. In embodiments, the miR126-mimic has at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to native miR126.

As used herein, the term "phosphorothioated oligodeoxynucleotide (ODN)" refers to a nucleic acid sequence, e.g., "CpG nucleic acid sequence" or "GpC nucleic acid sequence", in which some or all the internucleotide linkages constitute a phosphorothioate linkage. In embodiments, phosphorothioated oligodeoxynucleotide (ODN) is 15 to 30 bases long, single-stranded, partly or completely phosphorothioated. The partly phosphorothioated ODN is an ODN in which 1, 2, 3, 4, 5, 6, 7, 8, 9, 10, 11, 12, 13, 14, 15, 16, 17, 18, 19, 20, 21, 22, 23, 24, 25, 26, 27, or 28, internucleotide linkages constitute a phosphorothioate linkage.

In embodiments, the term "CpG motif" in a nucleic acid refers to a nucleic acid in which a 5' C nucleotide connected to a 3' G nucleotide through a phosphodiester internucleotide linkage or a phosphodiester derivative internucleotide linkage. In embodiments, the term "CpG motif" in a nucleic acid refers to a nucleic acid in which a 5' G nucleotide connected to a 3' C nucleotide through a phosphodiester internucleotide linkage or a phosphodiester derivative internucleotide linkage (aka a "GpC nucleic acid sequence"). In embodiments, a CpG motif includes a phosphodiester internucleotide linkage. In embodiments, a CpG motif includes a phosphodiester derivative internucleotide linkage. In embodiments, a CpG motif includes a phosphorothioate linkage.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide including one or more of poly-G sequence at the 5', 3', or both ends; an internal palindrome sequence including CpG motif; or one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate. Examples of Class A CpG ODNs include ODN D19, ODN 1585, ODN 2216, and ODN 2336.

As used herein, the term "Class B CpG ODN" or "B-class CpG ODN" or "K-type CpG ODN" or "Class B CpG DNA sequence" is used in accordance with its common meaning in the biological and chemical sciences and refers to a CpG motif including oligodeoxynucleotide including one or more of a 6mer motif including a CpG motif; phosphodiester derivatives linking all deoxynucleotides. In embodiments, a 6mer motif comprises 5'-PuPyCGPyPu-3' (SEQ ID NO: 15), where Pu represents a purine containing nucleobase (e.g., A or G) and Py represents a pyrimidine containing nucleobase (e.g., T/U or C). In embodiments, a Class B CpG ODN includes one or more copies of a 6mer motif including a CpG motif and phosphodiester derivatives linking all deoxynucleotides. In embodiments, the phosphodiester derivative is phosphorothioate. In embodiments, a Class B CpG ODN includes one 6mer motif including a CpG motif. In embodiments, a Class B CpG ODN includes two copies of a 6mer motif including a CpG motif. In embodiments, a Class B CpG ODN includes three copies of a 6mer motif including a CpG motif. In embodiments, a Class B CpG ODN includes four copies of a 6mer motif including a CpG motif. Examples of Class B CpG ODNs include ODN 1668, ODN 1826, ODN 2006, and ODN 2007.

As used herein, the term "Class C CpG ODN" or "C-class CpG ODN"" or "C-type CpG DNA sequence" is used in accordance with its common meaning in the biological and chemical sciences and refers to an oligodeoxynucleotide including a palindrome sequence including a CpG motif and phosphodiester derivatives (phosphorothioate) linking all deoxynucleotides. Examples of Class C CpG ODNs include ODN 2395 and ODN M362.

A "label" or a "detectable moiety" is a composition detectable by spectroscopic, photochemical, biochemical, immunochemical, chemical, magnetic resonance imaging, or other physical means. For example, useful detectable moieties include $^{32}P$, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monocrystalline SPIO, monocrystalline SPIO aggregates, monocrystalline iron oxide nanoparticles, monocrystalline iron oxide, other nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g., compound described herein). Any method known in the art for conjugating an oligonucleotide or protein to the label may be employed, e.g., using methods described in Hermanson, Bioconjugate Techniques 1996, Academic Press, Inc., San Diego.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —$NO_2$, in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O) NR'R", —NR"C(O)R', —NR'—C(O)NR"R"', —NR"C(O)$_2$R', —NR—C(NR'R"R"')=NR"", —NR—C(NR'R")=N R"', —S(O)R', —S(O)$_2$R', —S(O)$_2$NR'R", —NRSO$_2$R', —NR'NR"R"', —ONR'R", —NR'C=(O)NR"NR"'R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A—($CH_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
(i) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:
  (a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=(O)$NHNH_2$, —NHC=(O)$NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and
  (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der waal's bond(s)/interactions, hydrogen bond(s), polar bond(s), or combinations or mixtures thereof).

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would most likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

The term "inhibiting" also means reducing an effect (disease state or expression level of a gene/protein/mRNA) relative to the state in the absence of a compound or composition of the present disclosure.

The terms "phenotype" and "phenotypic" as used herein refer to an organism's observable characteristics such as onset or progression of disease symptoms, biochemical properties, or physiological properties.

For specific proteins described herein (e.g., CD34 or CD38), the named protein includes any of the protein's naturally occurring forms, variants or homologs (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "CD34" refers to hematopoietic progenitor cell antigen CD34 also known as CD34 antigen that is encoded by the CD34 gene in humans. It is a cell surface glycoprotein and functions as a cell-cell adhesion factor. The term "CD34" as provided herein includes any of the CD34 protein naturally occurring forms, homologs or variants that maintain the activity of CD34 (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD34 protein is the protein as identified by the NCBI sequence reference NP_001764 or NP_001020280.1, homolog or functional fragment thereof.

The term "CD38" refers to cluster of differentiation 38, also known as cyclic ADP ribose hydrolase that is encoded by the CD38 gene in humans. It is a cell surface glycoprotein and functions in cell-cell adhesion and signaling transduction. The term "CD38" as provided herein includes any of the CD38 protein naturally occurring forms, homologs or variants that maintain the activity of CD38 (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD38 protein is the protein as identified by the NCBI sequence reference NP_001766.2, homolog or functional fragment thereof.

The term "an amount of" in reference to a polynucleotide or polypeptide, refers to an amount at which a component or element is detected. The amount may be measured against a control, for example, wherein an increased level of a particular polynucleotide or polypeptide in relation to the control, demonstrates enrichment of the polynucleotide or polypeptide. Thus, in embodiments, an increased amount indicates a greater level or efficiency of grafting HSPCs described herein into a host (e.g., mouse). The term refers to quantitative measurement of the enrichment as well as qualitative measurement of an increase or decrease relative to a control.

Throughout the description and claims of this specification the word "comprise" and other forms of the word, such as "comprising" and "comprises," means including but not limited to, and is not intended to exclude, for example, other components.

"Analog," "analogue," or "derivative" is used in accordance with its plain ordinary meaning within Chemistry and Biology and refers to a chemical agent that is structurally similar to another agent (i.e., a so-called "reference" agent) but differs in composition, e.g., in the replacement of one atom by an atom of a different element, or in the presence of a particular functional group, or the replacement of one functional group by another functional group, or the absolute stereochemistry of a chiral center of the reference agent. In some embodiments, a derivative may be a conjugate with a pharmaceutically acceptable agent, for example, phosphate or phosphonate.

As used herein, the term "salt" refers to acid or base salts of the agents used herein. Illustrative but non-limiting examples of acceptable salts are mineral acid (hydrochloric acid, hydrobromic acid, phosphoric acid, sulfuric acid, and the like) salts, organic acid (acetic acid, propionic acid, glutamic acid, citric acid, and the like) salts, and quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

An "adjuvant" (from Latin, adiuvare: to aid) is a pharmacological and/or immunological agent that modifies the effect of other agents.

A "diluent" (also referred to as a filler, dilutant or thinner) is a diluting agent. Certain fluids are too viscous to be pumped easily or too dense to flow from one particular point to the other. This can be problematic, because it might not be economically feasible to transport such fluids in this state. To ease this restricted movement, diluents are added. This decreases the viscosity of the fluids, thereby also decreasing the pumping/transportation costs.

The terms "administration" or "administering" refer to the act of providing an agent of the current embodiments or pharmaceutical composition including an agent of the current embodiments to the individual in need of treatment.

By "co-administer" it is meant that a composition described herein is administered at the same time, just prior to, or just after the administration of additional therapies. The compound or the composition of the disclosure can be administered alone or can be co-administered to the patient. Co-administration is meant to include simultaneous or sequential administration of the compound individually or in combination (more than one compound or agent). The preparations can also be combined, when desired, with other active substances (e.g. to reduce metabolic degradation).

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and. Other modes of delivery include, but are not limited to, the use of liposomal formulations, intravenous infusion, transdermal patches, etc.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Bioniater Sci. Polym. Ed.* 7:623-645, 1995; as biodegradable and injectable gel formulations (see, e.g., Gao *Phann. Res.* 12:857-863, 1995); or, as microspheres for oral administration (see, e.g., Eyles, *J. Phann. Pharmacol.* 49:669-674, 1997).

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

Pharmaceutical compositions may include compositions wherein the therapeutic drug (e.g., agents described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of therapeutic drug effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and agents of this disclosure. Adjustment and manipulation of established dosages (e.g., frequency and duration) are well within the ability of those skilled in the art.

For any therapeutic agent described herein, the therapeutically effective amount can be initially determined from cell culture assays. Target concentrations will be those concentrations of therapeutic drug(s) that are capable of achieving the methods described herein, as measured using the methods described herein or known in the art.

The term "about" refers to any minimal alteration in the concentration or amount of an agent that does not change the efficacy of the agent in preparation of a formulation and in treatment of a disease or disorder. The term "about" with respect to concentration range of the agents (e.g., therapeutic/active agents) of the current disclosure also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Methods

Provided herein is a method of treating a red blood cell disease in a subject in need thereof, the method including administering to the subject an effective amount of an anti-miR126 compound or a pharmaceutical composition including an anti-miR126 compound disclosed herein. In embodiments, the disease is anemia. Thus, in one aspect, a method of treating anemia in a subject in need thereof is provided. The method includes administering to the subject an effective amount of an anti-microRNA126 (miR126) compound.

In one aspect, a method of treating a red blood cell disease in a subject in need thereof is provided. The method includes administering to the subject an effective amount of an anti-microRNA126 (miR126) compound.

In one aspect, a method of treating or preventing anemia in a subject in need thereof is provided. The method includes (i) isolating a hematopoietic stem cell (HSC) from a subject, thereby forming an isolated HSC; (ii) contacting the isolated HSC with an anti-microRNA126 (miR126) compound thereby forming a contacted HSC; and (iii) administering the contacted HSC to the subject, thereby treating or preventing anemia in the subject.

In embodiments, the contacting step is free of viral transduction. In embodiments, the contacted HSC is allowed to divide prior to the administering of step (iii). In embodiments, the isolating includes obtaining a biological sample from the subject and isolating the HSC from the biological sample. In embodiments, the biological sample is a blood sample or a bone marrow sample.

In one aspect, a method of forming a red blood cell is provided. The method includes: (i) contacting a hematopoietic stem cell (HSC) with an anti-microRNA126 (miR126) compound, thereby forming a contacted HSC; and allowing the contacted HSC to divide, thereby forming a red blood cell. In embodiments, the contacting occurs in a subject. In embodiments, the HSC is derived from a biological sample. In embodiments, the biological sample is a blood sample or a bone marrow sample. In embodiments, the contacting occurs in vitro. In embodiments, the contacted HSC is administered to a subject. In embodiments, the contacting step is free of viral transduction and the HSC is contacted with the compound. In embodiments, the HSC is contacted with about 1-100 nanomolar concentration of the compound.

In embodiments, the anti-miR126 compound includes: (i) a phosphorothioated CpG oligodeoxynucleotide (CpG-ODN) conjugated to an anti-miR126 nucleic acid sequence; (ii) a CpG-ODN conjugated to a miRNA126 mimic nucleic acid sequence; or (iii) an unconjugated anti-miR126 nucleic acid sequence, wherein the unconjugated anti-miR126 nucleic acid sequence includes one or more phosphorothioate linkages and one or more chemically modified nucleotides.

In embodiments, the anti-miR126 compound further includes a covalent linker between the CpG-ODN and the anti-miR126 nucleic acid sequence or between the CpG-ODN and the miRNA126 mimic nucleic acid sequence. In embodiments, the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the id linker is an unsubstituted $C_1$-$C_{40}$ alkylene, unsubstituted 2 to 40 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the linker is a substituted 2 to 40 membered heteroalkylene.

In embodiments, the anti-miR126 nucleic acid sequence, the miRNA126 mimic nucleic acid sequence or the unconjugated anti-miR126 nucleic acid sequence are independently chemically modified. In embodiments, the anti-miR126 nucleic acid sequence, the miRNA126 mimic nucleic acid sequence or the unconjugated anti-miR126 nucleic acid sequence independently include a chemical modification selected for the group consisting of a 2' O-Methyl, 2'-deoxy-2'fluoro, 2'-deoxy, a universal base, 5-C-methyl, an inverted deoxy abasic residue incorporation, and a locked nucleic acid. In embodiments, the modification is positioned at the terminal nucleobase of the anti-miR126 nucleic acid sequence, the miRNA126 mimic nucleic acid sequence or the unconjugated anti-miR126 nucleic acid sequence. In embodiments, the modification is not positioned at the terminal nucleobase of the anti-miR126 nucleic acid sequence, the miRNA126 mimic nucleic acid sequence or the unconjugated anti-miR126 nucleic acid sequence. In embodiments, the modification protects against serum-derived nucleases.

In embodiments, the compound is administered to the subject by intravenous, parenteral, subcutaneous, intramuscular, transdermal, intraperitoneal, intranasal, aerosol, oral, or topical administration. In embodiments, the compound is administered to the subject by intravenous, parenteral, subcutaneous, intramuscular, transdermal, intraperitoneal, intranasal, aerosol, oral, or topical administration. In embodiments, the treatment is dose-dependent of the compound or composition. In embodiments, about 0.001 mg/kg to about 100 mg/kg of the compound are administered to the subject.

The compounds used for the methods provided herein including embodiments thereof may include an anti-microRNA (anti-miR) sequence, where the anti-miR sequence includes one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more), phosphorothioate linkages and one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) chemically modified nucleotides.

In embodiments, the anti-miR is anti-miR126. In embodiments, the miRNA-mimic is miR126-mimic.

In embodiments, the linker represented by "xxxxx" or the like described herein is a bond, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, substituted (e.g. substituted with a substituent group, size-limited substituent group or lower substituent group) or unsubstituted cycloheteroalkylene or —$(CH_2)_n$—$PO_4$—$[(CH_2)_nPO_4]_z$—$(CH_2)_n$, in which the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5 or 1 to 5. In embodiments, n is 3 and z is 0 to 4 or 1 to 4. In embodiments, n is 3 and z is 0 to 3 or 1 to 3. In embodiments, n is 3 and z is 3. 2'OMe (2'-O-Methylnucleoside; Hydroxyl in 2'-position replaced with 2'-OMethyl); PS is phoshorothioation. One none-bridging oxygen replaced with sulfur; PS+3 represents three phosphates in the sequence modified, had one none-bridging oxygen replaced with sulfur; PS+5 represents five phosphates in the sequence modified, had one none-bridging oxygen replaced with sulfur.

For example, as shown below, in embodiments, nucleobases in the phosphorothioated oligonucleotide of the present disclosure sequence may include a phosphorothioate internucleotide linkage. A portion of such a phosphorothioated oligonucleotide is shown below.

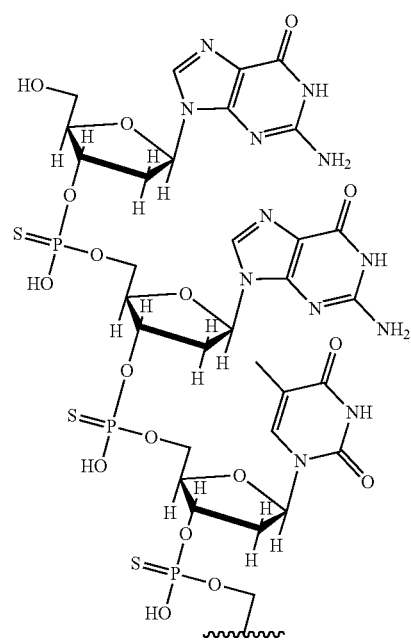

The linker may have the structure below, where the linker connects with the 3' phosphate of the guanine on one end and the 5' phosphate of the thymidine on the other end, and the nucleobases in the antisense part may be modified with 2'OMe.

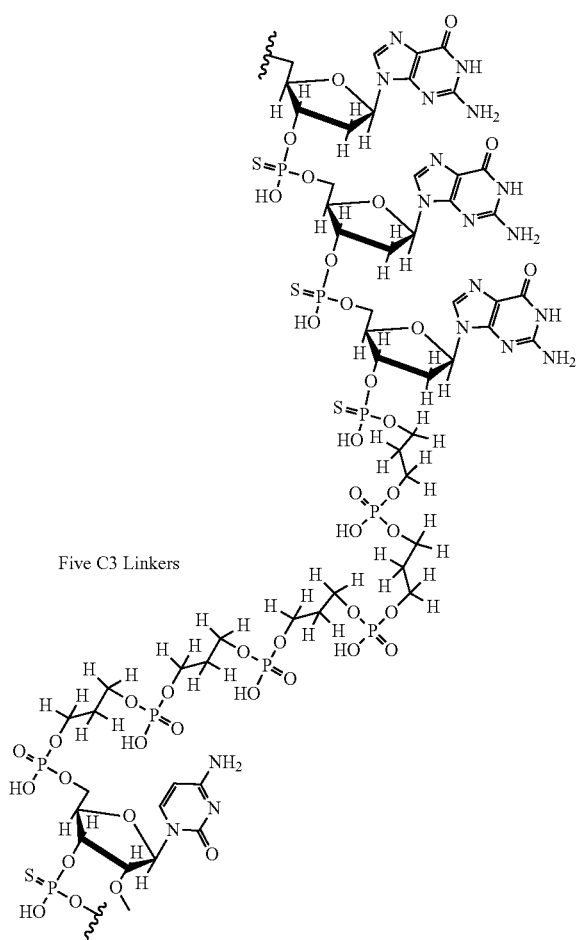

Five C3 Linkers

The above formula represents a portion of the CpG-ODN linked at the 3'-OH end with a $(CH_2)_3$ linker (also referred to herein as the C3 linker), which links to the 5'-phosphate of the antisense RNA.

The linker may be a bond, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted or unsubstituted heteroarylene.

In embodiments, the compound including a nucleic acid sequence (CpG-ODN) is conjugated to an anti-miR or miRNA-mimic sequence, with one or more linkers described herein.

In embodiments, the compound including a nucleic acid sequence of an anti-miR or miRNA-mimic sequence, where the nucleic acid sequence contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) phosphorothioate linkages and/or one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more) chemically modified nucleotides. In embodiments, a chemical modification is selected from the group consisting of a 2' O-Methyl, 2'-deoxy-2'fluoro, 2'-deoxy, a universal base, 5-C-methyl, an inverted deoxy abasic residue incorporation, and a locked nucleic acid.

In embodiments, the linker is a covalent linker (i.e. a linker that covalently attaches at least two (e.g. 2) portions of a compound). In embodiments, the linker is or includes a substituted (e.g. substituted with a substituent group, size-limited substituent group or lower substituent group) or unsubstituted alkylene or heteroalkylene linker. In embodiments, the nucleic acid conjugated to anti-miRs and miRNA mimics includes more than one substituted (e.g. substituted with a substituent group, size-limited substituent group or lower substituent group) or unsubstituted heteroalkylene linkers. Linkers may be added during the synthesis in sequence. In embodiments, heteroalkylene linkers are connected to each other with an intervening phosphate bond. In embodiments, the covalent linker is a substituted (e.g. substituted with a substituent group, size-limited substituent group or lower substituent group) or unsubstituted heteroalkylene linker.

In embodiments, the linker is a substituted (e.g. substituted with a substituent group, size-limited substituent group or lower substituent group) or unsubstituted heteroalkylene or substituted (e.g. substituted with a substituent group, size-limited substituent group or lower substituent group) or unsubstituted cyclo-heteroalkylene. A "cyclo-heteroalkylene," as used herein is a heteroalkylene having a one or more divalent cyclic moieties within the heteroalkylene chain. The cyclic moiety may be a substituted (e.g. substituted with a substituent group, size-limited substituent group or lower substituent group) or unsubstituted cycloalklylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene or substituted (e.g. substituted with a substituent group, size-limited substituent group or lower substituent group) or unsubstituted heteroarylene. In embodiments, the cyclic moiety is a substituted (e.g. substituted with a substituent group, size-limited substituent group or lower substituent group) or unsubstituted ribose (e.g., a nucleoside). In embodiments, the cyclic moiety serves as a branch point of the linker thereby forming a branched linker. The cyclic moiety branch point may be used to attach additional functional moieties to the conjugates provided herein, such as detectable moieties, drug moieties or biomolecule. As explained in more detail below, the additional functional moieties may be connected using click chemistry techniques as known in the art.

For example, the linker may have the structure below, where the linker connects with the 3' phosphate of the guanine on one end and the 5' phosphate of the thymidine on the other end:

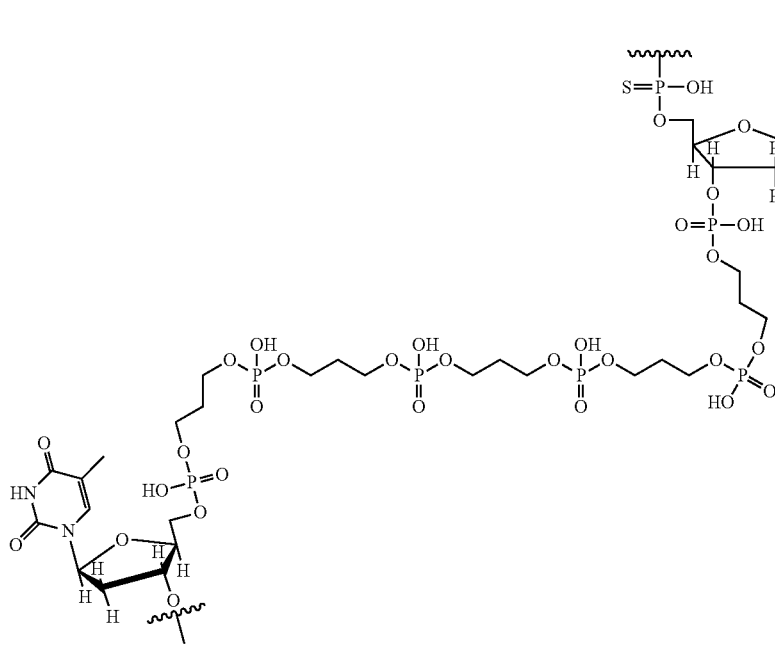

In embodiments, the guanidine above is connected to the nucleic acid sequence (CpG-ODN), and the thymidine is connected to an anti-miR or miRNA-mimic sequence.

In embodiments, the linker may include a moiety selected from an azide group, a protected amino group, N-hydroxysuccinimide (NHS) group, and a protected sulfhydryl group.

In embodiments, the linker may include a protected sulfhydryl group that is conjugated to a moiety selected from the group consisting of divinyl sulfone derivative, acryloyl derivative, and/or maleimido derivative. In embodiments, the acryloyl derivative is acryloyl chloride.

In embodiments, linker may be conjugated to polyethylene glycol (PEG) or bisphosphonate moiety.

In embodiments, linker may include an unsubstituted $C_3$ heteroalkylene.

In embodiments, linker may include an unsubstituted $C_6$ to $C_{12}$ heteroalkylene.

In embodiments, the linker may be substituted with a reactive group (e.g. a click chemistry reactive group) or a protected reactive group. The reactive group may be used to conjugate the CpG-ODN to an anti-miR or miRNA-mimic and/or to an additional functional moiety as described herein, such as a detectable moiety or biomolecule (e.g. a targeting moiety).

Thus, the linker may include further modification, conjugation, or attachment of additional moieties.

The reactive group used to conjugate the CpG-ODN to an anti-miR or miRNA-mimic compound to an additional functional moiety may be any applicable reactive group useful in bioconjugate chemistry. See Hermanson, *Bioconjugate Techniques* 1996, Academic Press, Inc., San Diego.

In embodiments, the reactive group is a click chemistry reactive group. Click chemistry refers to a group of reactions that are fast, simple to use, easy to purify, versatile, regio- specific, and give high product yields. Four different click reactions are possible: (1) Cycloadditions—these primarily refer to 1,3-dipolar cycloadditions, but also include hetero-Diels-Alder cycloadditions; (2) Nucleophilic ring-openings—these refer to the opening of strained heterocyclic electrophiles, such as aziridines, epoxides, cyclic sulfates, aziridinium ions, episulfonium ions; (3) carbonyl chemistry of the non-aldol type—examples include the formations of ureas, thioureas, hydrazones, oxime ethers, amides, aromatic heterocycles; (4) additions of carbon-carbon multiple bonds—examples include epoxidations, aziridinations, dihydrooxylations, sulfenyl halide additions, nitrosyl halide additions, and certain Michael additions. In embodiments, the click reaction used may be Cu'-catalyzed Huisgen 1,3-dipolar cycloaddition (HDC) of azides or terminal alkynes to form 1,2,3-triazoles. In embodiments, the click reaction may be a copper-free reaction.

In embodiments, the click chemistry reactive group is or includes an azide groups, an alkene group, an amino groups, an N-hydroxysuccinimide group, a sulfhydryl group, a divinyl sulfone derivative, or a maleimido derivative. Thus, in embodiments, the linker is substituted with a reactive group (e.g. a click chemistry reactive group) or a protected reactive group, including, for example, a protected amino group or a N-hydroxysuccinimide group, suitable for conjugation by N-hydroxysuccinimide (NHS) chemistry; a sulfhydryl group that may be conjugated with divinyl sulfone; a protected sulfhydryl group, which may be conjugated with 1-alkyl-3-methylacryloyl (acryloyl) chloride or acryloyl derivatives; a protected sulfhydryl group, which may be conjugated with maleimido derivatives.

Provided below is a structural example of a cyclo-heteroalkylene branched linker:

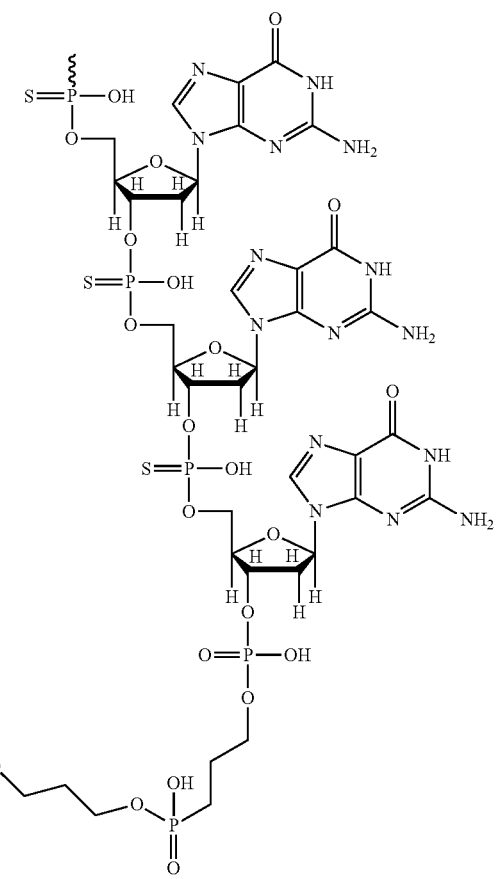
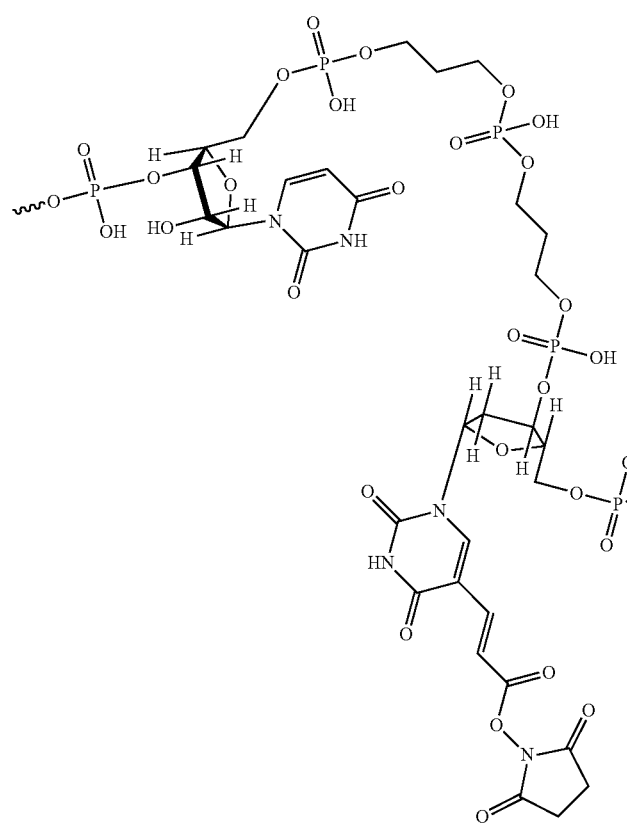

Substitution with NHS-Carboxy-dT

NHS esters react with nucleophiles, e.g., amines. NHS ester can be used for the introduction of the substituent, e.g., PEG (reaction with PEG-amine).

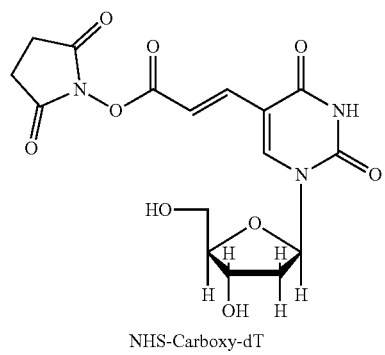

NHS-Carboxy-dT

As shown above, a cyclo-heteroalkylene branched linker connects with the 3' phosphate of the guanine on one end and the 5' phosphate of the thymidine on the other end. The moiety of the cyclo-heteroalkylene branched linker is a branch point and is a 5-substituted thymidine. The thymidine is substituted in position 5 with a reactive group containing an NHS moiety, which can serve as a reactive group to connect to an additional functional moiety As set forth above, the reactive group may be used to conjugate the CpG-ODN to an anti-miR or miRNA mimic nucleic acid sequence and/or to an additional functional moiety such as a detectable moiety, therapeutic moiety (e.g., drug moiety), targeting moiety or biomolecule. Additional functional moieties include a fluorescent label, a targeting compound (bone targeting bisphosphonates), a drug, or an antibody. In embodiments, additional moiety is a chemically reactive moiety, detectable moiety, therapeutic moiety (e.g. anti-cancer agent or anti-viral agent), nucleic acid sequence, DNA sequence, or nucleic acid analogs. In embodiments, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, an additional moiety is a therapeutic moiety (e.g. anti-cancer agent or anti-viral agent).

A linker may be a bond, nucleic acid sequence, two nucleic acid sequences, DNA sequence, two DNA sequences, nucleic acid analog sequence, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted (e.g. substituted with a substituent group, size-limited substituent group or lower substituent group) or unsubstituted heteroarylene.

In embodiments, anti-miR and miRNA mimics may include modifications such as 2' O-Methyl, 2'-deoxy-2'fluoro, 2'-deoxy, a universal base, 5-C-methyl, an inverted deoxy abasic residue incorporation, or a locked nucleic acid, or any combination(s) thereof. In embodiments, the anti-miR and miRNA mimics may have a modification positioned at the terminal nucleobase of the anti-miR and miRNA mimics. In embodiments, the anti-miR and miRNA mimics may not have a modification positioned at the terminal nucleobase of the anti-miR and miRNA mimics. In embodiments, the modification of the anti-miR and miRNA mimics protects the compound against serum-derived nucleases (e.g. is nuclease resistant).

In embodiments, the (CpG-ODN) conjugated to an anti-miR or miRNA mimic has a terminal moiety. A terminal moiety is a chemically reactive moiety, detectable moiety, therapeutic moiety (e.g. anti-cancer agent or anti-viral agent), nucleic acid sequence, DNA sequence, substituted (e.g. substituted with a substituent group, size-limited substituent group or lower substituent group) or unsubstituted alkyl, substituted (e.g. substituted with a substituent group, size-limited substituent group or lower substituent group) or unsubstituted heteroalkyl, substituted (e.g. substituted with a substituent group, size-limited substituent group or lower substituent group) or unsubstituted cycloalkyl, substituted (e.g. substituted with a substituent group, size-limited substituent group or lower substituent group) or unsubstituted heterocycloalkyl, substituted (e.g. substituted with a substituent group, size-limited substituent group or lower substituent group) or unsubstituted aryl, or substituted (e.g. substituted with a substituent group, size-limited substituent group or lower substituent group) or unsubstituted heteroaryl.

In embodiments, a terminal moiety is a chemically reactive moiety, detectable moiety, therapeutic moiety (e.g. anti-cancer agent or anti-viral agent), nucleic acid sequence, DNA sequence, nucleic acid analogs, $R^1$-substituted or unsubstituted alkyl, $R^1$-substituted or unsubstituted heteroalkyl, $R^1$-substituted or unsubstituted cycloalkyl, $R^1$-substituted or unsubstituted heterocycloalkyl, $R^1$-substituted or unsubstituted aryl, or $R^1$-substituted or unsubstituted heteroaryl.

In embodiments, a CpG-ODN nucleic acid sequence conjugated to an anti-miR or miRNA-mimic conjugates includes a terminal moiety, wherein the terminal moiety is a detectable moiety. In embodiments, the CpG-ODN conjugated to an anti-miR or miRNA-mimic includes a terminal detectable moiety such as, a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, the CpG-ODN conjugated to an anti-miR or miRNA-mimic includes a terminal moiety, which is a therapeutic moiety (e.g., anti-cancer agent or anti-viral agent).

In embodiments, the CpG-ODN conjugated to an anti-miR or miRNA-mimic includes a terminal moiety, which is a hydrogen, oxo, halogen, —CN, —CF$_3$, —NH$_2$, —OH, —SH, —N$_3$, substituted (e.g. substituted with a substituent group, size-limited substituent group or lower substituent group) or unsubstituted alkyl, substituted (e.g. substituted with a substituent group, size-limited substituent group or lower substituent group) or unsubstituted heteroalkyl, substituted (e.g. substituted with a substituent group, size-limited substituent group or lower substituent group) or unsubstituted cycloalkyl, substituted (e.g. substituted with a substituent group, size-limited substituent group or lower substituent group) or unsubstituted heterocycloalkyl, substituted (e.g. substituted with a substituent group, size-limited substituent group or lower substituent group) or unsubstituted aryl, or substituted (e.g. substituted with a substituent group, size-limited substituent group or lower substituent group) or unsubstituted heteroaryl. In embodiments, the CpG-ODN conjugated to an anti-miR or miRNA-mimic includes a terminal moiety, which is a substituted (e.g. substituted with a substituent group, size-limited substituent group or lower substituent group) or unsubstituted $C_1$-$C_{40}$ alkyl, substituted (e.g. substituted with a substituent group, size-limited substituent group or lower substituent group) or unsubstituted 2 to 40 membered heteroalkyl, substituted (e.g. substituted with a substituent group, size-limited substituent group or lower substituent group) or unsubstituted $C_3$-$C_8$ cycloalkyl, substituted (e.g. substituted with a substituent group, size-limited substituent group or lower substituent group) or unsubstituted 3 to 8 membered heterocycloalkyl, substituted (e.g. substituted with a substituent group, size-limited substituent group or lower substituent group) or unsubstituted $C_6$-$C_{10}$ aryl, or substituted (e.g. substituted with a substituent group, size-limited substituent group or lower substituent group) or unsubstituted 5 to 10 membered heteroaryl. In embodiments, the CpG-ODN conjugated to an anti-miR or miRNA-mimic includes a terminal moiety, which is a substituted (e.g. substituted with a substituent group, size-limited substituent group or lower substituent group) $C_1$-$C_{40}$ alkyl, substituted (e.g. substituted with a substituent group, size-limited substituent group or lower substituent group) 2 to 40 membered heteroalkyl, substituted (e.g. substituted with a substituent group, size-limited substituent group or lower substituent group) $C_3$-$C_8$ cycloalkyl, substituted (e.g. substituted with a substituent group, size-limited substituent group or lower substituent group) 3 to 8 membered heterocycloalkyl, substituted (e.g. substituted with a substituent group, size-limited substituent group or lower substituent group) $C_6$-$C_{10}$ aryl, or substituted (e.g. substituted with a substituent group, size-limited substituent group or lower substituent group) 5 to 10 membered heteroaryl. In embodiments, the terminal moiety is an $R^1$-substituted $C_1$-$C_{40}$ alkyl, $R^1$-substituted 2 to 40 membered heteroalkyl, $R^1$-substituted $C_3$-$C_8$ cycloalkyl, $R^1$-substituted 3 to 8 membered heterocycloalkyl, $R^1$-substituted $C_6$-$C_{10}$ aryl, or $R^1$-substituted 5 to 10 membered heteroaryl. In embodiments, the terminal moiety is an $R^1$-substituted $C_1$-$C_{40}$ alkyl. In embodiments, the terminal moiety is an -(unsubstituted $C_1$-$C_{40}$ alkylene)-$R^1$. In embodiments, the terminal moiety is an -(unsubstituted linear $C_1$-$C_{40}$ alkylene)-$R^1$. In embodiments, the terminal moiety is an -(unsubstituted $C_3$-$C_{21}$ alkylene)-$R^1$. In embodiments, the terminal moiety is an -(unsubstituted $C_3$-$C_{18}$ alkylene)-$R^1$. In embodiments, the terminal moiety is an -(unsubstituted linear $C_3$-$C_{15}$ alkylene)-$R^1$. In embodiments, the terminal moiety is an -(unsubstituted linear $C_6$-$C_{21}$ alkylene)-$R^1$. In embodiments, the terminal moiety is an -(unsubstituted linear $C_9$-$C_{21}$ alkylene)-$R^1$. In embodiments, the terminal moiety is an -(unsubstituted linear $C_9$-$C_{18}$ alkylene)-$R^1$. In embodiments, the terminal moiety is an -(unsubstituted linear $C_9$-$C_{15}$ alkylene)-$R^1$. In embodiments, the terminal moiety is an -(unsubstituted linear $C_{12}$-$C_{15}$ alkylene)-$R^1$. In embodiments, the terminal moiety is an -(unsubstituted linear $C_{12}$ alkylene)-$R^1$. In embodiments, the terminal moiety is an -(unsubstituted linear $C_{13}$ alkylene)-$R^1$. In embodiments, the terminal moiety is an -(unsubstituted linear $C_{14}$ alkylene)-$R^1$. In embodiments, the terminal moiety is an -(unsubstituted linear $C_{15}$ alkylene)-$R^1$. In embodiments, the terminal moiety is an $R^1$-substituted 2 to 40 membered heteroalkyl. The terminal moiety is an -(unsubstituted 2 to 40 membered heteroalkylene)-$R^1$. In embodiments, the terminal moiety is a -(substituted linear 2 to 40 membered heteroalkylene)-$R^1$. In embodiments, the terminal moiety is a -(substituted 5 to 40 membered heteroalkylene)-$R^1$. In embodiments, the terminal moiety is a -(substituted 10 to 40 membered heteroalkylene)-$R^1$. In embodiments, the terminal moiety is a -(substituted 15 to 40 membered heteroalkylene)-$R^1$. In embodiments, the terminal moiety is a -(substituted 20 to 40 membered heteroalkylene)-$R^1$. In embodiments, the terminal moiety is a -(substituted 30 to 40 membered heteroalkylene)-$R^1$. In embodiments, the terminal moiety is a -(substituted 2 to 35 membered heteroalkylene)-$R^1$. In embodiments, the terminal moiety is a -(substituted 2 to 30 membered heteroalkylene)-$R^1$. In embodiments, the terminal moiety is a -(substituted 2 to 25 membered heteroalkylene)-$R^1$. In embodiments, the terminal moiety is a -(substituted 2 to 20 membered heteroalkylene)-$R^1$. In embodiments, the terminal moiety is a -(substituted 2 to 10 membered heteroalkylene)-$R^1$. In embodiments, the terminal moiety is a -(substituted 2 to 50 membered heteroalkylene)-$R^1$. In embodiments, the terminal moiety is a -(substituted 2 to 60 membered heteroalkylene)-$R^1$.

In embodiments, the CpG-ODN conjugated to an anti-miR or miRNA-mimic includes a terminal moiety, which is a substituted (e.g. substituted with a substituent group, size-limited substituent group or lower substituent group) 2 to 40 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 10 to 50 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 20 to 40 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 25 to 40 membered heteroalkyl. In embodiments, the CpG-ODN conjugated to an anti-miR or miRNA-mimic includes a terminal moiety, which is a substituted (e.g. substituted with a substituent group, size-limited substituent group or lower substituent group) 30 to 40 membered heteroalkyl.

In embodiments, the CpG-ODN conjugated to an anti-miR or miRNA-mimic includes a terminal moiety with a $R^1$ group, in which $R^1$ is a detectable moiety or a therapeutic moiety. In embodiments, $R^1$ in the CpG-ODN conjugated to an anti-miR or miRNA-mimic includes a terminal moiety, which is a detectable moiety. In embodiments, $R^1$ in the CpG-ODN conjugated to an anti-miR or miRNA-mimic includes a detectable moiety, which is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, $R^1$ in the CpG-ODN conjugated to an anti-miR or miRNA-mimic includes a terminal moiety, which is a therapeutic moiety (e.g., anti-cancer agent or anti-viral agent). In embodiments, $R^1$ in the CpG-ODN conjugated to an anti-miR or miRNA-mimic includes a terminal moiety, which is H. In embodiments, $R^1$ in the CpG-ODN conjugated to an anti-miR or miRNA-mimic includes an oxo as a terminal moiety. In embodiments, $R^1$ in the CpG-ODN conjugated to an anti-miR or miRNA-mimic includes oxygen as a terminal moiety. In embodiments, $R^1$ in the CpG-ODN conjugated to an anti-miR or miRNA-mimic includes sulfur as a terminal moiety. In embodiments, $R^1$ in the CpG-ODN conjugated to an anti-miR or miRNA-mimic includes =S as a terminal moiety.

In embodiments, the CpG-ODN nucleic acid sequence of the compound includes unmethylated CpG motif (e.g., a CpG nucleic acid sequence or a GpC nucleic acid sequence). In embodiments, the CpG-ODN nucleic acid sequence includes a Class A CpG nucleic acid sequence, a Class B CpG nucleic acid sequence, or a Class C CpG nucleic acid sequence.

In embodiments, the compound includes CpG-ODN, in which C and G are nucleotides connected by a phosphodiester internucleotide linkage. In embodiments, the compound includes CpG, wherein C and G are nucleotides connected by a phosphodiester derivative internucleotide linkage. In embodiments, the CpG motif is unmethylated. In embodiments, C and G are connected as 5'C-G 3'. In embodiments, C and G are connected as 5'G-C 3'.

In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In embodiments, the compound includes a plurality of phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof).

In embodiments, the phosphodiester derivative linkage in the compound may be phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage.

In embodiments, one or more of the nucleic acid internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g., 1, 2, 3, 4, 5, 6, 7, 8, 9, 10, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)).

In embodiments, the compound includes a CpG-ODN linked to an anti-miR targeting miR-126 or an miRNA-mimic of miR-142. In embodiments, the compound includes the sequence of SEQ ID NO:6. In embodiments, the compound is the sequence of SEQ ID NO:6.

Methods of Treating Anemia

In embodiments of any of the methods and uses, the disclosure includes treating a red blood cell disorder (e.g., anemia), by administering effective amounts of an anti-miR126 compound. Any of the anti-miR126 compounds described in international application PCT/US2016/057143 published as WO 2017/066639A1 may be used for the methods provided herein including embodiments thereof.

For the methods provided herein the anti-miR126 compounds may be administered with an effective dose between about 0.001 mg/kg to about 100 mg/kg of the agent (e.g., 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/kg).

In embodiments, an effective dose of an anti-miR126 compound is administered to a subject in need thereof for treating a disease (e.g., anemia). The anti-miR suppresses expression/activity of a miR (e.g., miR126) in a cell, and induces the growth of HSCs and formation of red blood cells.

The anti-miR126 compound may be administered to a subject in need thereof, at a dose between about 0.001 mg/kg to about 0.01 mg/kg of the compound, between about 0.01 mg/kg to about 0.1 mg/kg of the compound, between about 0.1 mg/kg to about 1.0 mg/kg of the compound, between about 1.0 mg/kg to about 5.0 mg/kg of the compound, between about 5.0 mg/kg to about 10 mg/kg of the compound, between about 10 mg/kg to about 15 mg/kg of the compound, between about 15 mg/kg to about 20 mg/kg of the compound, between about 20 mg/kg to about 25 mg/kg of the compound, between about 25 mg/kg to about 30 mg/kg of the compound, between about 30 mg/kg to about 35 mg/kg of the compound, between about 35 mg/kg to about 40 mg/kg of the compound, between about 40 mg/kg to about 45 mg/kg of the compound, between about 45 mg/kg to about 50 mg/kg of the compound, between about 50 mg/kg to about 55 mg/kg of the compound, between about 55 mg/kg to about 60 mg/kg of the compound, between about 60 mg/kg to about 65 mg/kg of the compound, between about 65 mg/kg to about 70 mg/kg of the compound, between about 70 mg/kg to about 75 mg/kg of the compound, between about 75 mg/kg to about 80 mg/kg of the compound, between about 80 mg/kg to about 85 mg/kg of the compound, between about 85 mg/kg to about 90 mg/kg of the compound, between about 90 mg/kg to about 95 mg/kg of the compound, or between about 95 mg/kg to about 100 mg/kg of the compound.

In embodiments, the present disclosure includes compositions with an effective dose of an anti-miR126 compound between about 0.1% to about 20% w/v of the composition.

For example, the effective dose of the anti-miR126 compound may be between about 0.001%-about 0.01%, between about 0.01%-about 0.1%, between about 0.1%-about 1.0%, between about 1.0%-about 2.0%, between about 2.0%-about 3.0%, between about 3.0%-about 4.0%, between about 4.0%-about 5.0%, between about 5.0%-about 6.0%, between about 6.0%-about 7.0%, between about 7.0%-about 8.0%, between about 8.0%-about 9.0%, between about 9.0%-about 10%, between about 10%-about 11%, between about 11%-about 12%, between about 12%-about 13%, between about 13%-about 14%, between about 14%-about 15%, between about 15%-about 16%, between about 16%-about 17%, between about 17%-about 18%, between about 18%-about 19%, or between about 19%-about 20% w/v of the composition.

Methods of Treating Cancer

As described above, inhibition of BCR-ABL by TKI treatment causes an undesired increase in endogenous miR-126 levels, thereby enhancing LSC quiescence and persistence. miR-126 KO in LSCs and/or ECs, or treatment with a CpG-miR-126 inhibitor targeting miR-126 in both LSCs and ECs, enhances the in vivo anti-leukemic effects of TKI treatment and strongly diminishes LSC leukemia-initiating capacity, providing a new strategy for the elimination of LSCs in CML. Applicants are the first to show that the efficacy of tyrosine kinase inhibitors (e.g., BCR-ABL) used to treat cancer (e.g., CML) can be enhanced by concurrent targeting of miR-126.

Thus, in an aspect is provided a method of treating cancer in a subject in need thereof, the method including administering to the subject a therapeutically effective amount of a tyrosine kinase inhibitor and a therapeutically effective amount of an anti-microRNA126 (miR126) compound.

In another aspect, is provided a method of treating cancer in a subject in need thereof, the method including administering to the subject a therapeutically effective amount of an anti-microRNA126 (miR126) compound, wherein the subject has been treated with a tyrosine kinase inhibitor prior to the administering a therapeutically effective amount of an anti-microRNA126 (miR126) compound.

In another aspect, is provided a method of treating cancer in a subject undergoing cancer treatment, the method including administering to the subject a therapeutically effective amount of an anti-microRNA126 (miR126) compound.

In another aspect, is provided a method of treating a chemoresistant cancer in a subject in need thereof, the method including administering to the subject a therapeutically effective amount of an anti-microRNA126 (miR126) compound. In embodiments, the subject has been treated with a tyrosine kinase inhibitor prior to said administering a therapeutically effective amount of the anti-microRNA126 (miR126) compound.

In embodiments, the subject has a relapsed cancer. In embodiments, the subject has been treated with asatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, panitumumab, pazopanib, trastuzumab or sorafenib.

For the methods provided herein (e.g., methods of treating anemia, methods of treating cancer) the anti-microRNA126 (miR126) compound may be any anti-microRNA126 (miR126) compound provided herein including embodiments thereof. In embodiments, the anti-microRNA126 (miR126) compound is an anti-miR126 nucleic acid. In embodiments, the anti-microRNA126 (miR126) compound includes the sequence of SEQ ID NO:6. In embodiments, the anti-microRNA126 (miR126) compound is the sequence of SEQ ID NO:6. In embodiments, the anti-miR126 nucleic acid includes the sequence of SEQ ID NO:6. In embodiments, the anti-miR126 nucleic acid is the sequence of SEQ ID NO:6. Any of the anti-miR126 compounds described in international application PCT/US2016/057143 published as WO 2017/066639A1 may be used for the methods provided herein including embodiments thereof.

In embodiments, the method includes prior to the administering a therapeutically effective amount of an anti-microRNA126 (miR126) compound, detecting a level of miR126 in the subject. In embodiments, the method includes prior to the administering a therapeutically effective amount of an anti-microRNA126 (miR126) compound, selecting a subject expressing an increased level of miR126 relative to a standard control.

In embodiments, the cancer is a hematopoietic cell cancer. In embodiments, the cancer is not a hematopoietic cell cancer. In embodiments, the cancer is myeloma or acute myeloid leukemia. In embodiments, the cancer is prostate cancer, breast cancer, glioblastoma, ovarian cancer, lung cancer, head and neck cancer, esophageal cancer, skin cancer, melanoma, brain cancer, colorectal cancer, lymphoma, or myeloma, pancreatic cancer, chronic myeloid leukemia (CML), or myelodysplastic syndromes (MDS). In embodiments, the cancer is myeloma. In embodiments, the cancer is acute myeloid leukemia. In embodiments, the cancer is prostate cancer. In embodiments, the cancer is breast cancer. In embodiments, the cancer is glioblastoma. In embodiments, the cancer is ovarian cancer. In embodiments, the cancer is lung cancer. In embodiments, the cancer is head and neck cancer. In embodiments, the cancer is esophageal cancer. In embodiments, the cancer is skin cancer. In embodiments, the cancer is melanoma. In embodiments, the cancer is brain cancer. In embodiments, the cancer is colorectal cancer. In embodiments, the cancer is lymphoma. In embodiments, the cancer is pancreatic cancer. In embodiments, the cancer is chronic myeloid leukemia (CML). In embodiments, the cancer is myelodysplastic syndromes (MDS).

A "tyrosine kinase inhibitor" or "TKI inhibitor" as referred to herein is a substance capable of detectably decreasing the expression or activity of a given tyrosine kinase (e.g., ABL). The TKI inhibitor can decrease expression or activity of a tyrosine kinase 10%, 20%, 30%, 40%, 50%, 60%, 70%, 80%, 90% or more in comparison to a control in the absence of the TKI inhibitor. In certain instances, expression or activity of the tyrosine kinase is 1.5-fold, 2-fold, 3-fold, 4-fold, 5-fold, 10-fold or lower than the expression or activity in the absence of the TKI inhibitor.

As defined herein, the term "inhibition", "inhibit", "inhibiting" and the like in reference to a tyrosine kinase inhibitor means negatively affecting (e.g. decreasing) the activity or function of a tyrosine kinase relative to the activity or function of the tyrosine kinase in the absence of the inhibitor. In embodiments inhibition means negatively affecting (e.g. decreasing) the concentration or levels of the tyrosine kinase relative to the concentration or level of the tyrosine kinase in the absence of the inhibitor. In embodiments, inhibition refers to reduction of a disease or symptoms of disease (e.g., leukemia). In embodiments, inhibition refers to a reduction in the activity of a particular tyrosine kinase. Thus, inhibition includes, at least in part, partially or totally blocking stimulation, decreasing, preventing, or delaying activation, or inactivating, desensitizing, or down-regulating signal transduction or enzymatic activity or the amount of a tyrosine kinase. In embodiments, inhibition refers to a reduction of activity of a tyrosine kinase resulting from a direct interaction (e.g. an inhibitor binds to the tyrosine kinase). In embodiments, inhibition refers to a reduction of activity of a tyrosine kinase from an indirect interaction (e.g. an inhibitor binds to a protein that activates the tyrosine kinase, thereby preventing tyrosine kinase activation).

In embodiments, the tyrosine kinase inhibitor is a multi-kinase inhibitor. In embodiments, the tyrosine kinase inhibitor is dasatinib. In embodiments, the tyrosine kinase inhibitor is sunitinib. In embodiments, the tyrosine kinase inhibitor is erlotinib. In embodiments, the tyrosine kinase inhibitor is bevacizumab. In embodiments, the tyrosine kinase inhibitor is vatalanib. In embodiments, the tyrosine kinase inhibitor is vemurafenib. In embodiments, the tyrosine kinase inhibitor is vandetanib. In embodiments, the tyrosine kinase inhibitor is cabozantinib. In embodiments, the tyrosine kinase inhibitor is poatinib. In embodiments, the tyrosine kinase inhibitor is axitinib. In embodiments, the tyrosine kinase inhibitor is ruxolitinib. In embodiments, the tyrosine kinase inhibitor is regorafenib. In embodiments, the tyrosine kinase inhibitor is crizotinib. In embodiments, the tyrosine kinase inhibitor is bosutinib. In embodiments, the tyrosine kinase inhibitor is cetuximab. In embodiments, the tyrosine kinase inhibitor is gefitinib. In embodiments, the tyrosine kinase inhibitor is imatinib. In embodiments, the tyrosine kinase inhibitor is lapatinib. In embodiments, the tyrosine kinase inhibitor is lenvatinib. In embodiments, the tyrosine kinase inhibitor is mubritinib. In embodiments, the tyrosine kinase inhibitor is panitumumab. In embodiments, the tyrosine kinase inhibitor is pazopanib. In embodiments, the tyrosine kinase inhibitor is trastuzumab. In embodiments, the tyrosine kinase inhibitor is or sorafenib.

In embodiments, the tyrosine kinase inhibitor is dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib. In embodiments, the tyrosine kinase inhibitor is dasatinib, bevacizumab, vatalanib, vemurafenib, vandetanib, cabozantinib, poatinib, axitinib, ruxolitinib, regorafenib, crizotinib, bosutinib, lapatinib, lenvatinib, mubritinib, nilotinib, panitumumab, or pazopanib.

The terms asatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab and sorafenib, refer in the usual and customary sense, to the compounds listed in the CAS registry under that term. For example, mubritinib refers in the usual and customary sense to the compound identified by CAS registry number 366017-09-6.

In embodiments, a therapeutically effective amount of dasatinib and a therapeutically effective amount of an anti-microRNA126 (miR126) compound (e.g., an anti-miR126 nucleic acid) is administered. In embodiments, a therapeutically effective amount of sunitinib and a therapeutically effective amount of an anti-microRNA126 (miR126) compound is administered. In embodiments, a therapeutically effective amount of erlotinib and a therapeutically effective amount of an anti-microRNA126 (miR126) compound is administered. In embodiments, a therapeutically effective amount of bevacizumab and a therapeutically effective amount of an anti-microRNA126 (miR126) compound is administered. In embodiments, a therapeutically effective amount of vatalanib and a therapeutically effective amount of an anti-microRNA126 (miR126) compound is administered. In embodiments, a therapeutically effective amount of vemurafenib and a therapeutically effective amount of an anti-microRNA126 (miR126) compound is administered. In embodiments, a therapeutically effective amount of vandetanib and a therapeutically effective amount of an anti-microRNA126 (miR126) compound is administered. In embodiments, a therapeutically effective amount of cabozantinib and a therapeutically effective amount of an anti-microRNA126 (miR126) compound is administered. In embodiments, a therapeutically effective amount of poatinib and a therapeutically effective amount of an anti-microRNA126 (miR126) compound is administered. In embodiments, a therapeutically effective amount of axitinib and a therapeutically effective amount of an anti-microRNA126 (miR126) compound is administered. In embodiments, a therapeutically effective amount of ruxolitinib and a therapeutically effective amount of an anti-microRNA126 (miR126) compound is administered. In embodiments, a therapeutically effective amount of regorafenib and a therapeutically effective amount of an anti-microRNA126 (miR126) compound is administered.

In embodiments, a therapeutically effective amount of crizotinib and a therapeutically effective amount of an anti-microRNA126 (miR126) compound is administered. In embodiments, a therapeutically effective amount of bosutinib and a therapeutically effective amount of an anti-microRNA126 (miR126) compound is administered. In embodiments, a therapeutically effective amount of cetuximab and a therapeutically effective amount of an anti-microRNA126 (miR126) compound is administered. In embodiments, a therapeutically effective amount of gefitinib and a therapeutically effective amount of an anti-microRNA126 (miR126) compound is administered. In embodiments, a therapeutically effective amount of imatinib and a therapeutically effective amount of an anti-microRNA126 (miR126) compound is administered. In embodiments, a therapeutically effective amount of lapatinib and a therapeutically effective amount of an anti-microRNA126 (miR126) compound is administered. In embodiments, a therapeutically effective amount of lenvatinib and a therapeutically effective amount of an anti-microRNA126 (miR126) compound is administered. In embodiments, a therapeutically effective amount of mubritinib and a therapeutically effective amount of an anti-microRNA126 (miR126) compound is administered. In embodiments, a therapeutically effective amount of panitumumab and a therapeutically effective amount of an anti-microRNA126 (miR126) compound is administered. In embodiments, a therapeutically effective amount of pazopanib and a therapeutically effective amount of an anti-microRNA126 (miR126) compound is administered. In embodiments, a therapeutically effective amount of trastuzumab and a therapeutically effective amount of an anti-microRNA126 (miR126) compound is administered. In embodiments, a therapeutically effective amount of sorafenib and a therapeutically effective amount of an anti-microRNA126 (miR126) compound is administered. In embodiments, the anti-microRNA126 (miR126) compound is an anti-miR126 nucleic acid. In further embodiments, the anti-microRNA126 (miR126) compound includes the sequence of SEQ ID NO:6. In other further embodiments, the anti-microRNA126 (miR126) compound is the sequence of SEQ ID NO:6.

In embodiments, the compound and the inhibitor are administered to the subject by intravenous, parenteral, subcutaneous, intramuscular, transdermal, intraperitoneal, intranasal, aerosol, oral, or topical administration. In embodiments, the compound is administered at about 0.001 mg/kg to about 100 mg/kg. In embodiments, the cancer is a relapsed cancer after chemotherapy. In embodiments, the relapsed cancer is chemotherapy resistant.

In embodiments, the anti-microRNA126 (miR126) compound and the tyrosine kinase inhibitor are administered in a combined synergistic amount. A "combined synergistic amount" as used herein refers to the sum of a first amount (e.g., an amount of an anti-microRNA126 (miR126) compound) and a second amount (e.g., an amount of a tyrosine kinase inhibitor) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the anti-microRNA126 (miR126) compound when used separately from the tyrosine kinase inhibitor. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the tyrosine kinase inhibitor when used separately from the anti-microRNA126 (miR126) compound.

The synergistic effect may be a miR126 activity decreasing effect and/or a tyrosine kinase activity decreasing effect. In embodiments, synergy between the anti-microRNA126 (miR126) compound and the tyrosine kinase inhibitor may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease (e.g., decrease of miR126 activity or decrease of tyrosine kinase activity) than the sum of the decrease of the anti-microRNA126 (miR126) compound or the tyrosine kinase inhibitor when used individually and separately. In embodiments, synergy between the anti-microRNA126 (miR126) compound and the tyrosine kinase inhibitor may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of miR126 and/or the tyrosine kinase than the sum of the inhibition of the anti-microRNA126 (miR126) compound or the tyrosine kinase inhibitor when used individually and separately.

The synergistic effect may be a cancer-treating effect such as a myeloma (i.e. a myeloma-treating synergistic effect), acute myeloid leukemia (i.e. an acute myeloid leukemia-treating synergistic effect), prostate cancer (i.e. a prostate cancer-treating synergistic effect), breast cancer (i.e. a breast cancer-treating synergistic effect), glioblastoma (i.e. a glioblastoma-treating synergistic effect), ovarian cancer (i.e. an ovarian cancer-treating synergistic effect), lung cancer (i.e. a lung cancer-treating synergistic effect), head and neck cancer (i.e. a head and neck cancer-treating synergistic effect), esophageal cancer (i.e. a esophageal cancer-treating synergistic effect), skin cancer (i.e. a skin cancer-treating synergistic effect), melanoma (i.e. a melanoma-treating synergistic effect), brain cancer (i.e. a brain cancer-treating synergistic effect), colorectal cancer (i.e. a colorectal cancer-treating synergistic effect), lymphoma (i.e. a lymphoma-treating synergistic effect), pancreatic cancer (i.e. a pancreatic cancer-treating synergistic effect), chronic myeloid leukemia (CML) (i.e. a CML-treating synergistic effect), or myelodysplastic syndromes (MDS) (i.e. a MDS-treating synergistic effect) treating effect.

The anti-microRNA126 (miR126) compound and the tyrosine kinase inhibitor may be administered in combination either simultaneously (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of the anti-microRNA126 (miR126) compound and the tyrosine kinase inhibitor.

In embodiments, the anti-microRNA126 (miR126) compound and the tyrosine kinase inhibitor are administered simultaneously or sequentially. In embodiments, the anti-microRNA126 (miR126) compound and the tyrosine kinase inhibitor are administered simultaneously. In embodiments, the anti-microRNA126 (miR126) compound and the tyrosine kinase inhibitor are administered sequentially. During the course of treatment the anti-microRNA126 (miR126) compound and tyrosine kinase inhibitor may at times be administered sequentially and at other times be administered simultaneously.

In embodiments, where the anti-microRNA126 (miR126) compound and the tyrosine kinase inhibitor are administered sequentially, the tyrosine kinase inhibitor is administered at a first time point and the anti-microRNA126 (miR126) compound is administered at a second time point, wherein the first time point precedes the second time point. Alternatively, in embodiments, where the anti-microRNA126 (miR126) compound and the tyrosine kinase inhibitor are administered sequentially, the anti-microRNA126 (miR126) compound is administered at a first time point and the tyrosine kinase inhibitor is administered at a second time point, wherein the first time point precedes the second time point.

The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

In instances where the anti-microRNA126 (miR126) compound and tyrosine kinase inhibitor are administered simultaneously, the anti-microRNA126 (miR126) compound and tyrosine kinase inhibitor may be administered as a mixture. Thus, in embodiments, the anti-microRNA126 (miR126) compound and the tyrosine kinase inhibitor are admixed prior to administration.

Pharmaceutical Compositions

The compositions including an anti-microRNA126 (miR126) compound and a tyrosine kinase inhibitor as provided herein, including embodiments thereof, are further contemplated as pharmaceutical compositions. Thus, in an aspect, a pharmaceutical composition including a pharmaceutically acceptable excipient, an anti-microRNA126 (miR126) compound and a tyrosine kinase inhibitor is provided. The anti-microRNA126 (miR126) compound may be any of the anti-microRNA126 (miR126) compounds provided herein and the tyrosine kinase inhibitor may be any of the tyrosine kinase inhibitors provided herein. In embodiments, the tyrosine kinase inhibitor is dasatinib, bevacizumab, vatalanib, vemurafenib, vandetanib, cabozantinib, poatinib, axitinib, ruxolitinib, regorafenib, crizotinib, bosutinib, lapatinib, lenvatinib, mubritinib, nilotinib, panitumumab, or pazopanib.

The anti-microRNA126 (miR126) compound and tyrosine kinase inhibitor included in the pharmaceutical compositions provided herein may be any one of the anti-microRNA126 (miR126) compounds or tyrosine kinase inhibitors described herein including embodiments thereof. For example, the anti-microRNA126 (miR126) compound may be an anti-miR126 nucleic acid. In embodiments, the anti-miR126 nucleic acid includes the sequence of SEQ ID NO:6 and the tyrosine kinase inhibitor may be dasatinib, bevacizumab, vatalanib, vemurafenib, vandetanib, cabozantinib, poatinib, axitinib, ruxolitinib, regorafenib, crizotinib, bosutinib, lapatinib, lenvatinib, mubritinib, nilotinib, panitumumab, or pazopanib.

The provided compositions are, inter alia, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Pharmaceutical compositions provided herein include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

Provided compositions can include a single agent or more than one agent. The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

EXAMPLES

Chronic myelogenous leukemia (CML) stem cells (LSCs) are responsible for initiating and maintaining clonal hematopoiesis. These cells persist in the bone marrow (BM) despite effective inhibition of BCR-ABL kinase activity by tyrosine kinase inhibitors (TKIs). Here, we show that although miR-126 supports the quiescence, self-renewal and engraftment capacity of CML LSCs, miR-126 levels are lower in CML LSCs as compared to normal long-term hematopoietic stem cells (LT-HSCs). Down-regulation of miR-126 levels in CML LSCs is due to phosphorylation of SPRED1 by BCR-ABL, leading to inhibition of the RAN/EXP-5/RCC1 complex that mediates miRNA maturation. Endothelial cells (ECs) in the BM supply miR-126 to CML LSCs to support quiescence and leukemia growth, as shown using CML mouse models with conditional miR-126 knockout (KO) in ECs and/or LSCs. Inhibition of BCR-ABL by TKI treatment causes an undesired increase in endogenous miR-126 levels, thereby enhancing LSC quiescence and persistence. miR-126 KO in LSCs and/or ECs, or treatment with a CpG-miR-126 inhibitor targeting miR-126 in both LSCs and ECs, enhances the in vivo anti-leukemic effects of TKI treatment and strongly diminishes LSC leukemia-initiating capacity, providing a new strategy for the elimination of LSCs in CML.

In chronic myelogenous leukemia (CML), miR-126 is needed to maintain the quiescence and leukemogenic capacity of leukemia stem cells (LSCs). However, BCR-ABL inhibits miR-126 maturation in these stem cells, such that they depend on trafficking of miR-126 from endothelial cells in the bone marrow. Because BCR-ABL tyrosine kinase inhibitors used to treat CML have the undesired effect of raising miR-126 levels thereby preserving LSCs, the efficacy of this treatment in mice can be enhanced by concurrent targeting of miR-126.

Figure 1B:
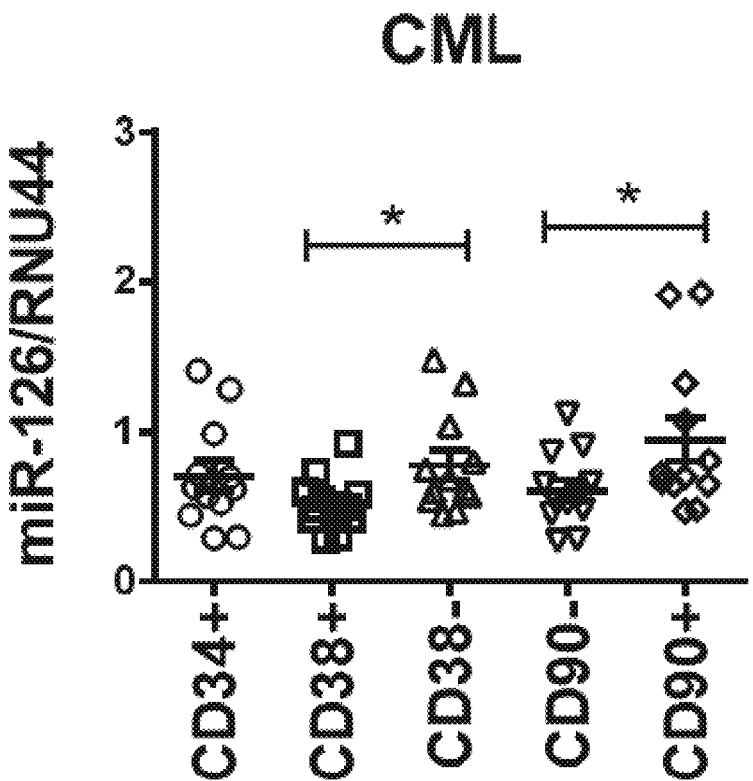
Figure 1C:
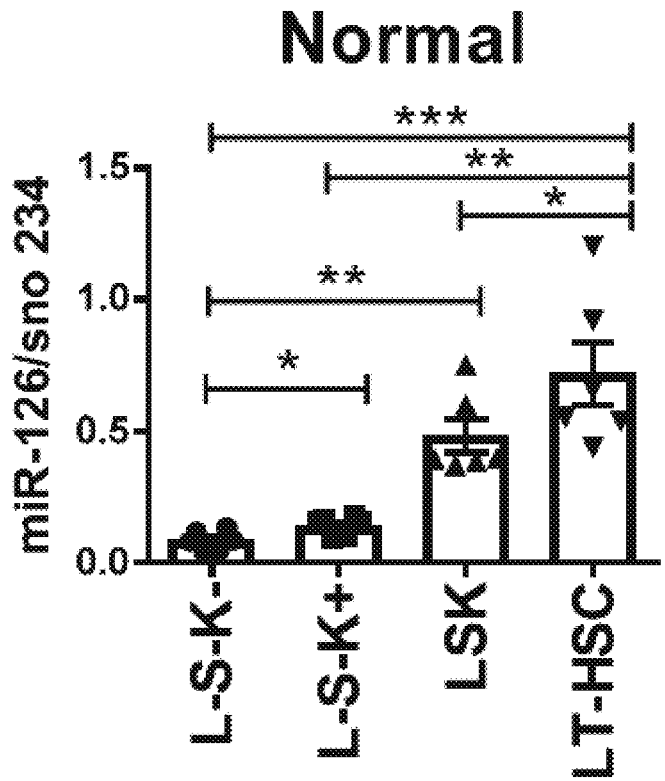
FIG. 1C and FIG. 1D show miR-126 expression, as assessed by QPCR, in the indicated BM subpopulations from normal (FIG. 1C) and CML (FIG. 1D) mice (n=6).
Figure 1D:
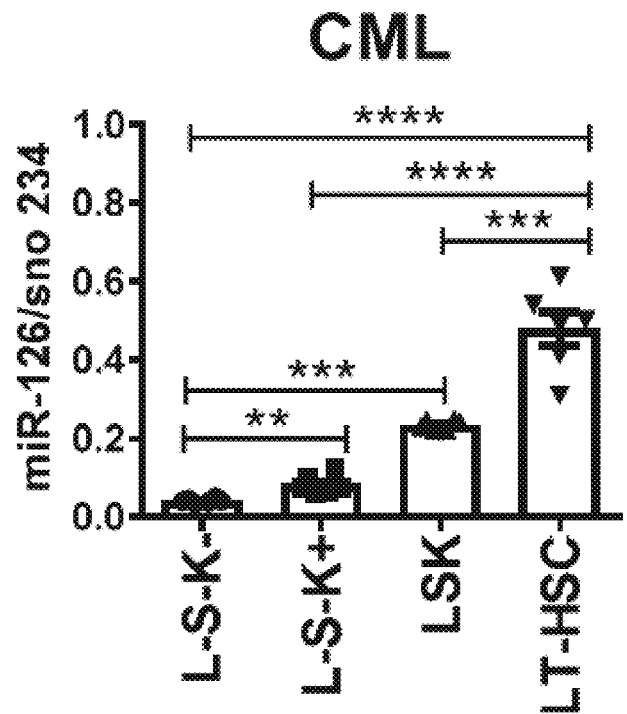
Figure 1E:
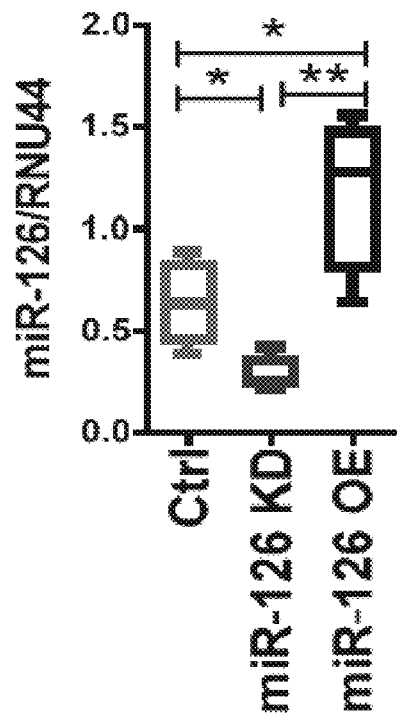
FIGS. 1E-1I show miR-126 expression (FIG. 1E), cell cycle analysis, where the legend from top to bottom represents each group of three data points from left to right (FIG. 1F), apoptosis (FIG. 1G), CFCs (FIG. 1H) and CFC replating efficiency (FIG. 1I) of CML Lin-CD34+ CD38− cells transduced with anti-miR-126 (KD), miR-126 precursor (OE) or control (Ctrl) lentiviruses (n=4 biologically independent samples).
Figure 1F:
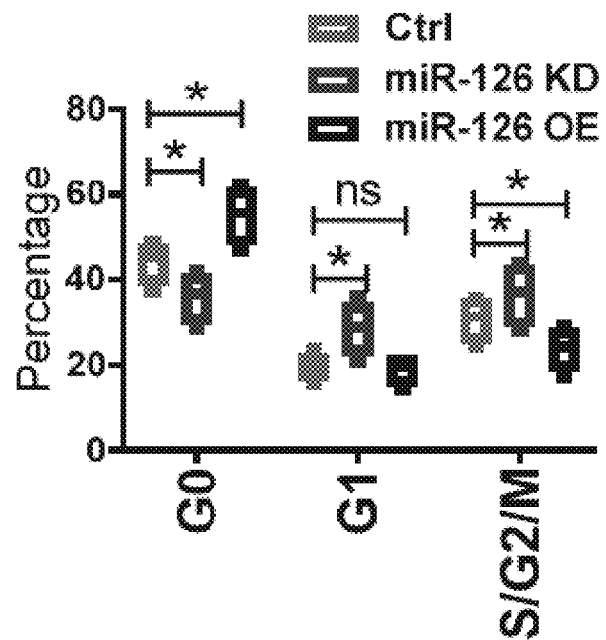
Figure 1G:
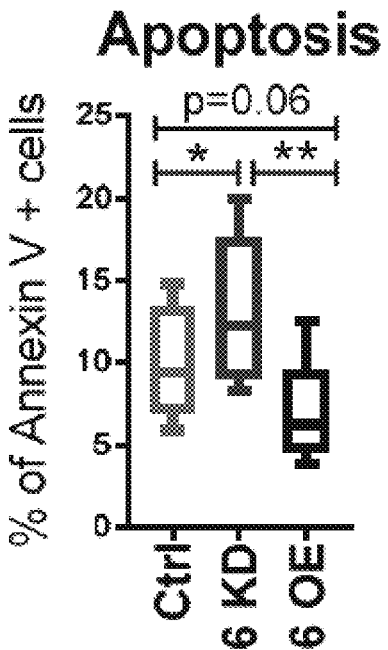
Figure 1H:
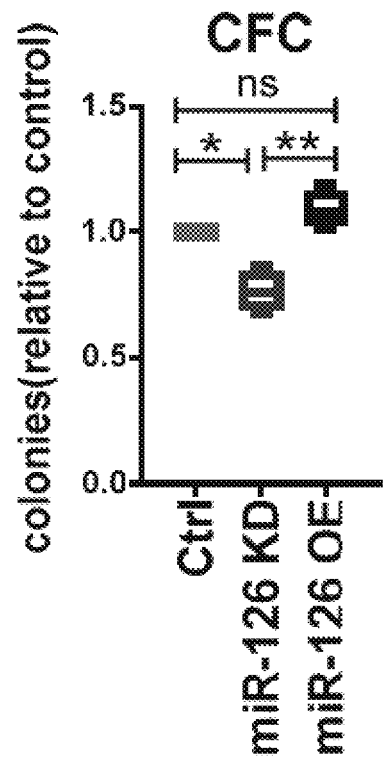
Figure 1I:
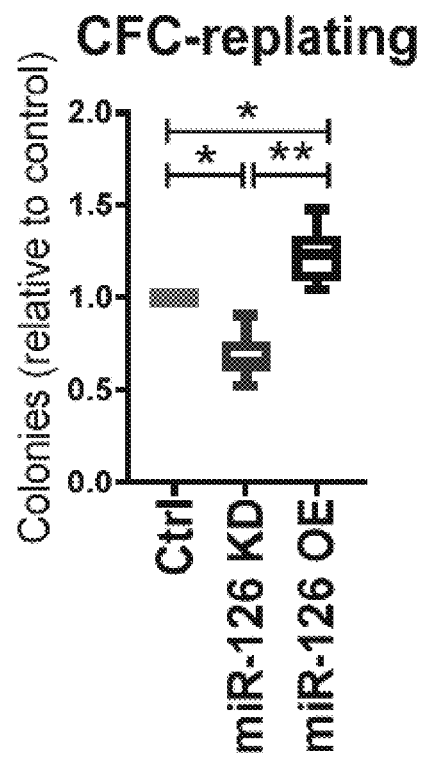
Figure 1J:
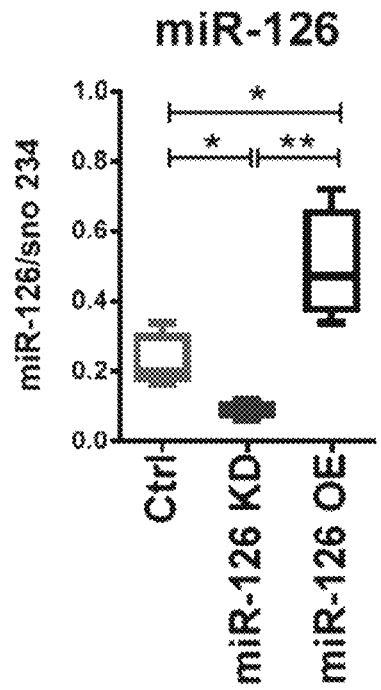
FIGS. 1J-1M show miR-126 expression (FIG. 1J), cell cycle analysis, wherein the legend from top to bottom represents each group of three data points from left to right (FIG. 1K), apoptosis (FIG. 1L), and CFCs (FIG. 1M) of LT-HSCs from induced SCLtTA/BCR-ABL mice after transduction with miR-126 KD, miR-126 OE, or control lentiviruses (n=4 independent experiments).
Figure 1K:
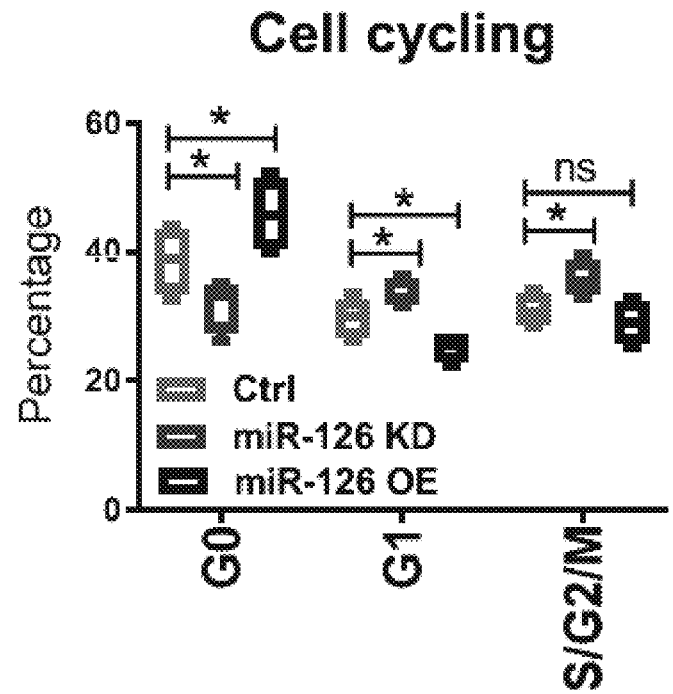
Figure 1L:
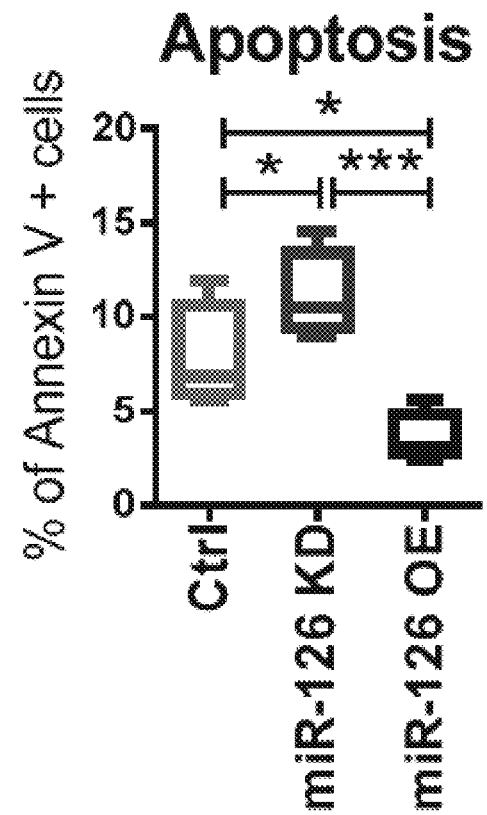
Figure 1M:
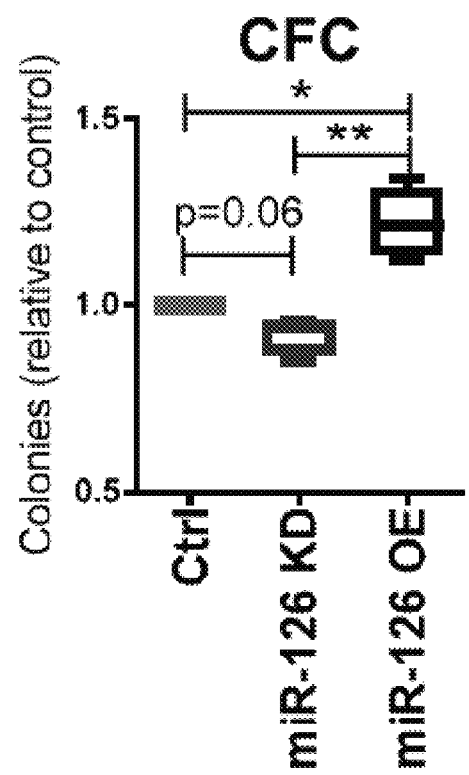
Figure 7B:
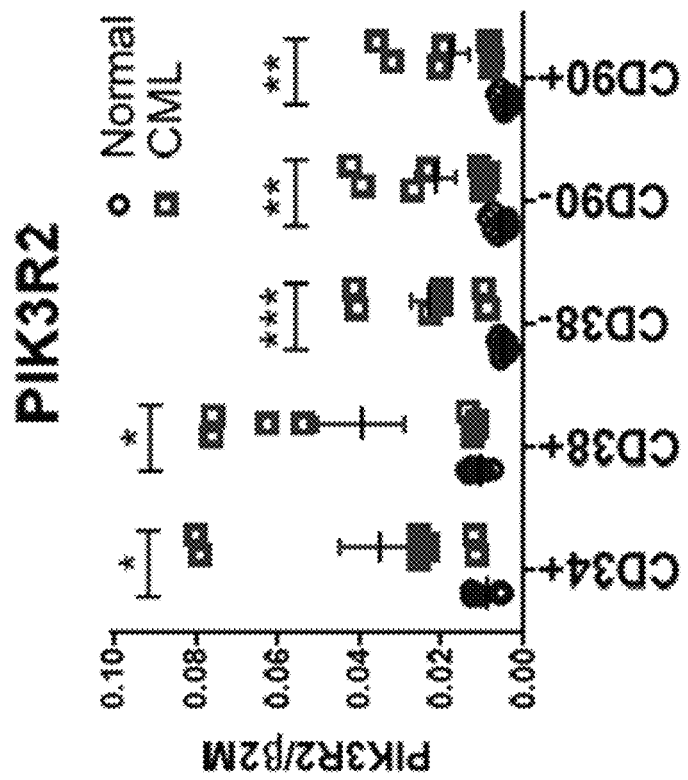
Figure 7A:
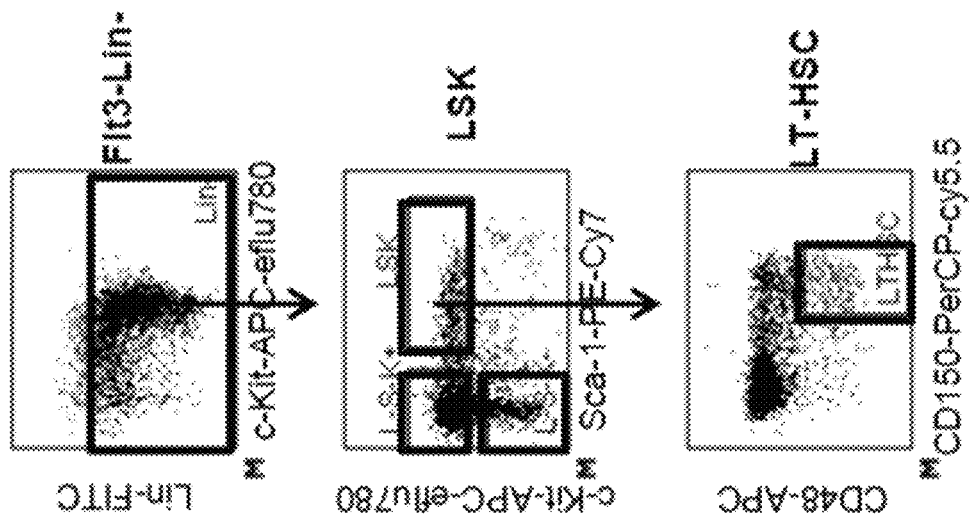

Example 1: Bone Marrow Niche Trafficking of miR-126 Controls Self-Renewal of Leukemia Stem Cells in Chronic Myelogenous Leukemia Higher miR-126 Levels are Associated with Human and Mouse CML LSCs.

miR-126 has been shown to contribute to leukemogenesis in acute leukemia[6,11,12]. To determine miR-126 expression in CIVIL cell subpopulations, we sorted immunophenotypically defined subsets of HPCs [Lin-CD34+(CD34+) and Lin-CD34+CD38+(CD38+)], HSCs [Lin-CD34+CD38-(CD38-) and Lin-CD34+CD38-CD90- (CD90-)] and LT-HSCs [Lin-CD34+CD38-CD90+(CD90+)] from peripheral blood (PB) and BM samples of normal donors (n=12) and newly diagnosed chronic phase (CP) CML patients (n=12). LT-HSCs in both normal and CML samples showed the highest expression of miR-126 (FIG. 1A and FIG. 1B). Similar results were obtained in wild-type (WT) B6 and inducible SCLtTA/BCR-ABL transgenic B6 mice, a well-established CML mouse model[13]. We isolated Lin-Sca-1-c-Kit-(L-S-K-), Lin-Sca-1-c-Kit+(L-S-K+) [including common myeloid progenitors (CMP), granulocyte-macrophage progenitors (GMP) and megakaryocyte-erythrocyte progenitors (MEP)], Lin-Sca-1+c-Kit+(LSK) and LSK Flt3-CD150+CD48- (LT-HSC) cells from the BM of WT mice and CML mice after BCR-ABL induction by tetracycline withdrawal (FIG. 7a). As in the human samples, mouse normal and CIVIL LT-HSCs showed the highest expression of miR-126 (FIG. 1C and FIG. 1D).

Figure 1N:
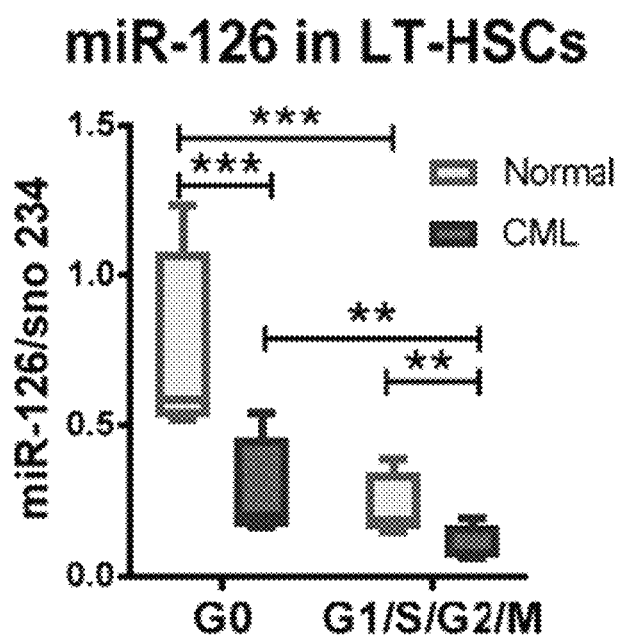
FIG. 1N shows miR-126 expression, as assessed by QPCR, in quiescent Hoechst-Pyronin-(G0) LT-HSCs and proliferating Hoechst+/−Pyronin+(G1/S/G2/M) LT-HSCs from normal or SCLtTA/BCR-ABL mice (n=4 independent samples).
Figure 1O:
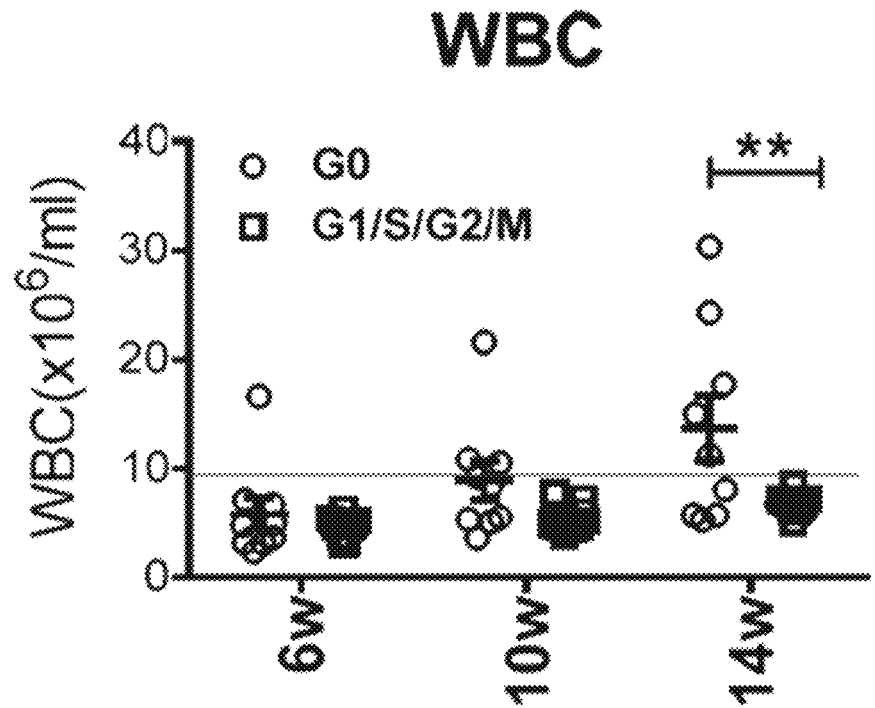
Figure 1P:
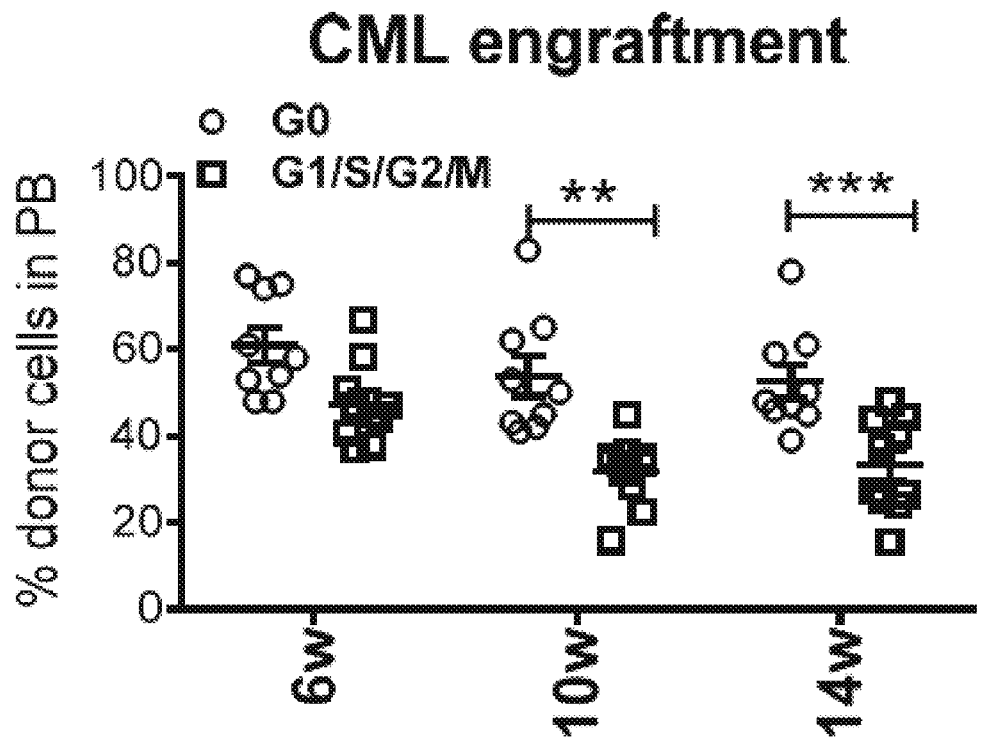

To test the effects of miR-126 on quiescence of CML LSCs, we knocked down miR-126 expression in human CML Lin-CD34+CD38- cells (HSCs) and mouse CML LT-HSCs using GFP-expressing miRZip anti-miR-126 (miR-126 KD) or miR-126 precursor (overexpression, OE) lentiviral vectors. After transduction, GFP+ cells were selected and cultured for 72 hours (h). miR-126 KD increased cell cycling and apoptosis, decreased the number of colony forming cells (CFCs) and CFC replating efficiency of both human CML HSCs (FIGS. 1E-1I) and mouse CML LT-HSCs (FIGS. 1J-1M); conversely, miR-126 OE decreased cell cycling and apoptosis and increased CFC replating efficiency. We validated these results in vivo, first by showing that the quiescent Hoechst-Pyronin-(G0) fraction of CML LT-HSCs from induced SCLtTA/BCR-ABL mice (CD45.2) expressed significantly higher miR-126 levels than the proliferating Hoechst+/−Pyronin+ (G1/G2/S/M) fraction of CML LT-HSCs (p=0.0019; FIG. 1N). The association of miR-126 with LSC activity was then demonstrated by showing that quiescent CML LT-HSCs had a significantly higher rate of long-term engraftment and leukemogenic capacity than did proliferating CML LT-HSCs after transplantation into CD45.1 congenic recipient mice (FIGS. 1I-1P).

BCR-ABL Down-Regulates miR-126 Expression in CML Cells.

Figure 2A:
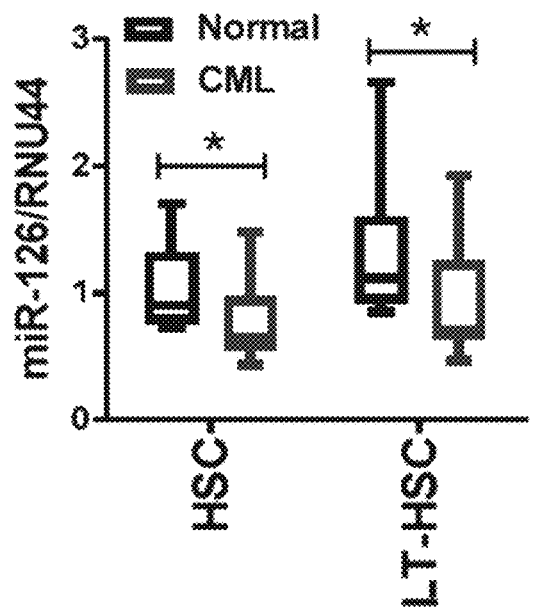
FIGS. 2A-2O. The figure shows that BCR-ABL downregulates miR-126 expression in CML cells.
Figure 2B:
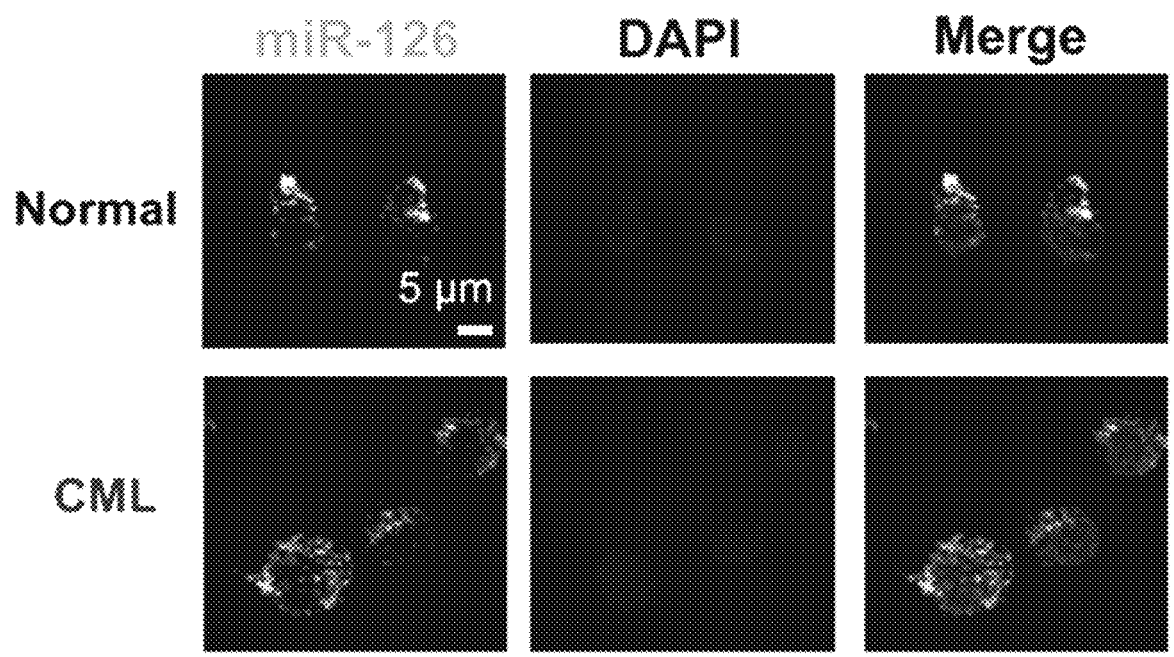
Figure 2C:
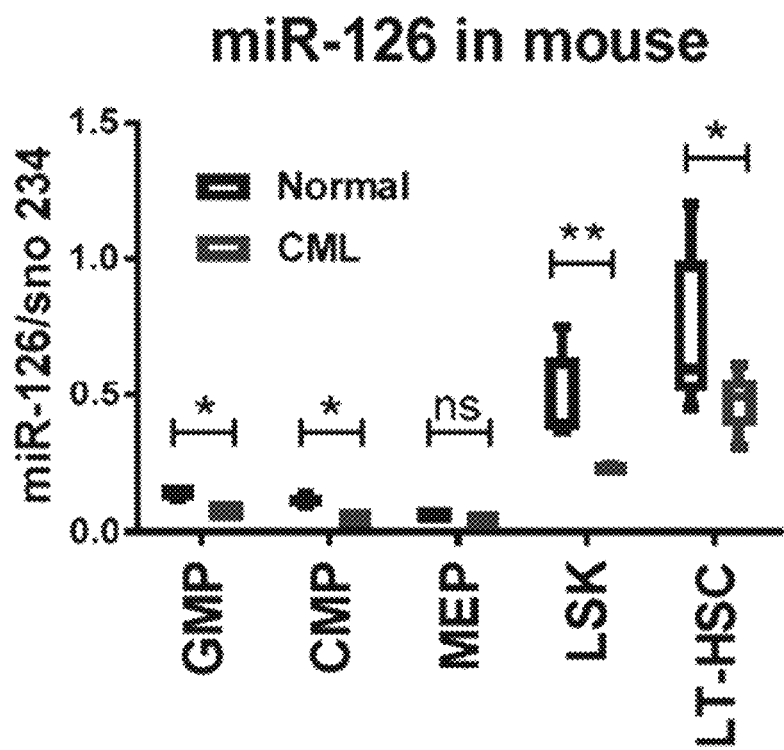
FIG. 2C shows miR-126 expression, as assessed by QPCR, in the indicated BM cell populations from normal and CML mice (n=6) wherein for each group of two data points, the data point on the left represents data for normal cells and the data point on the right represents data for CML cells.

Although miR-126 has similar patterns of expression and function in CIVIL as in normal hematopoiesis[4], we noted that human CML Lin-CD34+CD38− (HSCs) and Lin-CD34+CD38−CD90+ cells (LT-HSCs) had significantly lower miR-126 levels than their normal counterparts (FIG. 2A and FIG. 2B); similar differences were also observed in mouse samples (FIG. 2C). Consistent with this finding, CML HSCs and LT-HSCs expressed higher levels of PIK3R2 and SPRED1, two validated targets of miR-126[4,7,9,14,15], as compared to their normal counterparts (FIG. 7B and FIG. 7C).

Figure 2D:
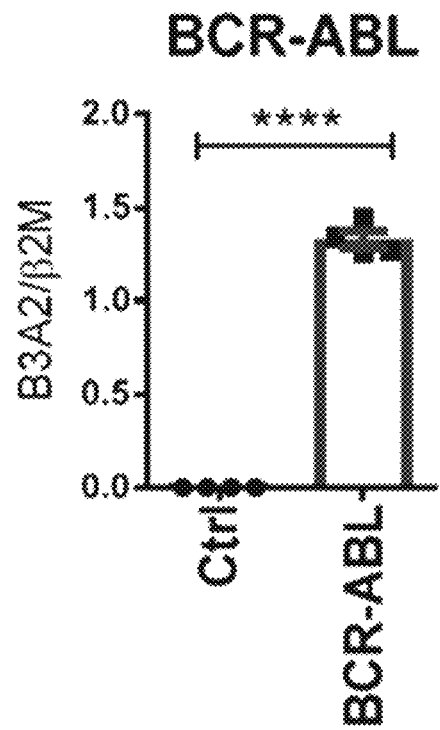
FIGS. 2D-2E show BCR-ABL (FIG. 2D) and miR-126 (FIG. 2E) expression in normal mouse BM LSK cells transduced with BCR-ABL or control (Ctrl) retroviruses, as assessed by QPCR at 24 h after transduction (n=4 independent experiments).
Figure 2E:
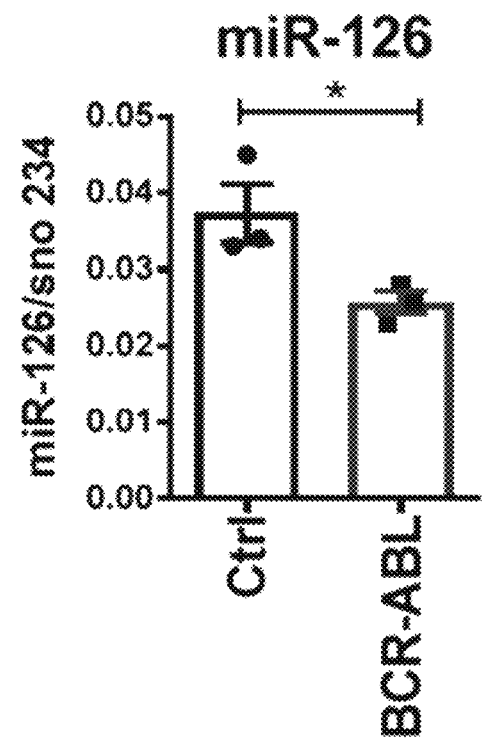
Figure 2F:
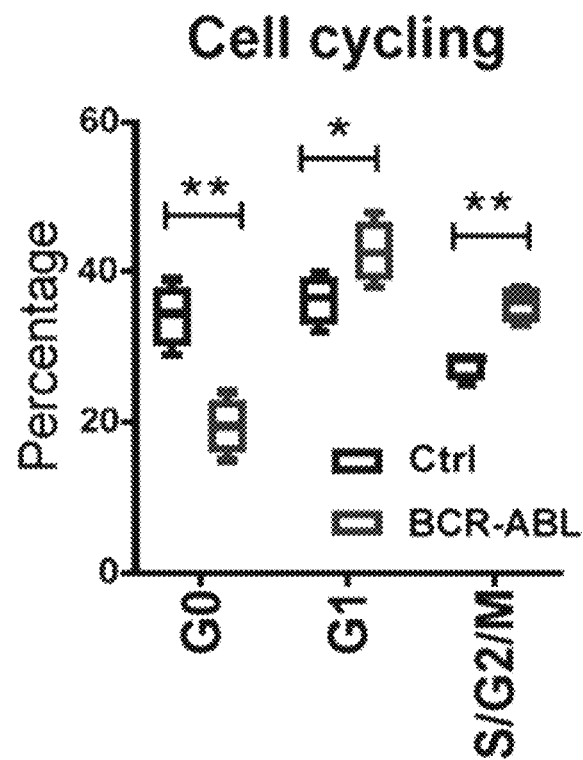
FIG. 2F and FIG. 2G show Cell cycle (FIG. 2F) and cell growth (FIG. 2G) analyses (n=4 independent experiments) of the cells from FIG. 2D and FIG. 2E at 48 h after transduction, wherein for each set of two data points, the data point on the left represents data for cells transduced with control retroviruses and the data point on the right represents data for cells transduced with BCR-ABL retroviruses.
Figure 2G:
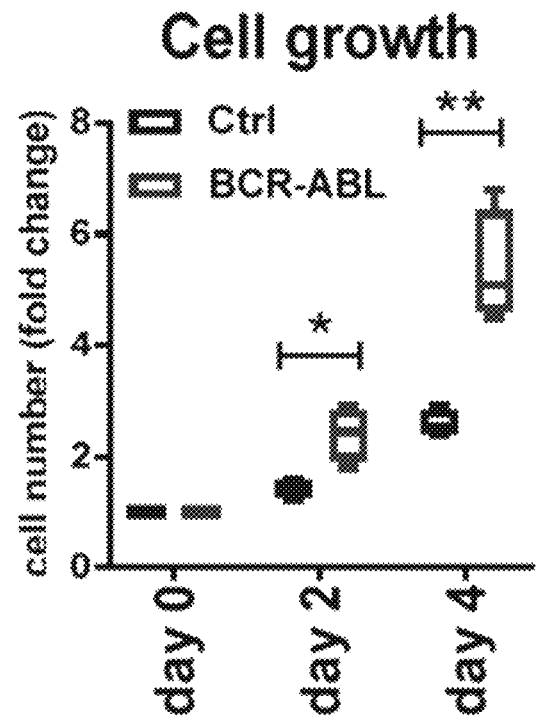
Figure 2H:
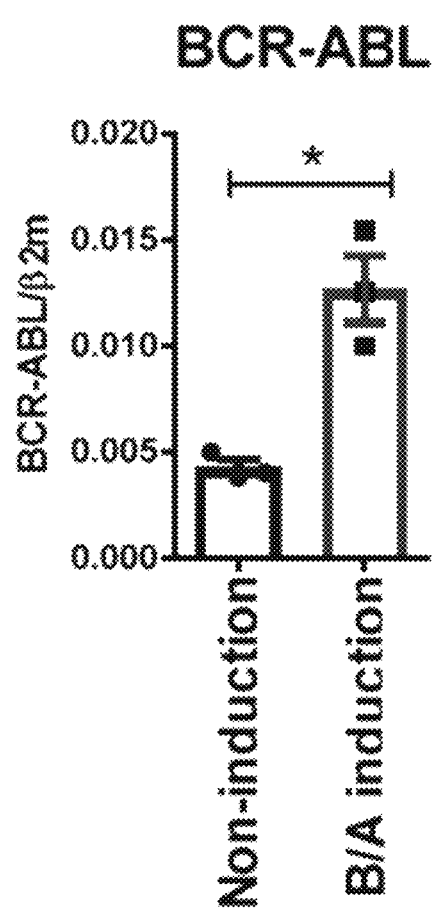
FIG. 2H and FIG. 2I show BCR-ABL (FIG. 2H) and miR-126 (FIG. 2I) expression, as assessed by QPCR, in LT-HSCs from non-induced CML mice (tet off) cultured for 24 h in the presence (non-induction) or absence (BCR-ABL (B/A) induction) of tetracycline (2 µg/ml) (n=3 independent animals in each group).
Figure 2I:
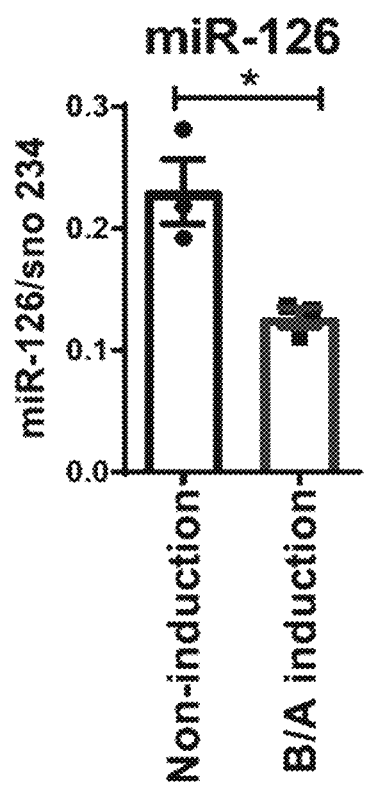
Figure 2J:
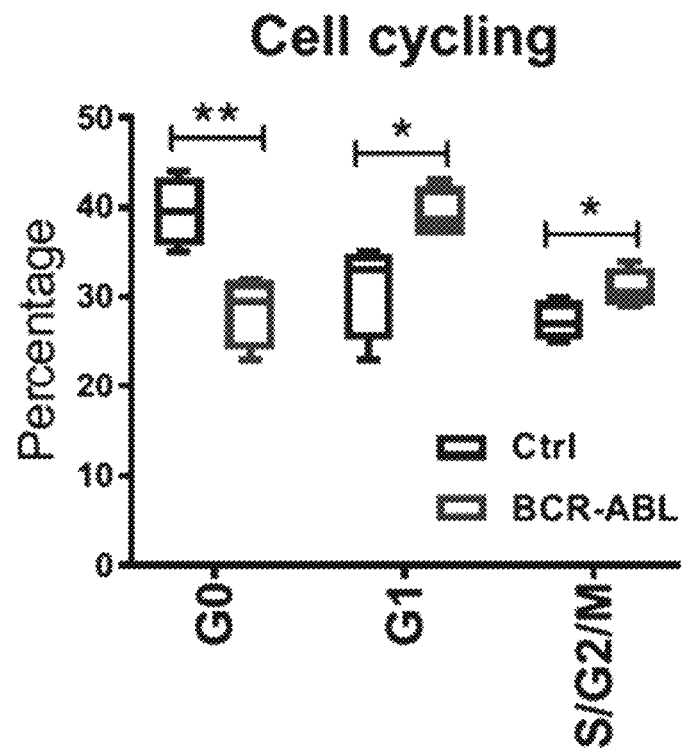
FIG. 2J and FIG. 2K show Cell cycle (FIG. 2J) and cell growth (FIG. 2K) analyses (n=4 independent experiments in each group) of the cells from FIG. 2H and FIG. 2I at 48 h after BCR-ABL induction, wherein for each set of two data points, the data point on the left represents data for non-induced cells and the data point on the right represents data for induced cells.
Figure 2K:
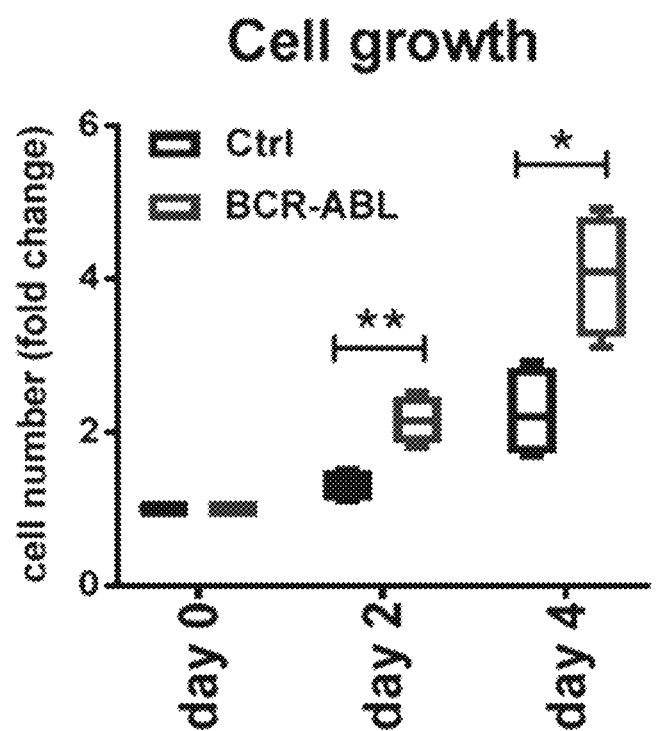
Figure 2L:
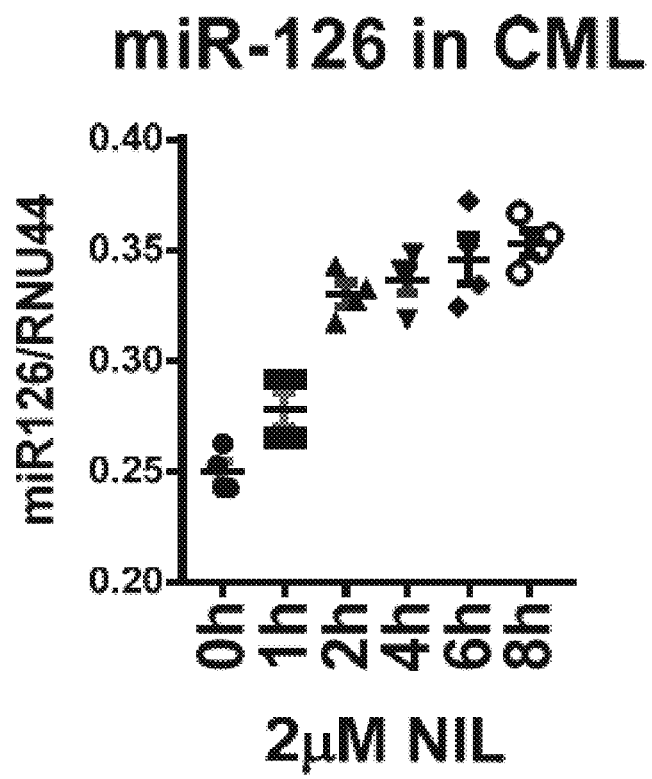
FIG. 2L shows miR-126 expression, as assessed by QPCR, in human CML Lin-CD34+CD38− cells treated with NIL (2 µM) for the indicated periods of time (n=4 independent experiments). Mean±SEM was shown.
Figure 2M:
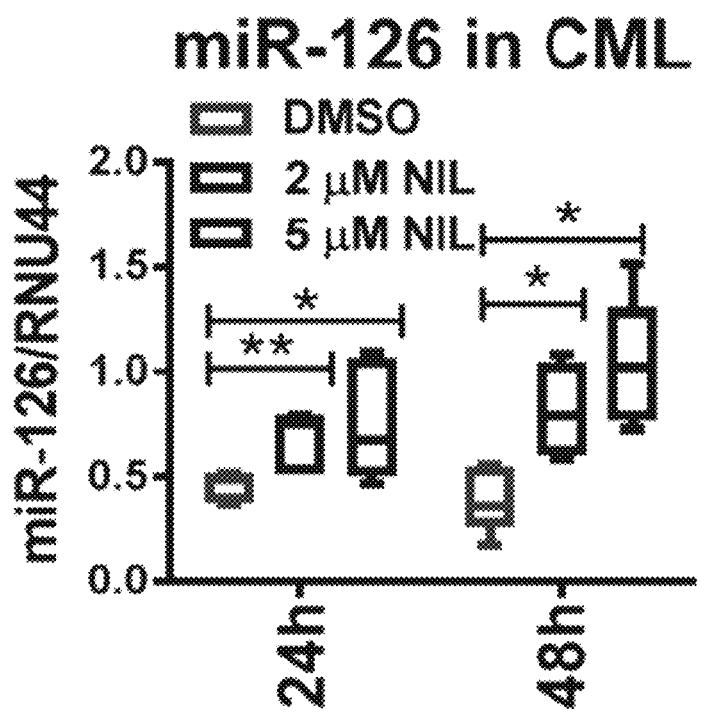
FIG. 2M shows miR-126 expression, as assessed by QPCR, in CML Lin-CD34+CD38− cells. For each group of three data points, the data points from left to right represent cells treated with DMSO (Ctrl), 2 µM or 5 µM NIL (n=5 independent samples).
Figure 2N:
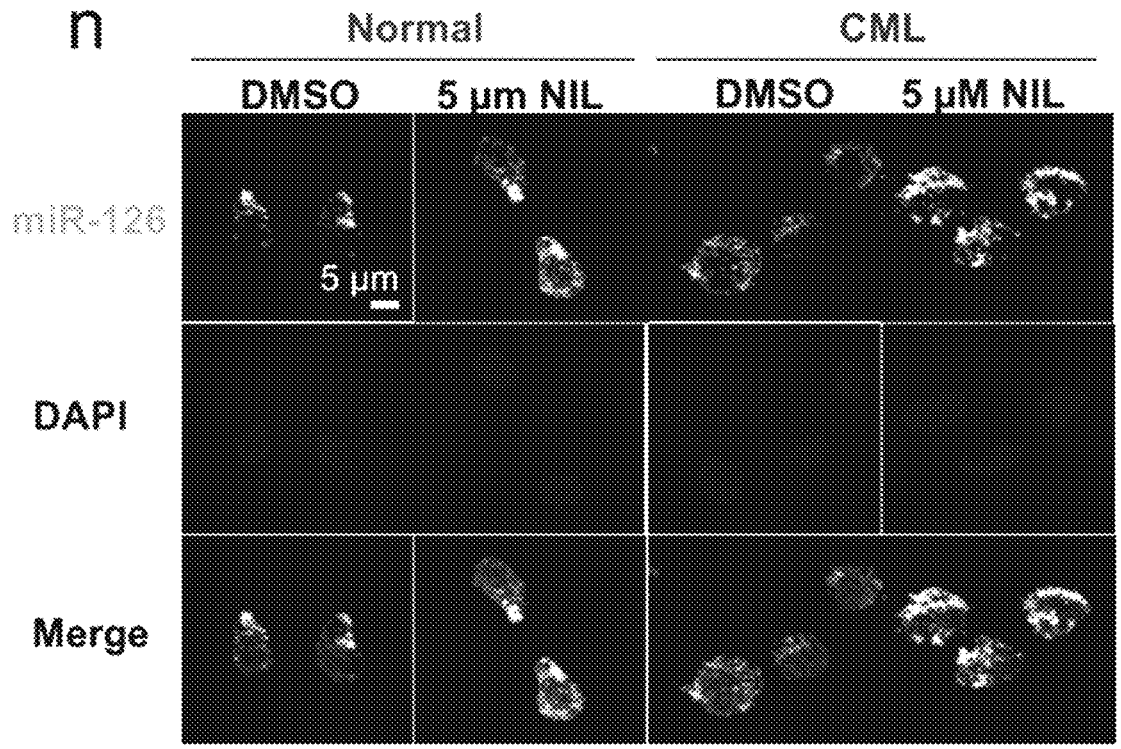
FIG. 2N shows miR-126 expression, as assessed by miRNA staining, in normal and CML Lin-CD34+CD38− cells treated with DMSO or NIL (5 µM) The experiments were repeated using 4 independent samples with similar results.
Figure 2O:
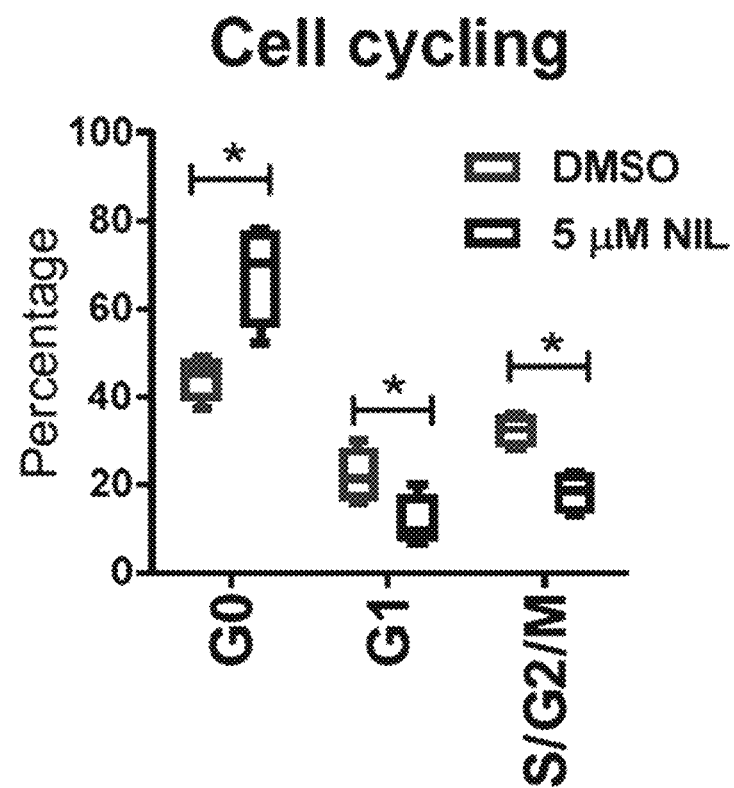
Figure 7E:
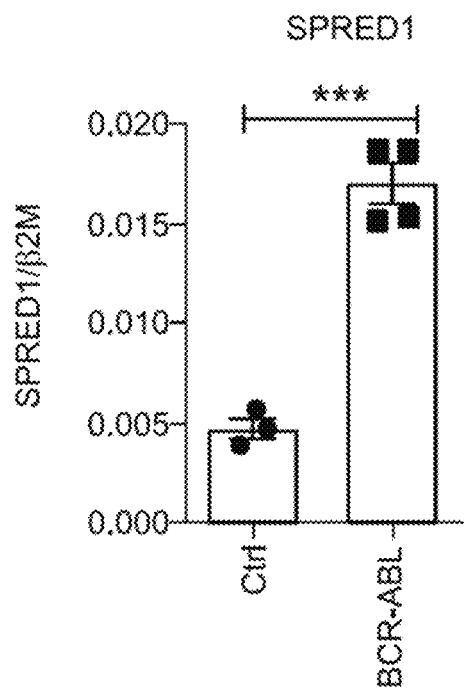
Figure 7F:
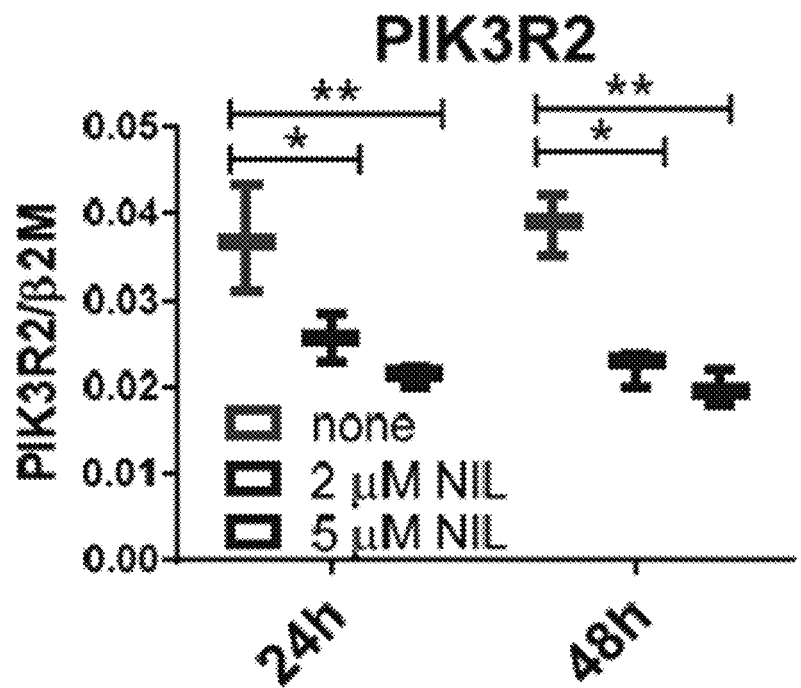
Figure 7G:
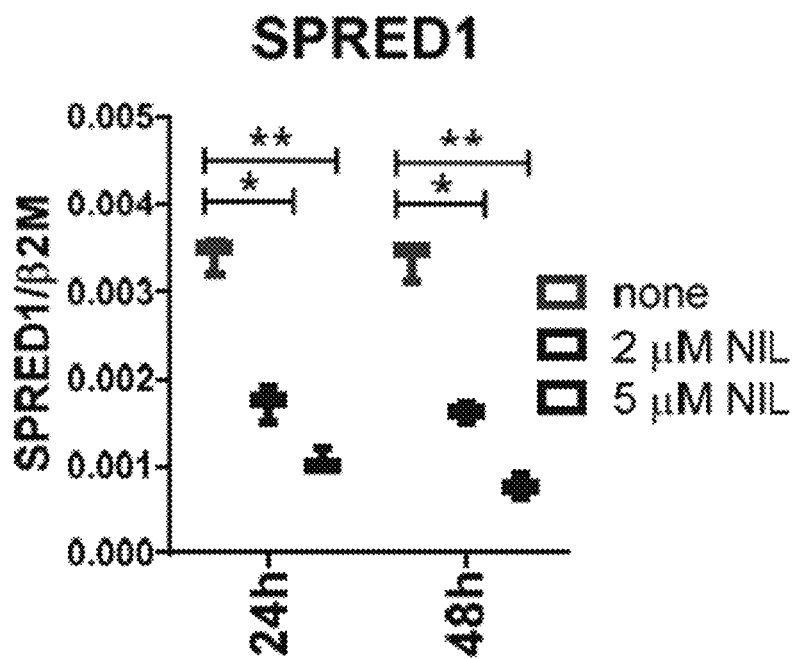
Figure 7H:
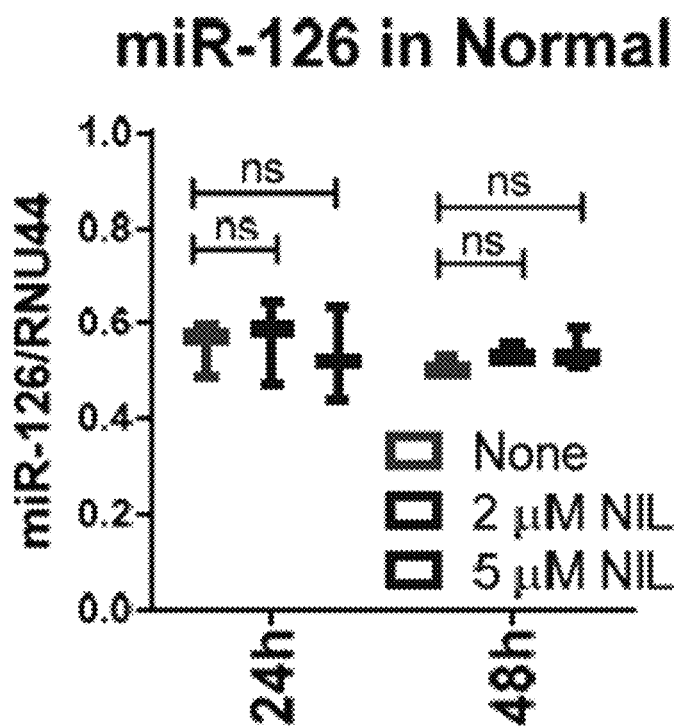
Figure 7I:
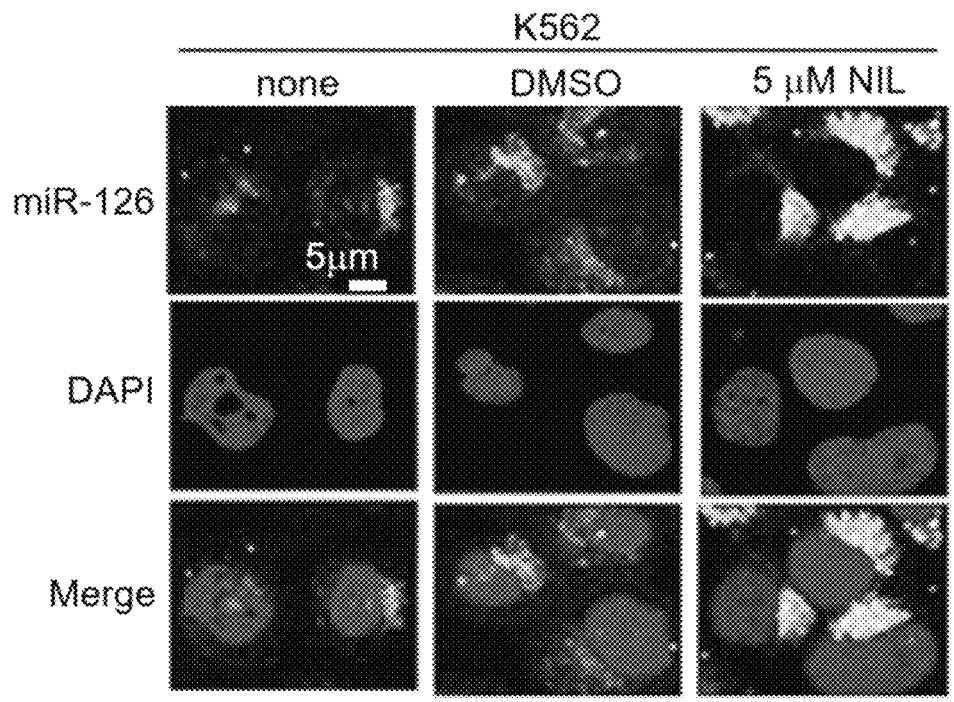

This differential expression of miR-126 observed led us to postulate that BCR-ABL itself might be involved in lowering miR-126 levels in CML cells. To test this hypothesis, we transduced normal mouse BM LSK cells with retroviral BCR-ABL or control vectors, and selected GFP+ cells and cultured them for 72 h. Upon BCR-ABL induction (FIG. 2D), miR-126 expression decreased (FIG. 2E) and PIK3R2 and SPRED1 expression increased compared to the control cells (FIG. 7D and FIG. 7E); this was associated with an increase in cell cycling (FIG. 2F) and cell growth (FIG. 2G). To further validate this finding, we sorted LT-HSCs from non-induced BCR-ABL transgenic mice and cultured them with or without tetracycline. Upon tetracycline withdrawal and BCR-ABL induction (FIG. 2H), we observed reduced miR-126 levels (FIG. 2I) and increased cell cycling (FIG. 2J) and cell growth (FIG. 2K) as compared with non-induced controls. Conversely, BCR-ABL inhibition by nilotinib (NIL), a first-line TKI for CML treatment, led to increased miR-126 expression (FIGS. 2L-2N), decreased PIK3R2 and SPRED1 levels (FIG. 1F and FIG. 1G) and an increased fraction of quiescent cells in human CML HSCs (FIG. 2O), but not in normal HSCs (FIG. 7H), as compared with vehicle alone. NIL treatment also resulted in increased miR-126 expression in human BCR-ABL+K562 cells (FIG. 7I).

BCR-ABL Deregulates miR-126 Biogenesis.

Figure 3A:
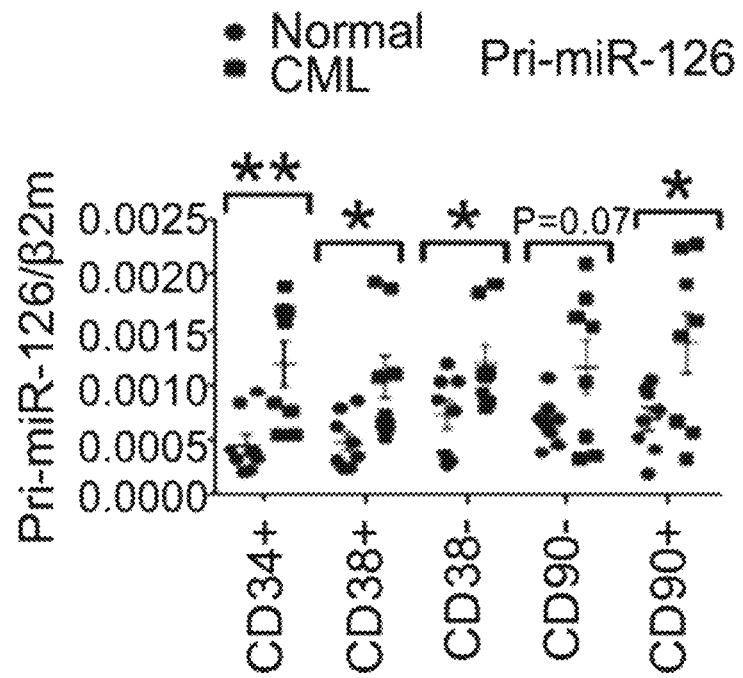
FIGS. 3A-3S. The figures show BCR-ABL deregulates miR-126 biogenesis.
Figure 3B:
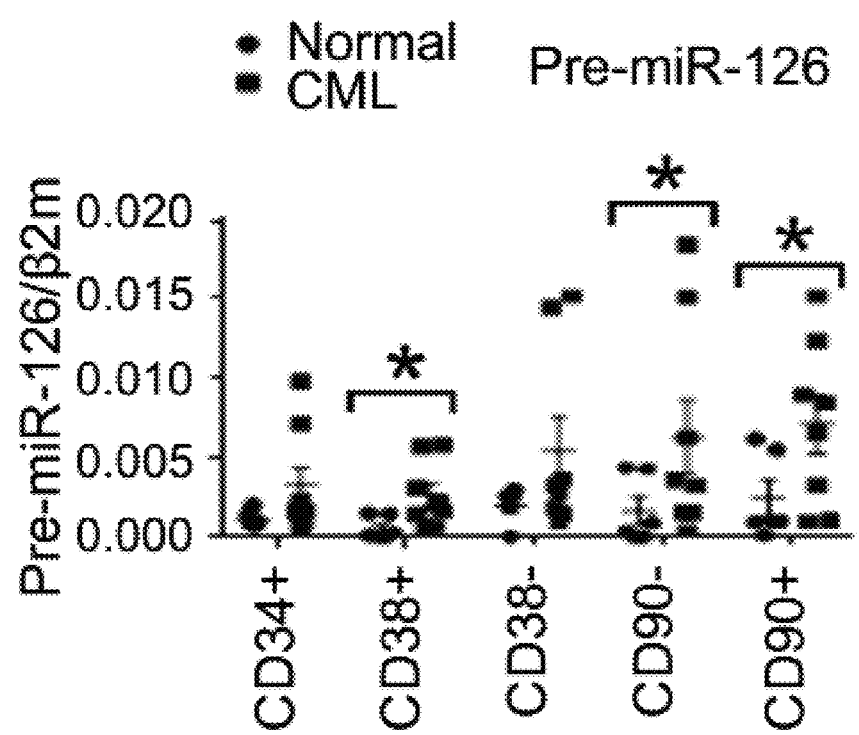
Figure 3C:
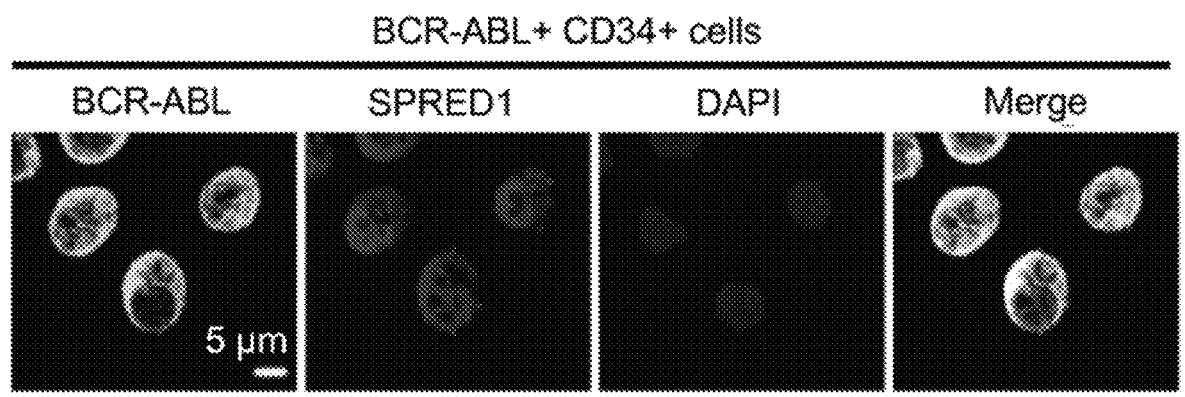
FIG. 3C shows BCR-ABL and SPRED1 staining in CML CD34+ cells by immunofluorescence (IF).
Figure 3D:
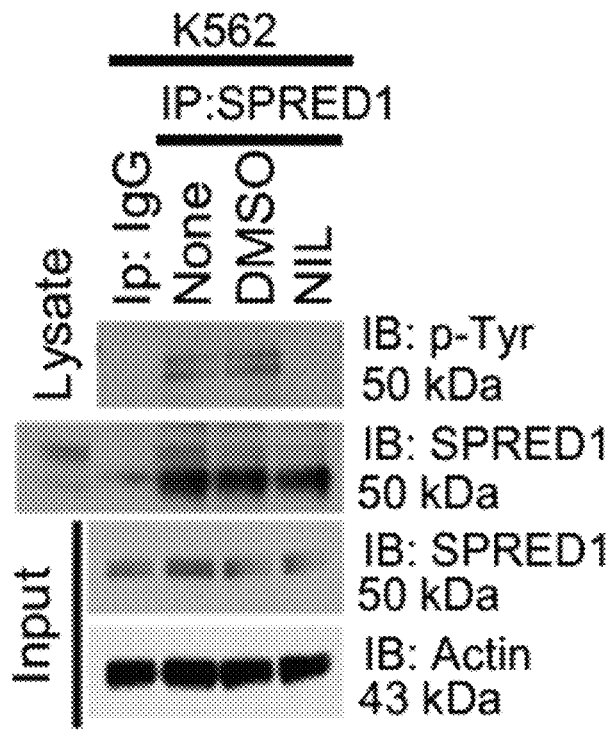
FIG. 3D shows immunoprecipitation (IP) with anti-SPRED1 followed by immunoblotting (IB) with anti-SPRED1 and anti-phosphotyrosine (p-Tyr) antibodies (left) and an in vitro kinase assay (right), as performed by IP with anti-c-Abl or anti-normal mouse IgG as control and immunoblotting with anti-SPRED1, in lysates of K562 cells treated with none, DMSO (vehicle) or NIL.
Figure 3E:
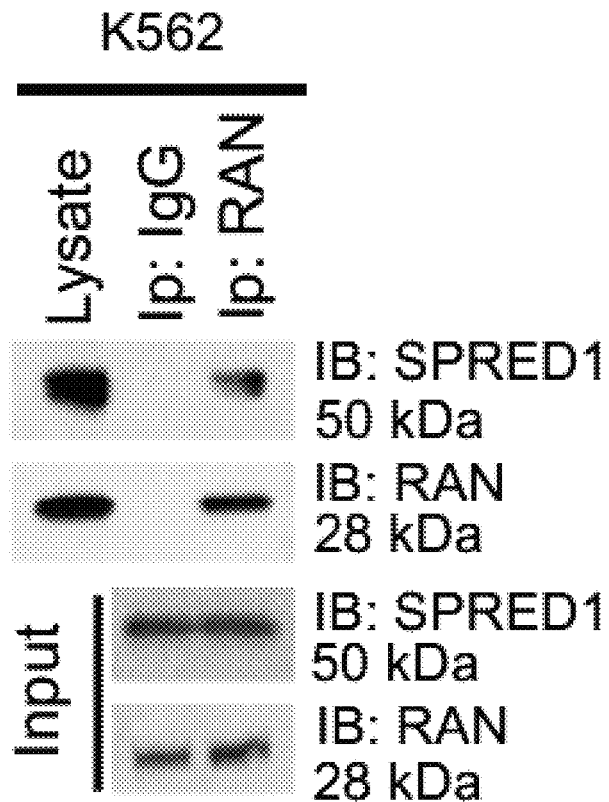
FIG. 3E shows IP with anti-RAN followed by D3 with anti-SPRED1 and anti-RAN antibodies in lysates of K562 cells.
Figure 3F:
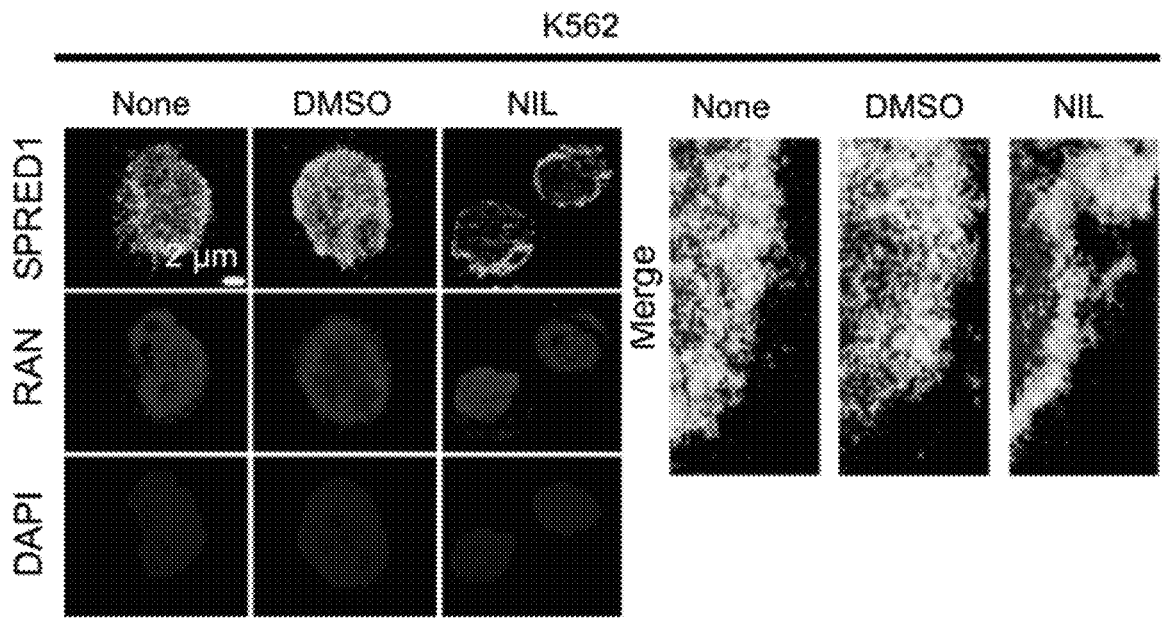
FIG. 3F shows SPRED1 and RAN staining by IF in K562 cells treated with none, DMSO or NIL.
Figure 3G:
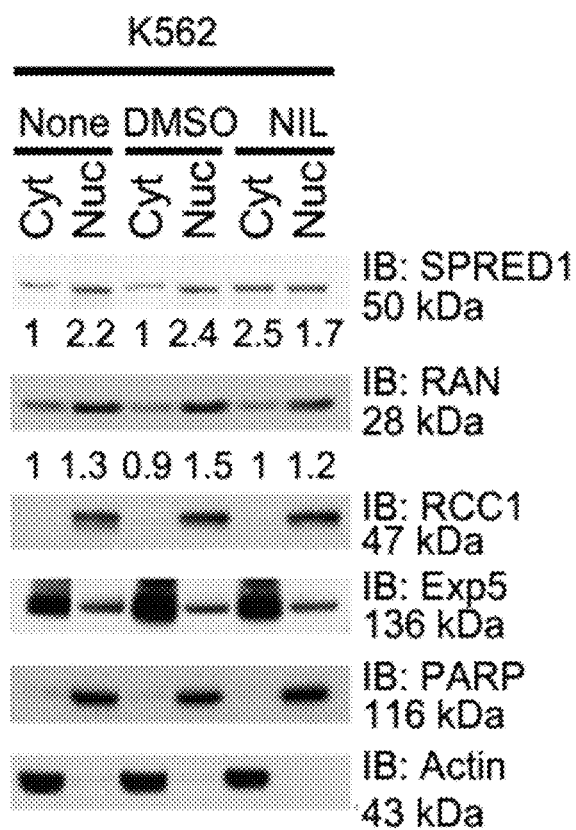
FIG. 3G shows SPRED1, RAN, RCC1 and Exp-5 expression in cytoplasmic (Cyt) and nuclear (Nu) fractions from K562 cells, treated with DMSO or NIL, as assessed by D3. Densitometric quantification of selected bands is shown (normalized to the actin loading control for total and Cyt lysates or to the PARP loading control for Nu lysates).
Figure 3H:
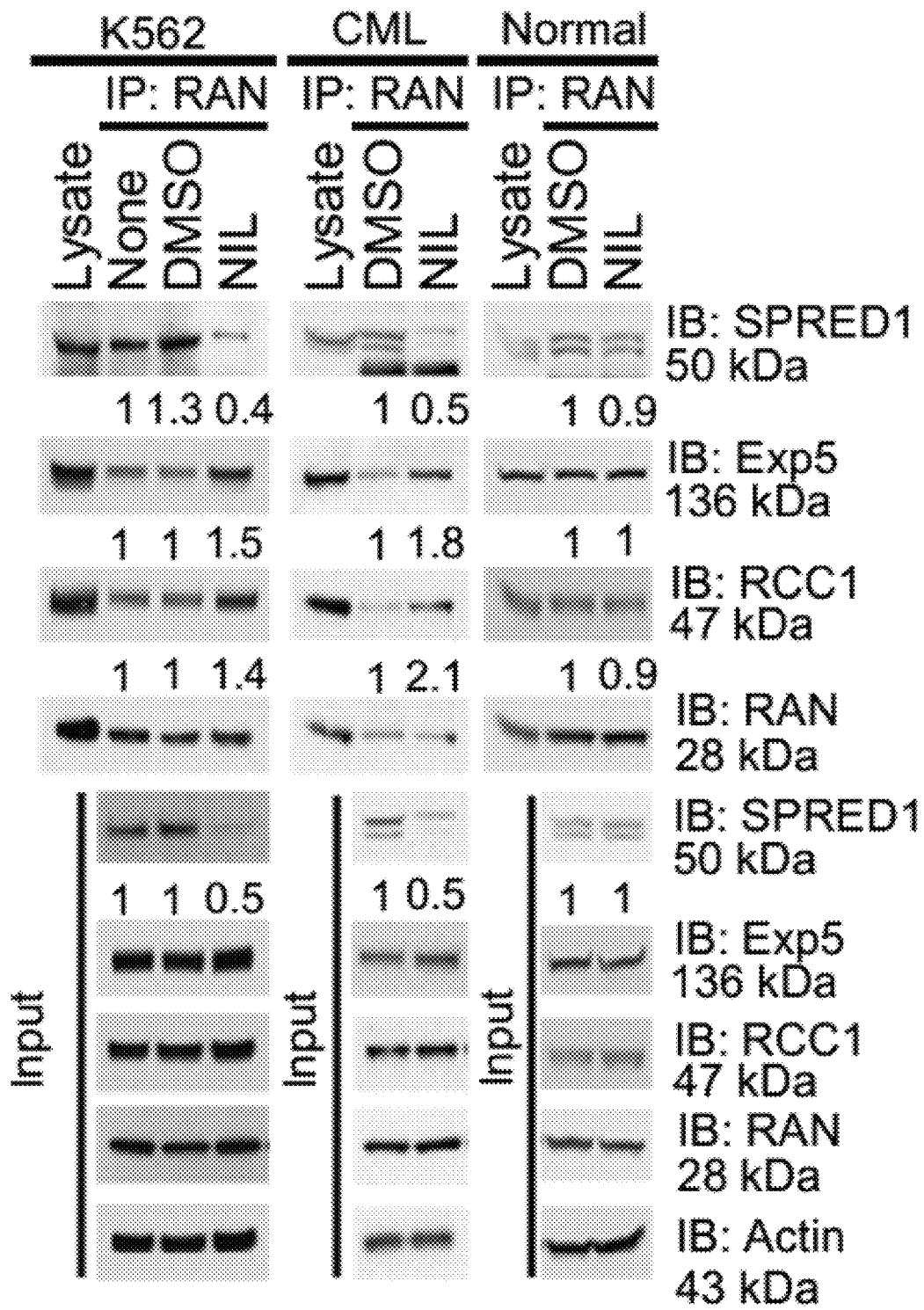
FIG. 3H shows IP with anti-RAN followed by D3 with anti-SPRED1, RAN, Exp-5 and RCC1 antibodies in lysates of K562 cells, CML CD34+ cells, and normal CD34+ cells treated with DMSO or NIL. Densitometric quantification of selected bands is shown (normalized to the actin loading control).
Figure 3I:
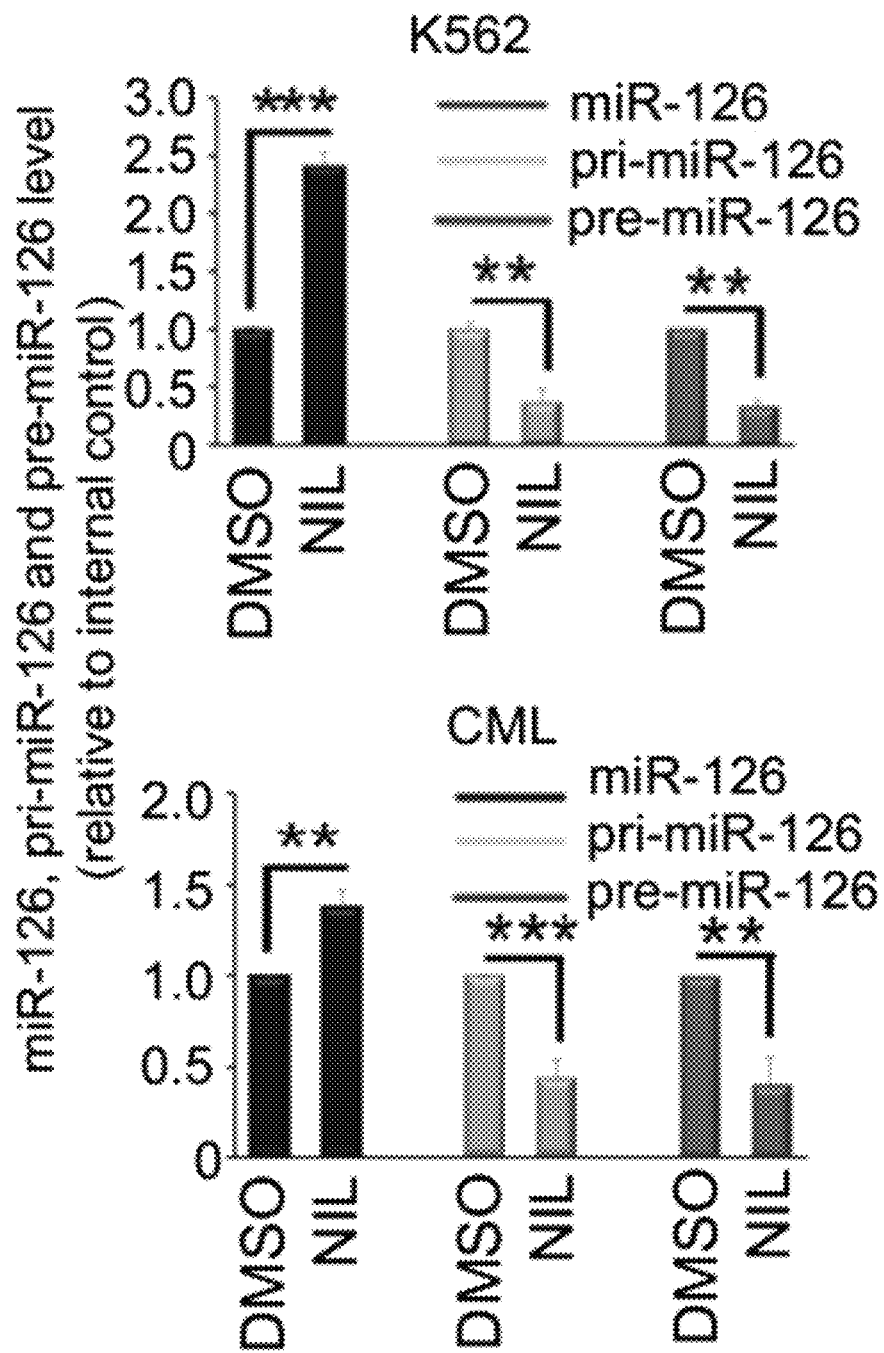
FIG. 3I shows mature (left two bars), pri- (middle two bars) and pre-miR-126 (right two bars) expression, as assessed by QPCR, in K562 and CML CD34+ cells treated with DMSO or NIL (n=3 independent experiments for K562 and 3 independent samples for CML cells).
Figure 3J:
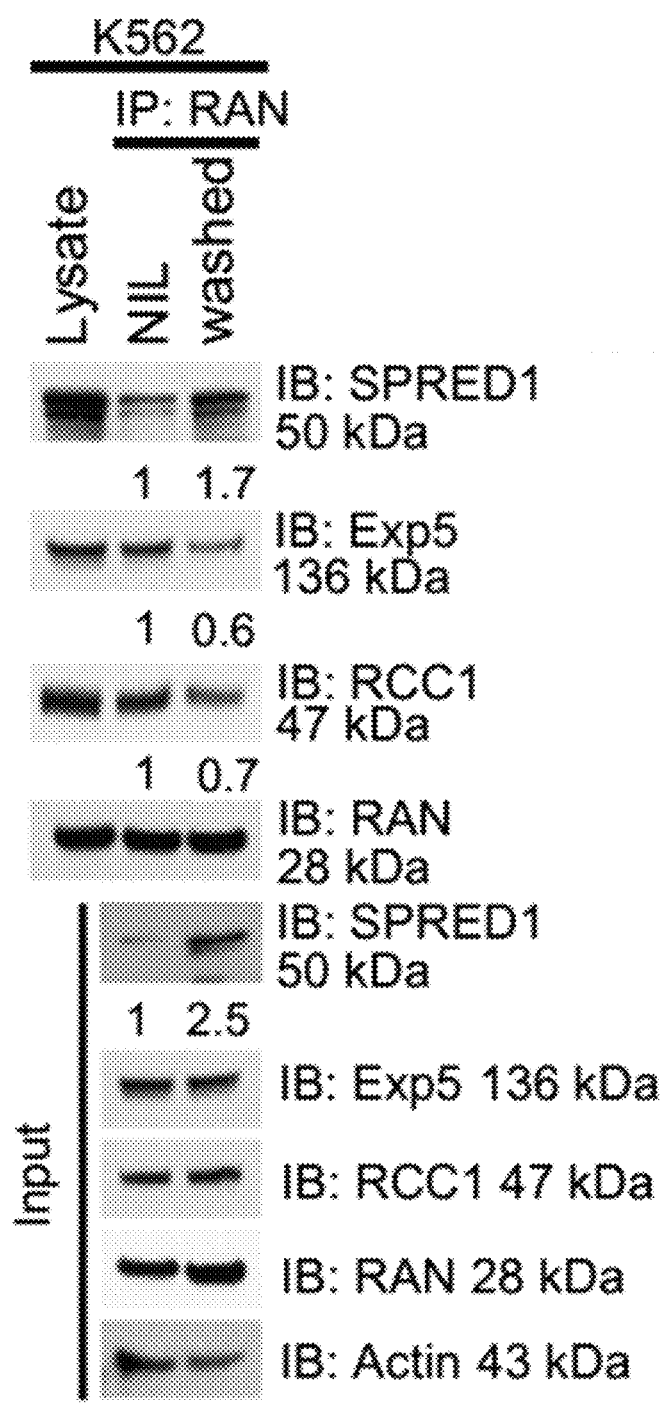
FIG. 3J shows IP with anti-RAN followed by D3 with anti-SPRED1, Exp-5, RCC1 and RAN antibodies in lysates of K562 cells without or with washing-off of NIL. Densitometric quantification of selected bands is shown (normalized to the actin loading control).
Figure 3K:
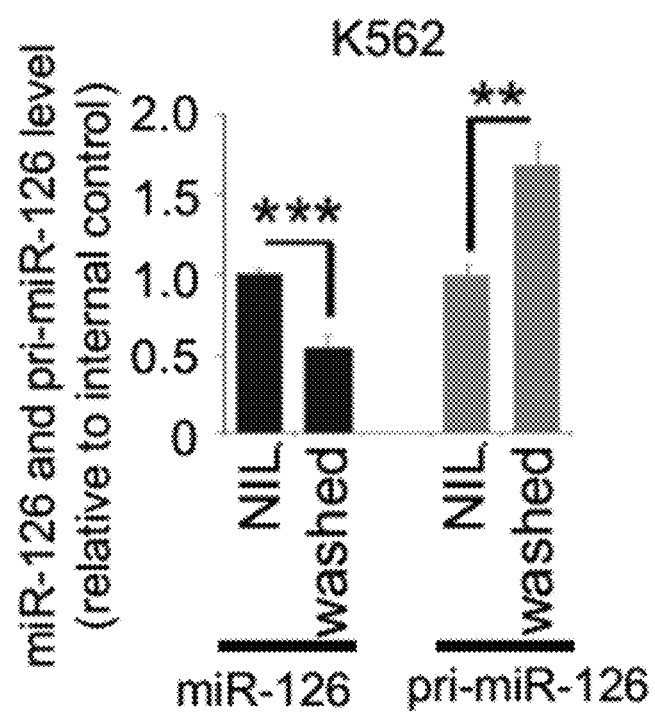
FIG. 3K and FIG. 3M show mature and pri-miR-126 expression as assessed by QPCR (n=3 independent experiments) (FIG. 3K), miR-126 staining (FIG. 3L), and mature and pre-miR-126 levels as assessed by Northern blotting (FIG. 3M) in K562 cells with or without washing-off of NIL.
Figure 3L:
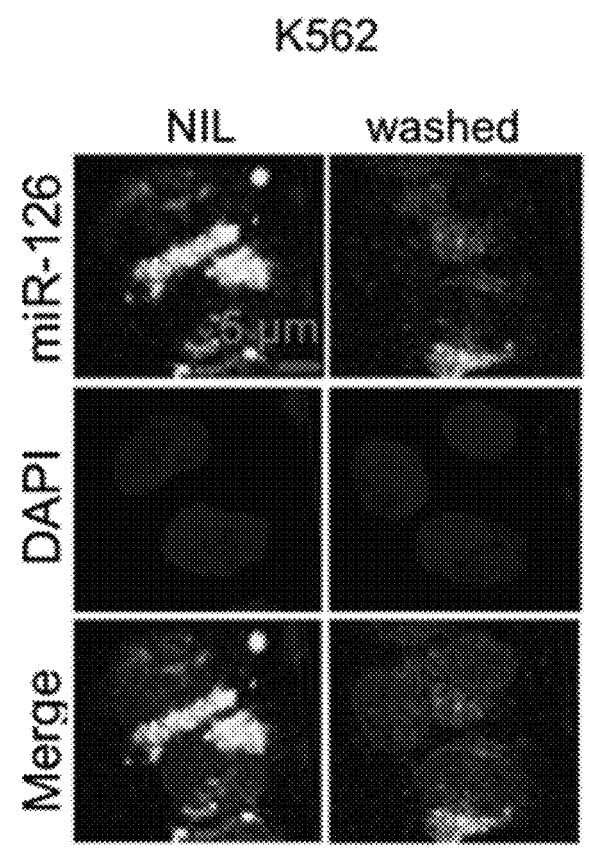
Figure 3M:
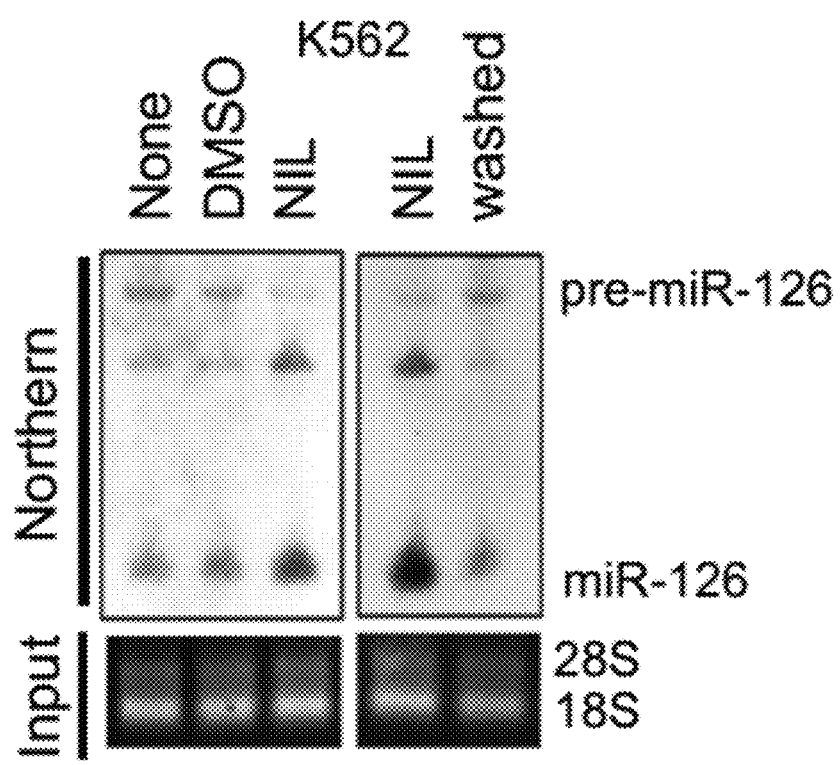
Figure 3N:
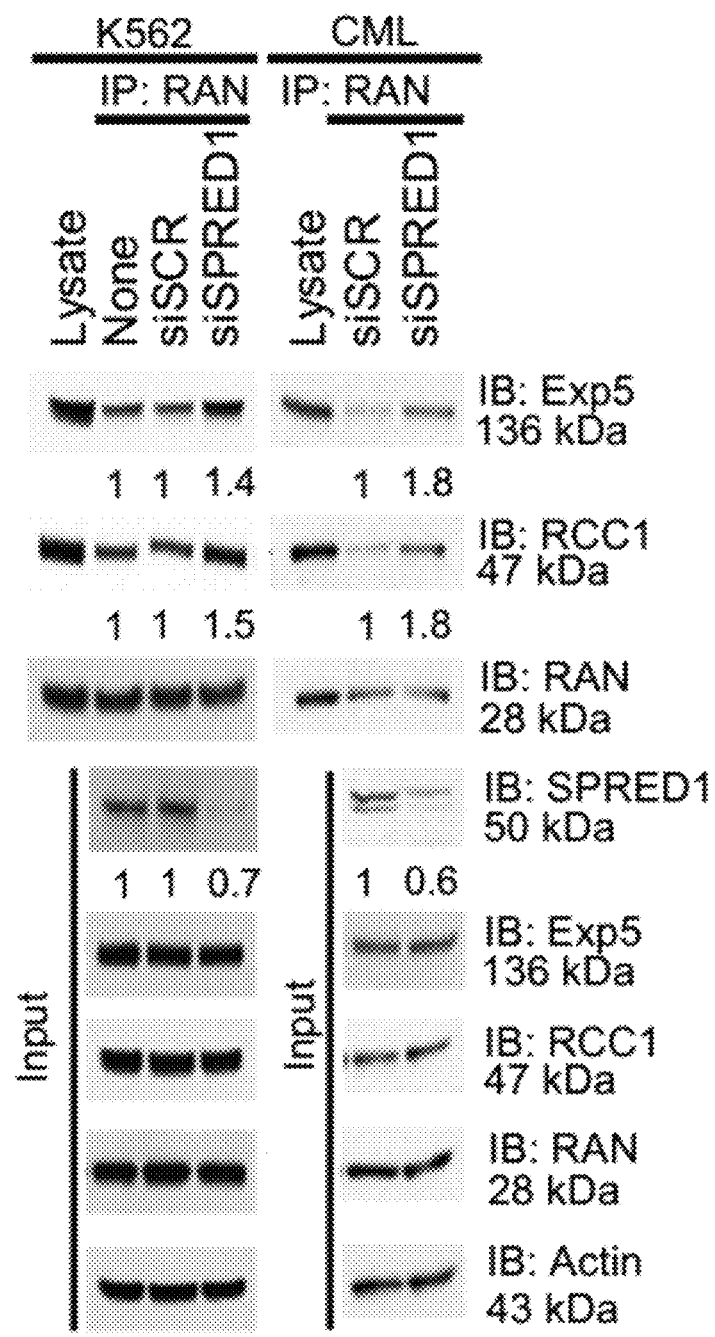
FIG. 3N shows IP with anti-RAN followed by D3 with anti-Exp-5, RCC1 and RAN antibodies in lysates of K562 and CML CD34+ cells with control (siSCR) or SPRED1 (siSPRED1) knockdown. Densitometric quantification of selected bands is shown (normalized to the actin loading control.
Figure 3O:
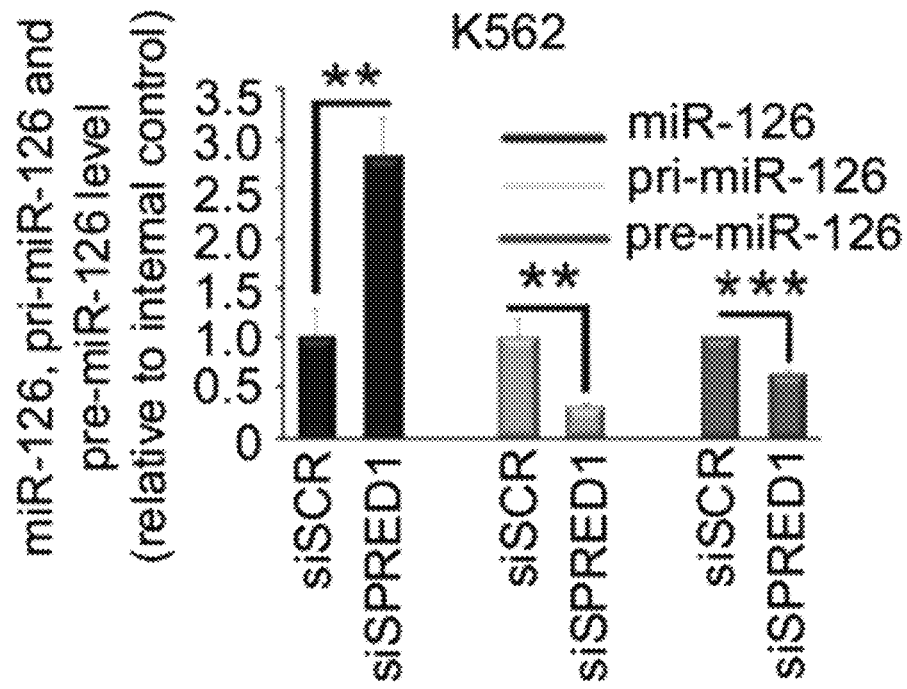
FIG. 3O and FIG. 3P show mature (left two bars), pri- (middle two bars) and pre-miR-126 (right two bars) expression, assessed by QPCR (n=3 independent experiments) (FIG. 3O) and miR-126 staining (FIG. 3P) in siSCR and siSPRED1 treated K562 cells.
Figure 3P:
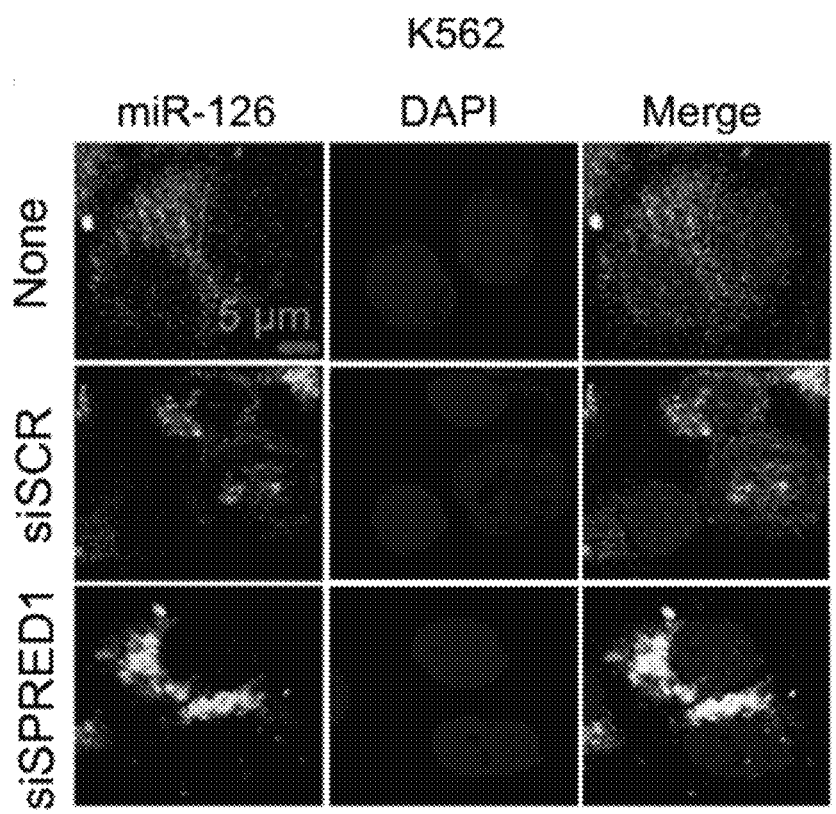
Figure 3Q:
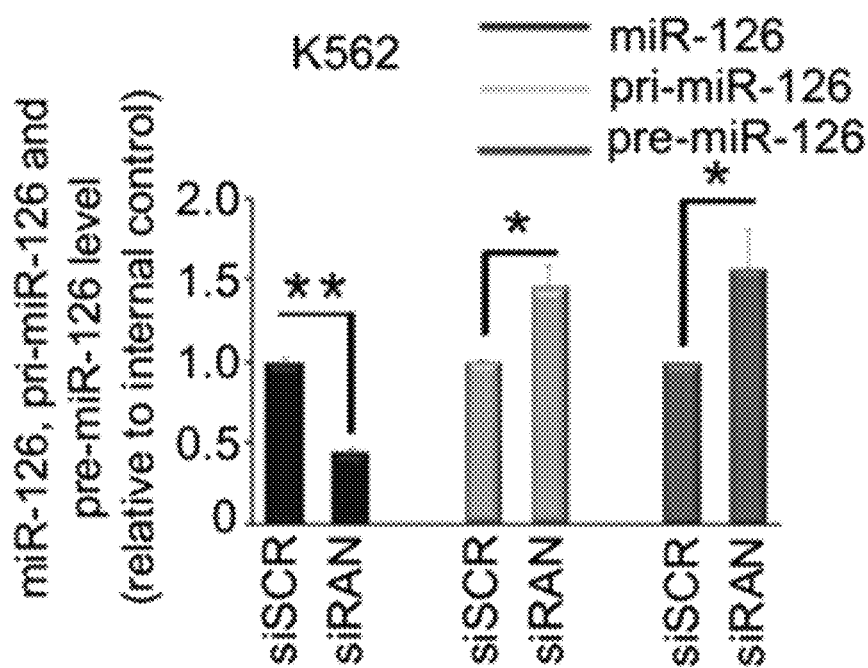
Figure 3R:
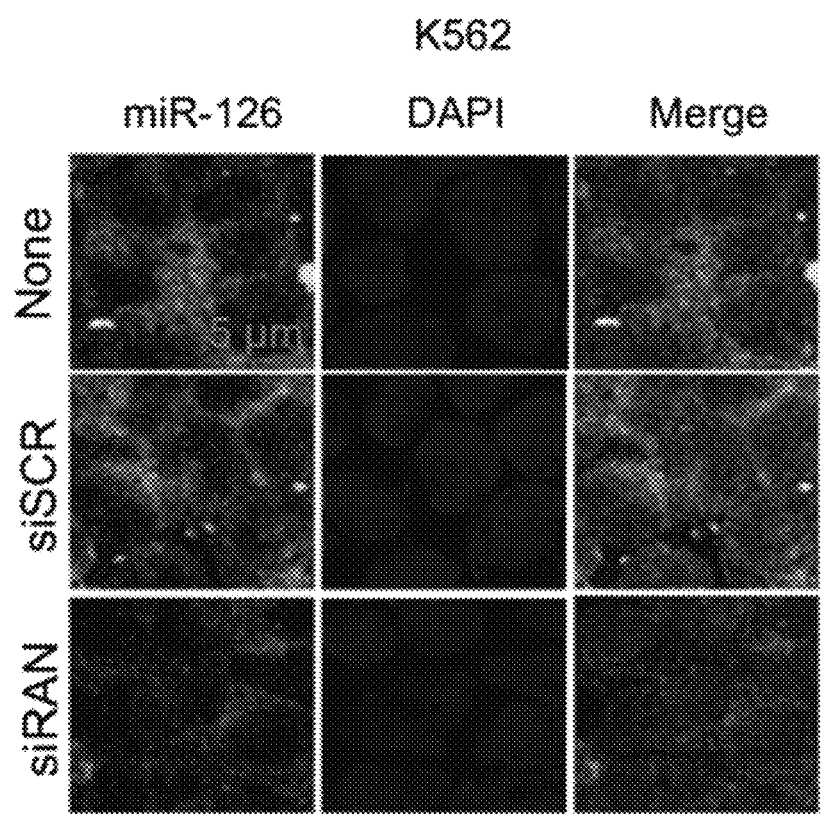
Figure 3S:
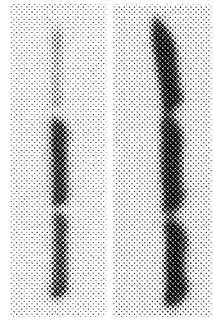
Figure 14:
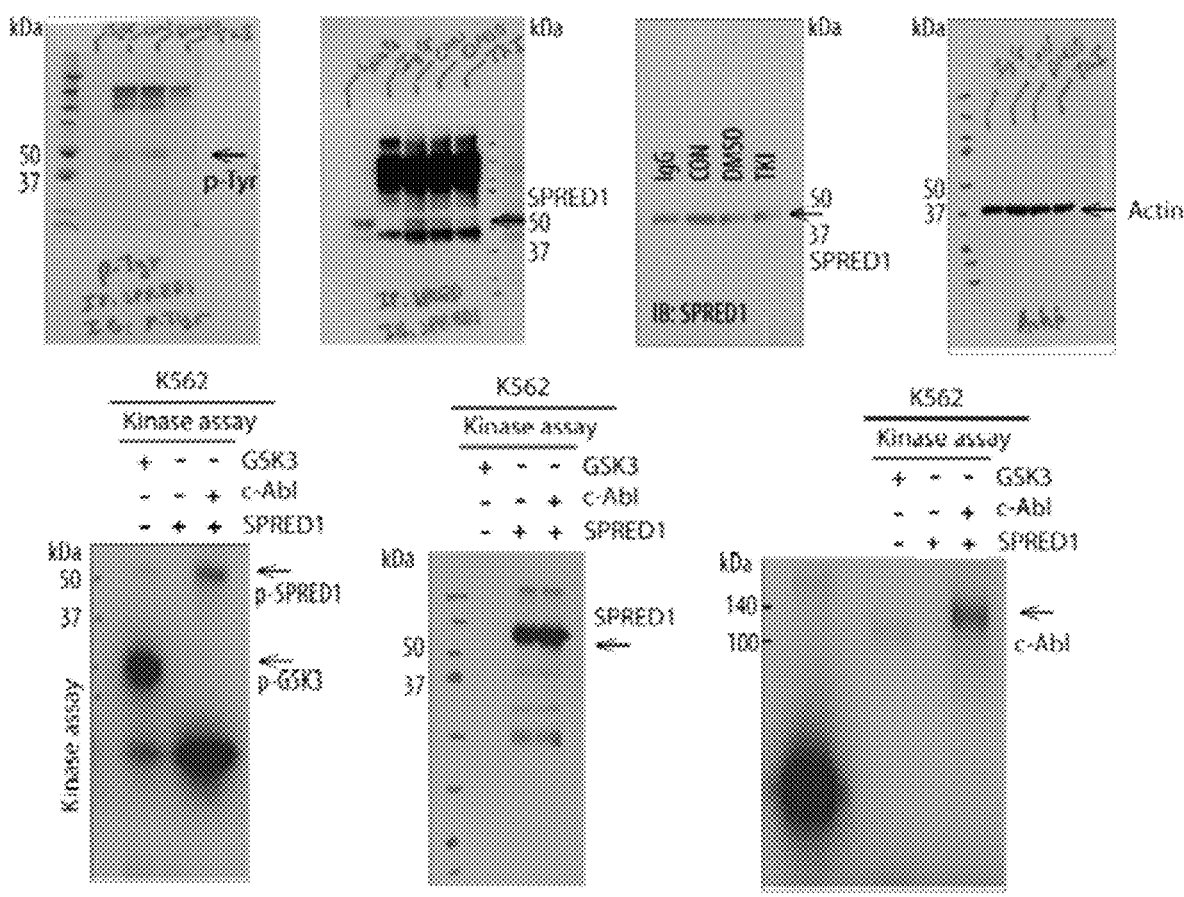
FIG. 14. The figure shows full-length gels and blots with molecular weight standards for FIGS. 3D, 3E, and 3G.
Figure 14:
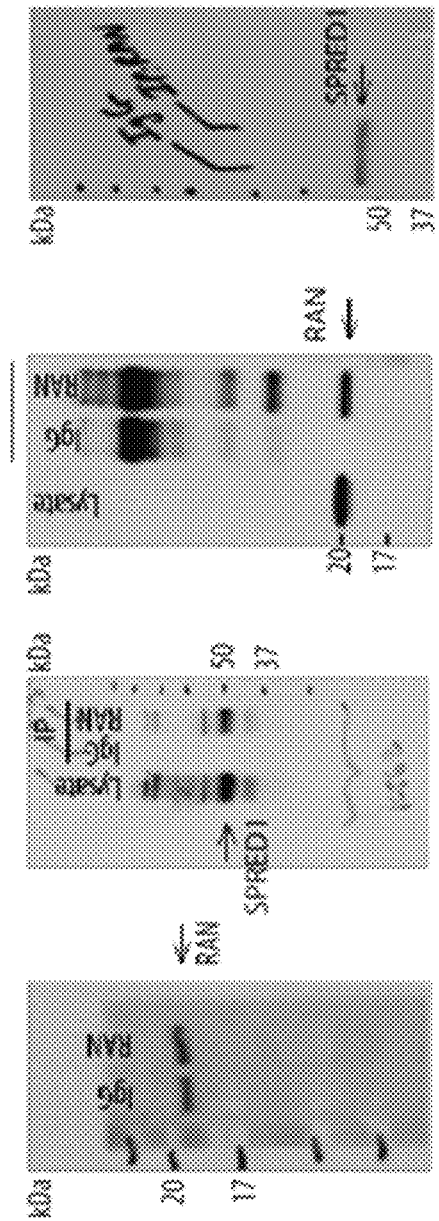
Figure 14:
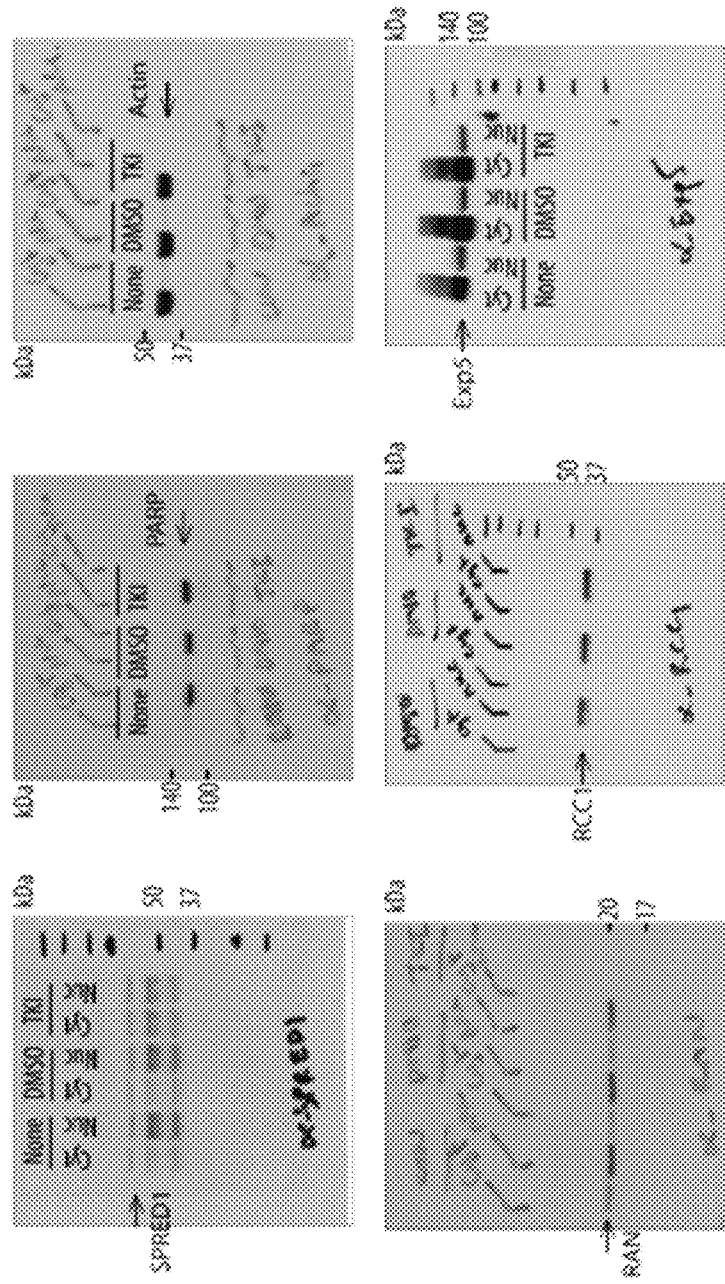
Figure 15:
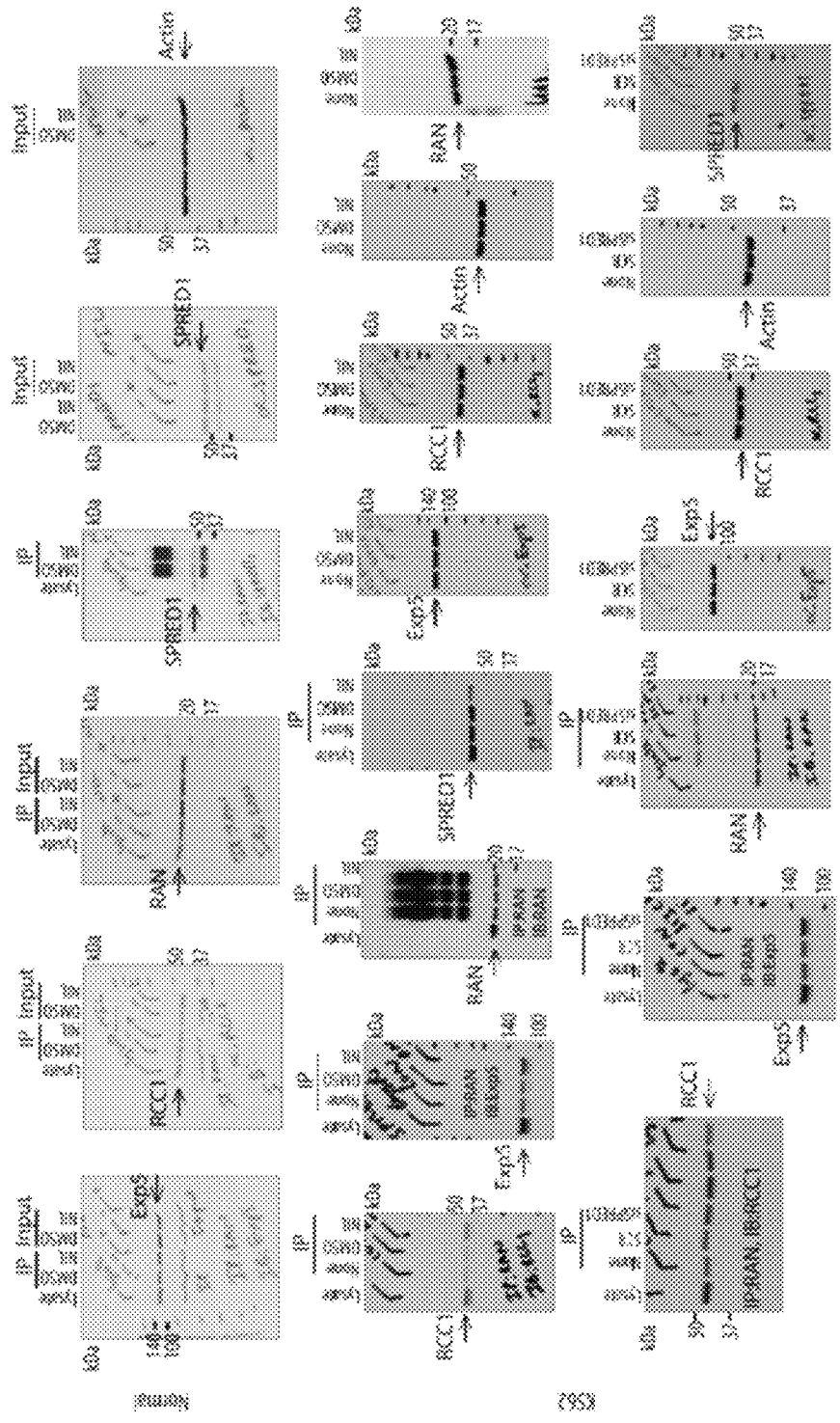
FIG. 15. The figure shows full-length gels and blots with molecular weight standards for FIGS. 3H, 3J, and 3N.
Figure 15:
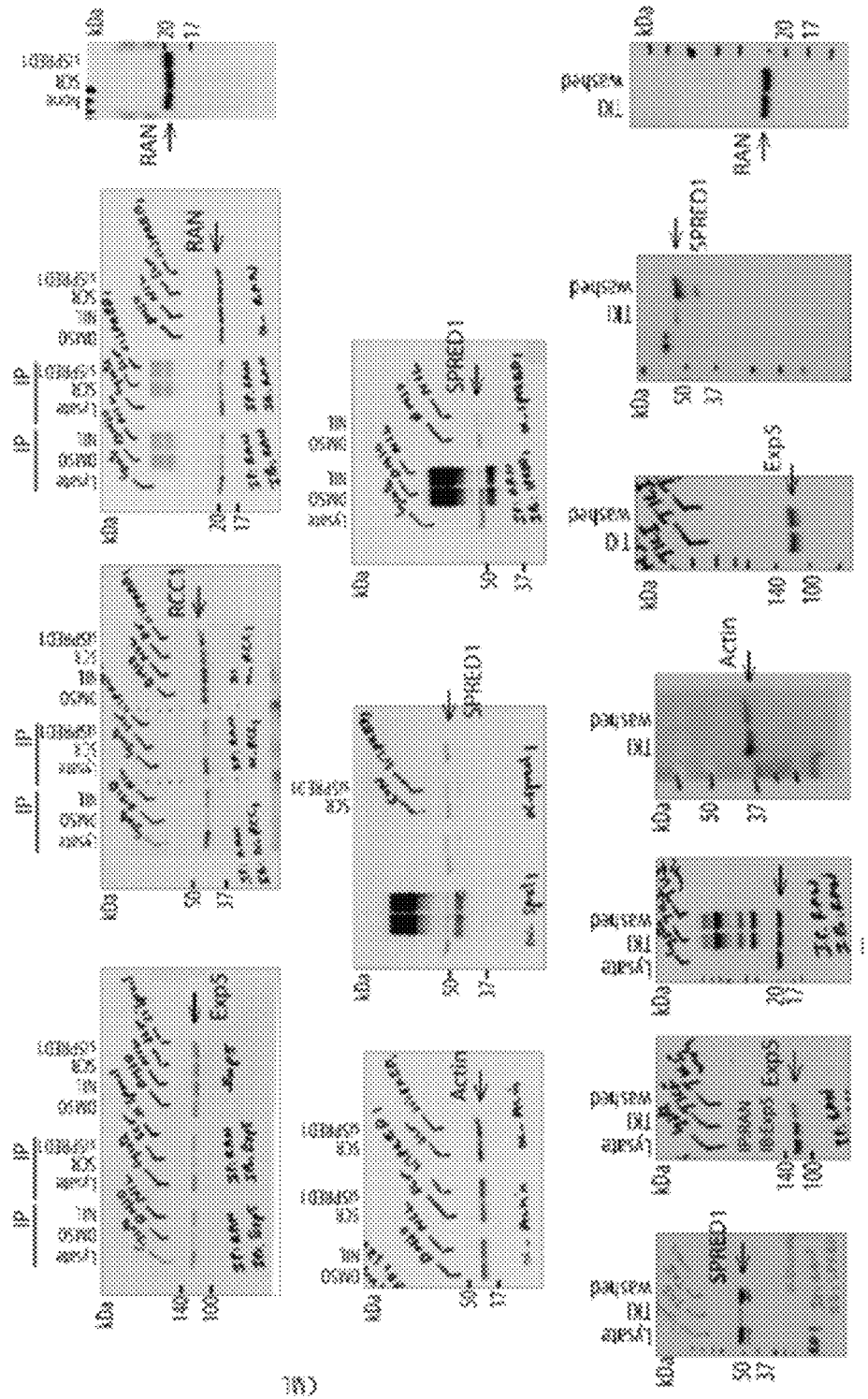
Figure 15:
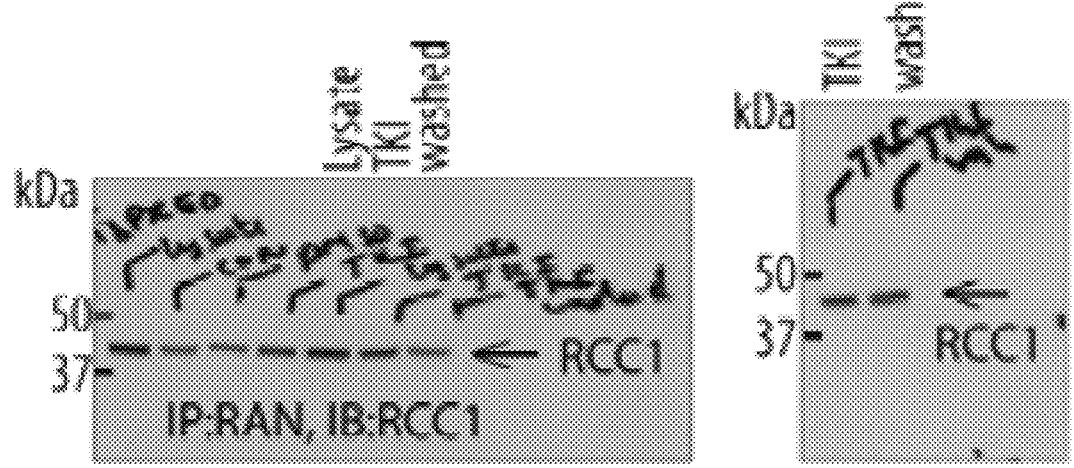
Figure 16:
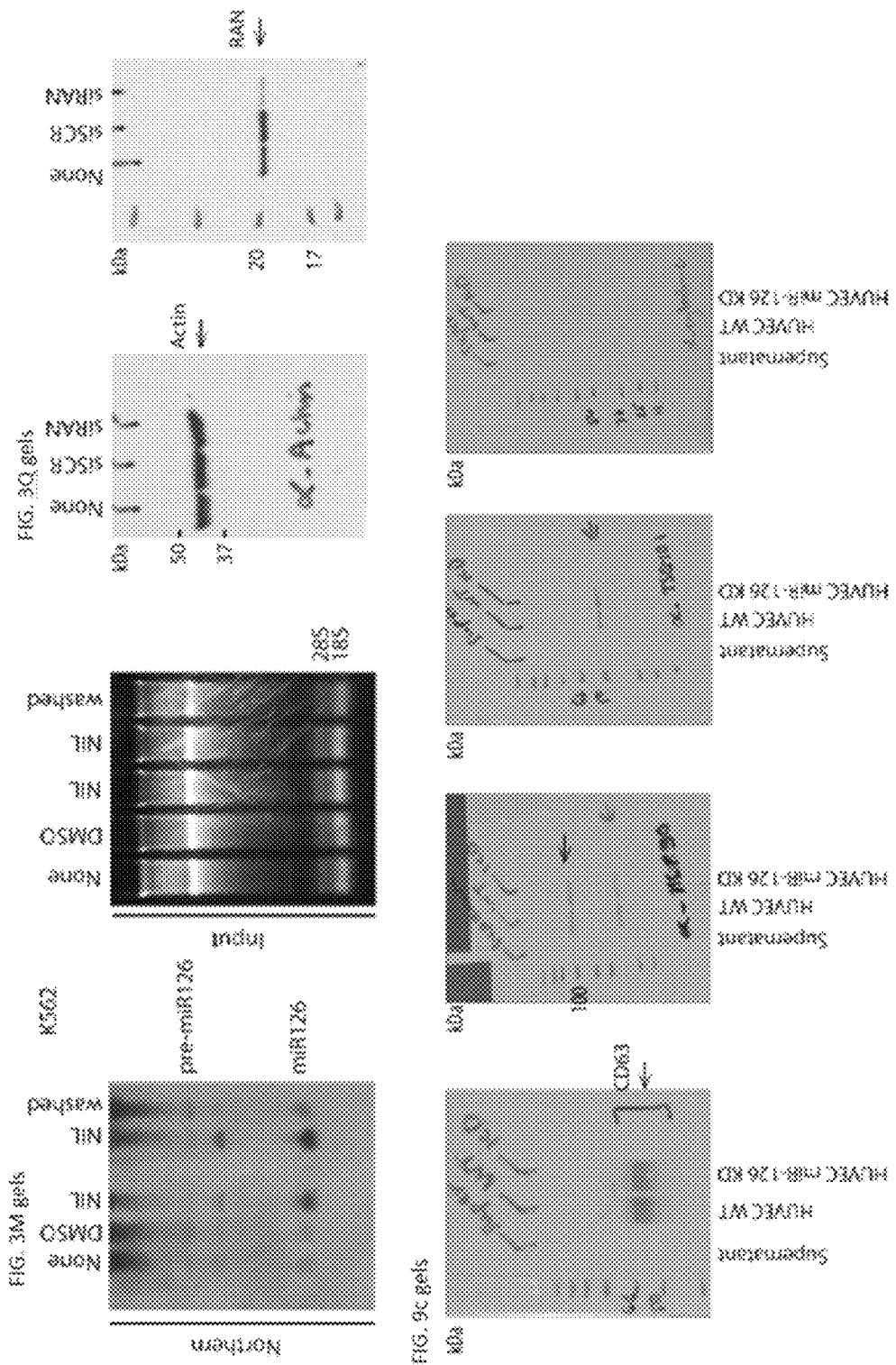
FIG. 16. The figure shows full-length gels and blots with molecular weight standards for FIGS. 3M and 3Q, FIG. 9C, and FIGS. 11H, 11K, 11M, and 11P.
Figure 16:
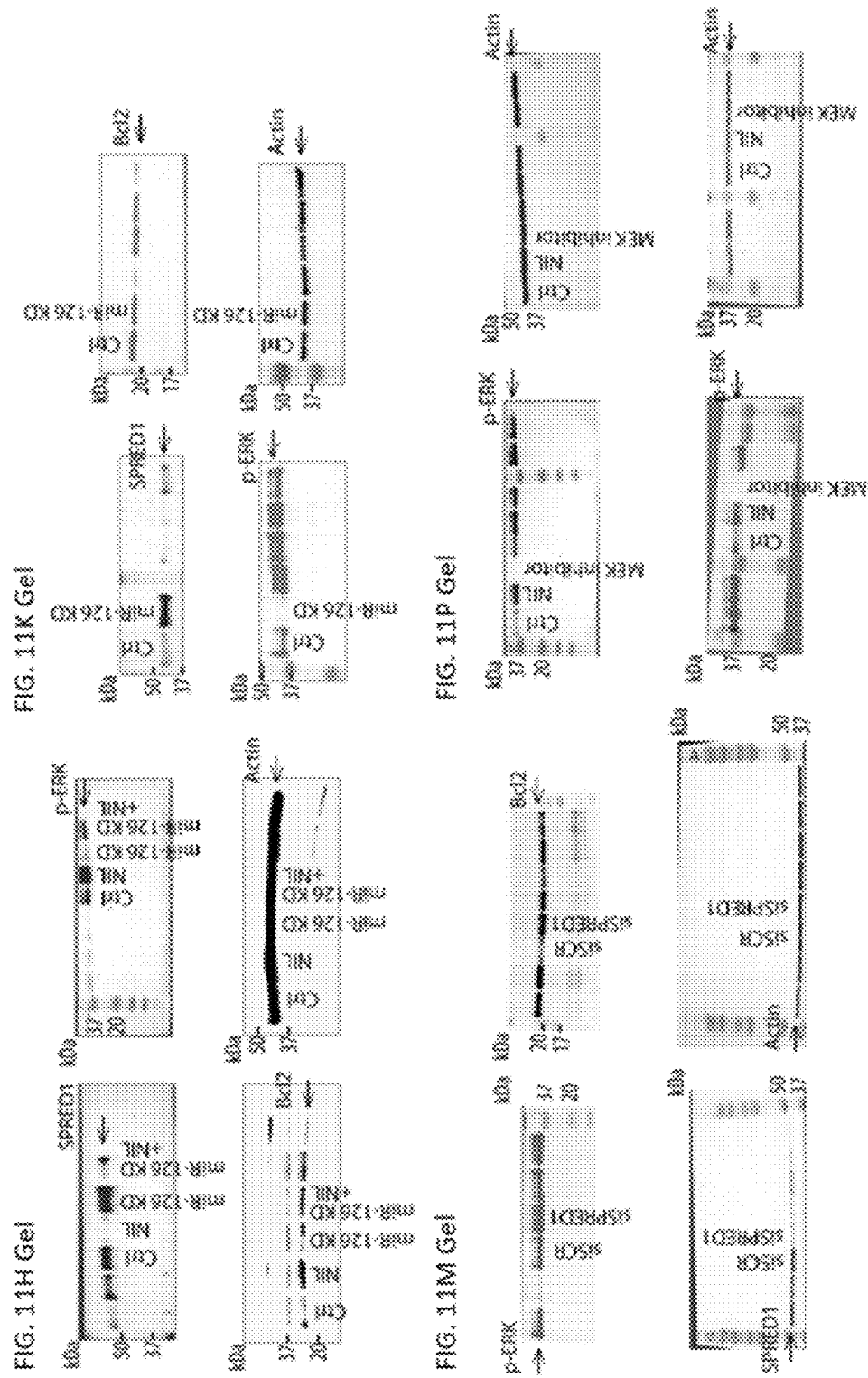
Figure 17:
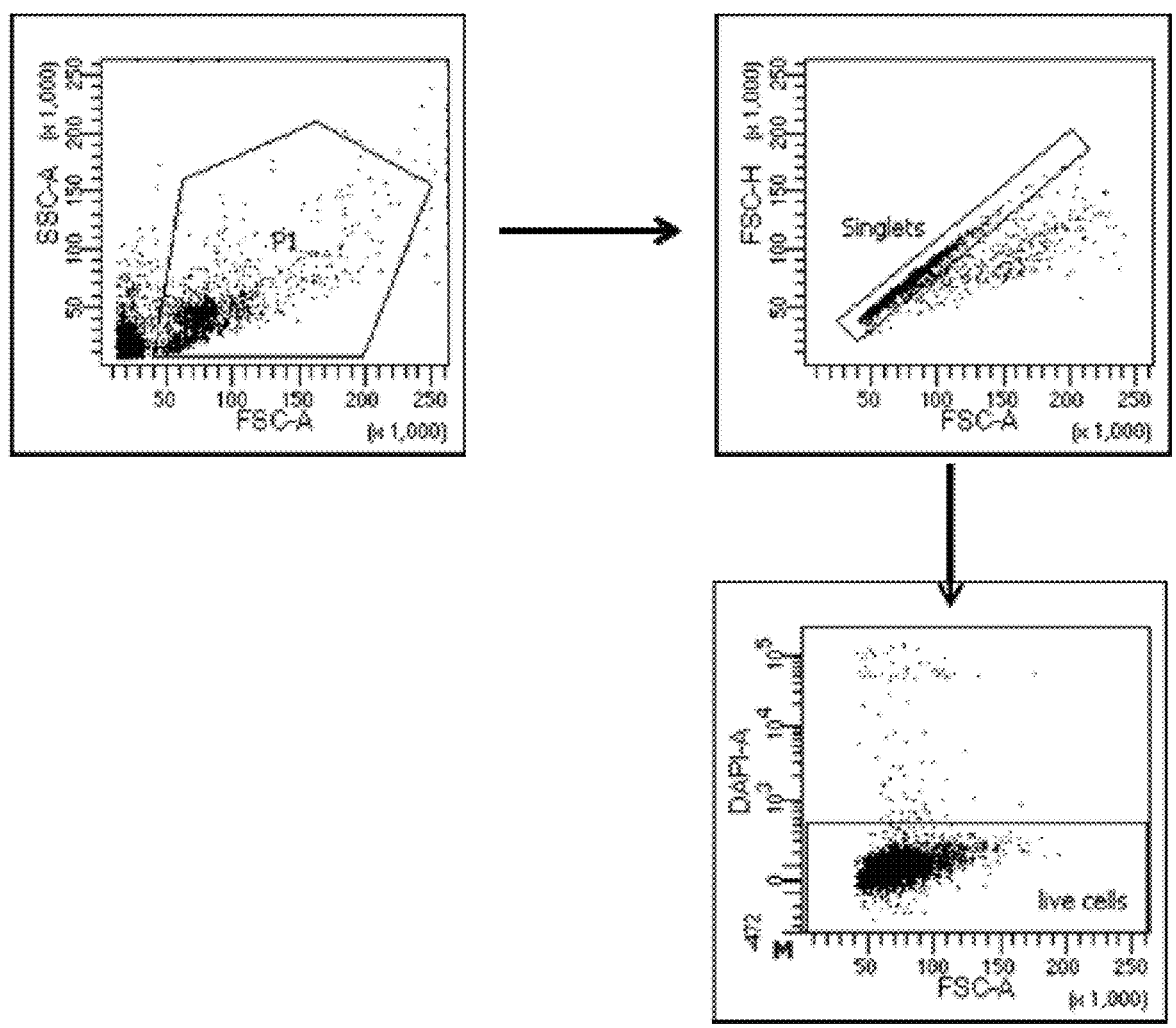
FIG. 17. The figure shows gating strategy for flow cytometry analysis. All samples were FSC-A and SSC-A gated, followed by FSC-A/FSC-H gating to select singlet cells. DAPI negative cells were then gated for subsequent relevant gating, shown in the other figures.

Whereas CML cells harbored lower levels of mature miR-126 than their normal counterparts, we noted that BCR-ABL-positive cells had higher levels of primary (pri-) and precursor (pre-) miR-126 than their normal counterparts (FIG. 3A and FIG. 3B). This result led us to hypothesize that BCR-ABL might interfere with miR-126 biogenesis.

miRNA nucleus-to-cytoplasm shuttling and maturation are mediated by a protein complex comprising the GTP-binding nuclear protein RAN (RAS-related nuclear protein, a member of the RAS superfamily), Exp-5 and RCC1[16]. After activation via tyrosine phosphorylation, SPRED1 acts as a negative regulator of RAS superfamily proteins[17]. We therefore postulated that the BCR-ABL tyrosine kinase can phosphorylate SPRED1, allowing SPRED1 to bind RAN, and that this binding interferes with RAN/Exp-5/RCC1-mediated shuttling and maturation of miR-126. Using immunofluorescence (IF), immunoprecipitation (IP) and in vitro kinase activity assays to analyze BCR-ABL+ primary CD34+ and/or K562 cells, we showed that SPRED1 co-localized with BCR-ABL to the cytoplasm (FIG. 3C), was directly phosphorylated by BCR-ABL (FIG. 3D and FIG. 14), and formed an intra/perinuclear protein complex with RAN (FIG. 3E, FIG. 3F and FIG. 14). NIL treatment reversed these effects, resulting in SPRED1 de-phosphorylation (FIG. 3D, FIG. 14), decreased binding and co-localization of SPRED1 with RAN (FIG. 3F), increased formation of RAN/Exp-5/RCC1 complex (FIGS. 3G-3H, FIG. 14, FIG. 15), decreased pri- and pre-miR-126 levels, and increased mature miR-126 levels (FIG. 3I). Cell washing to remove NIL restored the binding of SPRED1 with RAN, decreased the binding of RAN with Exp-5/RCC1 (FIG. 3j, FIG. 15), increased pri-miR-126 levels (FIG. 3k) and reduced mature miR-126 levels (FIG. 3K and FIG. 3L). Northern blotting confirmed that the ratio of pri- and pre-miR-126 to mature miR-126 levels decreased upon exposure of BCR-ABL+ cells to NIL and increased upon wash-off of NIL (FIG. 3M, FIG. 16). SPRED1 knock-down (KD) by siRNA in BCR-ABL+primary CD34+ and K562 cells enhanced formation of the RAN/Exp-5/RCC1 complex (FIG. 3N, FIG. 15) and resulted in decreased pri- and pre-miR-126 levels (FIG. 3O) and increased mature miR-126 levels (FIG. 3O and FIG. 3P). Conversely, RAN KD by siRNA resulted in increased pri- and pre-miR-126 levels and reduced mature miR-126 levels (FIGS. 3Q-3S, FIG. 16). These results indicate that, in CML cells, BCR-ABL-induced SPRED1 phosphorylation interferes with RAN/Exp-5/RCC1-mediated miR-126 biogenesis and lowers mature miR-126 levels. Given that miR-126 suppresses SPRED1 expression, this BCR-ABL-mediated reduction in miR-126 biogenesis may cause a further increase in SPRED1 levels, such that higher SPRED1 levels result in lower mature miR-126 levels (FIG. 7J) and that the endogenous levels of miR-126 are therefore controlled by its own target (SPRED1) in BCR-ABL+ cells.

Of note, BCR-ABL-dependent deregulation of miRNAs is unlikely to be restricted to down-regulation of miR-126. In fact, comparing LSK cells from non-induced versus induced CML mice, we found that a total of 33 miRNAs (including miR-126-3p and miR-126-5p, miR-125a-5p, 125b-5p, 181a-3p, 181b-5p, and 29b-3p) to be significantly decreased, and 75 miRNAs (including miR-142-3p and miR-142-5p, 146b-3p, 146b-5p, and 486-5p) to be significantly increased (GSE107431, FIG. 7K), suggesting distinct BCR-ABL-dependent mechanisms causing miRNA deregulation in CML.

Endothelial Cells in the BM Niche Supply miR-126 to CML LSCs.

Figure 4A:
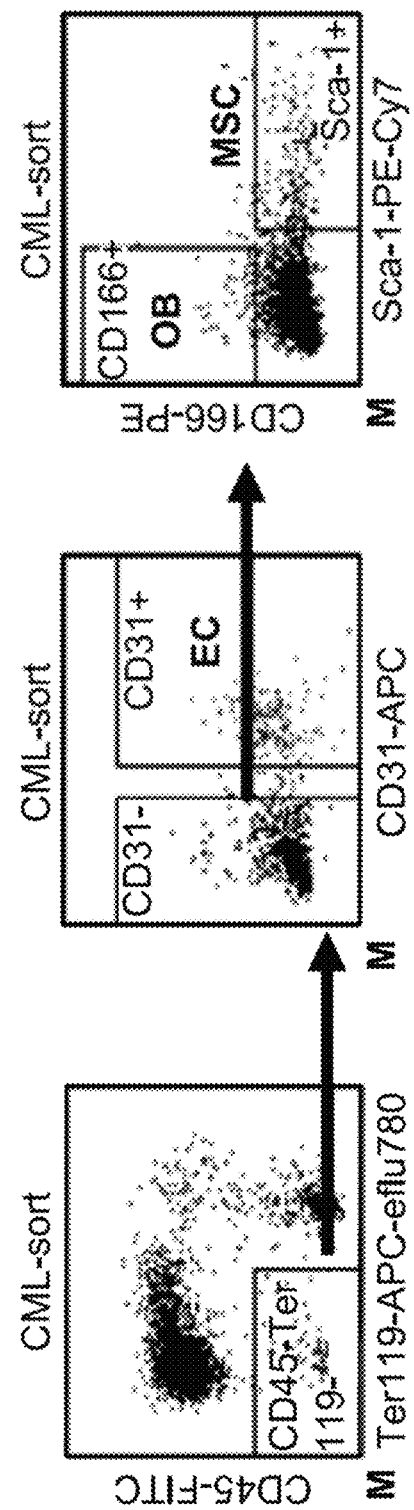
FIGS. 4A-4S. The figure shows endothelial cells in the niche supply miR-126 to normal and CML LT-HSCs.

Given that miR-126 is necessary for the quiescence of LSCs and that BCR-ABL activation causes down-regulation of mature miR-126 levels in LSCs, we reasoned that an exogenous source of miR-126 might be needed for BCR-ABL+LSCs to maintain quiescence and prevent clonal exhaustion. BCR-ABL+ LT-HSCs mainly reside in the BM niche, along with multiple regulatory non-hematopoietic cell types. miR-126 is one of the most abundantly expressed miRNAs in ECs and is involved in angiogenesis[18,19]. Consistent with this, we found that, in both normal and CML mice, BM ECs (CD45−Ter119-CD31+) expressed the highest levels of miR-126, as compared with LT-HSCs and other BM stromal cell populations, including osteoblasts (OB; CD45−Ter119-CD31−CD166+Sca-1-)[20] and mesenchymal stem cells (MSC; CD45−Ter119-CD31−CD166−Sca-1+)[21] (FIGS. 4A, 4B). We therefore hypothesized that ECs supply miR-126 to CML LT-HSCs.

Figure 4C:
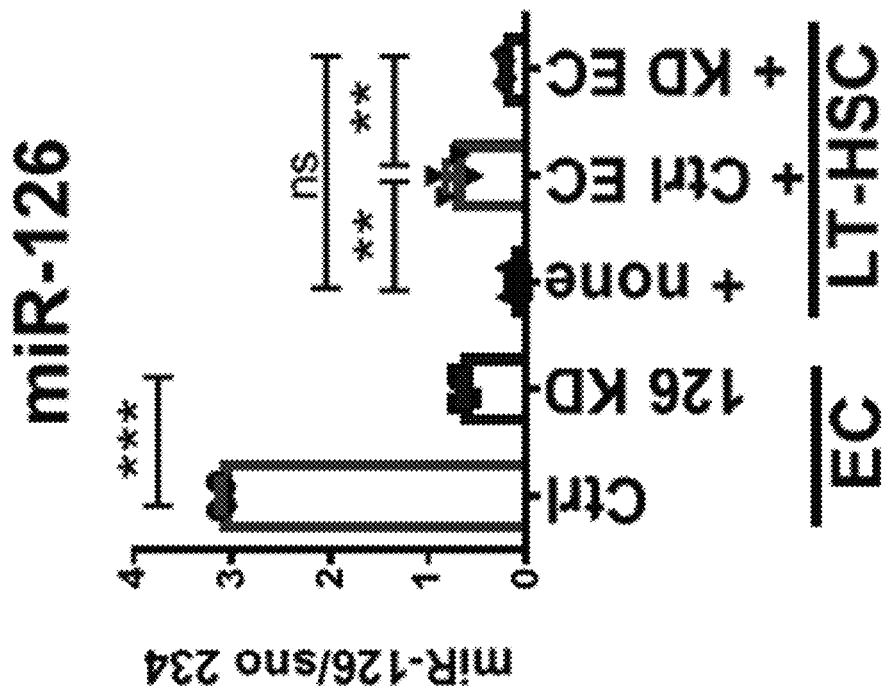
FIG. 4C shows miR-126 expression in ECs from the BM of CML mice that were transduced with miR-126 KD (126 KD) or control (Ctrl) lentiviruses, or in CML LT-HSCs that were cultured alone (none) or co-cultured with the ECs that had been transduced with control (Ctrl EC) or miR-126 KD (KD EC) lentiviruses (n=4 biologically independent samples).
Figure 4B:
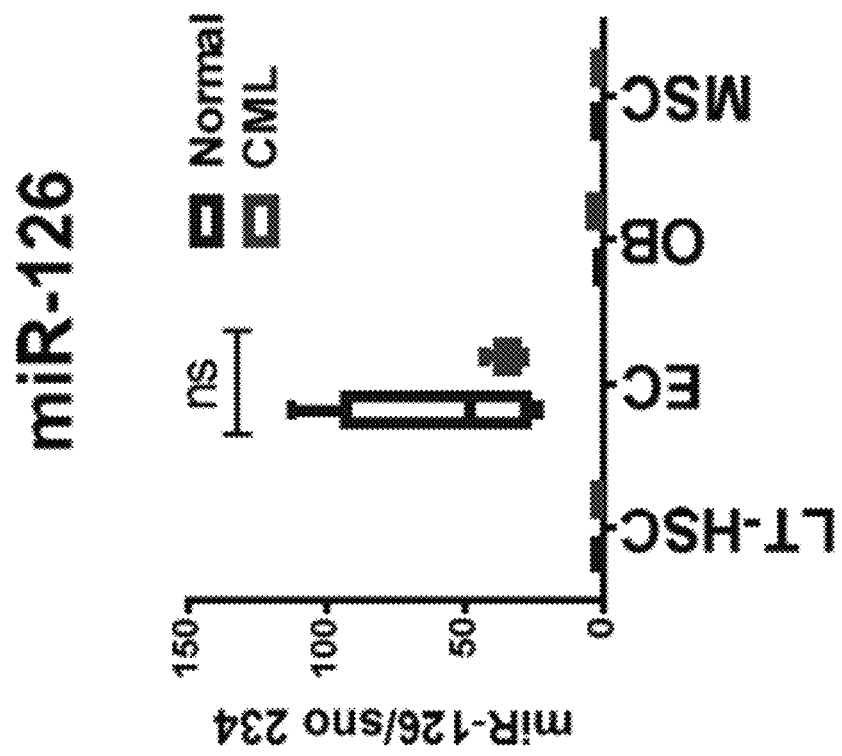
FIG. 4B shows miR-126 expression, as assessed by QPCR in LT-HSCs, ECs, OBs and MSCs from normal and CML mice (n=5 biologically independent samples). For each group of two data points, the data point on the left represents data for normal cells and the data point on the right represents data for CML cells.
Figure 4E:
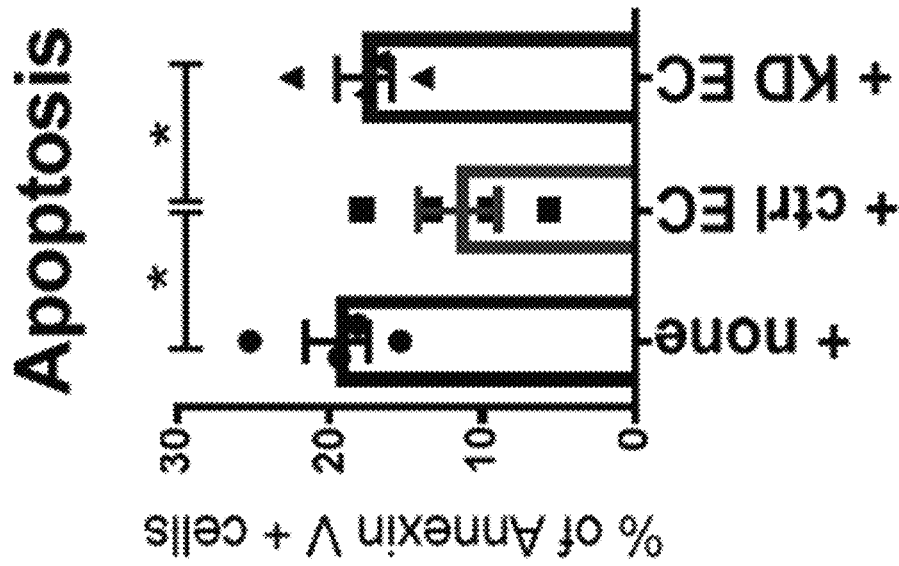
FIGS. 4D-4G show cell cycle analysis (n=4 biologically independent samples), wherein from top to bottom the legend represents each group of three data points from left to right (FIG. 4D), apoptosis (n=4) (FIG. 4E), cell growth (n=4) (FIG. 4F) and the percentage of Flt3-CD150+CD48– LSK cells (n=4) (FIG. 4G) in CML LT-HSCs cultured alone or with control or miR-126 KD ECs.
Figure 4D:
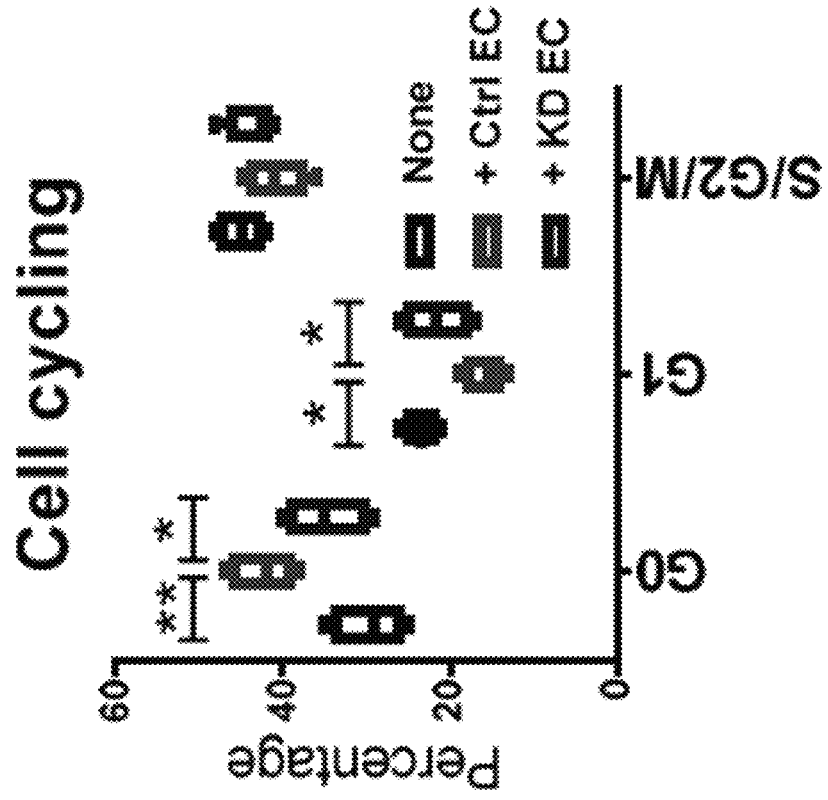
Figure 4F:
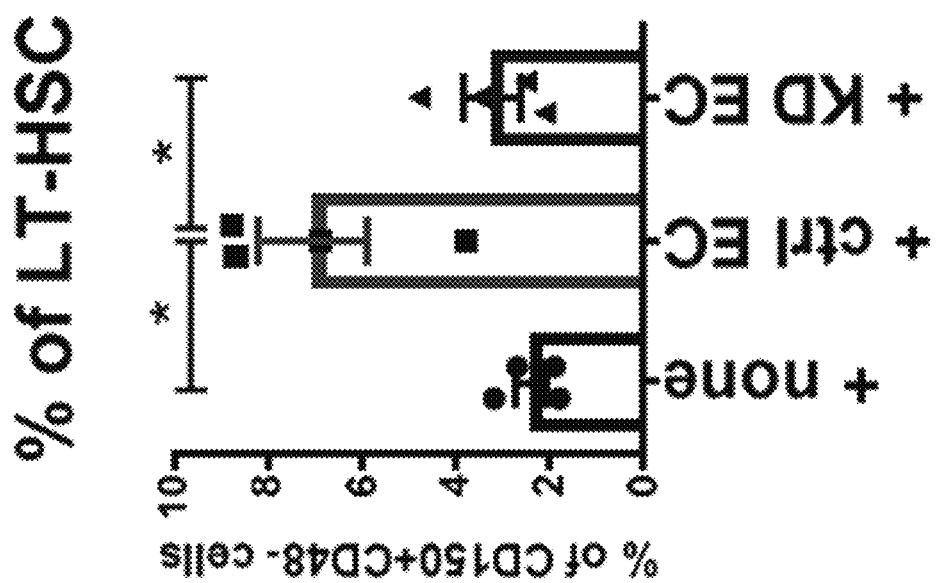
Figure 4G:
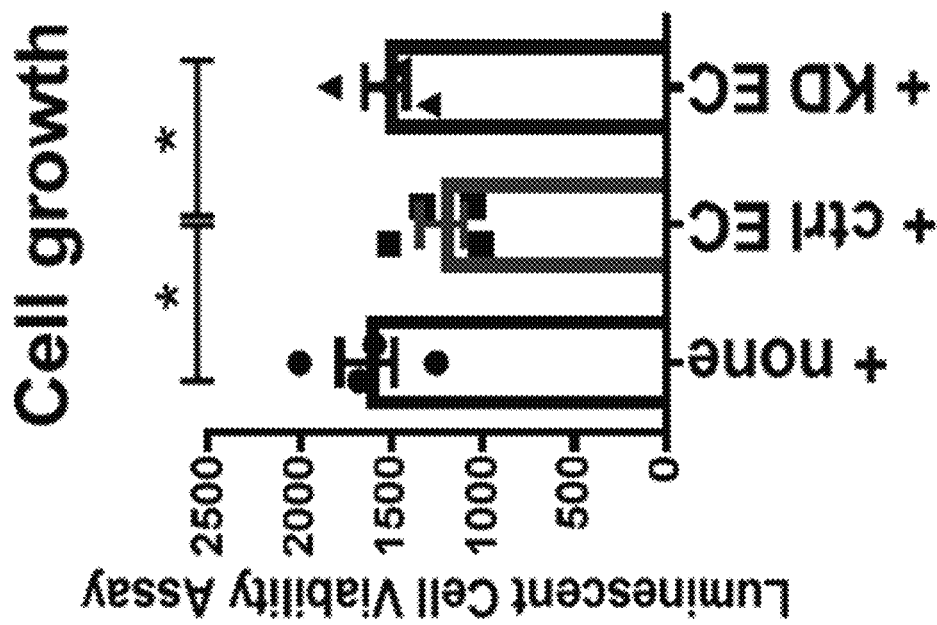
Figure 4I:
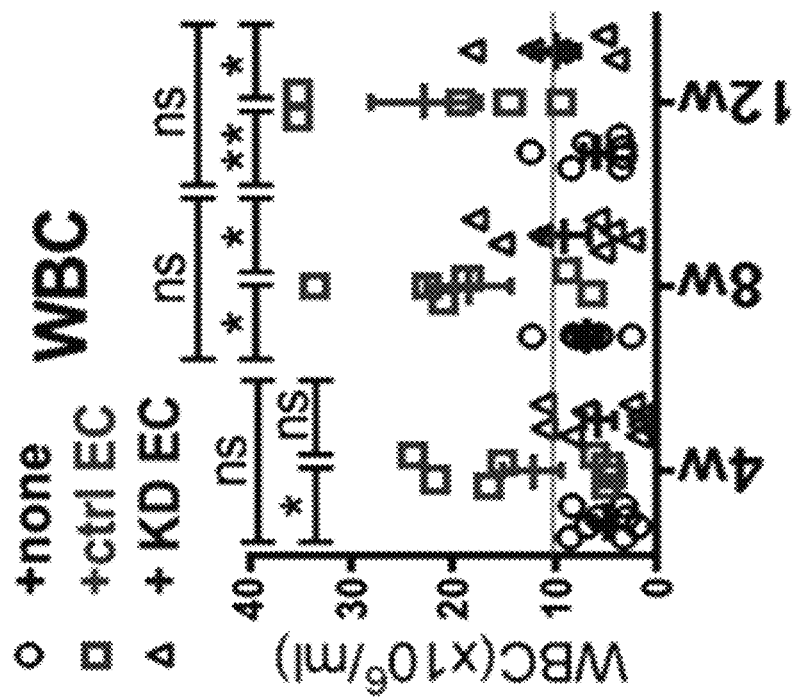
FIGS. 4I-4K show WBC counts (FIG. 4I) and CML donor cell engraftment in PB at the indicated times, wherein from top to bottom the legend represents each group of three data points from left to right (FIG. 4J) and survival (FIG. 4K) after recipient mice were transplanted with CML LT-HSCs that had been cultured alone (upper-most line at 100 days) or co-cultured with Ctrl EC (bottom line at 100 days) or KD EC (center line at 100 days) for 96 h (1,000 cells/mouse, n=8 in each group). Comparison between groups was performed by two-tailed, unpaired Student's t-test. The log-rank test was used to assess significant differences between survival curves.
Figure 4H:
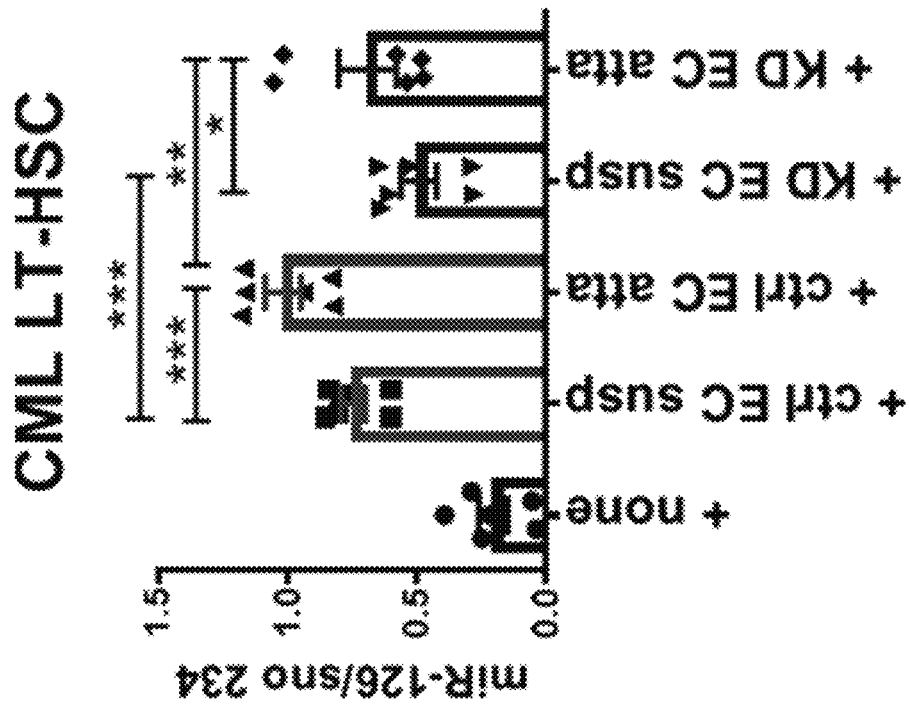
FIG. 4H shows miR-126 expression, as assessed by QPCR, in suspended (Susp) and EC-attached (Atta) sub-fractions of CML LT-HSCs (n=6 independent experiments).
Figure 4J:
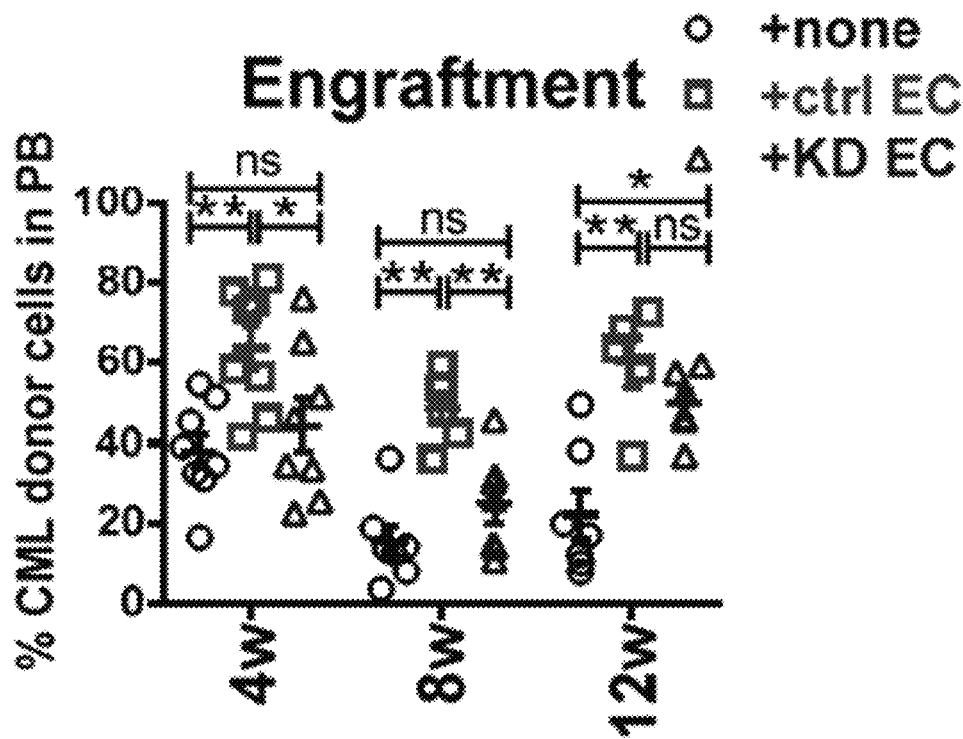
Figure 4K:
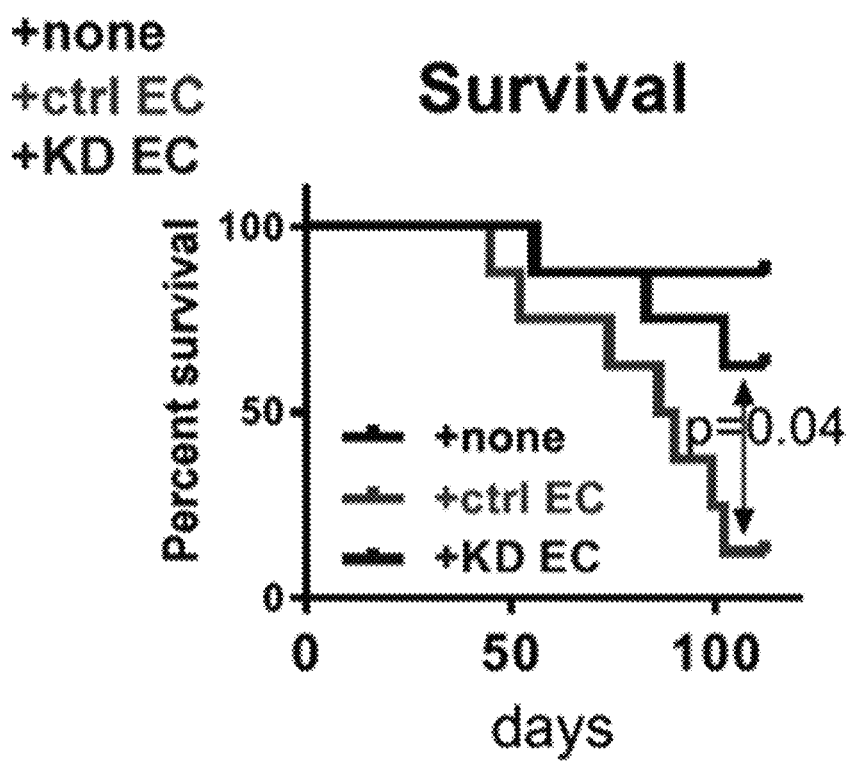
Figure 4L:
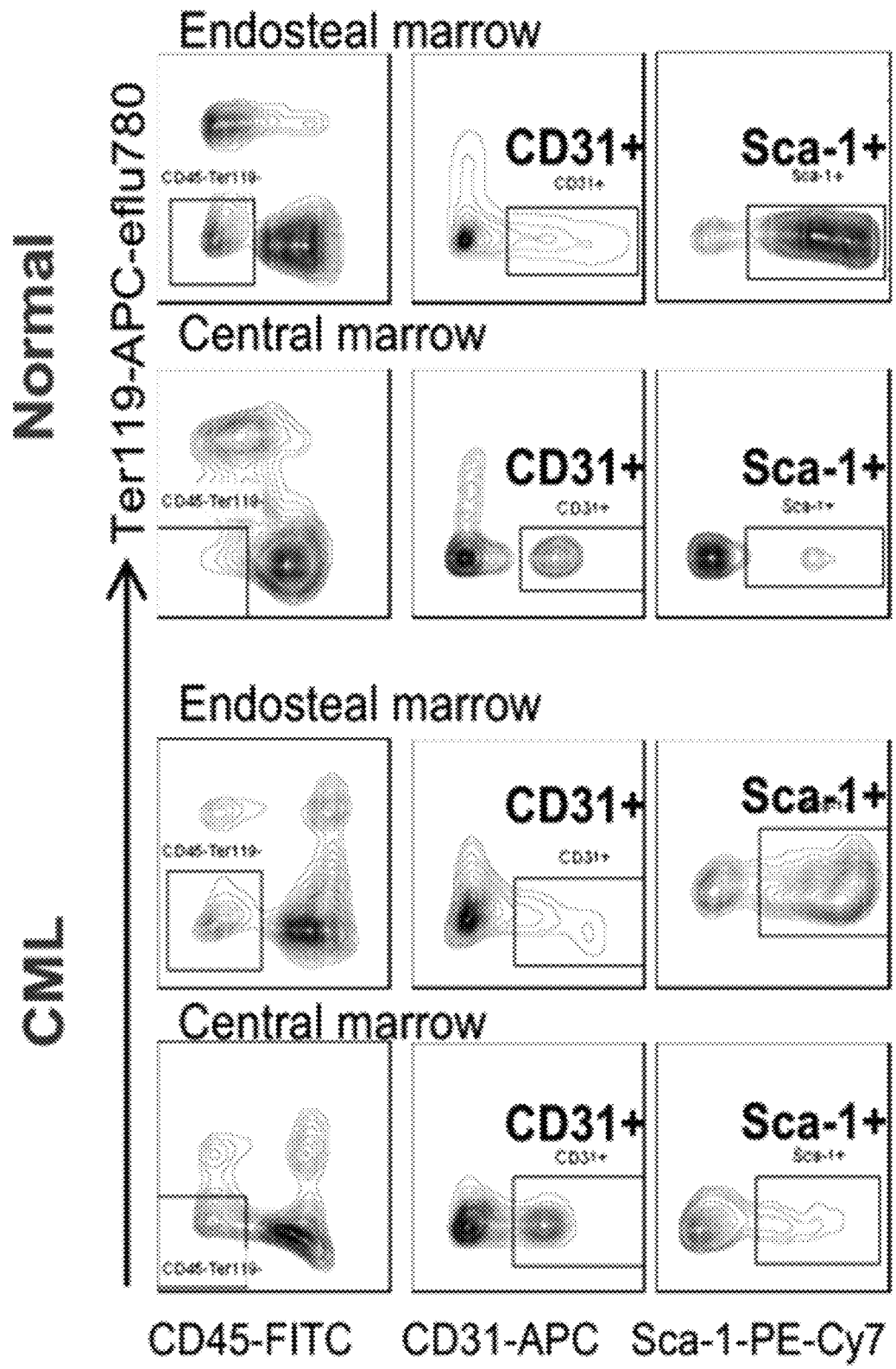
FIG. 4L and FIG. 4M show representative flow cytometry plots of EC staining (FIG. 4L) and frequency of Sca-1+ cells where the left two data points represent data from normal mice and the right two data points represent data from CML mice (FIG. 4M) in endosteal or central ECs from normal and CML mice (n=4 independent samples).
Figure 4N:
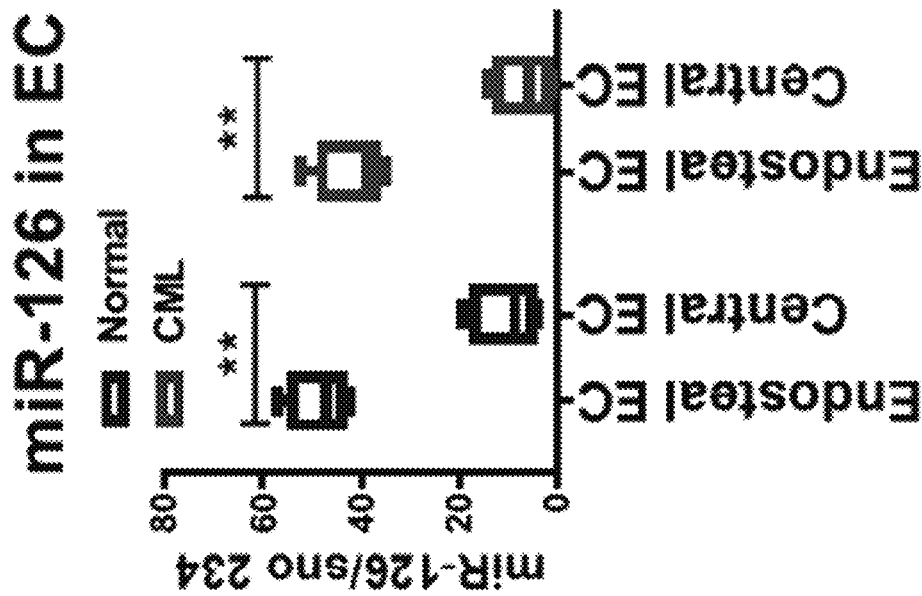
FIG. 4N and FIG. 4O show miR-126 expression, as assessed by QPCR, in endosteal or central ECs (n=4 independent samples) (FIG. 4N) and in Sca-1+ or Sca-1-ECs (n=4 independent samples) (FIG. 4O) from normal and CML mice, where the left two data points represent data from normal mice and the right two data points represent data from CML mice.
Figure 4M:
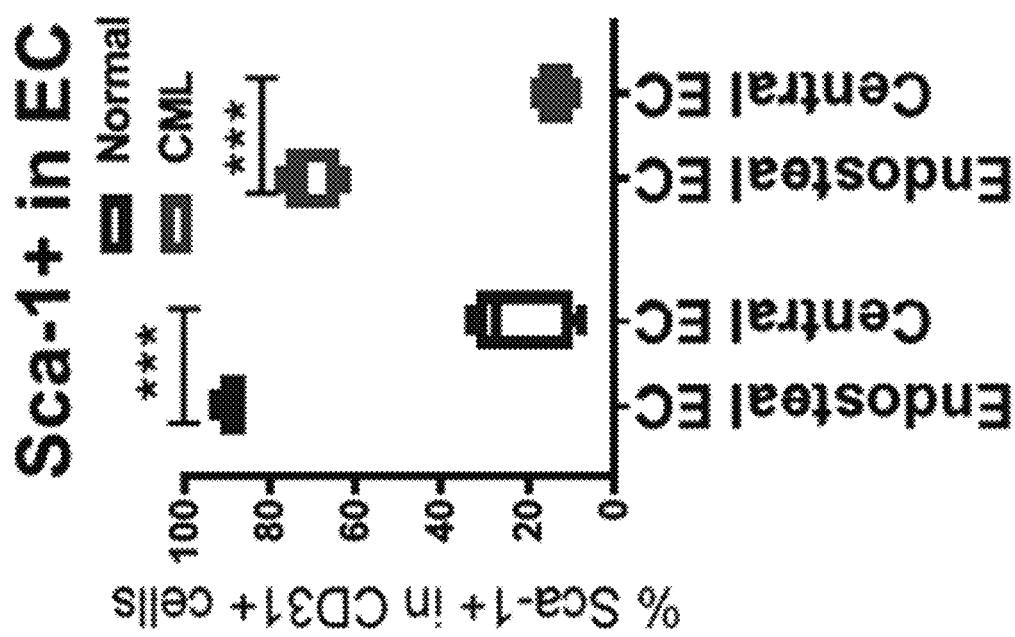

To test this hypothesis, we sorted ECs from endosteal and central marrow of SCLtTA/BCR-ABL mice and transduced these cells with lentiviral GFP-expressing miR-126 KD or control vectors (FIG. 4C). LT-HSCs from induced SCLtTA/BCR-ABL mice were then co-cultured with GFP+control or miR-126 KD ECs or were cultured without ECs for 96 h and analyzed for cell cycle and cell growth. After collecting the LT-HSCs that were in suspension, we separately collected the EC-attached LT-HSCs by flushing them gently from the culture flask with PBS buffer. EC-attached LT-HSCs were stained with CD45 to exclude EC contamination. CML cells co-cultured with control ECs showed higher miR-126 levels (FIG. 4C), decreased cell cycling (FIG. 4D), decreased apoptosis (FIG. 4E), decreased cell growth (FIG. 4F), and increased frequency of LT-HSCs (Flt3-CD150+CD48−LSK) (FIG. 4G) as compared to CML cells co-cultured with miR-126 KD ECs or cultured alone. The highest miR-126 levels were found in the LT-HSCs that were attached to control ECs (FIG. 4H). Next, we transplanted CML LT-HSCs (CD45.2, 1,000 cells/mouse) co-cultured for 96 h with control or miR-126 KD ECs, or cultured alone, into congenic CD45.1 recipient mice. CML LT-HSCs co-cultured with control ECs generated higher white blood cell (WBC) counts, higher CML engraftment levels and reduced survival ($p=0.04$) in recipient mice, as compared with CML LT-HSCs co-cultured with miR-126 KD ECs or cultured alone (FIGS. 4I-4K).

Figure 4P:
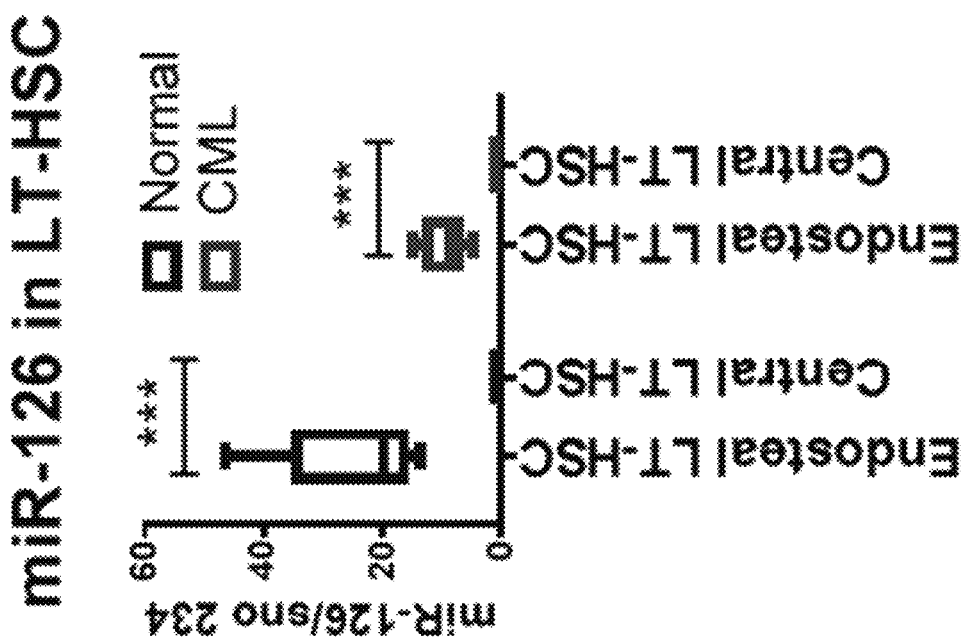
FIG. 4P shows miR-126 expression, as assessed by QPCR, in endosteal or central LT-HSCs from normal and CML mice (n=6 independent samples), where the left two data points represent data from normal mice and the right two data points represent data from CML mice.
Figure 4O:
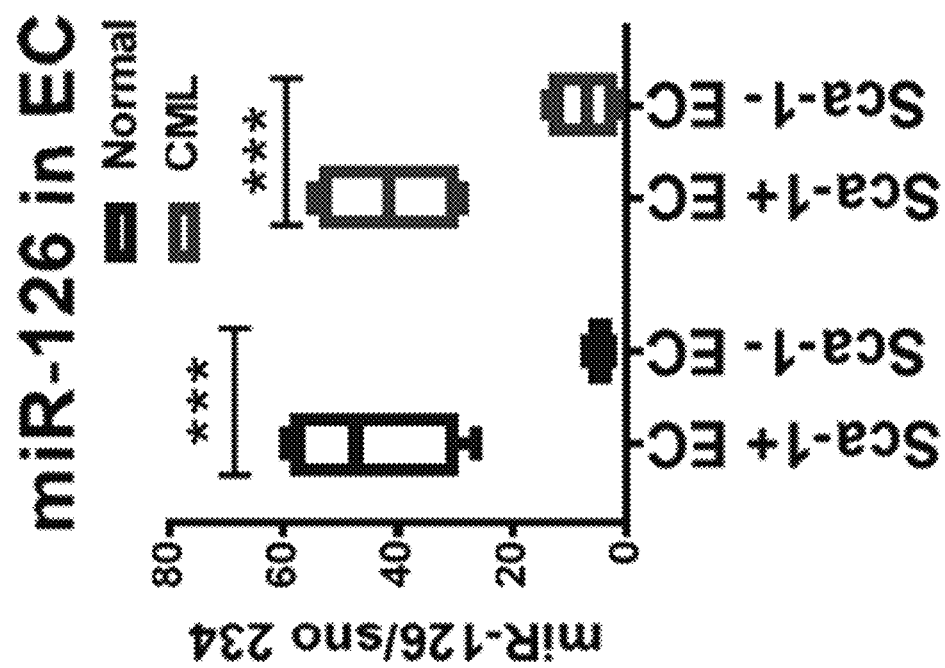
Figure 4R:
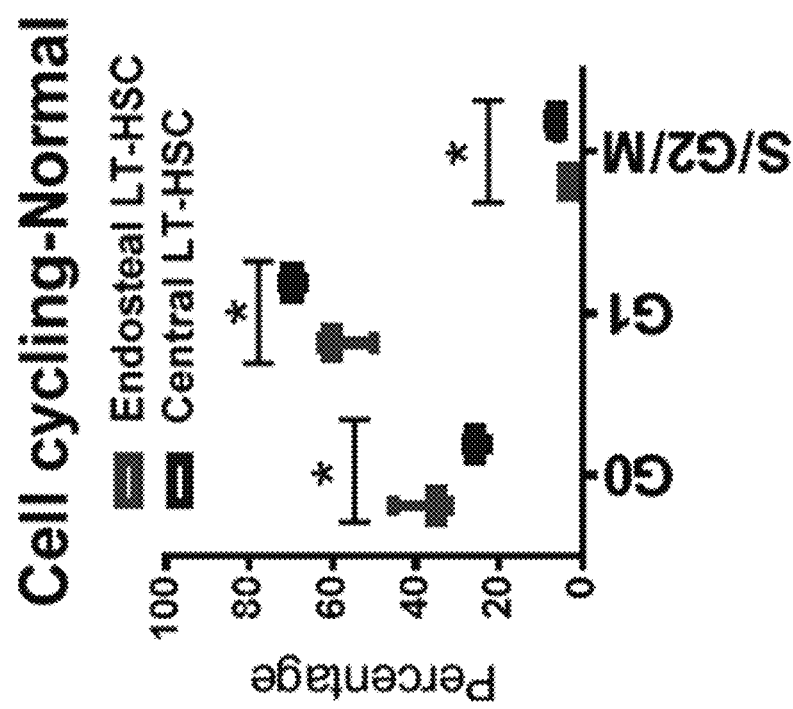
Figure 4Q:
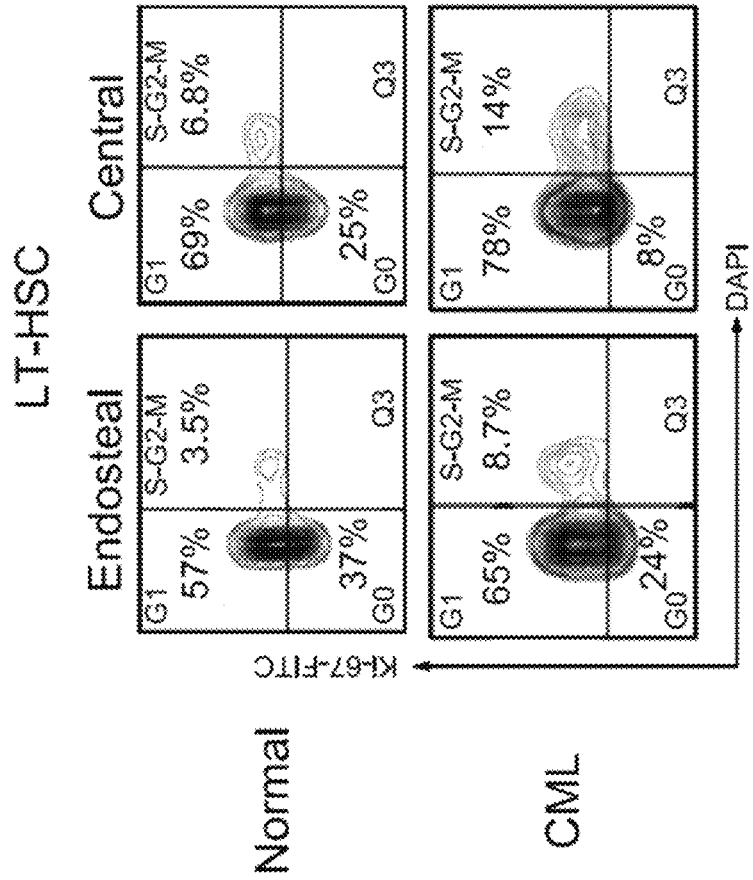
Figure 4S:
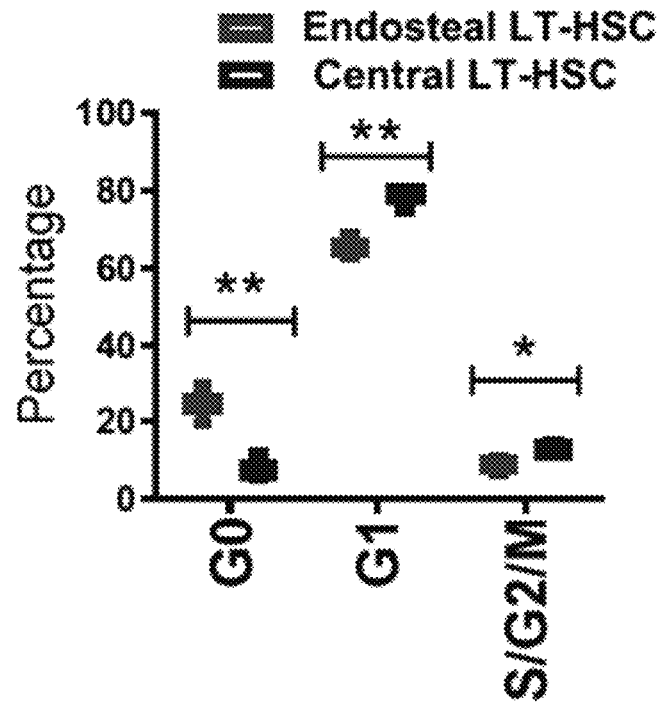

A recent report showed that in normal BM, Sca-1+ECs from arterial blood vessels are associated with quiescent HSCs, whereas Sca-1-ECs from permeable sinusoidal blood vessels are associated with proliferative HSCs[10]. We hypothesized that a similar association between EC immunophenotypic subpopulations and adjacent LT-HSC cell-cycle status may exist in CML mice and, given the role of miR-126 in cell quiescence, correlate with miR-126 levels. Upon sorting ECs and LT-HSCs from endosteal and central marrow of CML and normal mice, we found that >70% of endosteal ECs were Sca-1+ and >80% of central ECs were Sca-1−; furthermore, Sca-1+ECs expressed higher miR-126 levels than did Sca-1-ECs, and total endosteal ECs had higher miR-126 levels than did total central ECs (FIGS. 4L-4O). Accordingly, endosteal LT-HSCs had higher levels of miR-126 (FIG. 4P) and were more quiescent (FIGS. 4Q-4R) as compared to central LT-HSCs. These results demonstrate a direct association between miR-126 levels in ECs and the cell cycle status of adjacent LT-HSCs, and support the concept that there is active trafficking of miR-126 from ECs to LT-HSCs in vivo.

Figure 5A:
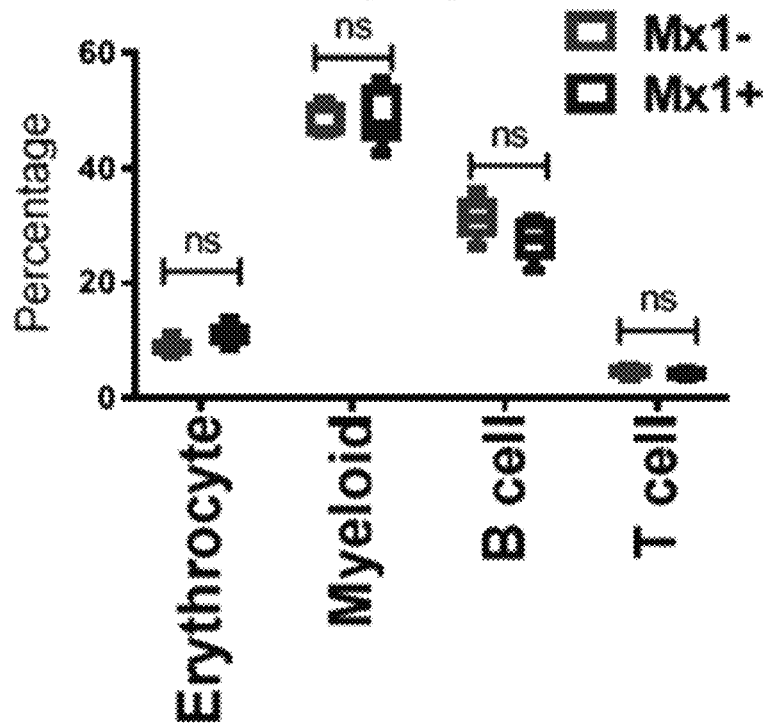
FIGS. 5A-5R. The figures show endothelial cells in the BM niche supply miR-126 to CIVIL LT-HSCs.
Figure 5B:
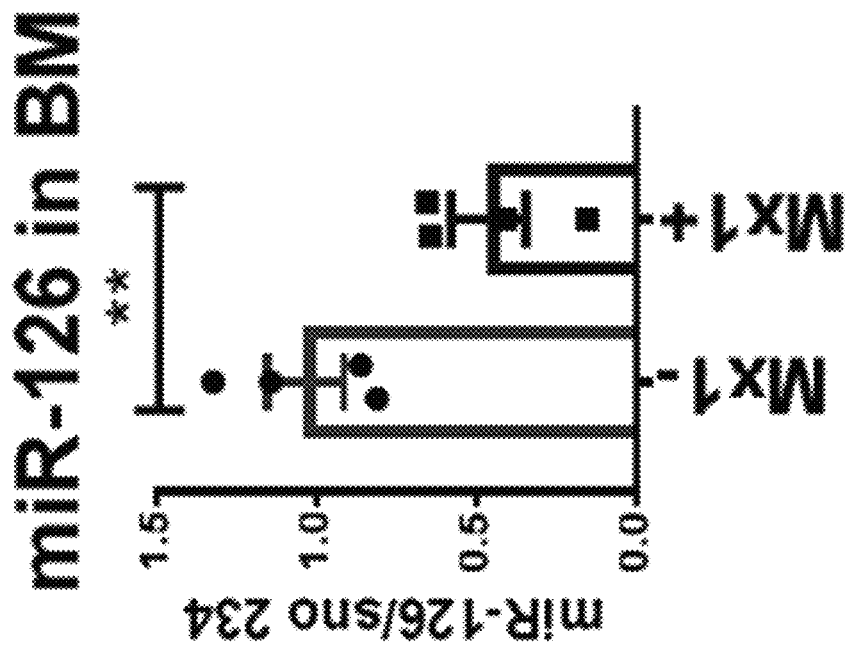
Figure 5C:
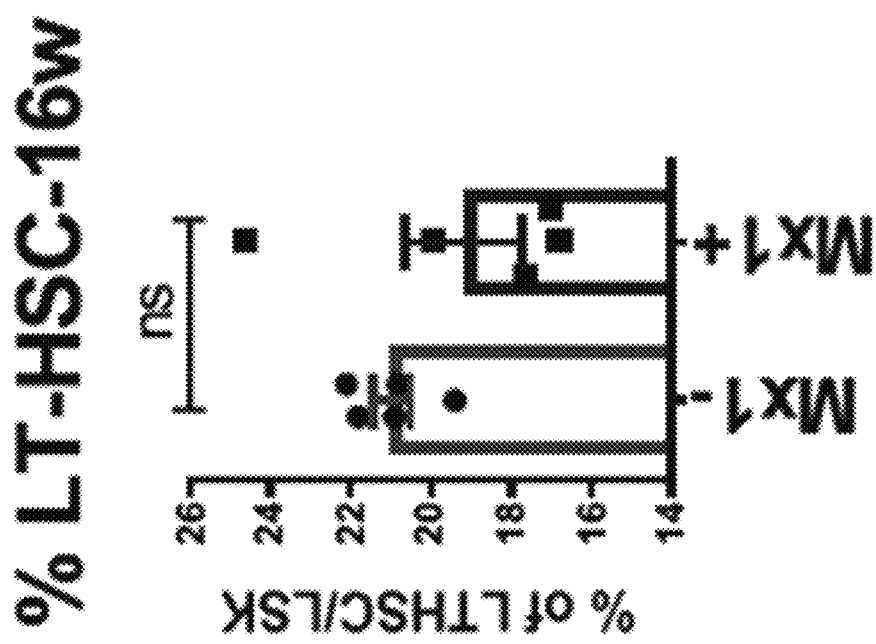
FIGS. 5C-5E show miR-126 expression in CIVIL BM cells (n=4 independent samples) (FIG. 5C), WBC counts where the legend from top to bottom represents each group of two data sets from left to right (FIG. 5D) and survival, where data for Mx1+ mice is represented by the line with higher percentage survival at day 60 and data for Mx1– mice is represented by the line with lower percentage survival at day 60 (FIG. 5E) of SCLtTA/BCR-ABL/miR-126flox/flox/Mx1+ or Mx1– mice subjected to tetracycline withdrawal and pIpC injection (n=9).
Figure 5D:
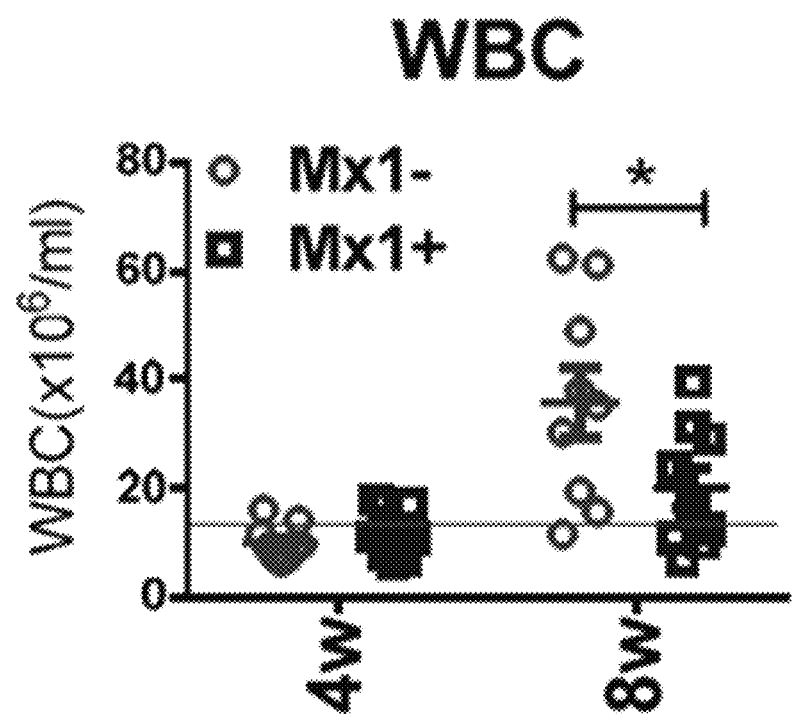
Figure 5E:
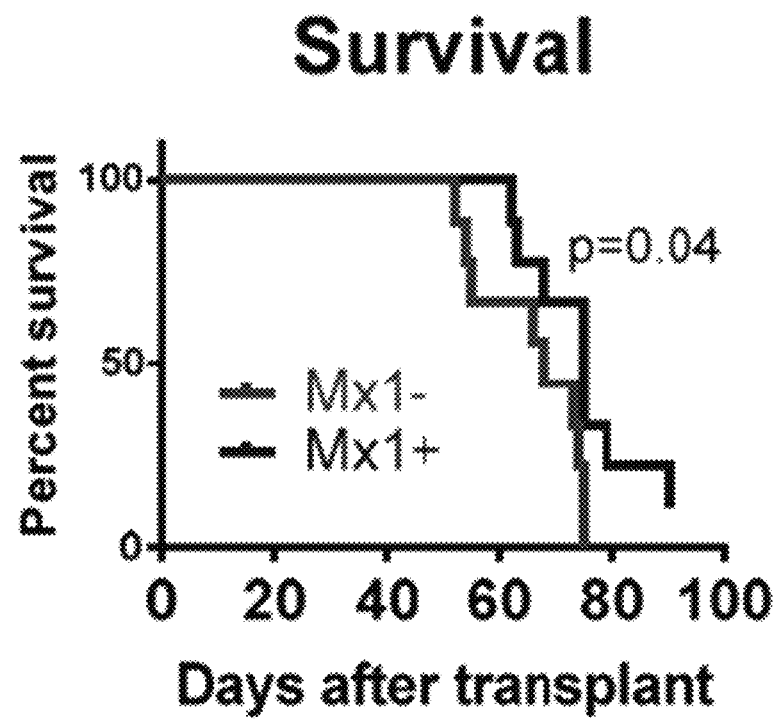
Figure 5F:
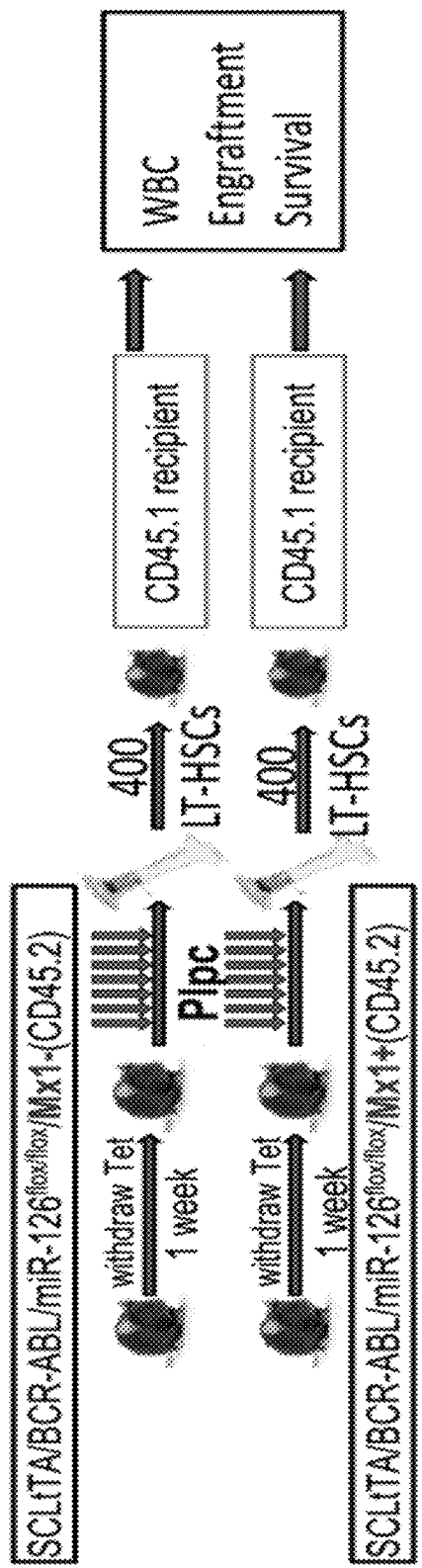
FIG. 5F shows CD45.2 CML LT-HSCs (400 cells/mouse) from BCR-ABL-induced and pIpC-injected SCL-tATA/BCR-ABL/miR-126flox/flox/Mx1+ or Mx1-mice were transplanted into CD45.1 congenic recipient mice (n=10 in each group).
Figure 5G:
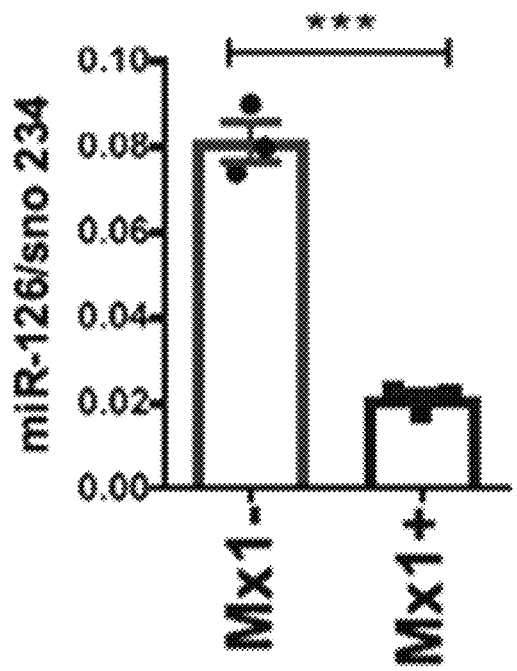
FIGS. 5G-5J show miR-126 expression, as assessed by QPCR, in donor CML LT-HSCs (n=3 independent samples) (FIG. 5G), WBC counts, where the legend from top to bottom represents each group of two data sets from left to right (FIG. 5H), CML cell engraftment in PB, where the legend from top to bottom represents each group of two data sets from left to right (FIG. 5I) and survival, where data for Mx1+ mice is represented by the line with higher percentage survival at day 150 and data for Mx1– mice is represented by the line with lower percentage survival at day 150 (FIG. 5J) of recipient mice from FIG. 5F (n=10 each).
Figure 5H:
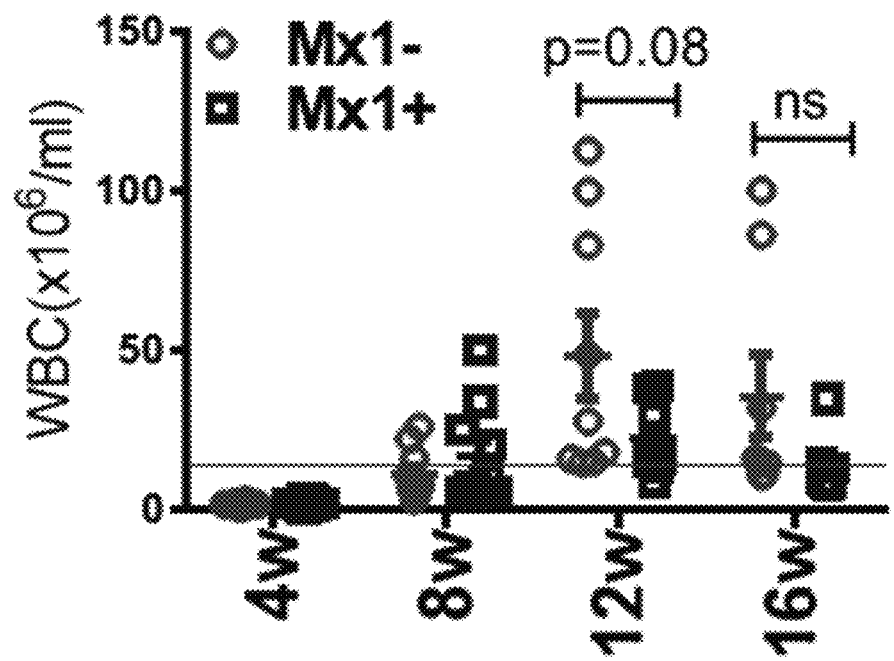
Figure 5I:
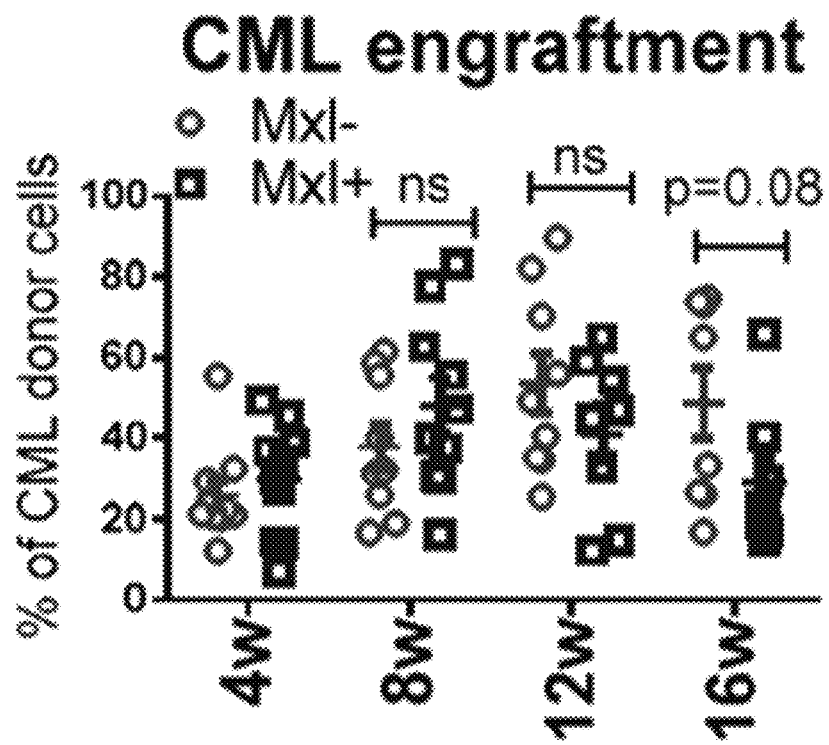
Figure 5J:
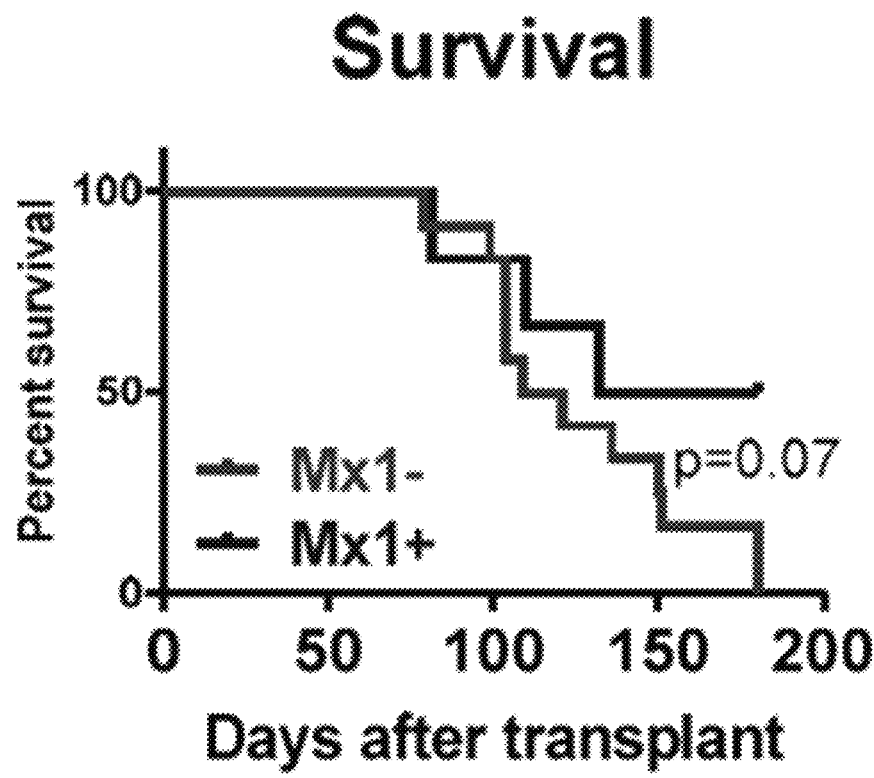

To test the functional role of EC-supplied miR-126 for leukemia growth, we generated CML or normal mice carrying miR-126 foxed alleles (flox) to enable conditional knock-out (c-KO) of miR-126 in LT-HSCs, in ECs, or in both. To generate these mice, we crossed miR-126$^{flox/flox}$ mice with Mx1-cre+ or Tie2-cre+ mice, followed by crossing with SCLtTA/BCR-ABL transgenic mice. These crosses led to the generation of the following strains: miR-126$^{flox/flox}$/Mx1-cre, SCLtTA/BCR-ABL/miR-126$^{flox/flox}$/Mx1-cre, miR-126$^{flox/flox}$/Tie2-cre and miR-126$^{flox/flox}$/Tie2-cre. After injecting miR-126$^{flox/flox}$/Mx1-cre+ (Mx1+) mice with polyinosine-polycytosine (pIpC) to delete miR-126 in normal HSCs, we observed no significant changes in WBC counts in PB (data not shown) or BM mononuclear cell subpopulations (including LT-HSCs) (FIG. 5A and FIG. 5B) after 16 weeks of follow-up, as compared to control (Mx1−) mice. Using SCLtTA/BCR-ABL/miR-126$^{flox/flox}$/Mx1+ mice, targeted miR-126 deletion in CML LSCs was obtained with tetracycline withdrawal to induce BCR-ABL expression and pIpC injection to induce cre expression. In these mice, miR-126 levels in BM cells were reduced by 60%, CML development was delayed ($p=0.047$) and survival was increased ($p=0.04$), as compared with similarly treated SCLtTA/BCR-ABL/miR-126$^{flox/flox}$/Mx1− controls (FIGS. 5C-5E). To confirm that these results were not attributable to "leaky" miR-126 down-regulation in the non-hematopoietic compartment, we sorted CD45.2 CML LT-HSCs from BCR-ABL-induced and pIpC-injected SCLtATA/BCR-ABL/miR-126$^{flox/flox}$/Mx1+ or Mx1− mice and transplanted these cells into CD45.1 congenic recipient mice (FIG. 5F). Recipients transplanted with Mx1+(miR-126 KO) CML LT-HSCs showed a trend for decreased CML development and increased survival as compared with recipient mice transplanted with Mx1− control CML LT-HSCs (FIGS. 5G-5J).

Figure 5K:
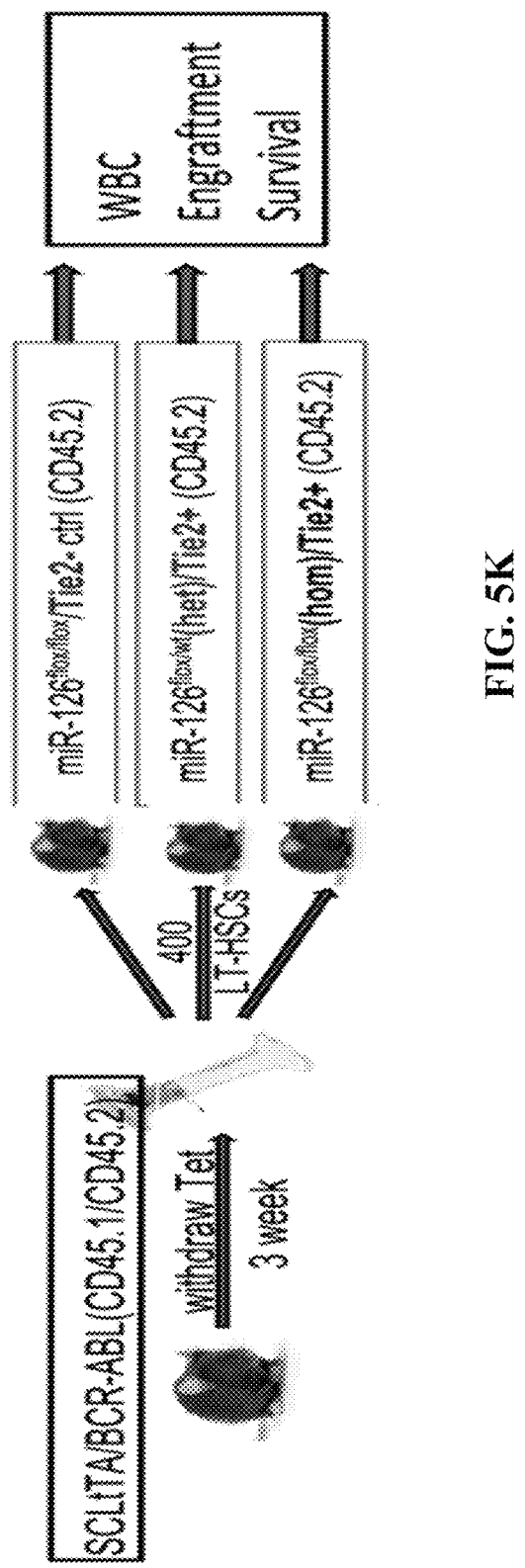
FIG. 5K shows CD45.1/CD45.2 CML LT-HSCs (400 cells/mouse) from induced CML mice were transplanted into CD45.2 congenic miR-126flox/flox/Tie2–
Figure 5L:
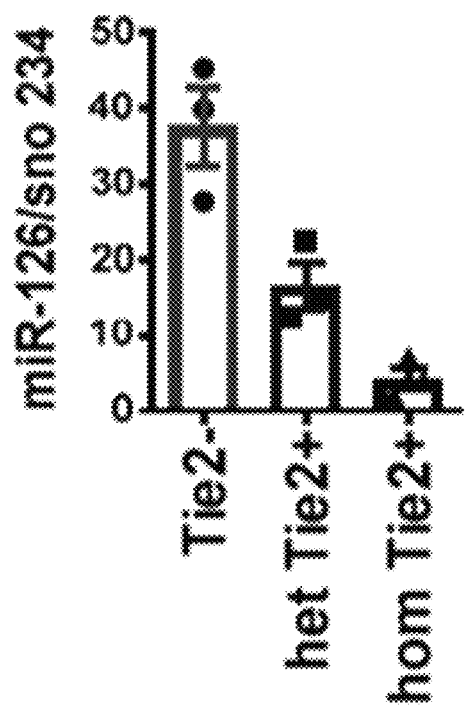
FIGS. 5L-5O show miR-126 expression, as assessed by QPCR, in ECs sorted from the recipient mice from FIG. 5K (n=3 independent samples) (FIG. 5L), WBC counts, wherein the legend from top to bottom represents each group of three data sets from left to right (FIG. 5M), CML cell engraftment in PB, wherein the legend from top to bottom represents each group of three data sets from left to right (FIG. 5N) and survival, where lines from top to bottom at 200 days represent data for hom Tie2+, het Tie2+ and Tie2− mice, respectively (FIG. 5O) of recipient mice from FIG. 5K.
Figure 5M:
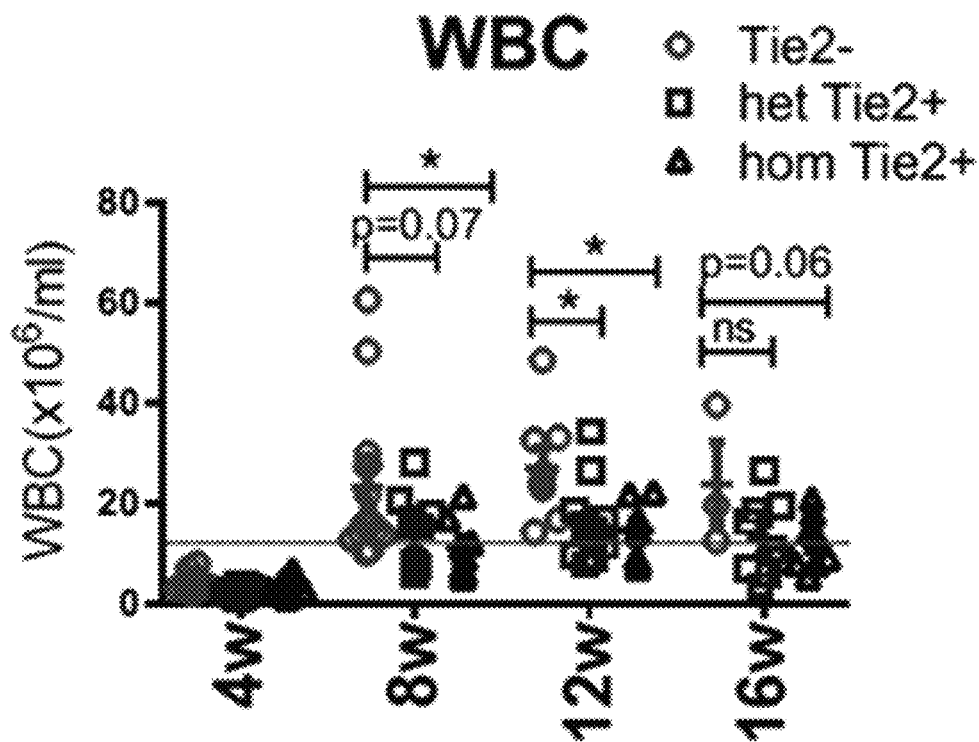
Figure 5N:
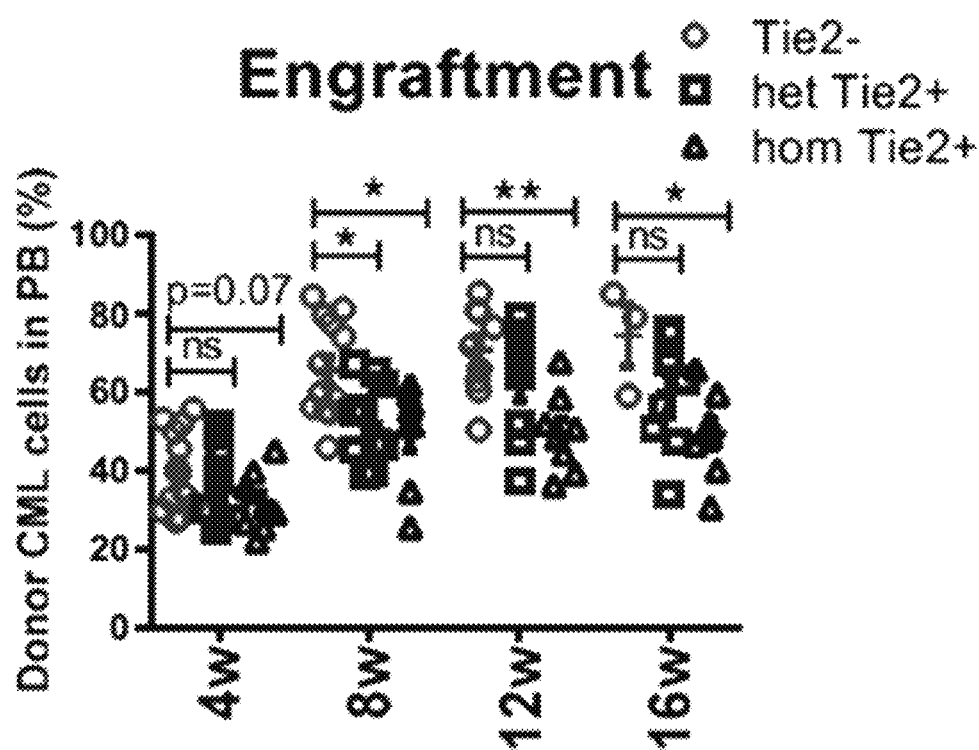
Figure 5O:
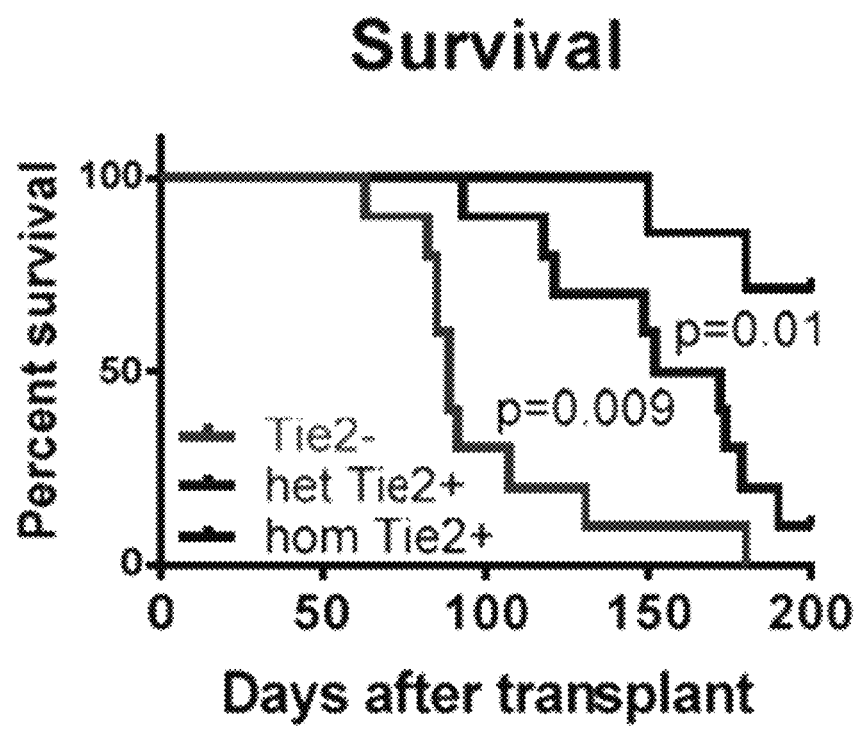

To assess the contribution of EC-derived miR-126 to leukemia growth, we sorted LT-HSCs from BCR-ABL-induced CD45.1/CD45.2 SCLtTA/BCR-ABL mice (used to track donor cells, and generated by crossing CD45.2 SCLtTA/BCR-ABL B6 mice with CD45.1 B6 mice) and transplanted these cells into CD45.2 congenic miR-126$^{flox/flox}$/Tie2-cre− (Tie2−) (WT miR-126 allele in ECs), miR-126$^{flox/wt(het)}$/Tie2-cre− (Tie2+) (heterozygous miR-126 KO allele in ECs), or miR-126$^{flox/flox(hom)}$/Tie2+ (homozygous miR-126 KO allele in ECs) recipient mice (FIG. 5K). Both het and hom Tie2+ recipient mice showed reduced CML cell engraftment, delayed CML development and significantly increased survival, as compared with Tie2− recipients at 16 weeks after transplantation (FIGS. 5L-5O; $p=0.009$ and $0.0003$ for survival of het Tie2+ and hom Tie2+ mice respectively); a miR-126 dosage effect was evident, as 70% of hom Tie2+ mice versus 10% of het Tie2+ mice were alive at 28 weeks (FIG. 5O). Of note, no significant differences in donor cell output from transplanted normal LT-HSCs (CD45.1) were observed in PB and BM from CD45.2 miR-126$^{flox/wt}$/Tie2+ recipients as compared with miR-126$^{flox/wt}$/Tie2− recipients after 16 weeks of follow-up (data not shown).

Figure 5P:
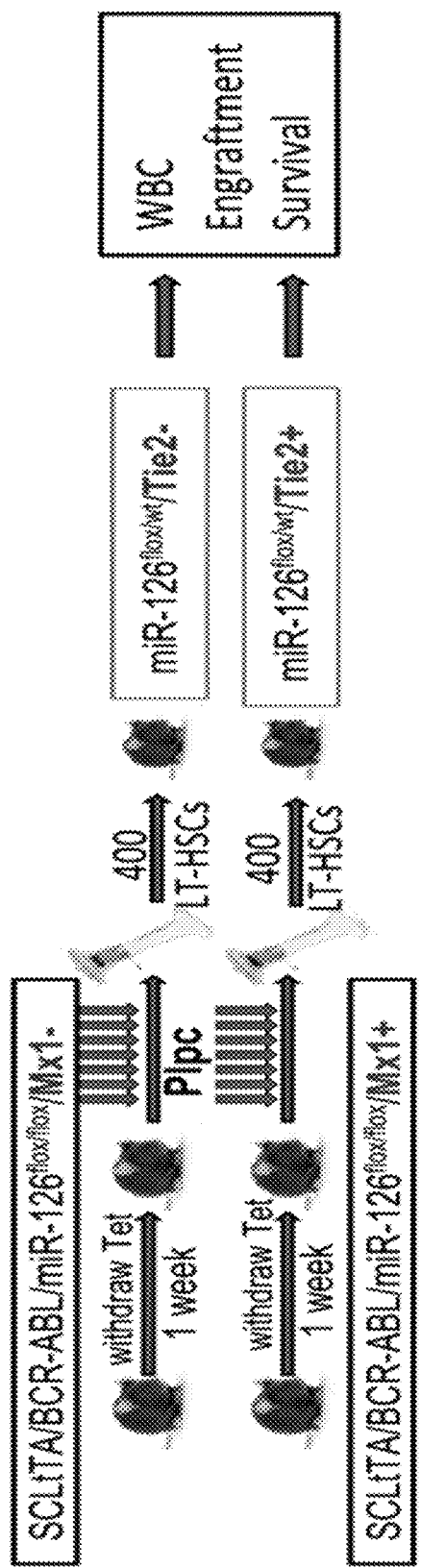
FIG. 5P shows CD45.2 CML LT-HSCs (400 cells/mouse) from BCR-ABL-induced and pIpC-injected SCLtTA/BCR-ABL/miR-126flox/flox/Mx1+ or Mx1− mice were transplanted into CD45.2 miR-126flox/wt/Tie2+ or Tie2− recipient mice (n=12 in each group), respectively.
Figure 5Q:
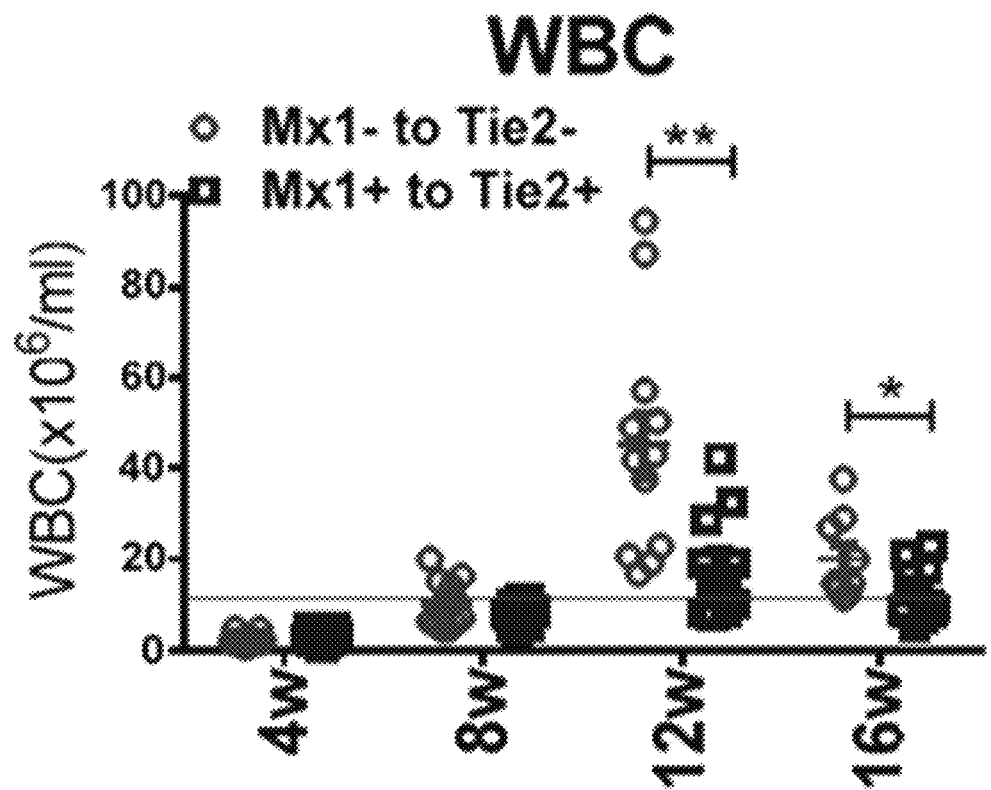
Figure 5R:
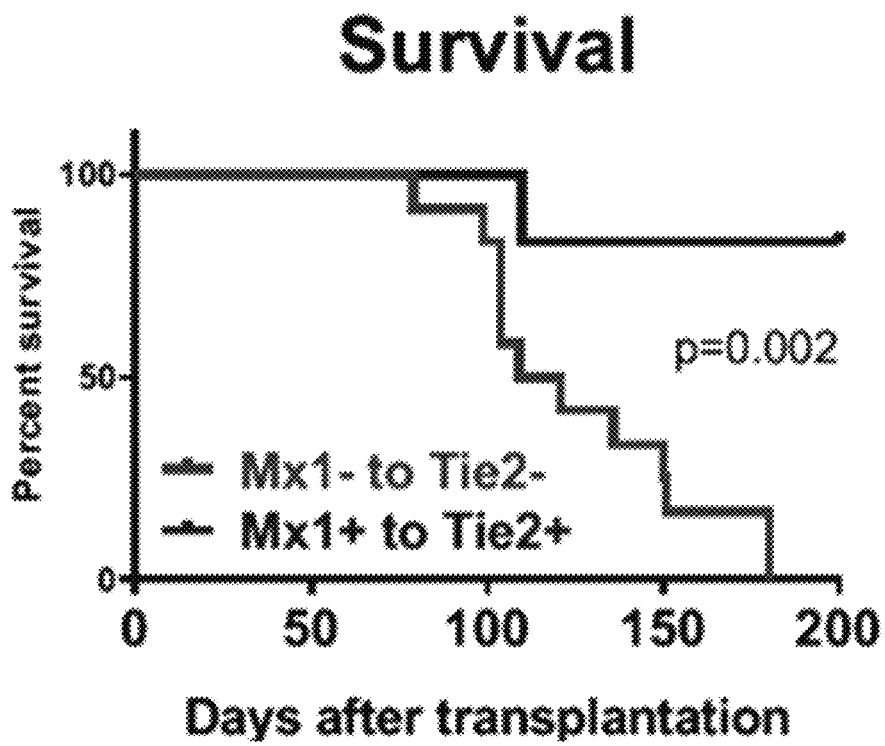

Next, to assess the functional impact of concurrent miR-126 KO in both LT-HSCs and ECs, CML LT-HSCs from BCR-ABL-induced and pIpC-injected SCLtATA/BCR-ABL/miR-126$^{flox/flox}$/Mx1+ or Mx1− mice were transplanted into miR-126$^{flox/wt}$/Tie2+ or Tie2− recipient mice, respectively (FIG. 5P). Tie2+ mice transplanted with Mx1+ CIVIL LT-HSCs showed a significantly delayed CML development ($p=0.007$) and prolonged survival ($p=0.002$) as compared with Tie2-mice transplanted with Mx1− CIVIL LT-HSCs (FIG. 5Q and FIG. 5R). At day 200, 83% of the mice with miR-126 KO in both ECs and LT-HSCs, but none of the controls with intact miR-126 in both ECs and LT-HSCs, were alive. Taken together, these results support a functional role of EC-derived miR-126 in sustaining leukemia growth in the CML LSC niche.

Figure 8A:
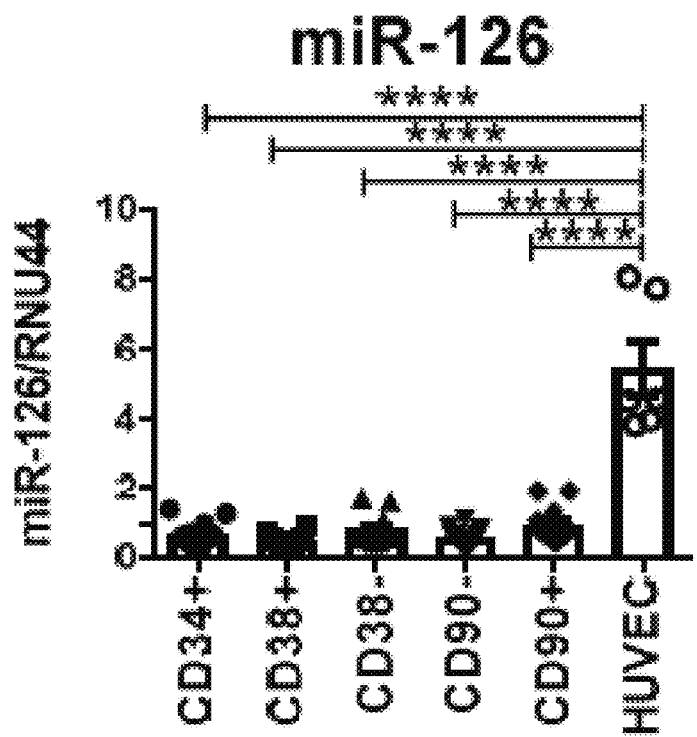
FIGS. 8A-8L. The figure shows endothelial cells in the niche supply miR-126 to CML LT-HSCs.
Figure 8B:
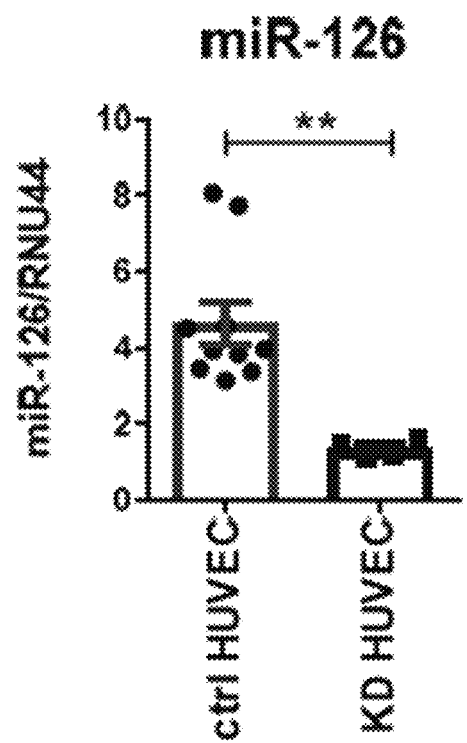
Figure 8C:
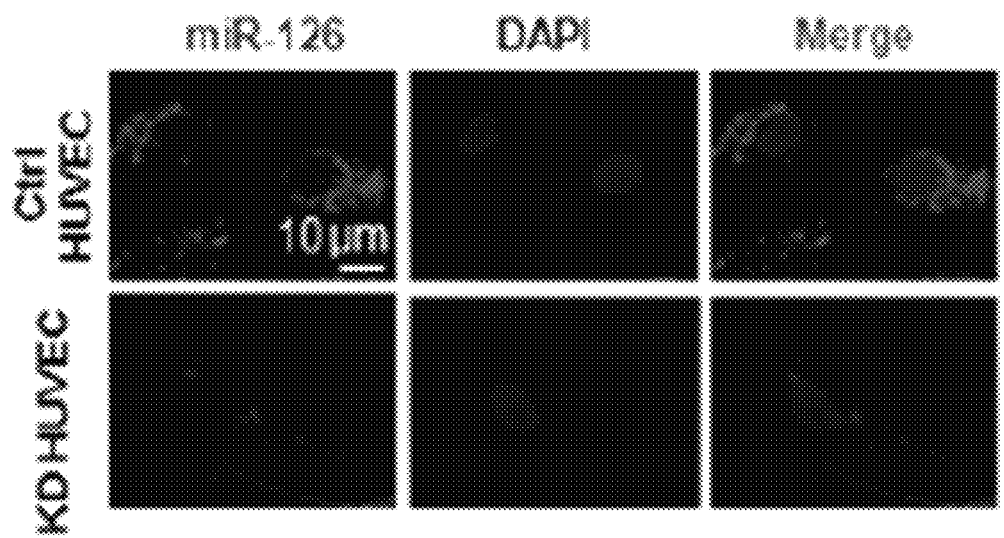
Figure 8D:
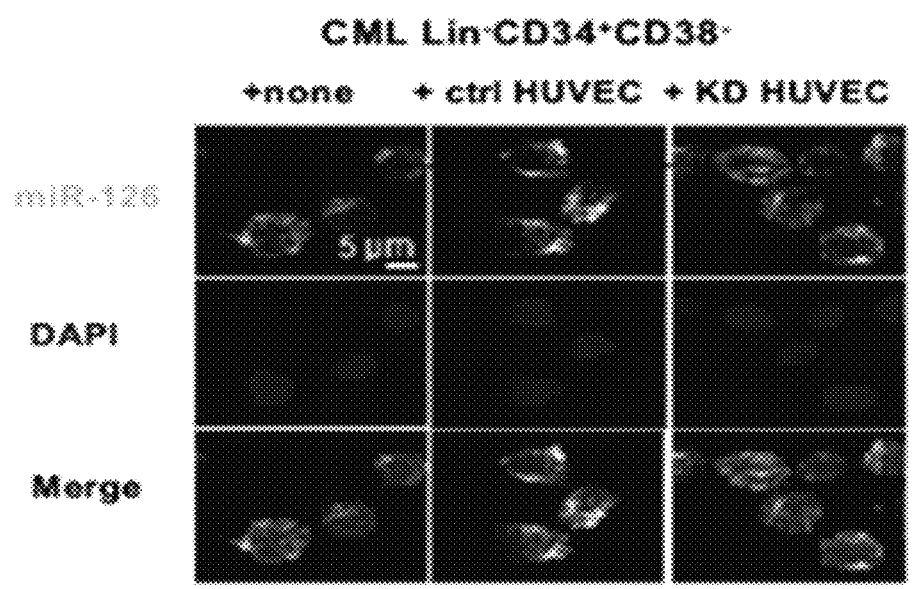
Figure 8E:
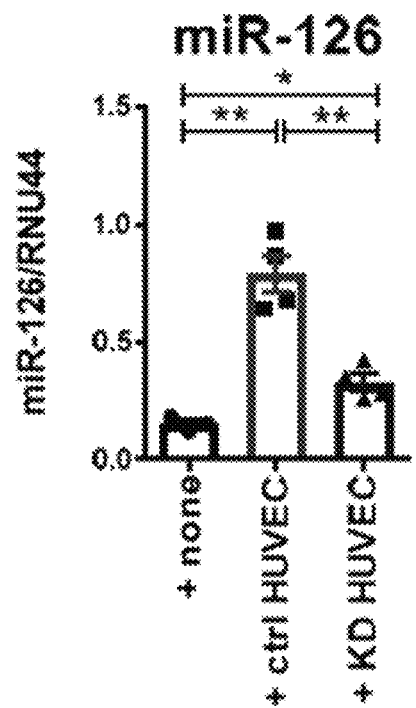
Figure 8F:
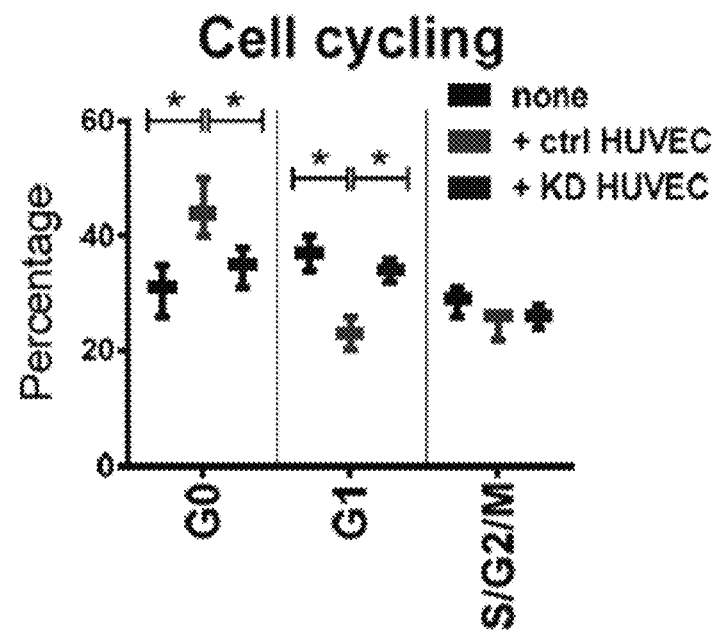
Figure 8G:
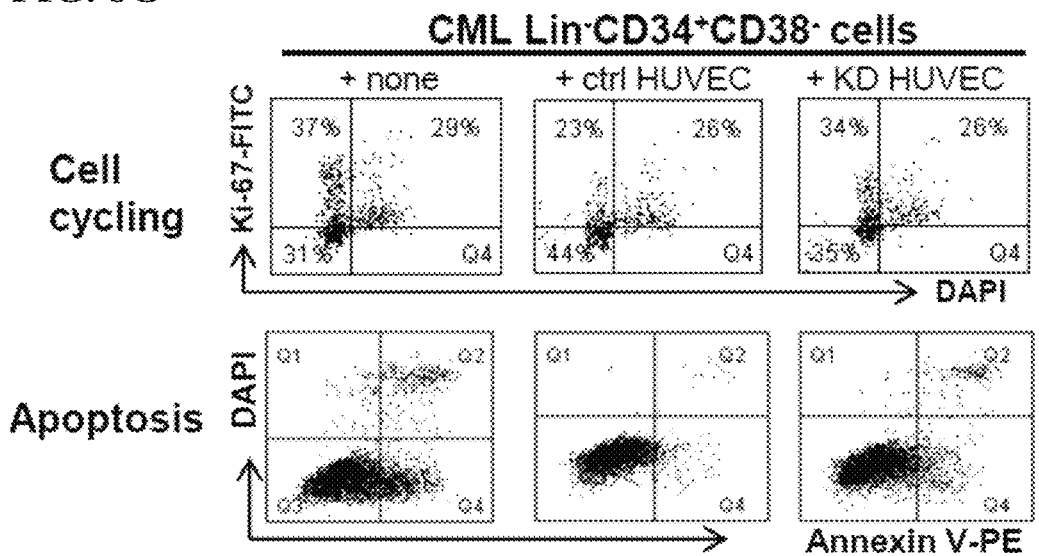
Figure 8H:
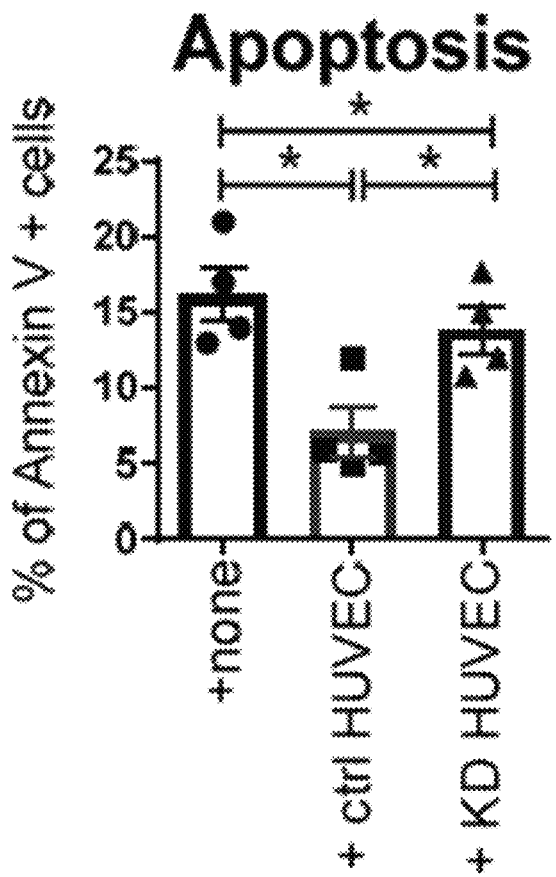
Figure 8I:
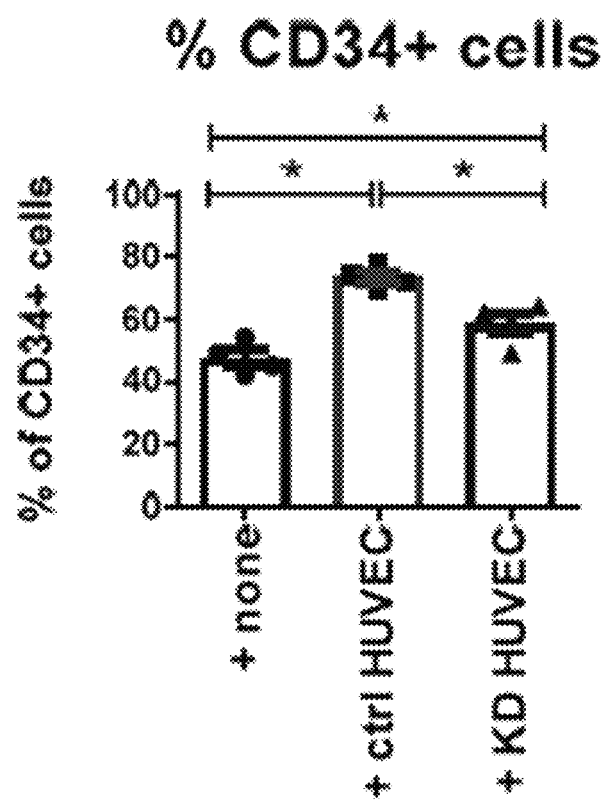

In assessing the relevance of these results to humans, we first showed that human umbilical vein EC (HUVECs) expressed significantly higher levels of miR-126 as compared with human CML CD34+ subpopulations (FIG. 8A). We next knocked down miR-126 in HUVECs by transduction with lentiviral miR-126 KD or control vectors (FIG. 8B and FIG. 8C) and then co-cultured CML Lin-CD34+CD38− cells (HSCs) with miR-126 KD or control HUVECs for 96 h. CML HSCs co-cultured for 96 h with control HUVECs had significantly higher miR-126 expression (FIG. 8D and FIG. 8E), decreased cell cycle entry and apoptosis (FIGS.

Figure 8J:
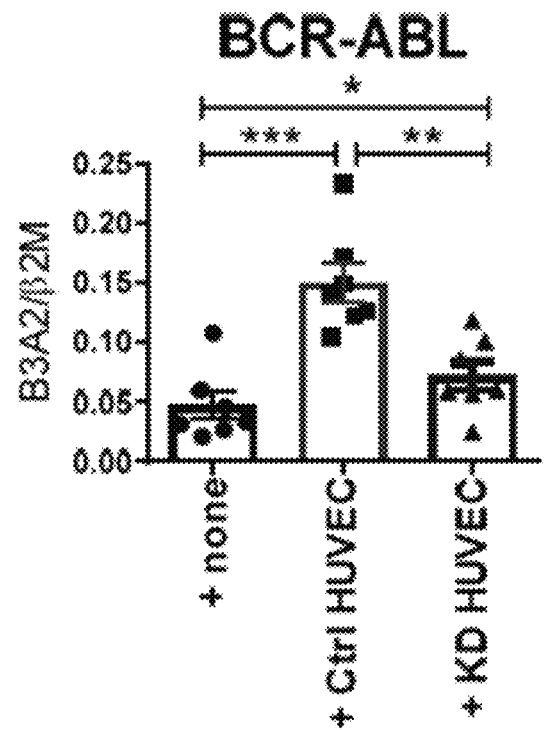
Figure 8K:
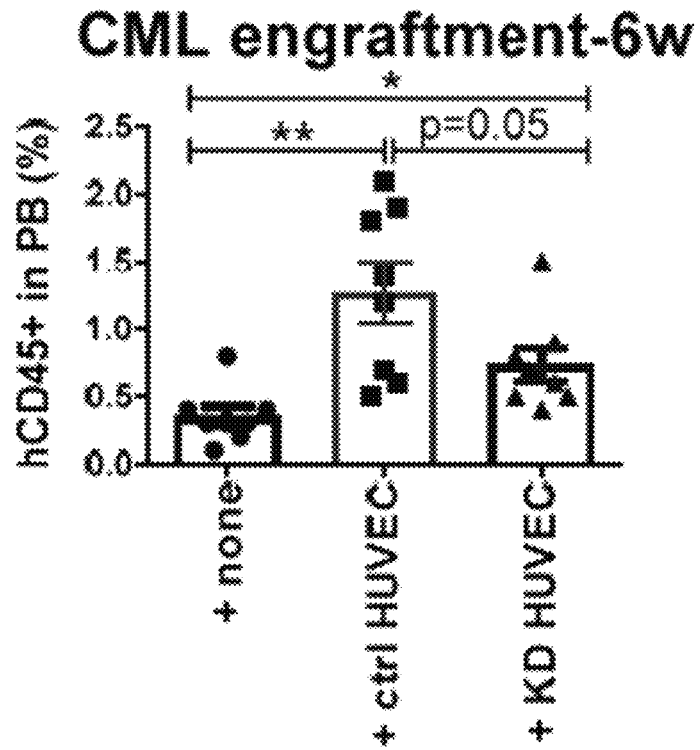
Figure 8L:
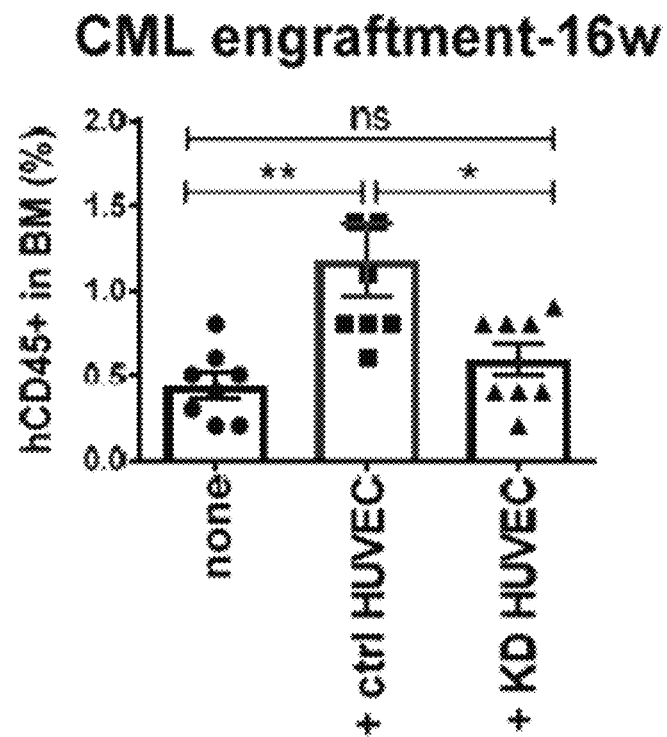

8F-8H) and an increased proportion of CD34+ cells (FIG. 8), as compared with CML cells co-cultured with KD HUVECs or cultured alone. Next, we transplanted CML CD34+ cells co-cultured with control or miR-126 KD HUVECs or cultured alone for 96 h into irradiated (300cGy) NSG-SGM3 (NOD-scid gamma IL3, GM-CSF, SCF triple transgenic) mice. At 16 weeks after transplantation, BCR-ABL expression in BM cells confirmed CIVIL cell engraftment in the recipient mice (FIG. 8J). Human CD45+ cell engraftment was significantly increased in mice receiving CML cells co-cultured with control HUVECs as compared with mice receiving CML cells co-cultured with KD HUVECs or cultured alone (FIG. 8K and FIG. 8L).

Extracellular Vesicles (EVs) Mediate miR-126 Trafficking from ECs to LT-HSCs.

Figure 9A:
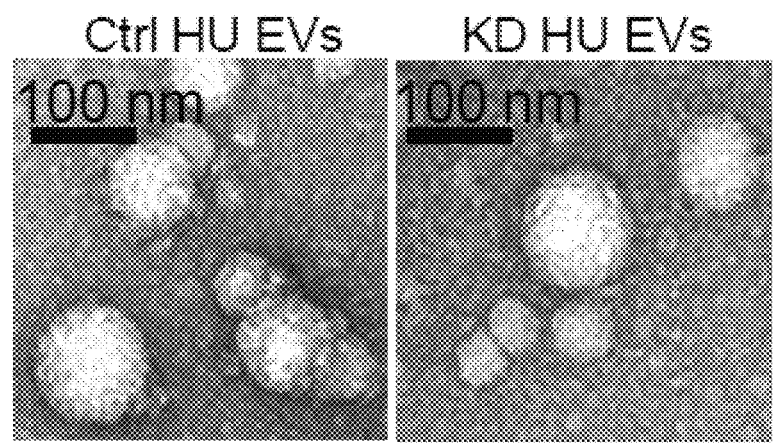
FIGS. 9A-9T. The figure shows endothelial cells in the nice supply miR-126 to CML LT-HSCs.
Figure 9B:
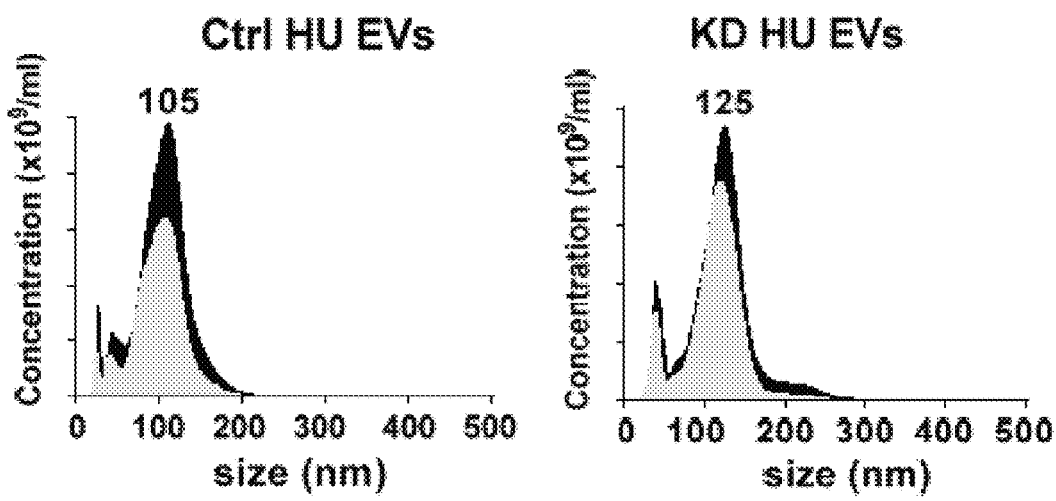
FIG. 9B shows the size and concentration of EVs isolated from the supernatants of both control (ctrl) and miR-126 KD HUVECs was analyzed by NanoSight using nanoparticle tracking assays (n=3 independent experiments).
Figure 9C:
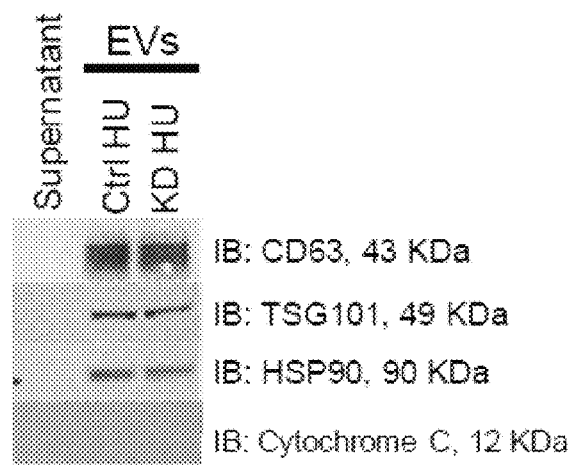
FIG. 9C shows expression of exosome-specific proteins (CD63, TSG101), EV-associated protein HSP90 and mitochondrial protein Cytochrome C in EVs isolated from ctrl or miR-126 KD HUVECs or in HUVEC supernatant (negative control), as assessed by western blot. The experiments were repeated twice with similar results. Full-length gels and blots with molecular weight standards were provided in Supplementary FIG. 10.
Figure 9E:
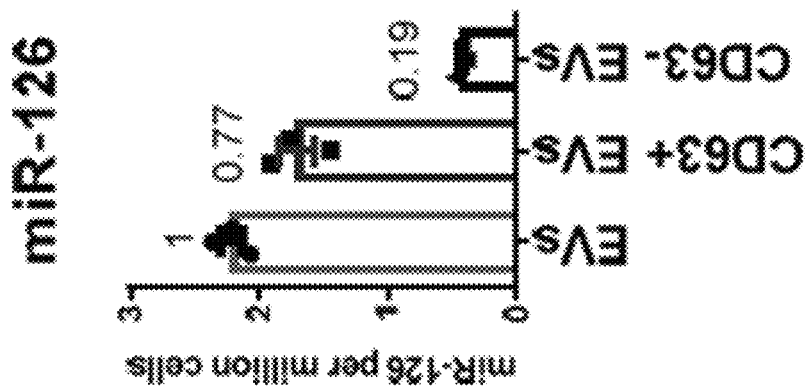
FIG. 9E shows miR-126 levels, as assessed by QPCR, in total EVs, CD63+ and CD63− HUVEC-derived EV fractions (n=3 independent experiments).
Figure 9D:
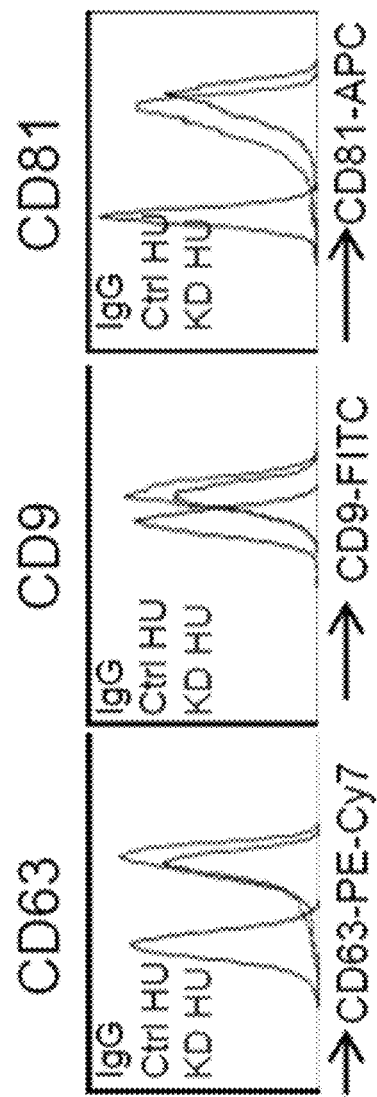
FIG. 9D shows expression of exosome-specific proteins on CD63+HUVEC-derived EV fraction, purified with magnetic beads coated with anti-CD63 antibody, as assessed by cytofluorimetric analyses using antibodies to tetraspanins (CD63, CD9 and CD81) (n=3 independent experiments with similar results).
Figure 9G:
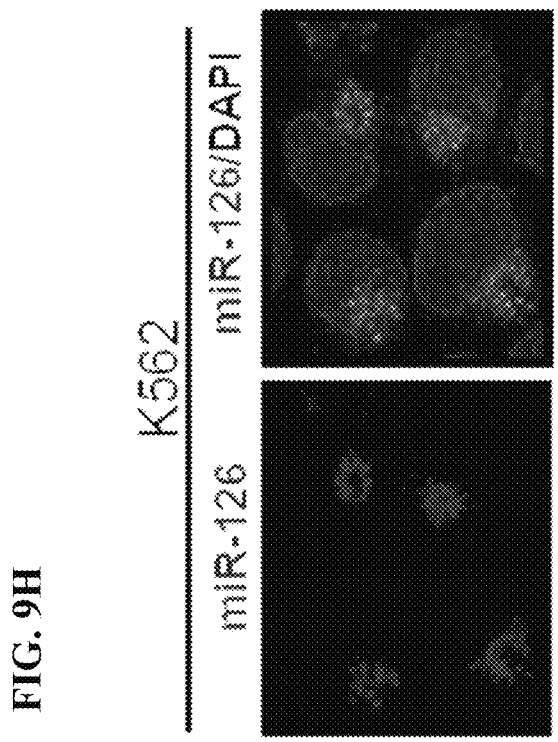
FIG. 9G and FIG. 9H show miR-126 fluorescence signal in HUVECs (FIG. 9G) and in K562 cells co-cultured with the pre-stained HUVEC-derived EVs (FIG. 9H). These experiments were repeated twice with similar results.

To test whether intercellular miR-126 trafficking between ECs and HSCs involves extracellular vesicles (EVs), we isolated EVs from control and miR-126 KD HUVECs by differential ultracentrifugation. Using electron microscopy and nanoparticle tracking analysis by NanoSight, the size range of the EVs isolated from the supernatants of both control and miR-126 KD HUVECs was 40-150 nm (peaks at 105 and 125 nm, respectively, FIG. 9A and FIG. 9B). By western blotting, EVs recovered from HUVECs showed expression of exosome-specific proteins (CD63, TSG101) and an EV-associated protein (HSP90)[22,23] and lack of a non EV-associated protein (the mitochondrial protein cytochrome C) (FIG. 9C, FIG. 16). Next, we fractionated EVs from HUVECs using magnetic beads coated with an anti-CD63 antibody and confirmed expression of exosome-specific proteins in the CD63+EV fraction using antibodies to tetraspanins (CD63, CD9 and CD81) by cytofluorimetric analysis (FIG. 9D). Significantly higher miR-126 levels were found in the CD63+EV fraction as compared with the CD63− EV fraction, as assessed by QPCR (0.77 versus 0.19, FIG. 9E). Notably, miR-126 levels were higher in EVs obtained from control HUVECs as compared to EVs from miR-126 KD HUVECs or EVs from human normal or CML Lin-CD34+CD38− HSC cells (FIG. 9F).

Figure 9H:
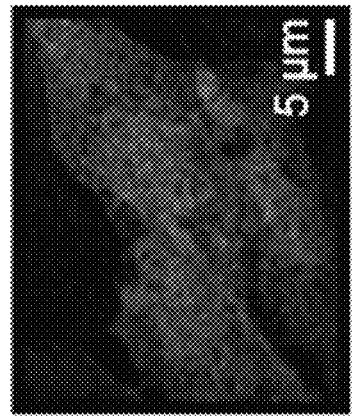
Figure 9F:
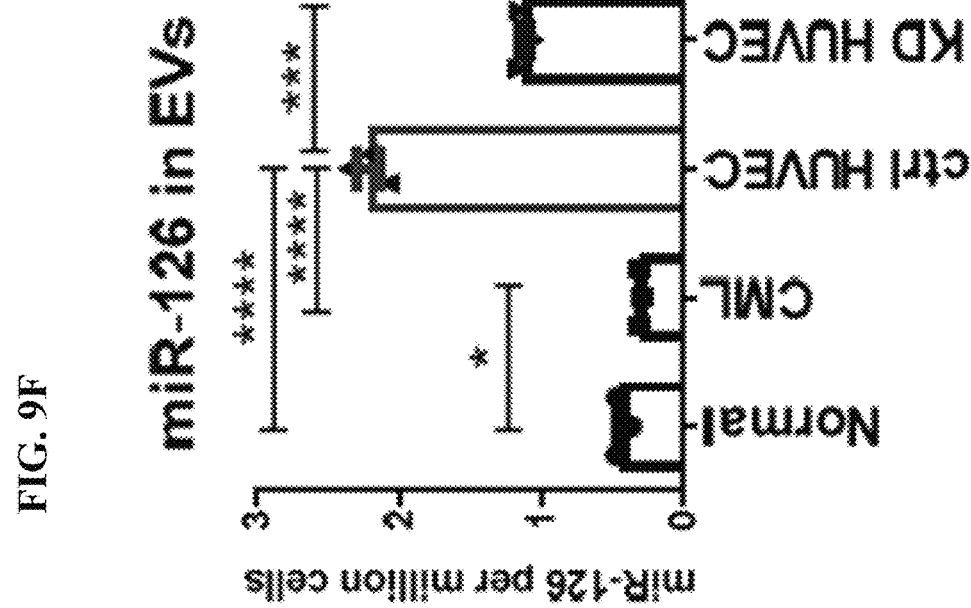
FIG. 9F shows miR-126 expression, as assessed by QPCR, in EVs harvested from human normal and CML Lin-CD34+CD38− HSCs as well as ctrl and miR-126 KD HUVECs (n=3 independent experiments).
Figure 9I:
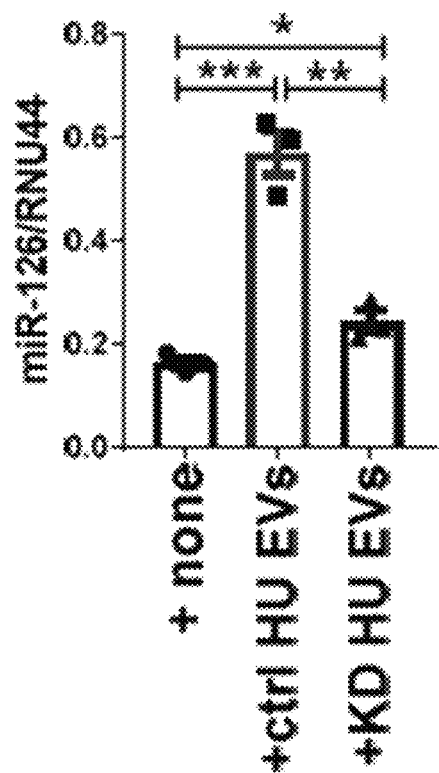
FIGS. 9I-9M show miR-126 levels as assessed by QPCR (n=3 independent samples) (FIG. 9I), representative plots (FIG. 9J) and accumulated results (FIG. 9K) of cell cycling (n=3), where the legend from top to bottom represents each group of two data sets from left to right, and representative plots (FIG. 9L) and accumulated results (FIG. 9M) of apoptosis (n=3) in human CML HSCs co-cultured with ctrl or KD HUVEC-derived EVs for 96 h.
Figure 9J:
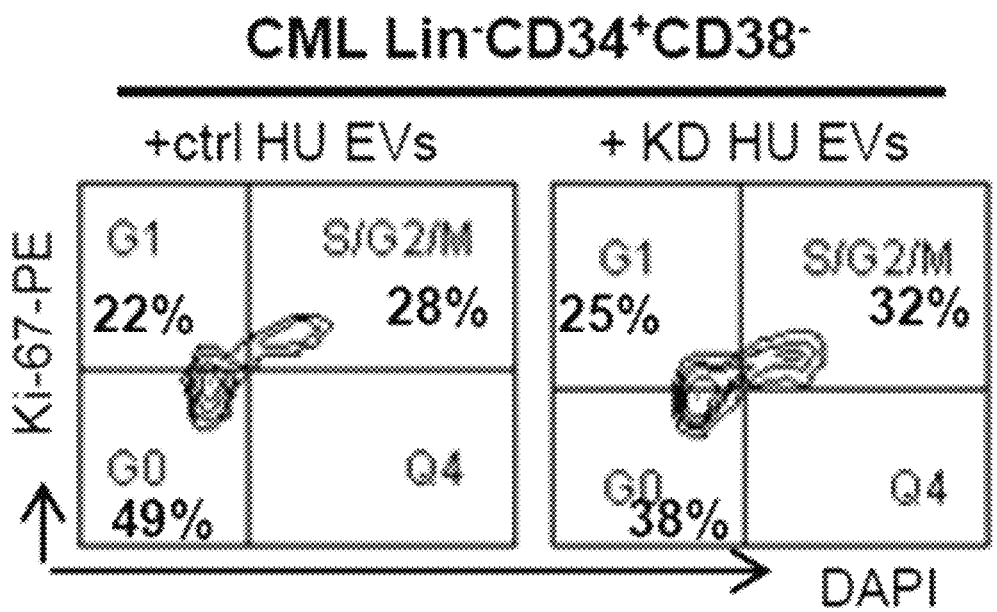
Figure 9K:
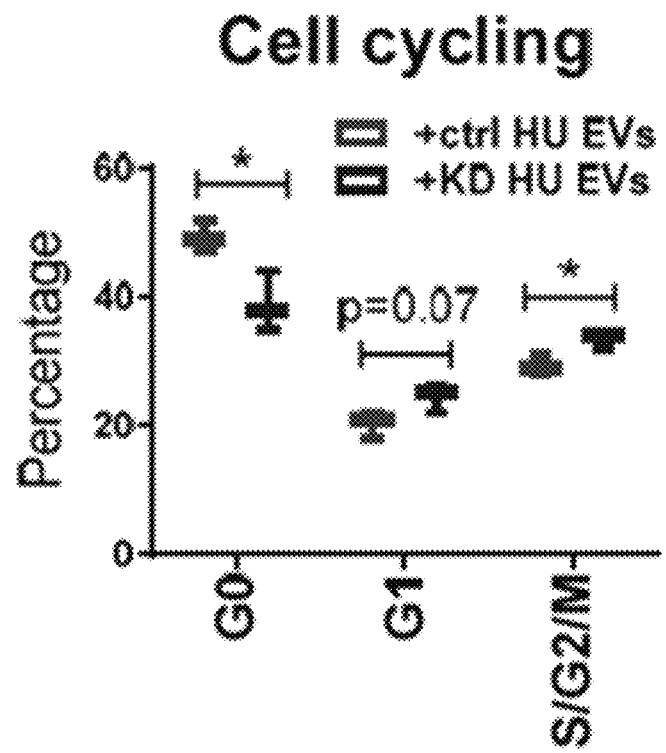
Figure 9L:
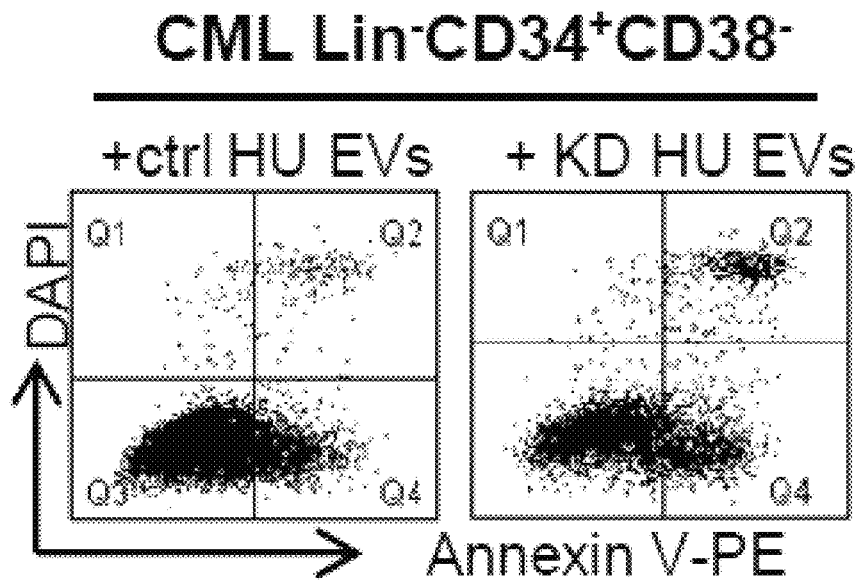
Figure 9N:
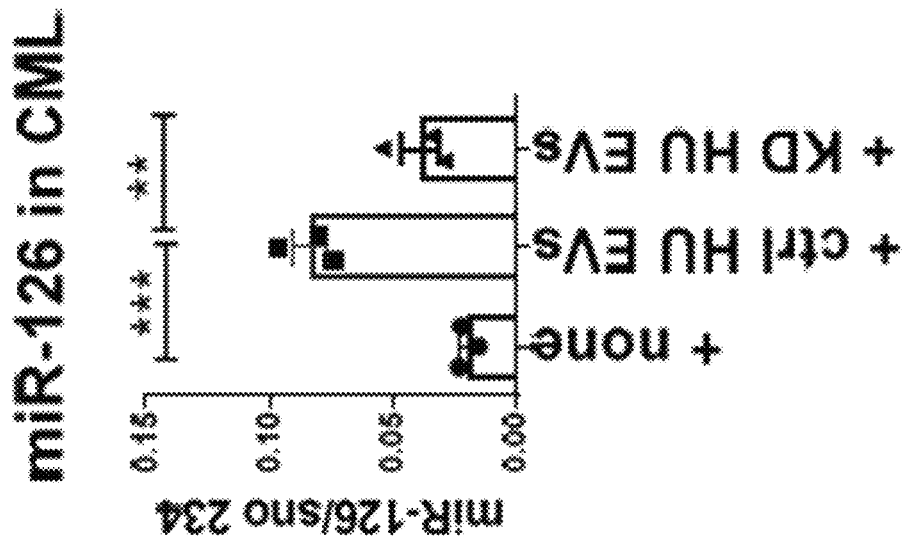
FIG. 9N shows miR-126 levels, as assessed by QPCR (n=3 independent experiments), in miR-126 KO CML LT-HSCs from BCR-ABL-induced and pIpC-injected SCLtTA/BCR-ABL/miR-126flox/flox/Mx1-cre+ mice co-cultured with ctrl or miR-126 KD HUVEC-derived EVs or cultured alone for 48 h.
Figure 9M:
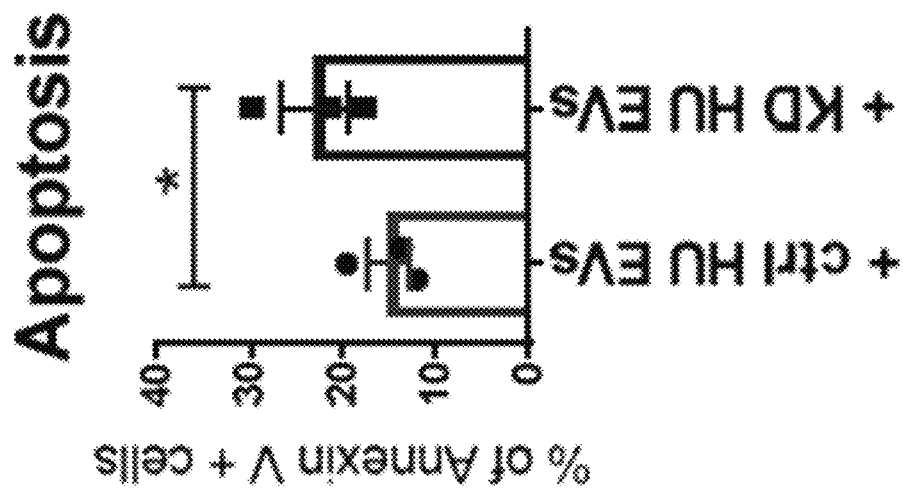

To demonstrate intercellular trafficking of miR-126, we labeled miR-126 with a fluorescence probe in cultured HUVECs (FIG. 9G) and subjected the supernatant from these cells to differential ultracentrifugation to collect EVs; treatment of BCR-ABL+K562 cells with the collected HUVEC EVs resulted in the presence of a miR-126 fluorescence signal in the K562 cells, as assessed by confocal microscopy (FIG. 9H). To corroborate these results, we cultured human CML HSCs for 96 h with EVs ($5 \times 10^9$ particles/ml as measured by NanoSight, equivalent to 5 μg/ml as measured by standard protein quantification methodology) isolated from control or KD HUVECs, or cultured the CML HSCs alone. CML HSCs co-cultured with control HUVEC-derived EVs had significantly increased miR-126 levels (FIG. 9I) and reduced cell cycling and apoptosis rates (FIGS. 9J-9M) as compared with CIVIL HSCs co-cultured with KD HUVEC-derived EVs or cultured alone. Next, we co-cultured miR-126 KO CML LT-HSCs from tetracycline-off and pIpC-injected SCLtTA/BCR-ABL/miR-126flox/flox/Mx1+ mice with control or miR-126 KD HUVEC-derived EVs for 48 h, or cultured the CML LT-HSCs alone. miR-126 KO CML cells co-cultured with control HUVEC-derived EVs showed significantly increased miR-126 levels (FIG. 9N) and reduced cell cycling and apoptosis rates as compared with miR-126 KO CML cells co-cultured with KD HUVEC-derived EVs or cultured alone.

Figure 9O:
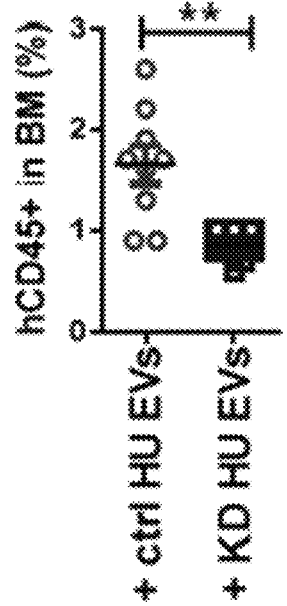
FIGS. 9O-9P show human CD45+(FIG. 9O) and CD45+ CD34+(FIG. 9P) cell engraftment in BM at 16 weeks from NSG-SGM3 mice transplanted with CML Lin-CD34+ cells co-cultured with ctrl (n=9) or KD (n=8) HUVEC-derived EVs for 96 h.
Figure 9P:
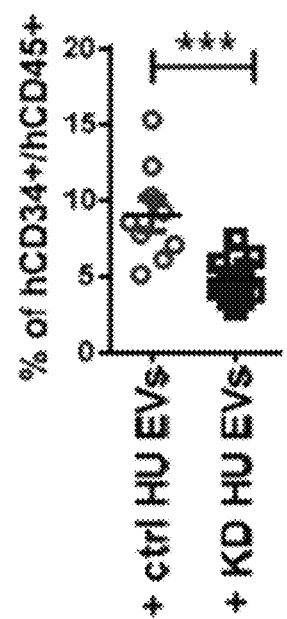
Figure 9Q:
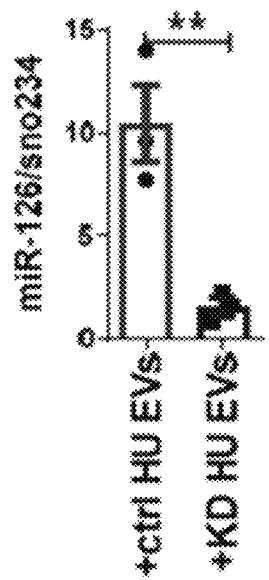
Figure 9R:
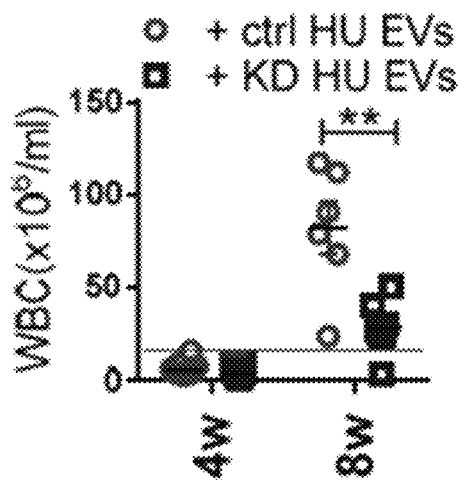
Figure 9S:
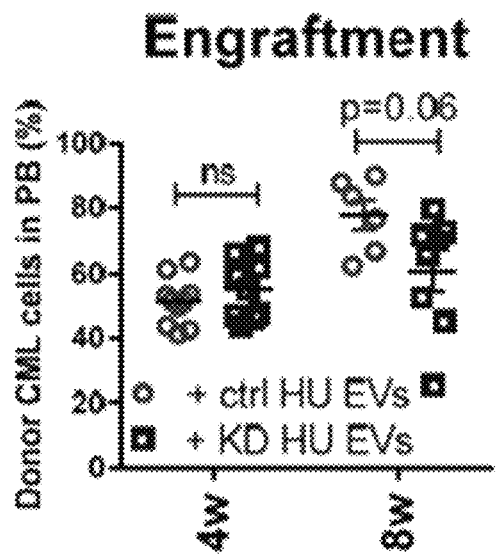
Figure 9T:
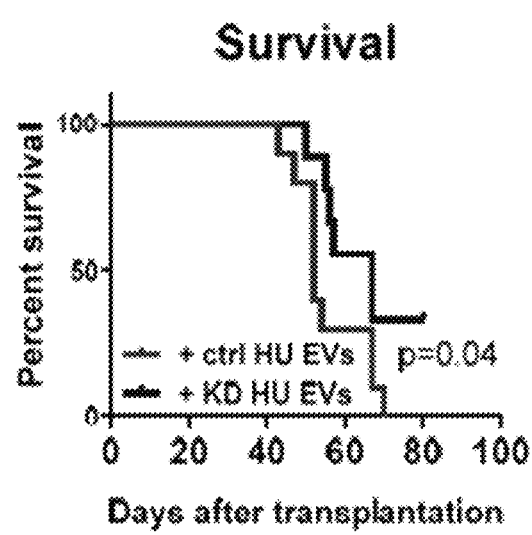

Next, we transplanted primary CML CD34+ cells co-cultured with EVs ($5 \times 10^9$ particles/ml) from control or miR-126 KD HUVECs for 96 h into NSG-SGM3 mice. Mice receiving cells co-cultured with control HUVEC-derived EVs showed enhanced human CD45+(p=0.001; FIG. 9O) and CD45+CD34+(p=0.0008; FIG. 9p) BM engraftment at 16 weeks, compared with mice receiving cells co-cultured with KD HUVEC-derived EVs. QPCR confirmed that the engrafted cells in both groups of mice were BCR-ABL+. We also sorted CML LT-HSCs from induced CD45.2 SCLtTA/BCR-ABL mice and co-cultured them with control or KD HUVEC-derived EVs for 96 h and then transplanted the cells into CD45.1 recipient mice. LT-HSCs co-cultured with control HUVEC-derived EVs showed increased miR-126 expression (p=0.009; FIG. 9Q), enhanced CML progression (p=0.002), an increased engraftment rate (p=0.06), and reduced survival (p=0.04) as compared with LT-HSCs co-cultured with KD HUVEC-derived EVs (FIGS. 9r-9t). Altogether, these observations suggest that EV-mediated trafficking is responsible for the transfer of miR-126 from ECs to LT-HSCs.

Of note, although we could not completely exclude the possibility that decreased CML LT-HSC quiescence and engraftment capacity results from functional changes in ECs induced by miR-126 KD, rather than from a decrease in miR-126 trafficking from ECs to LT-HSCs, Kuo et al. previously showed that miR-126 KO mice have no substantial changes in BM EC structure[9]. Moreover, we did not observe detectable changes in the morphology and growth rate of miR-126 KD HUVECs or miR-126 KD mouse ECs compared with controls (data not shown).

miR-126 Knockdown Enhances TKI-Mediated Targeting of CML LSC.

Figure 10A:
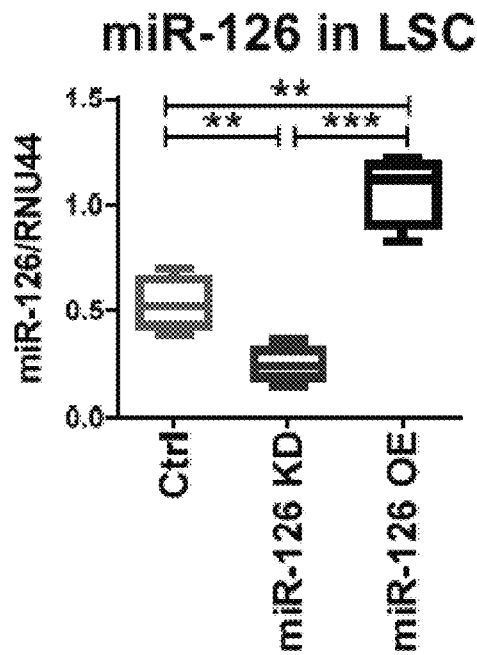
Figure 10B:
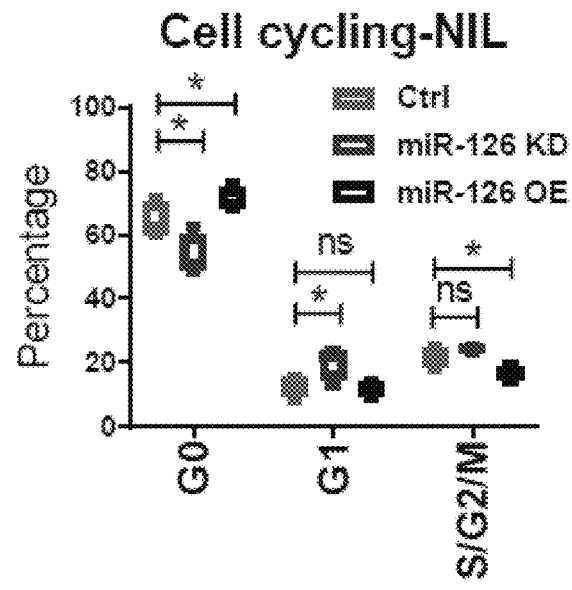
Figure 10E:
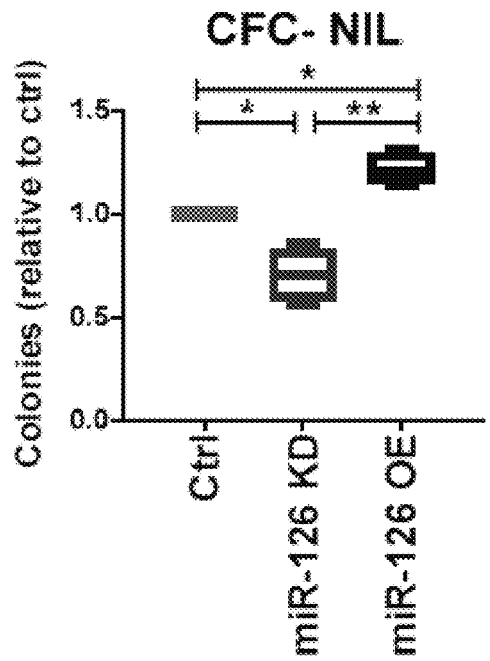
Figure 10F:
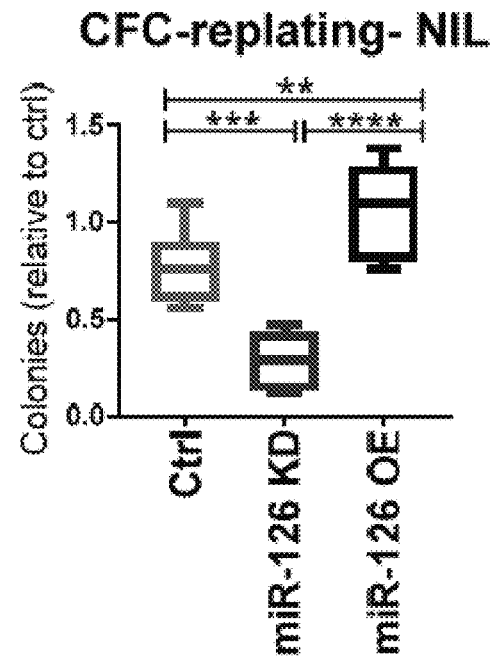
Figure 10G:
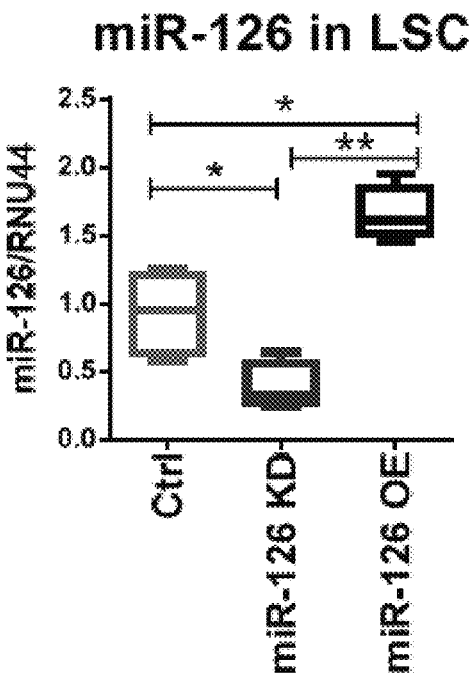
Figure 10H:
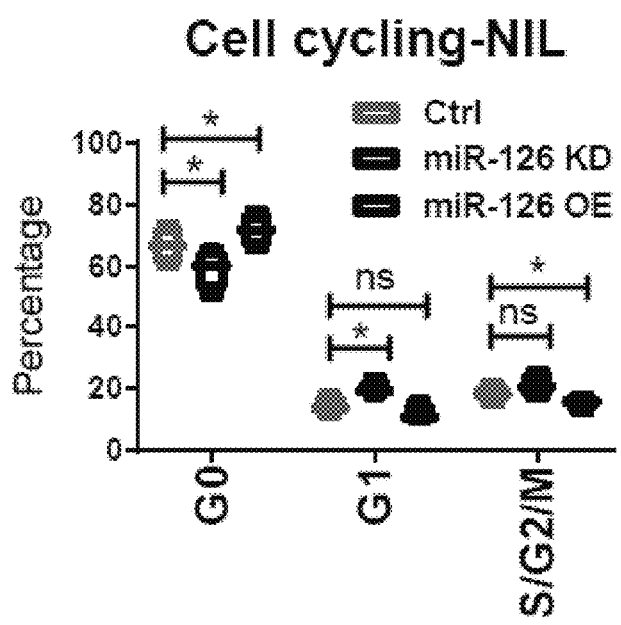
Figure 10K:
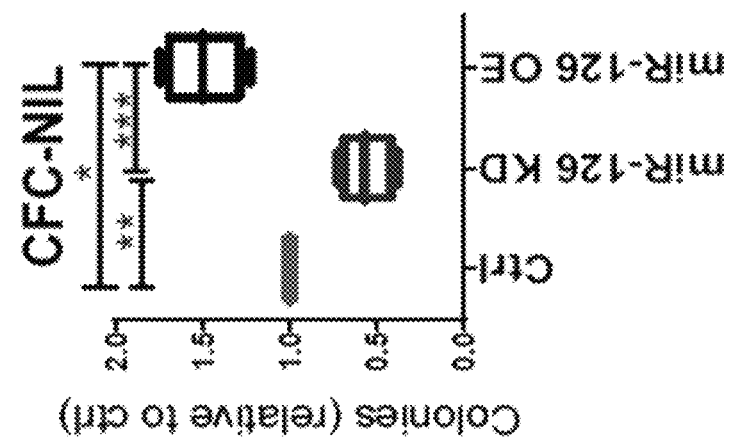
Figure 10J:
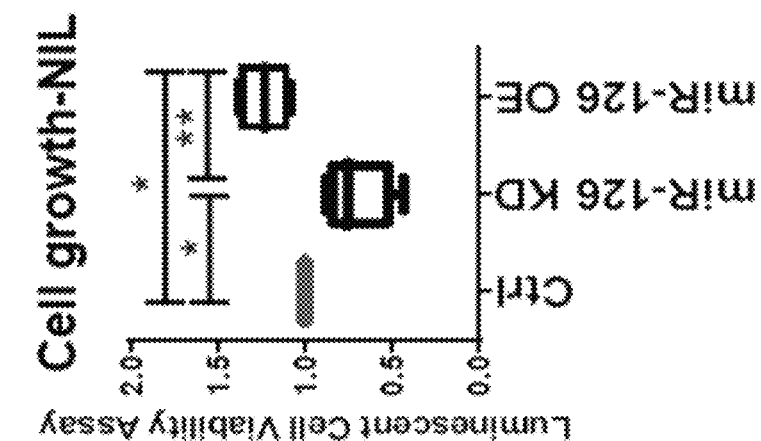
Figure 10I:
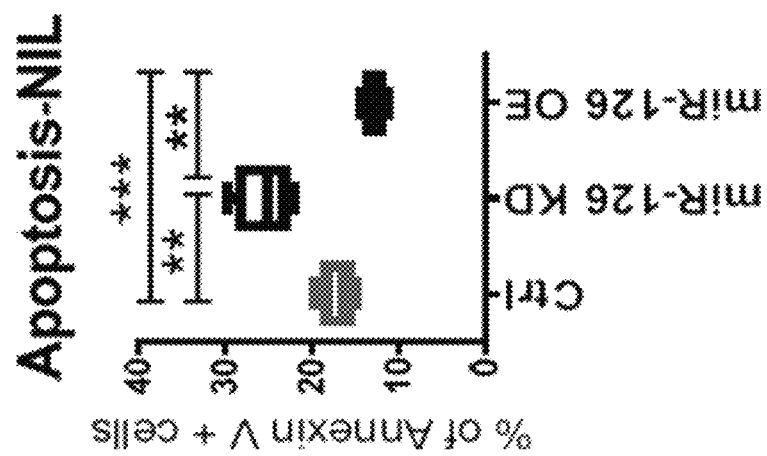

Given that BCR-ABL activity reduces endogenous levels of miR-126 in LT-HSCs and that pharmacologic inhibition of BCR-ABL by NIL increased miR-126 levels and the frequency of quiescent LT-HSCs (FIGS. 2D-2O), we postulated that miR-126 down-regulation may enhance the anti-leukemic activity of TKI treatment and eliminate CML LSCs. To test this hypothesis, we subjected human CML HSCs to miR-126 KD or OE by transduction of GFP-expressing lentiviruses (FIG. 10A). We selected GFP+ cells and cultured them for 96 h in the presence of NIL. Combined miR-126 KD and NIL treatment resulted in increased cell cycling and apoptosis (FIG. 10B and FIG. 10C) and decreased cell growth, CFC and CFC replating efficiency (FIGS. 10D-10F), as compared with only NIL-treated control cells. Conversely, combined miR-126 OE and NIL treatment resulted in decreased cell cycling and apoptosis and increased CFC and CFC replating efficiency (FIGS. 10B, 10C, 10E, 10F), as compared with only NIL-treated control cells. We obtained similar results for CML LT-HSCs from SCLtTA/BCR-ABL mice (FIGS. 10G-10K).

Figure 6B:
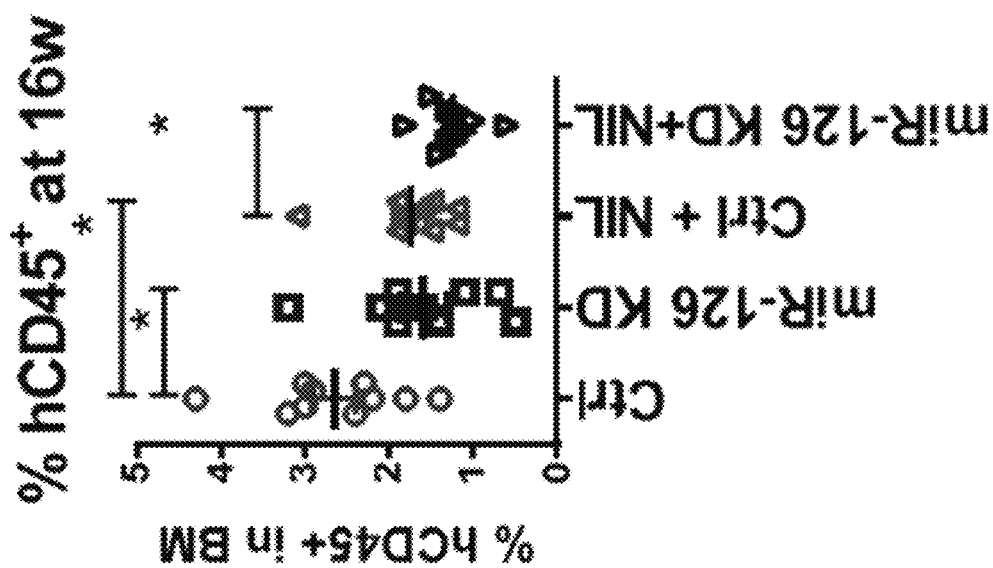
Figure 6A:
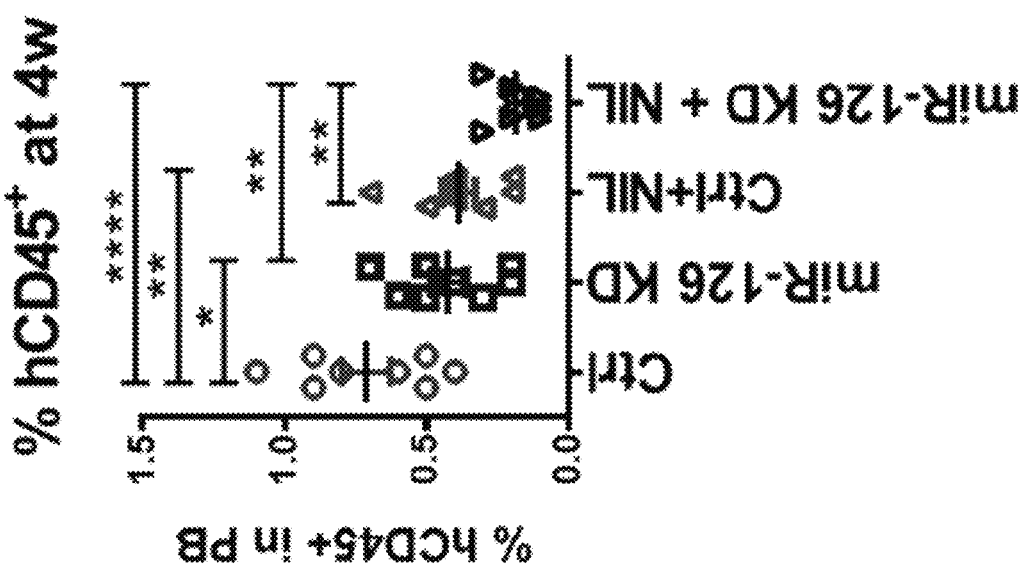
Figure 11A:
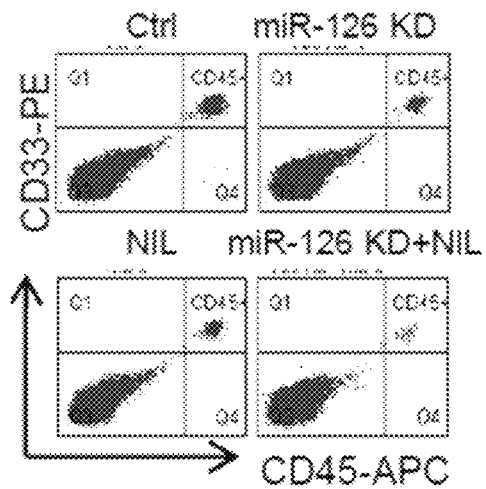
FIGS. 11A-11S. The figure shows miR-126 knockdown enhances TKI-mediated targeting of CML LSCs.
Figure 11B:
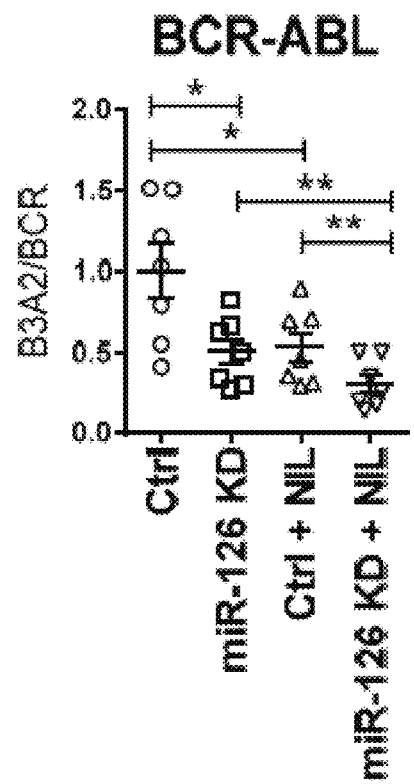

To further test the concept that miR-126 KD can enhance the anti-leukemic activity of TKI treatment, we transduced human CML HSCs with miR-126 KD or control lentiviral vectors; we selected GFP+ cells and treated them with NIL for 96 h and then transplanted them into irradiated NSG-SGM3 mice. Recipient mice receiving NIL-treated miR-126 KD cells showed reduced engraftment of human CD45+ cells in PB at 4 weeks (FIG. 6A) and in BM at 16 weeks (FIG. 6B and FIG. 11A), as compared to controls. BCR-ABL levels were reduced in BM cells from NSG-SGM3 mice transplanted with miR-126 KD CML cells as compared with mice transplanted with control CML cells (FIG. 11B).

Figure 6D:
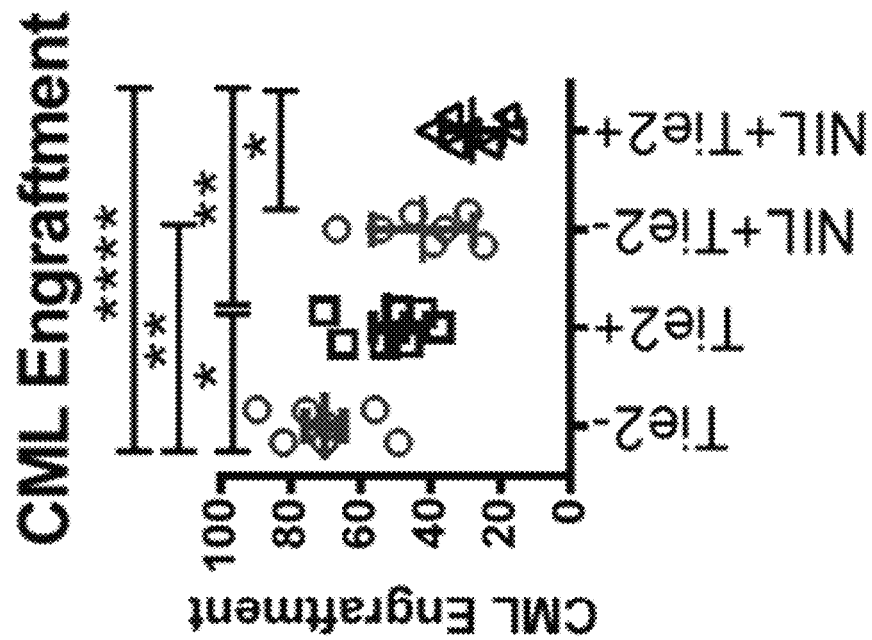
FIGS. 6C-6E show WBC counts (FIG. 6C), CML donor cell engraftment (FIG. 6D) and survival, where the line with 50 percent survival at approximately day 60 represents data for Tie2− mice, the line with 50 percent survival at approximately day 120 represents data for Tie2+ mice, the line with 50 percent survival at approximately day 150 represents data for NIL+Tie2−mice, and the remaining line represents data for NIL+Tie2+(FIG. 6E) of CD45.2 miR-126flox/wt/Tie2+ or Tie2− mice transplanted with CD45.1/CD45.2 CML LT-HSCs and treated with or without NIL (n=7 in each group) for 3 weeks. The log-rank test was used to assess significant differences between survival curves.
Figure 6C:
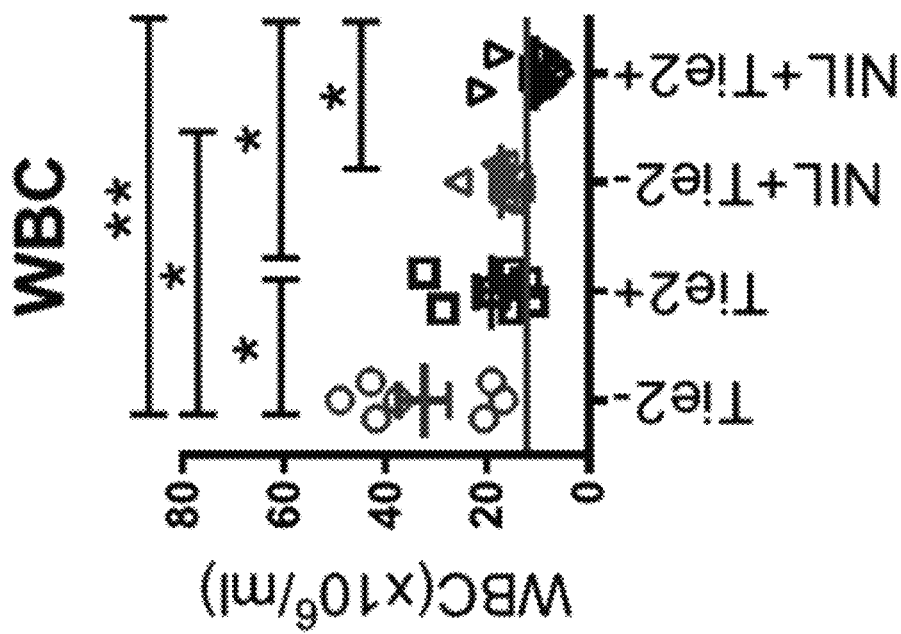
Figure 6E:
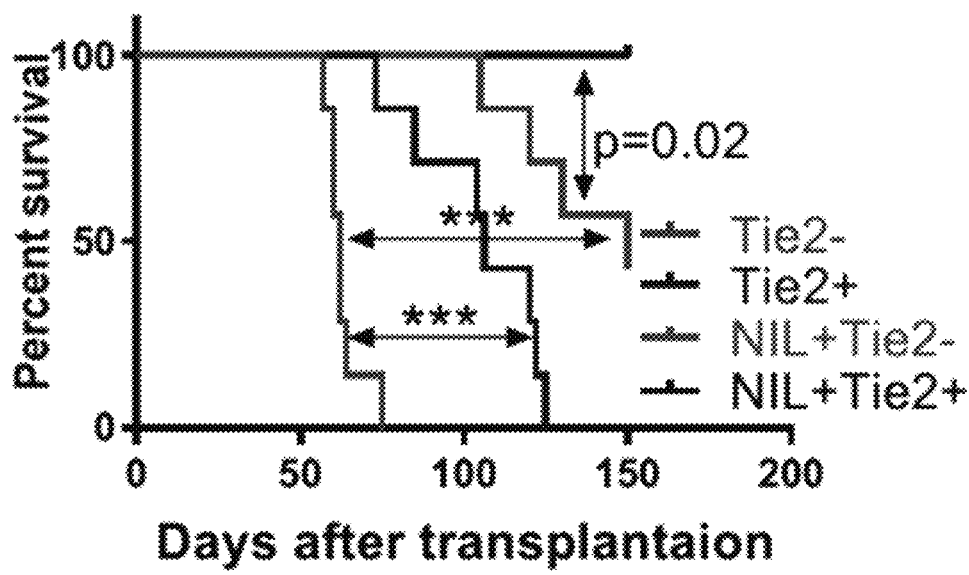
Figure 11C:
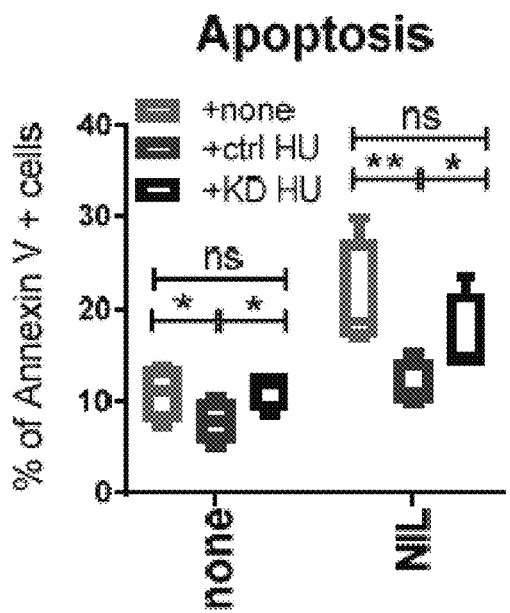
FIGS. 11C-11E show apoptosis (n=4 independent experiments) (FIG. 11C), cell growth (n=4) (FIG. 11D) and CFC (n=4) (FIG. 11E) in human CML HSCs co-cultured with ctrl or KD HUVECs or none, with or without NIL (5 for 96 h. The legends from top to bottom represent each group of three data sets from left to right.
Figure 11D:
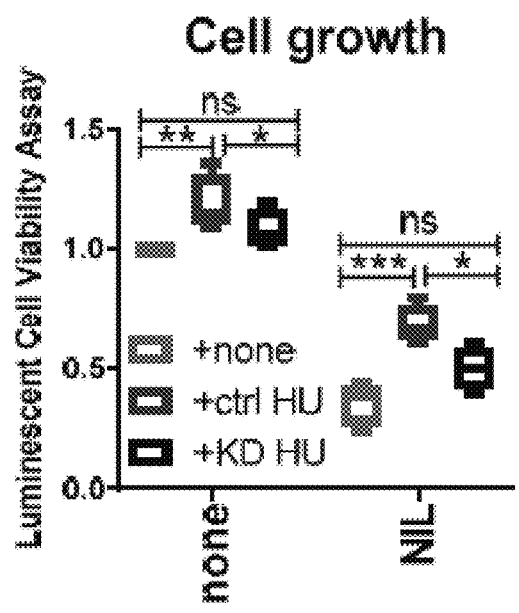
Figure 11E:
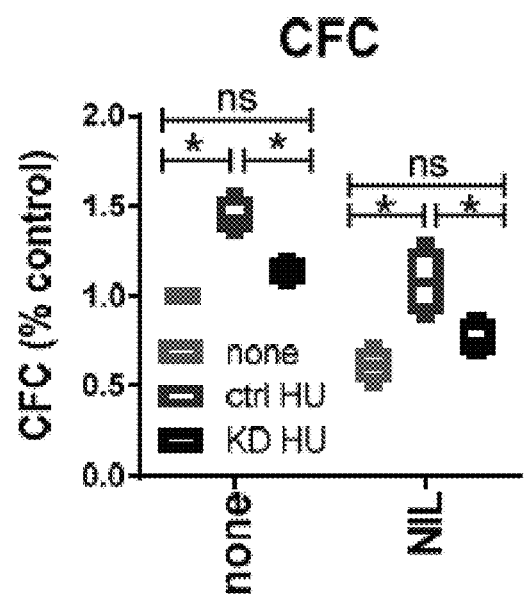
Figure 11F:
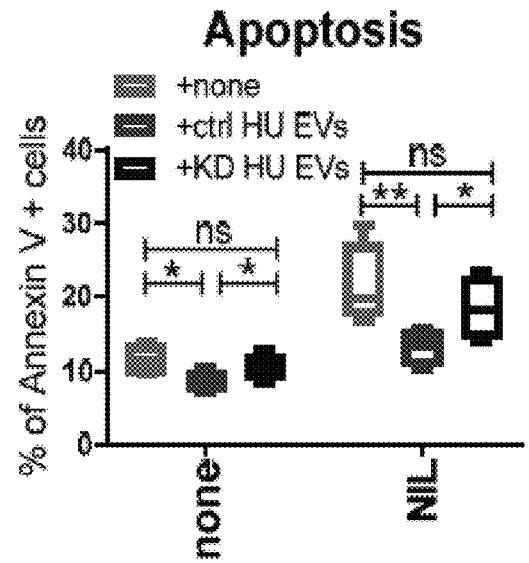
FIG. 11F and FIG. 11G show apoptosis (n=4 independent experiments) (FIG. 11F) and cell growth (n=4) (FIG. 11G) in human CML HSCs co-cultured with ctrl or KD HUVEC-derived EVs or cultured alone, with or without NIL (5 for 96 h. The legends from top to bottom represent each group of three data sets from left to right.
Figure 11G:
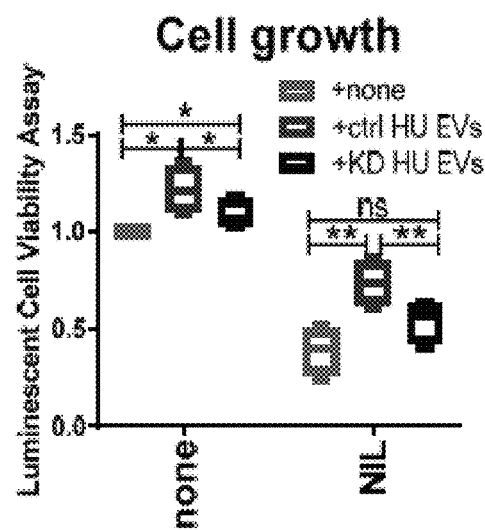

To test if miR-126 down-regulation in ECs also enhances the sensitivity of CML HSCs to TKI treatment, we cultured human CML HSCs alone or with HUVEC with or without miR-126 KD, and with or without NIL for 72 h. CML HSCs co-cultured with miR-126 KD HUVECs had significantly increased apoptosis and decreased cell growth and CFCs, as compared with CML HSCs co-cultured with control HUVECs with or without NIL (FIGS. 11C-11E). Of note, CML HSCs co-cultured with KD HUVEC-derived EVs also showed significantly increased apoptosis and decreased cell growth as compared to CML HSCs co-cultured with control HUVEC-derived EVs, with or without NIL (FIG. 11F and FIG. 11G). Next, we sorted CML LT-HSCs from induced CD45.1/CD45.2 SCLtTA/BCR-ABL mice and transplanted them into CD45.2 miR-126$^{flox/wt}$/Tie2+ (heterozygous miR-126 KO allele in ECs) or Tie2− (WT miR-126 allele in ECs) mice. After confirming CML development, we treated the mice with NIL (50 mg/kg, daily by oral gavage) or vehicle for 3 weeks. Vehicle-treated Tie2+ mice showed delayed CML development (p=0.02) and increased survival (p=0.001) as compared with vehicle-treated Tie2− mice (FIGS. 6C-6E). Moreover, NIL-treated Tie2+ mice showed significantly reduced WBC counts in PB (p=0.03) and increased survival (p=0.02) as compared with NIL-treated Tie2− mice (FIGS. 6C-6E), and all NIL-treated Tie2+ mice were alive at day 150 (FIG. 6E). Altogether, these results support the hypothesis that miR-126 down-regulation in ECs and CML HSCs enhances the anti-leukemic activity of TKI treatment.

Figure 11H:
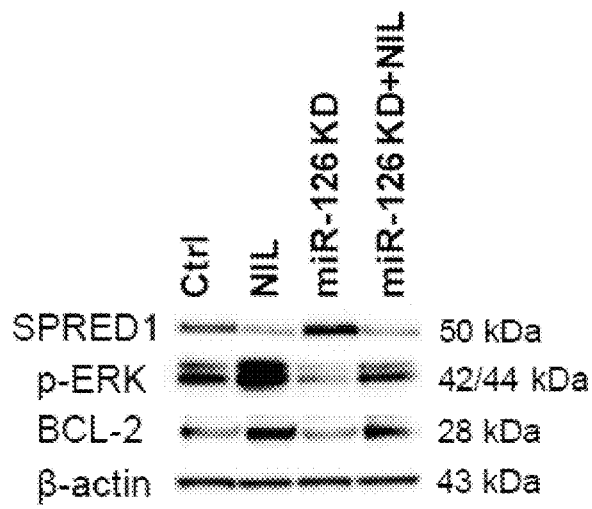
FIG. 11H shows SPRED1, p-ERK, BCL-2 and β-actin (loading control) proteins in human CML Lin-CD34+ cells with or without miR-126 KD and treated with or without NIL (2 as assessed by western blot. The experiments were repeated twice using independent samples with similar results.
Figure 11I:
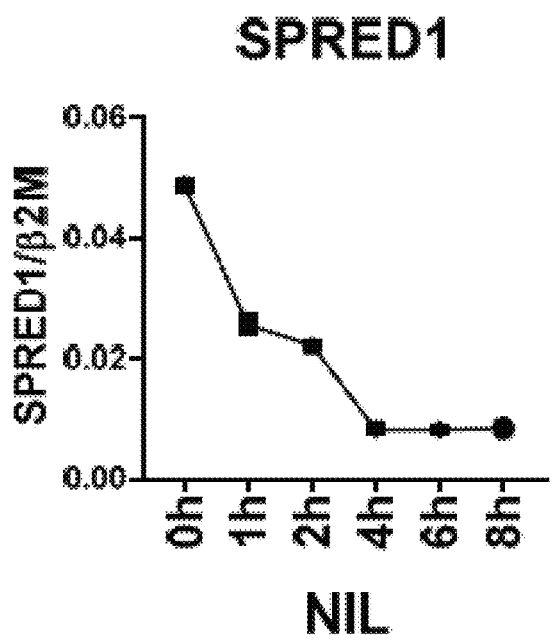
FIGS. 11I-11K show SPRED1 mRNA in NIL-treated cells at indicated times (n=4 independent experiments) (FIG. 11I) and in miR-126 KD cells (n=4 independent experiments) (FIG. 11J) from FIG. 11H, as assessed by QPCR.
Figure 11J:
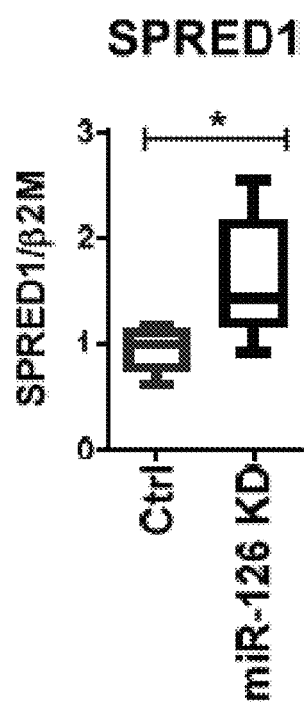
Figure 11K:
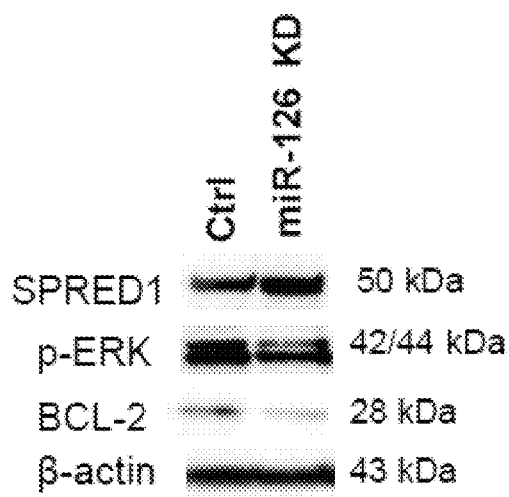
Figure 11L:
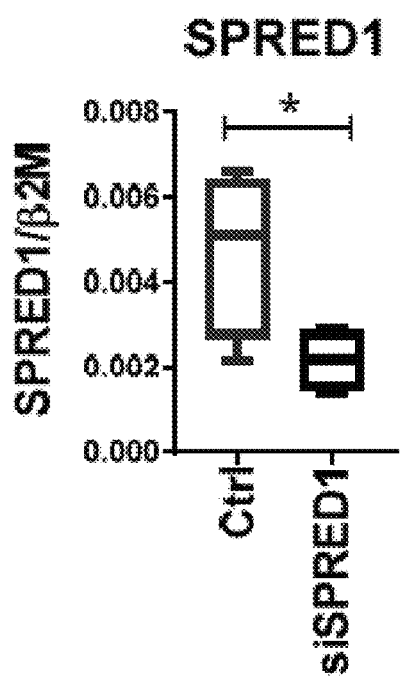
Figure 11M:
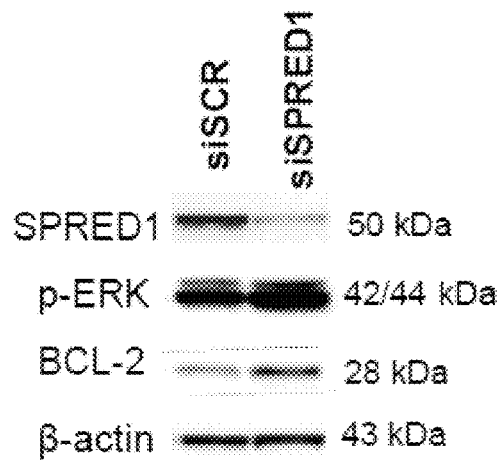
Figure 11N:
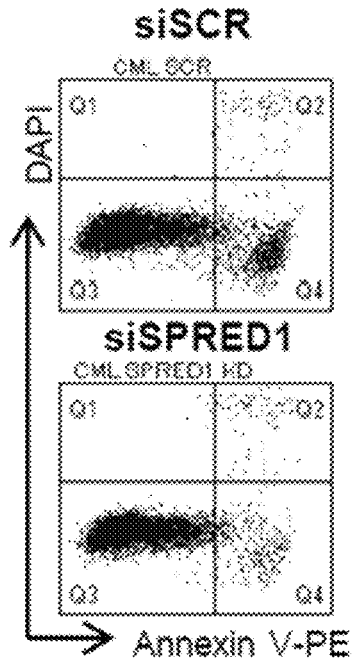
FIG. 11N and FIG. 11O show representative plots (FIG. 11N) and accumulated results (n=4 independent samples) (FIG. 11O) of apoptosis in SPRED1 KD CML Lin-CD34+ cells treated with and without NIL (2 μM) for 48 h.
Figure 11O:
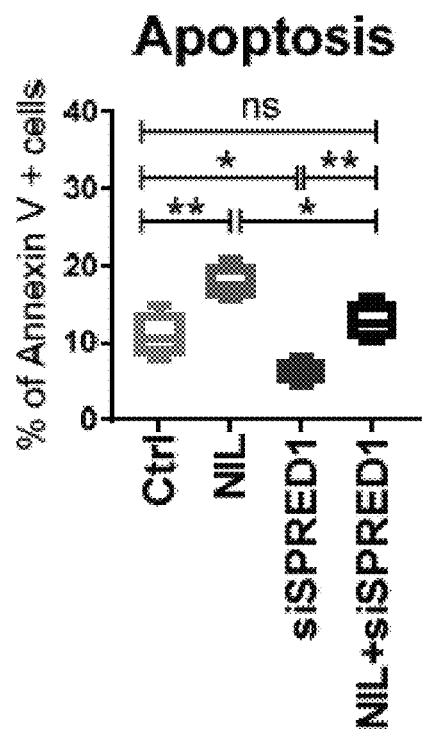
Figure 11P:
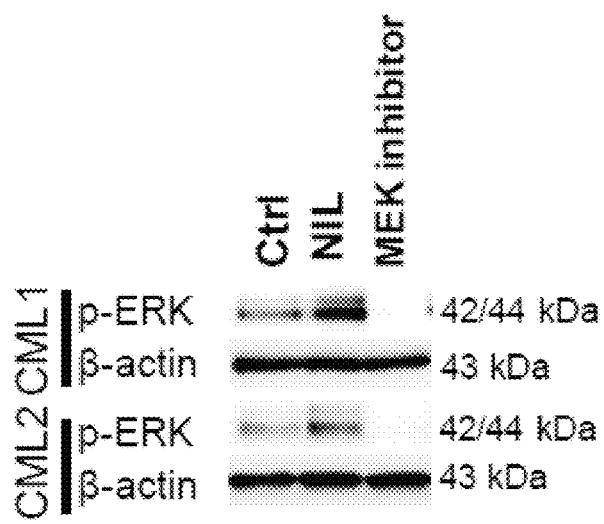
FIG. 11P and FIG. 11Q show p-ERK and β-actin expression by western blot (FIG. 11P) and apoptosis (n=4) (FIG. 11Q) in CML Lin-CD34+ cells treated with NIL (2 or MEK inhibitor PD0325901 (500 nM) or combination for 72 h. The experiments were repeated twice using independent samples with similar results.
Figure 11Q:
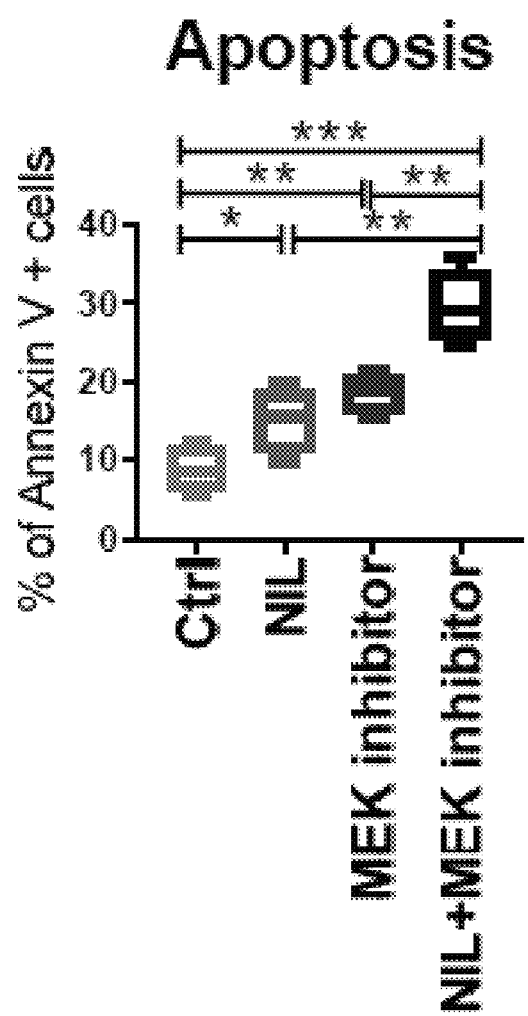
Figure 11R:
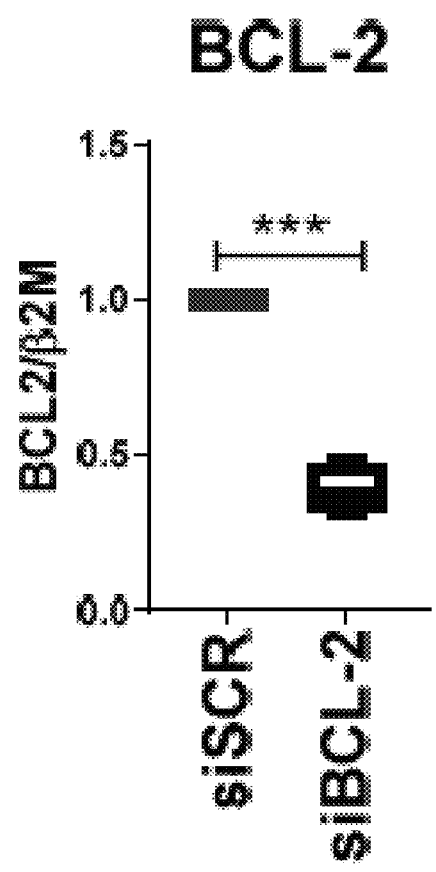
Figure 11S:
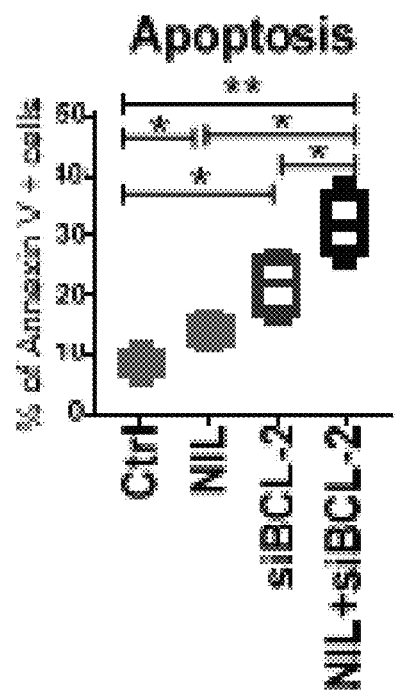

To sort out the mechanistic basis for the enhancement of TKI activity by miR-126 KD, we showed that, consistent with previous studies[24,25], NIL treatment enhanced MAPK/ERK activation, increased BCL-2 expression and promoted survival in CML CD34+ cells (FIG. 11H and FIG. 16). Thus, we reasoned that NIL could enhance MAPK/ERK activation through up-regulation of miR-126 and consequent down-regulation of SPRED1 (FIG. 11H and FIG. 11I), a reported inhibitor of the MAPK/ERK pathway. In fact miR-126 KD in CML CD34+ cells resulted in SPRED1 up-regulation and decreased phospho-ERK (p-ERK) and BCL-2 levels (FIGS. 11J-11K, FIG. 16), while SPRED1 KD increased p-ERK and BCL-2 levels and rescued NIL-induced apoptosis (FIGS. 11L-11O, FIG. 16). Moreover, NIL-induced apoptosis was enhanced by the MEK inhibitor PD0325901 or BCL-2 KD (FIGS. 11P-11S, FIG. 16). These results support a model in which NIL-induced up-regulation of miR-126 expression decreases SPRED1 expression and results in spurious activation of the MAPK/ERK pathway, and ultimate increase of BCL-2 levels. miR-126 KD counteracted these effects, thereby increasing the anti-leukemic activity of NIL.

Effective In Vitro and In Vivo Uptake and Gene Silencing Effects of the CpG-miR-126 Inhibitor.

Figure 12A:
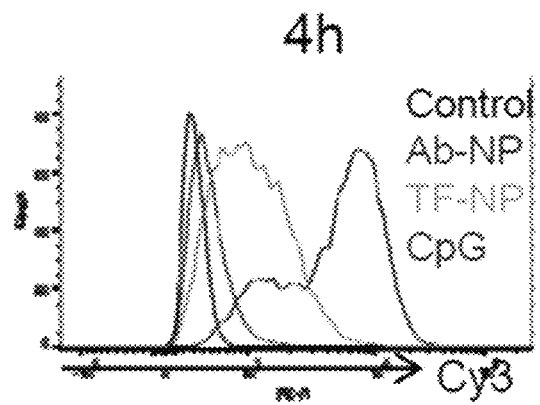
FIGS. 12A-12Q. The figure shows effective in vitro and in vivo uptake and gene silencing effects of the CpG-miR-126 inhibitor.
Figure 12B:
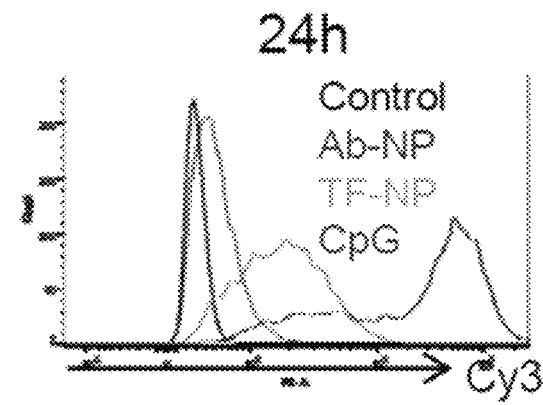
Figure 12C:
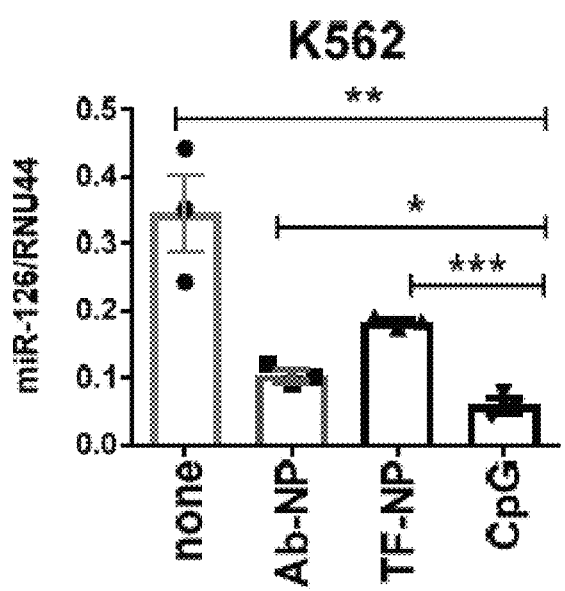
Figure 12D:
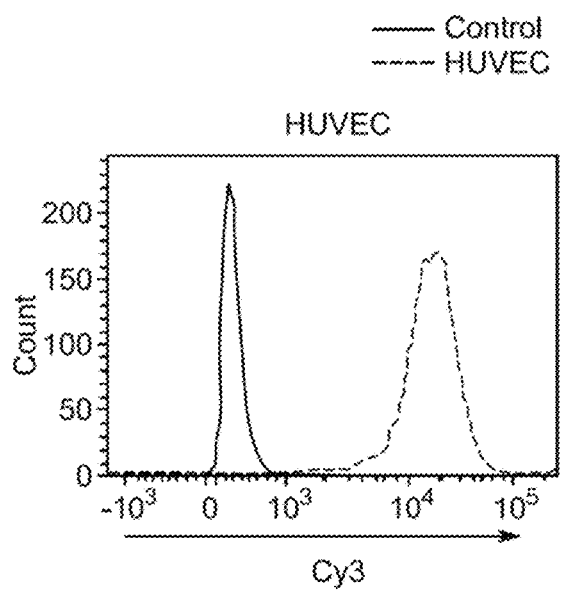
FIGS. 12D-12I show uptake of Cy3 in HUVECs (FIG. 12D), human normal (FIG. 12E) and CML (FIG. 12F) Lin-CD34+CD38−cells at 4 h and miR-126 expression in HUVECs (FIG. 12G), normal (FIG. 12H) and CML (FIG. 12I) Lin-CD34+CD38− cells at 24 h post treatment with CpG-miR-126 inhibitor-Cy3 (500 nM) (n=4 independent samples for all). For FIGS. 12D-12F, the legends from top to bottom represent the curves from left to right.
Figure 12E:
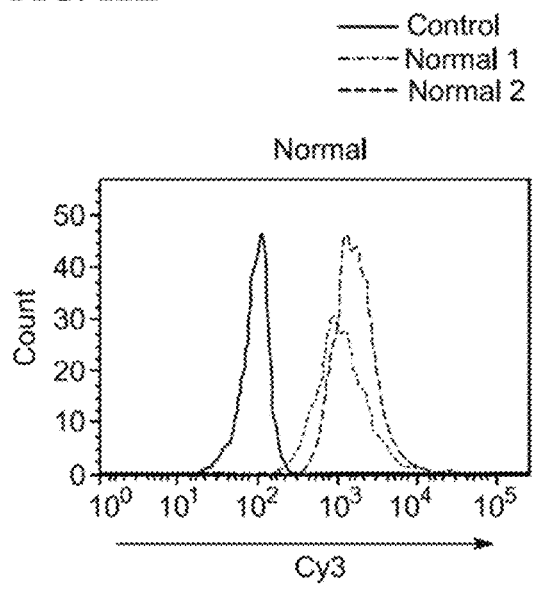
Figure 12F:
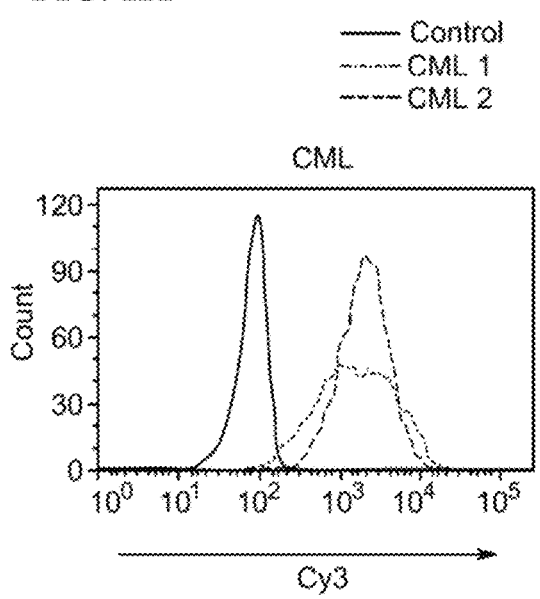
Figure 12G:
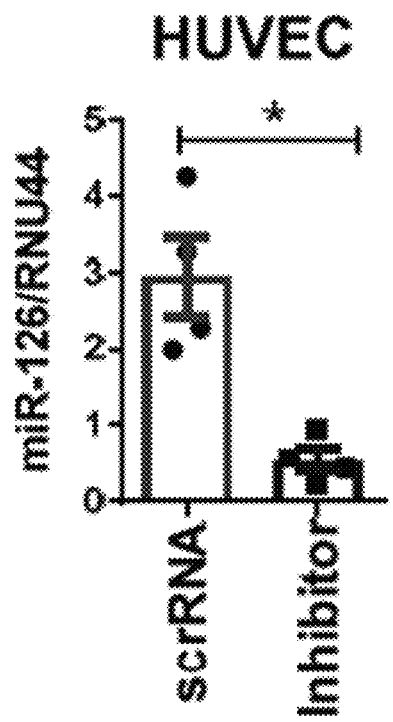
Figure 12H:
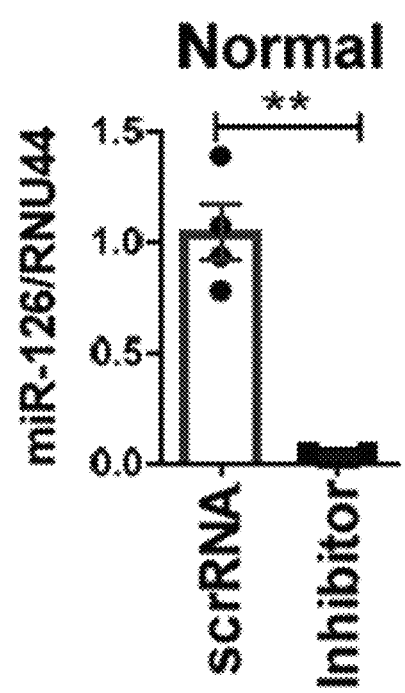
Figure 12I:
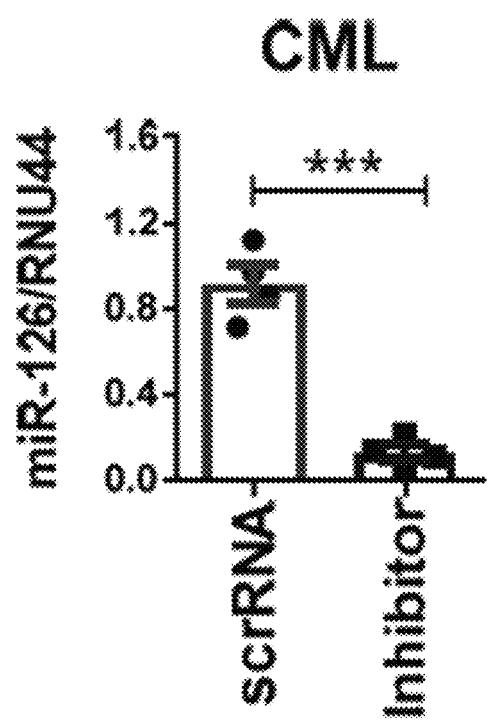
Figure 12J:
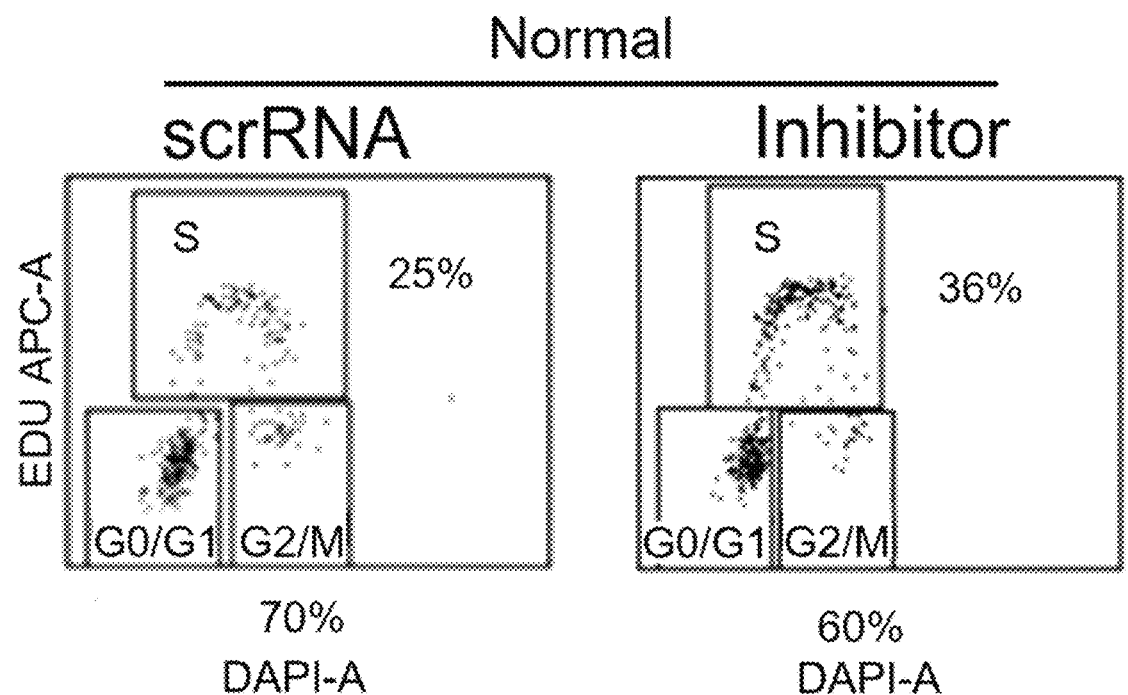
FIG. 12J and FIG. 12K show cell cycling in normal (FIG. 12J) and CML (FIG. 12K) Lin-CD34+CD38− cells treated with CpG-miR-126 inhibitor (500 nM), as assessed by EdU and DAPI staining. The experiments were repeated twice using biologically independent samples with similar results.
Figure 12K:
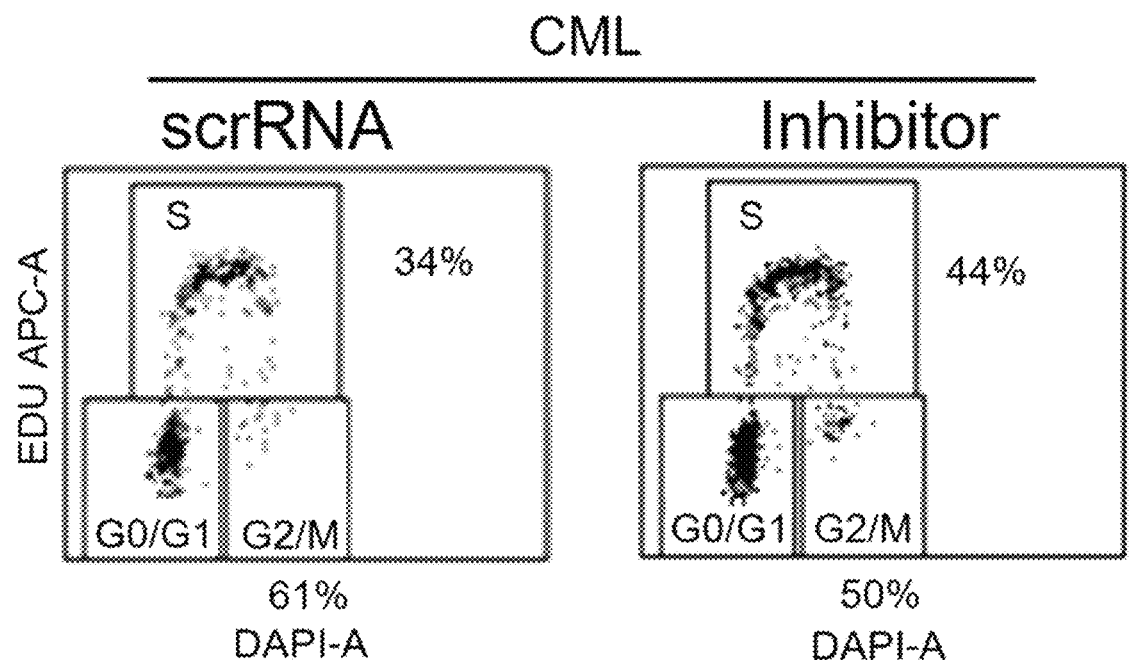

In view of the enhancing effects of miR-126 KD on the anti-leukemic activity of NIL, we reasoned that miR-126 could represent a therapeutic target for eliminating LSC. Although microRNAs can be targeted with oligonucleotide therapeutics (ONTs), it remains challenging to achieve efficient and cell-selective delivery of ONTs in vivo. Thus, we designed a novel miR-126 inhibitor by linking an anti-miR-126 oligodeoxynucleotide (ODN) to a cytosine guanine dinucleotide (CpG) ODN, a ligand for the intracellular protein Toll-like receptor 9 (TLR9). To allow for systemic administration, we chemically modified the CpG-miR-126 inhibitor to resist serum nucleases, using phosphothioation and 2'OMe-modified nucleotides in the CpG ODN and anti-miR-126 moieties, respectively. We compared the specificity and efficiency of CpG-miR-126 inhibitor uptake with a nanoparticle (NP) delivery method previously reported by our group[6]. We incubated K562 cells with fluorescently-labeled CpG-miR-126 inhibitor-Cy3 (CpG), human CD45 antibody (Ab)- or transferrin (TF)-conjugated NPs containing miR-126 inhibitor-Cy3 (Ab-NP or TF-NP), or naked miR-126 inhibitor-Cy3 (control), in the absence of any reagents routinely used for nucleic acid transfection. Flow cytometric analysis at 4 h and 24 h after treatment (FIG. 12A and FIG. 12B) showed that CpG-miR-126 inhibitor-Cy3 was taken up by 99% of the K562 cells at both 4 h and 24 h, compared with 24% and 30% of the cells incubated with Ab-NP and 74% and 88% of the cells incubated with TF-NP at 4 h and 24 h, respectively. K562 cells did not take up naked miR-126 inhibitor (control) (FIG. 12B). Efficient miR-126 down-regulation by CpG-miR-126 inhibitor-Cy3 in K562 cells was shown at 24 h (FIG. 12C). We further showed by flow cytometry that, even without routinely used transfection reagents, the CpG-miR-126 inhibitor-Cy3 was internalized by HUVECs as well as by human normal and CML Lin-CD34+CD38− cells at 4 h (FIGS. 12D-12F); >95% cells were positive for CpG-miR-126 inhibitor-Cy3 uptake in all three cell types. CpG-miR-126 inhibitor-Cy3 uptake led to efficient miR-126 down-regulation in HUVECs and HSCs (FIGS. 12G-12I). We also observed increased cell cycling in both CpG-miR-126 inhibitor-treated normal and CML HSCs, as compared to CpG-scrambled RNA (scrRNA)-treated controls (FIG. 12J and FIG. 12K).

Figure 12L:
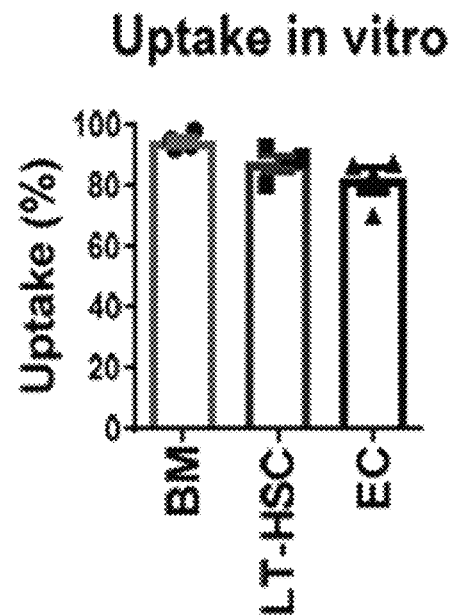
FIG. 12L and FIG. 12M show uptake of Cy3 by flow cytometry at 4 h (FIG. 12L) and miR-126 expression by QPCR at 24 h, where the legend from top to bottom represents each group of two data sets from left to right (FIG. 12M) in CIVIL BM mononuclear cells, LT-HSCs and ECs treated with CpG-miR-126 inhibitor-Cy3 (500 nM) (n=4 biologically independent samples for all).
Figure 12M:
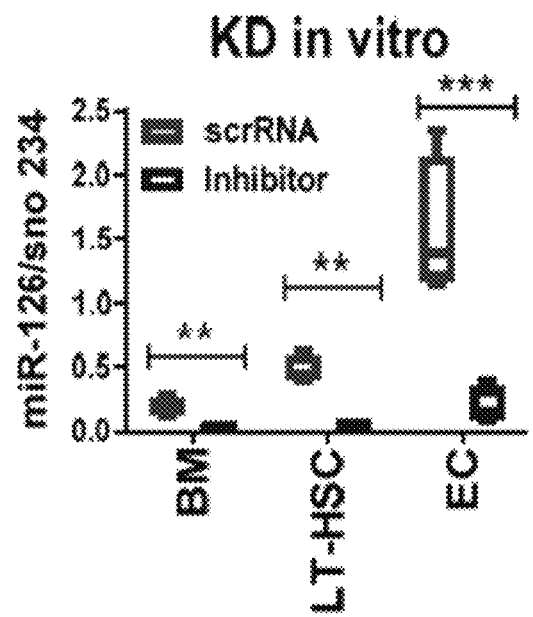
Figure 12N:
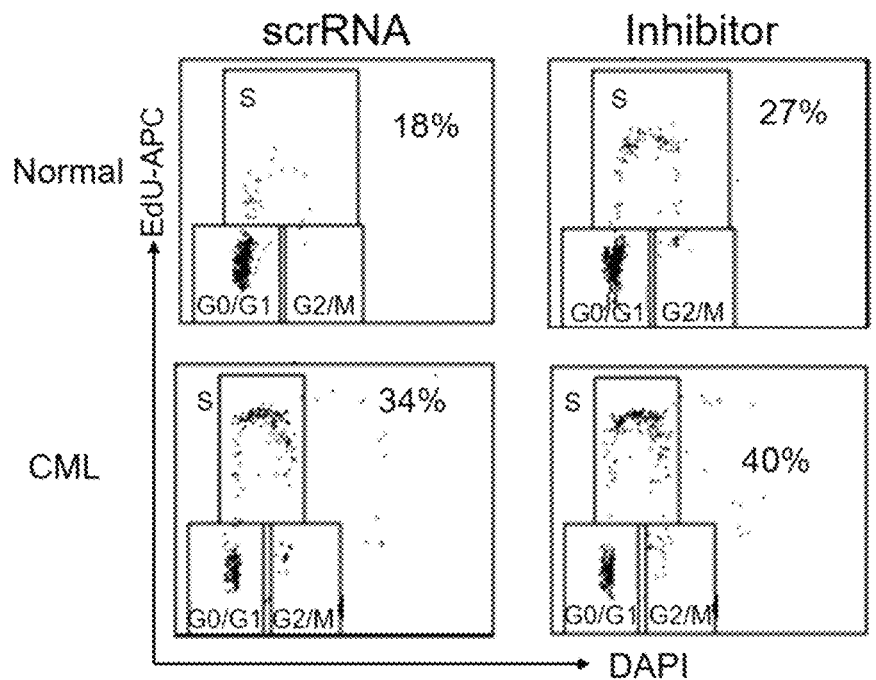
FIG. 12N shows cell cycling by EdU and DAPI staining at 72 h after addition of CpG-miR-126 inhibitor (500 nM) in normal and CML BM LT-HSCs. The experiments were repeated twice using biologically independent samples with similar results.
Figure 12O:
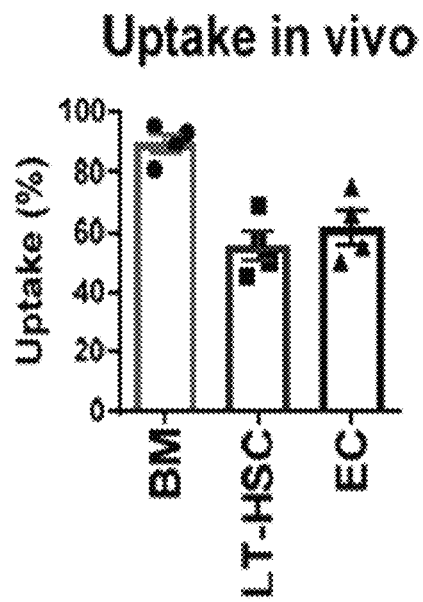
FIG. 12O shows Cy3 uptake in BM, LT-HSCs and ECs, as assessed at 16 h by flow cytometry, from CML mice treated with one dose (5 mg/kg, iv injection) of CpG-miR-126 inhibitor-Cy3 (n=3 independent samples).
Figure 12P:
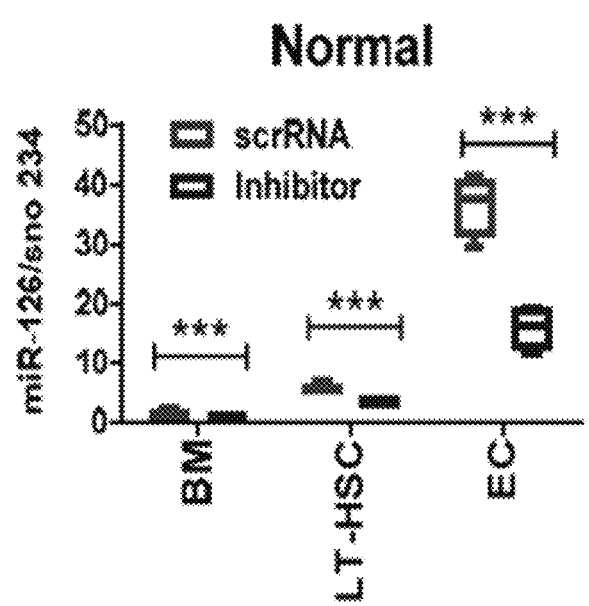
Figure 12Q:
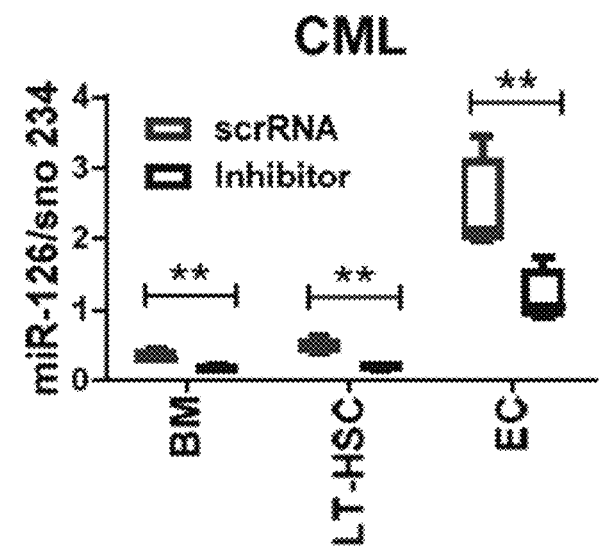

Next, we evaluated CpG-miR-126 inhibitor-Cy3 uptake in mouse LT-HSCs and ECs in vitro and in vivo. Following in vitro exposure to CpG-miR-126 inhibitor-Cy3, efficient uptake at 4 h and miR-126 down-regulation at 24 h were shown by flow cytometry and QPCR, respectively (FIG. 12L and FIG. 12M). We also observed increased cell cycling in normal and CML BM LT-HSCs treated with the CpG-miR-126 inhibitor (FIG. 12N). We treated normal and CML mice with one dose (5 mg/kg, iv injection) of CpG-miR-126 inhibitor-Cy3. At 16 h post-treatment, efficient in vivo uptake was demonstrated by flow cytometry in both LT-HSCs (56±5%) and ECs (62±3%) isolated from femurs (FIG. 12O). After CpG-miR-126 inhibitor treatment (5 mg/kg/day, iv, daily) for 3 days, we sorted LT-HSCs and ECs and found significant miR-126 down-regulation (FIG. 12P and FIG. 12Q).

CpG-miR-126 Inhibitor Enhances In Vivo Targeting of CML LSCs in Combination with TKI Treatment.

Figure 13A:
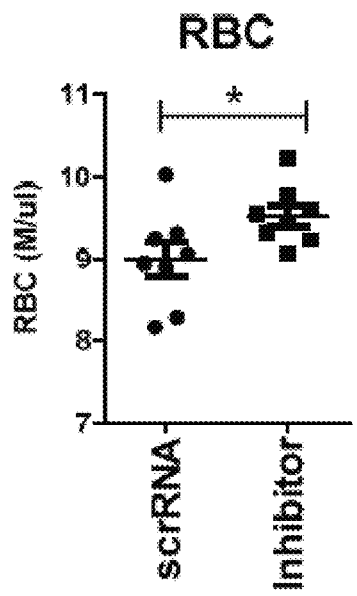
FIGS. 13A-13N. The figure shows CpG-miR-126 inhibitor in combination with Nilotinib enhances in vivo targeting of CML LSCs.
Figure 13B:
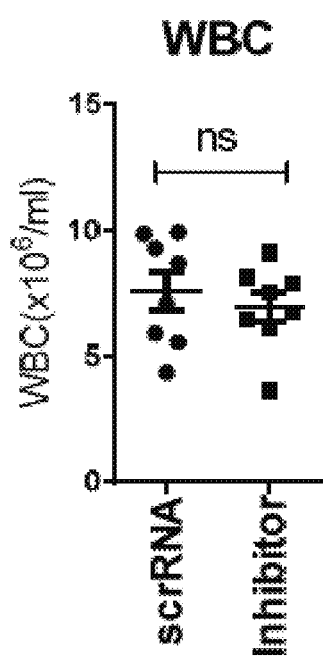
Figure 13C:
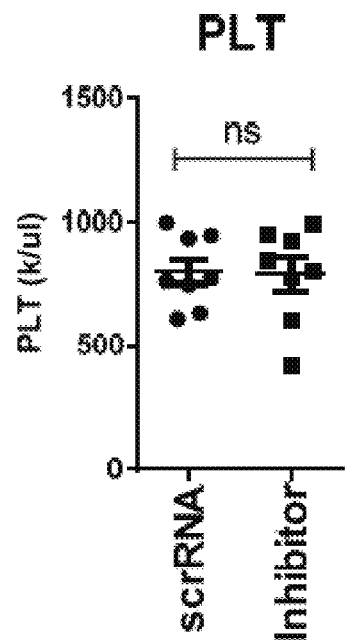
Figure 13D:
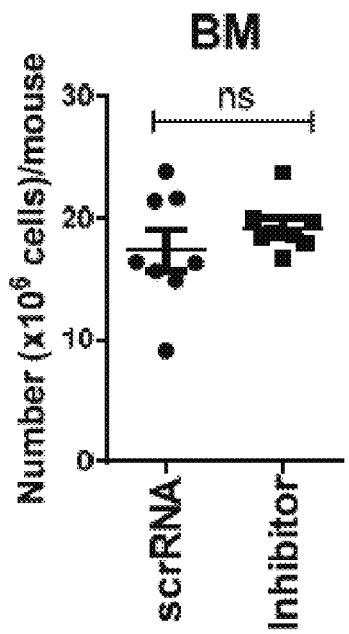
Figure 13E:
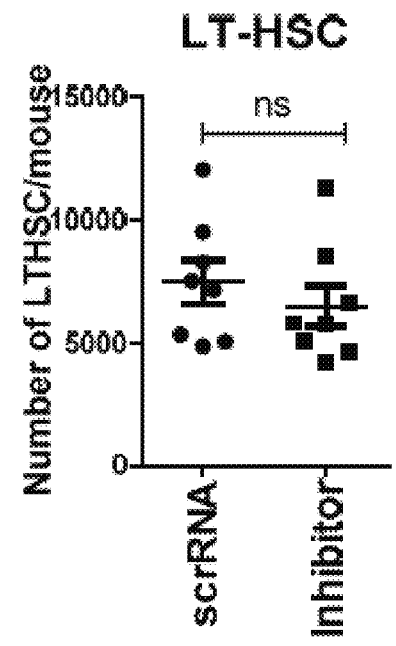
Figure 13F:
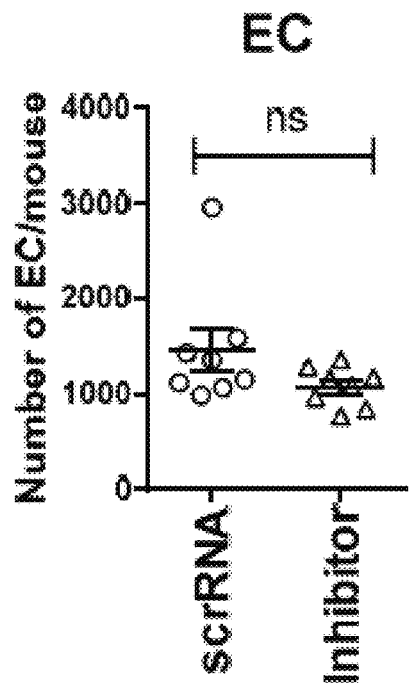
Figure 13G:
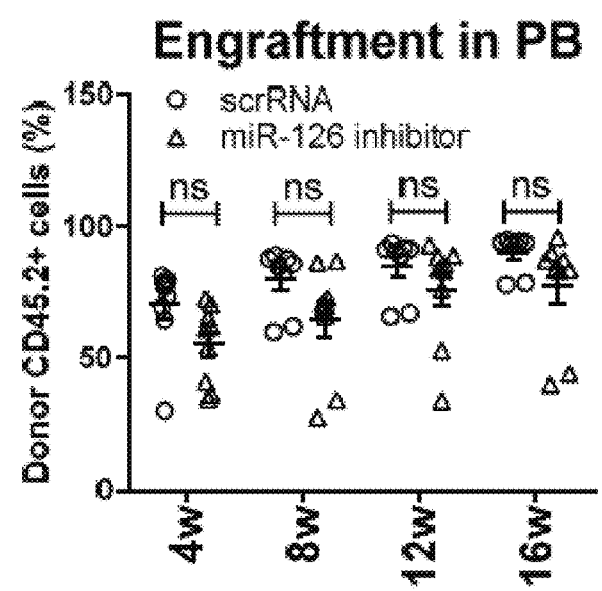
FIGS. 13G-13I show donor cell engraftment in PB every 4 weeks (FIG. 13G) and in BM and spleen at 16 weeks (FIG. 13H) and donor LT-HSC number in BM (FIG. 13I) from CD45.1 recipient mice transplanted with BM cells ($3 \times 10^5$/mouse, n=9 for each group) from treated CD45.2 B6 mice from FIGS. 13A-13F.
Figure 13H:
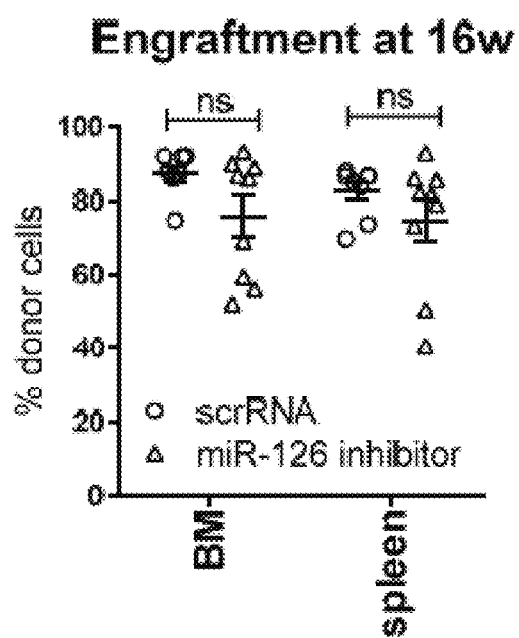
Figure 13I:
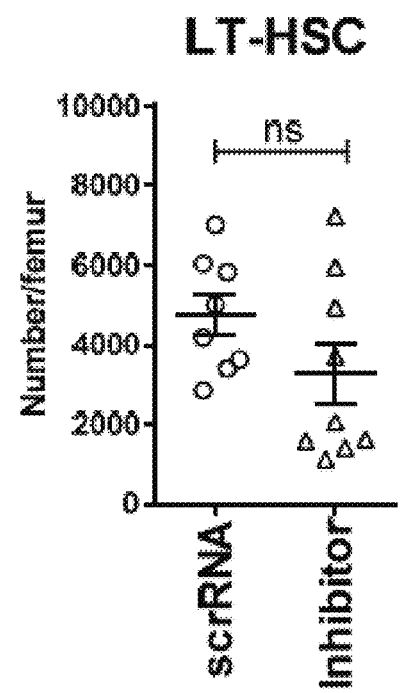

We next tested the effects of the CpG-miR-126 inhibitor in normal mice to ensure that the compound does not have hematologic toxicity. We treated WT B6 mice with CpG-scrRNA (scrRNA) or CpG-miR-126 inhibitor (inhibitor, 5 mg/kg/day i.v.) for 3 weeks, after which we collected their BM cells and transplanted them into recipient mice (3×10$^5$ BM cells/mouse). Compared with scrRNA-treated control mice, inhibitor-treated mice showed increased numbers of red blood cells (RBC), but no significant differences in the numbers of WBCs or platelets (PLT) in PB (FIGS. 13A-13C), or in the numbers of mononuclear cells, LT-HSCs, or ECs in the BM (FIG. 13D and FIG. 13F). These findings are in line with the observation that miR-126 down-regulation in normal HSCs increases hematological output[4]. In the recipient mice receiving BM cells from donor mice treated with scrRNA or inhibitor, we observed no significant differences in donor cell engraftment in PB, BM or spleen (FIG. 13G and FIG. 13H) or in donor LT-HSC numbers in BM (FIG. 13I) at 16 weeks after transplantation. These data demonstrate that the inhibitor lacks pre-clinical toxicity for normal hematopoiesis.

Figure 6F:
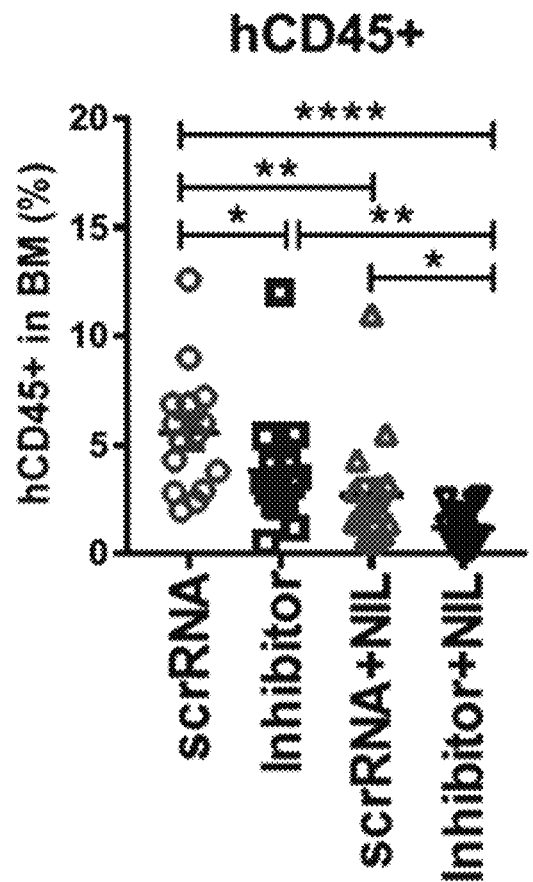
FIGS. 6F-6I show human CD45+(FIG. 6F), CD45+CD34+CD38− HSC (FIG. 6G) and CD45+CD34+CD38−CD90− LT-HSC (FIG. 6H) engraftment in BM of NSG-SGM3 mice transplanted with human CD34+ cells from CP CML patient samples and then treated with scrRNA (5 mg/kg, i.v. 4 times a week, n=15), inhibitor (5 mg/kg i.v. 4 times a week, n=14), scrRNA+NIL (50 mg/kg, daily by gavage, n=15), or inhibitor+NIL (n=16) for 3 weeks (total 60 mice).
Figure 6G:
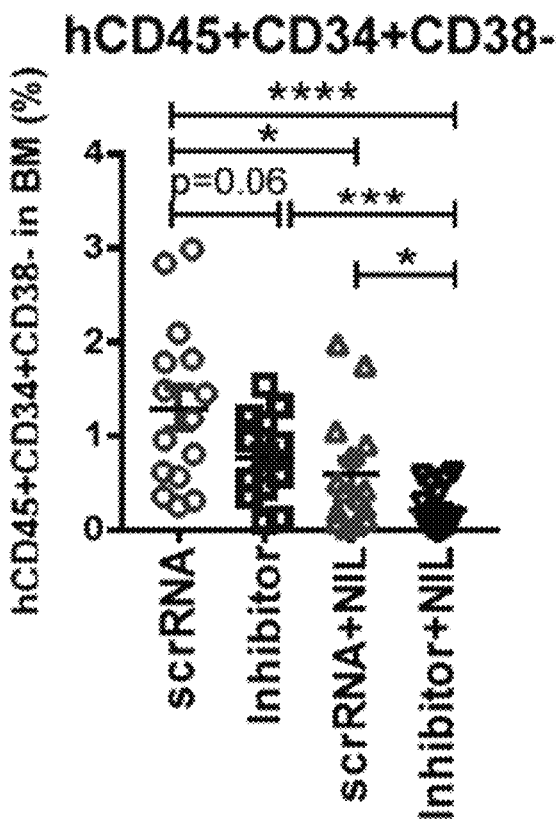
Figure 6H:
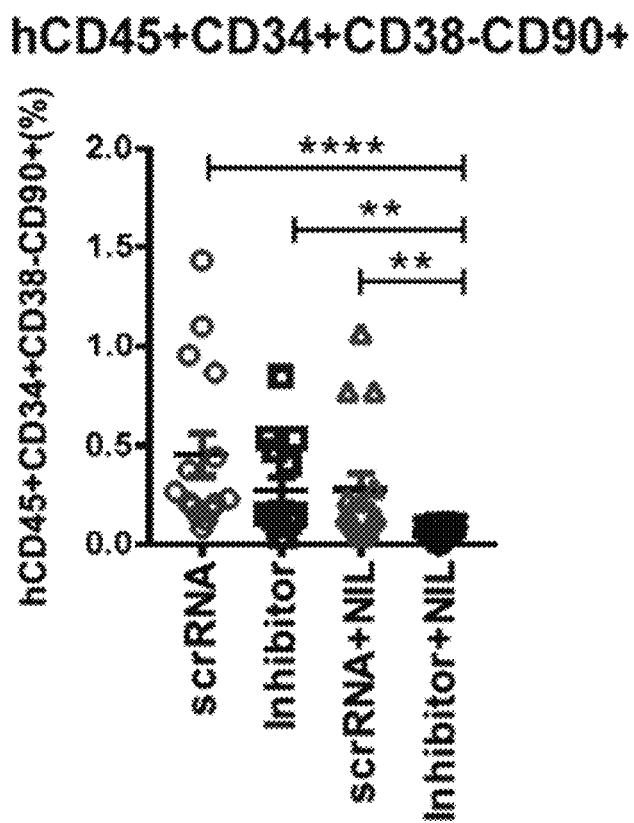
Figure 13J:
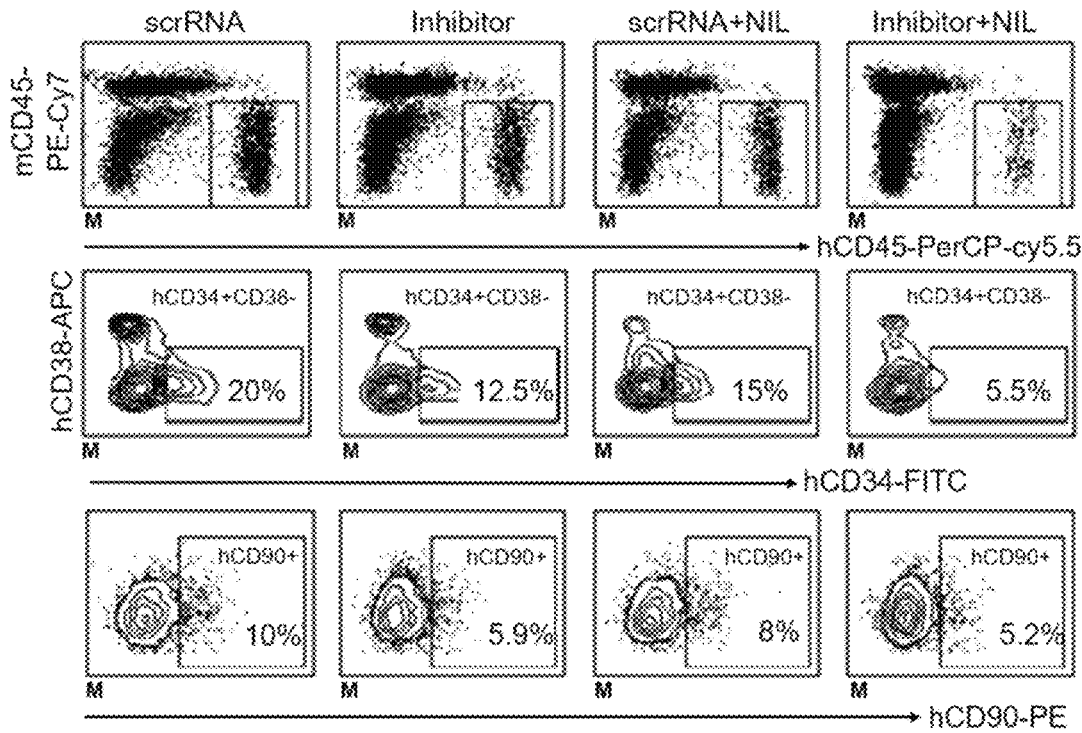
FIG. 13J shows reprehensive plots of human CD45+, CD45+CD34+CD38− and CD45+CD34+CD38−CD90+ cell engraftment in the BM of the NSG-SGM3 mice transplanted with human CP CML Lin-CD34+ cells (n=56) and then treated with scrRNA (5 mg/kg, i.v. 4 times a week), inhibitor (5 mg/kg i.v. 4 times a week), scrRNA+NIL (50 mg/kg, daily by oral gavage), or inhibitor+NIL for 3 weeks (n=14 for each group).
Figure 13K:
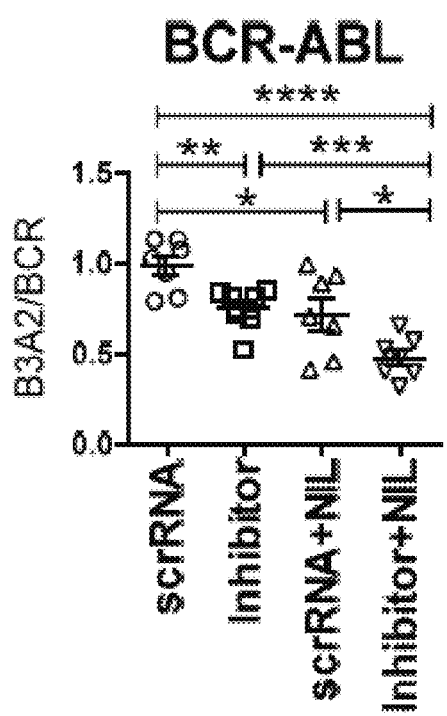

We then tested the effects of the inhibitor alone and in combination with NIL on human and mouse CML LT-HSCs in vivo. First, we transplanted human CD34+ cells from CP CML patients into NSG-SGM3 mice. At 6 weeks after transplantation, the mice were divided into 4 groups and treated with scrRNA (5 mg/kg i.v. 4 times a week), inhibitor (5 mg/kg, i.v. 4 times a week), scrRNA+NIL (50 mg/kg, daily by oral gavage), or inhibitor+NIL for 3 weeks, followed by assessment of human cell engraftment in PB, BM and spleen. We observed significantly reduced human CD45+, CD45+CD34+CD38− HSC and CD45+CD34+ CD38−CD90+ LT-HSC engraftment in the BM of inhibitor+ NIL treated mice as compared with scrRNA alone, inhibitor alone or scrRNA+NIL treated mice (FIG. 6F and FIG. 6H, FIG. 13J). QPCR analyses confirmed that the engrafted human CD45+ cells were BCR-ABL positive (FIG. 13K).

Figure 6J:
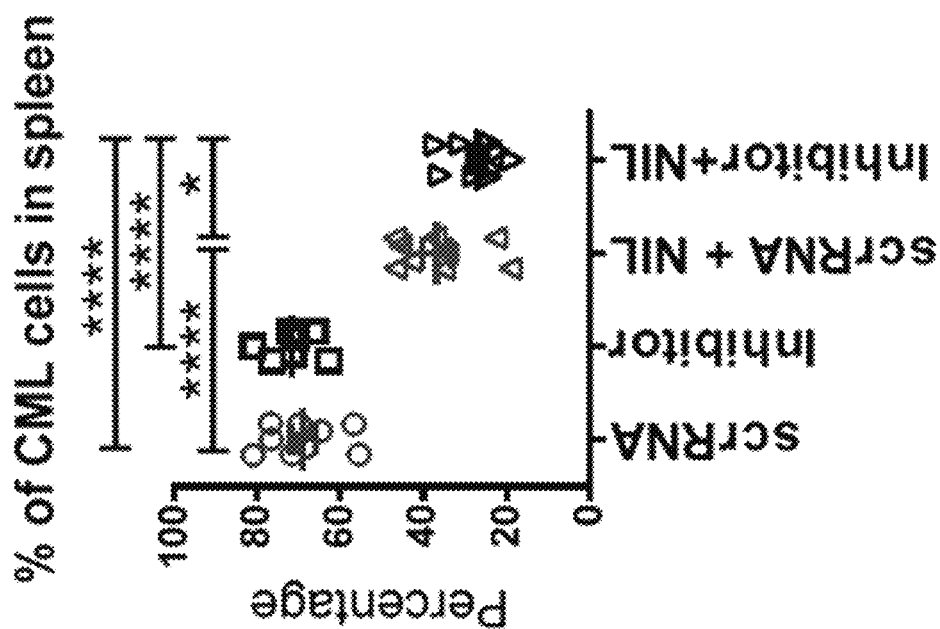
Figure 6I:
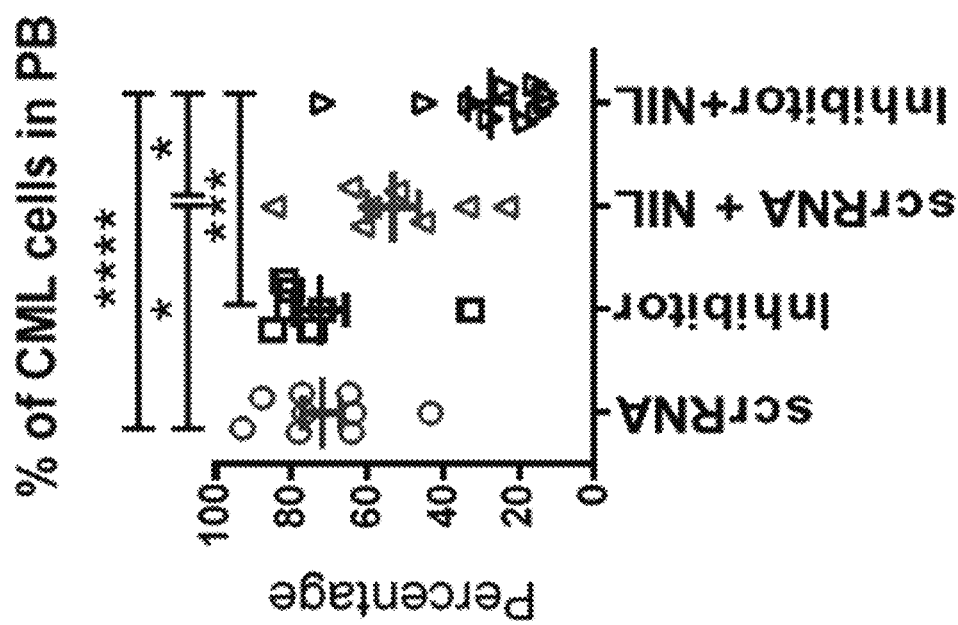
Figure 6L:
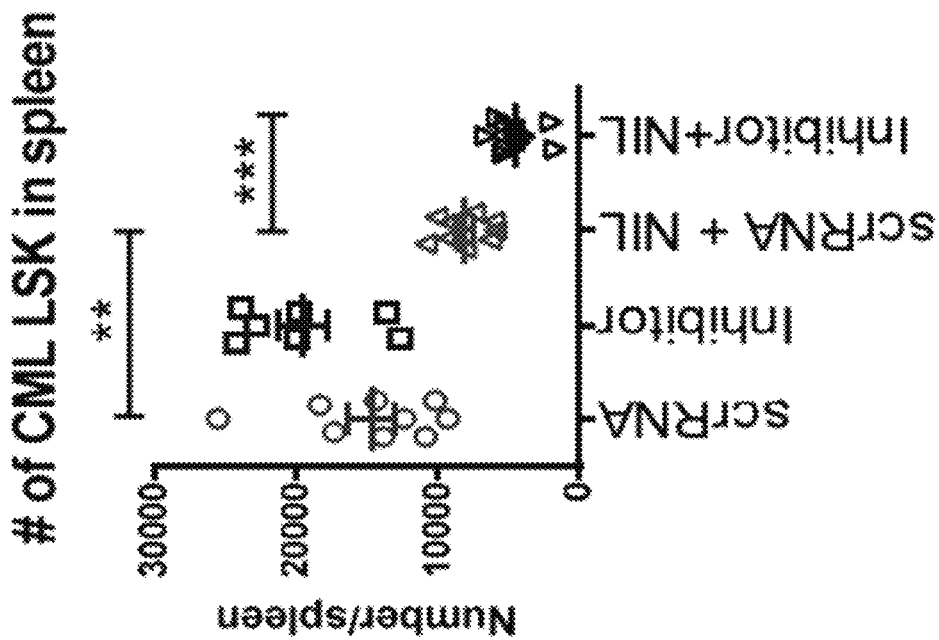
Figure 6K:
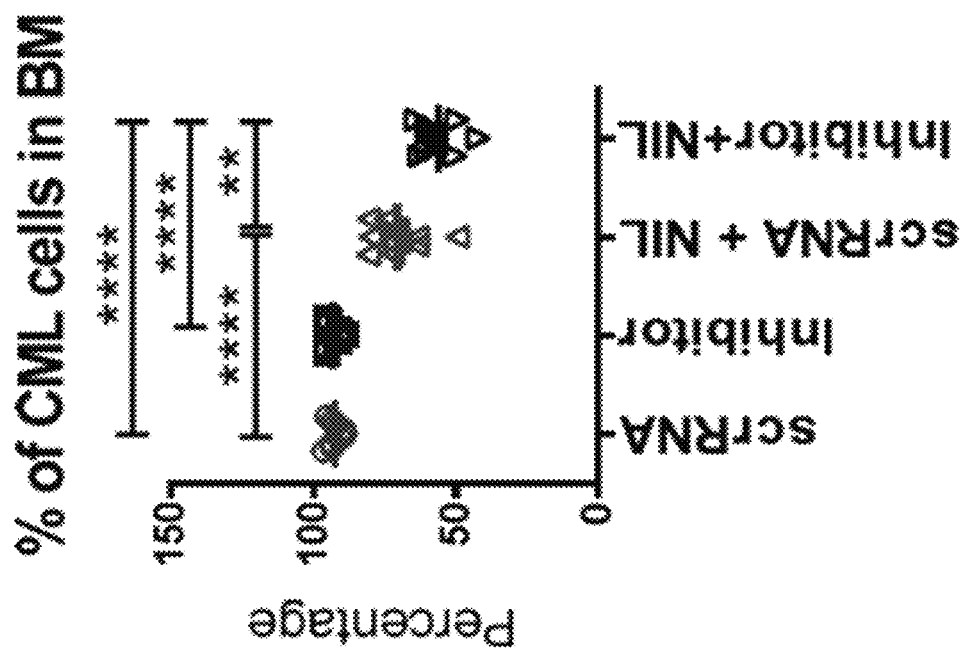
Figures 6M, 6N:
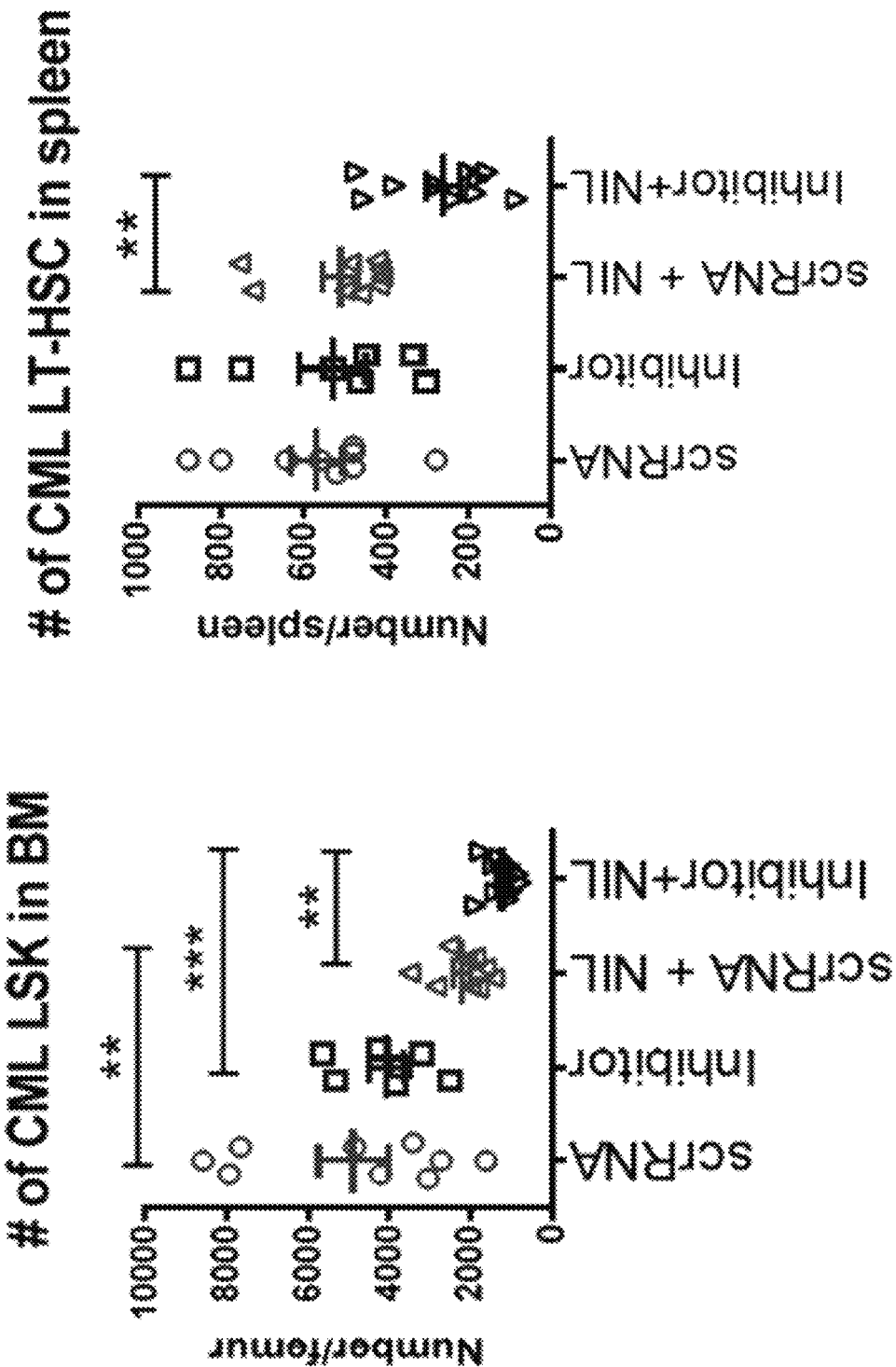
Figure 6O:
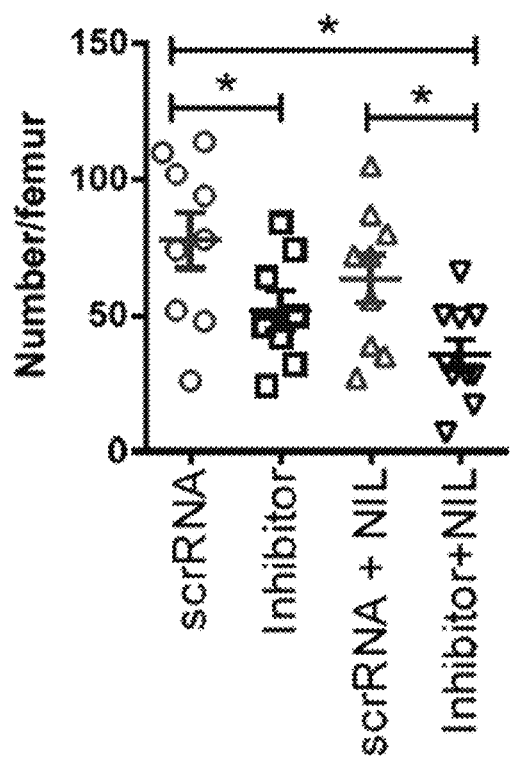
Figure 6P:
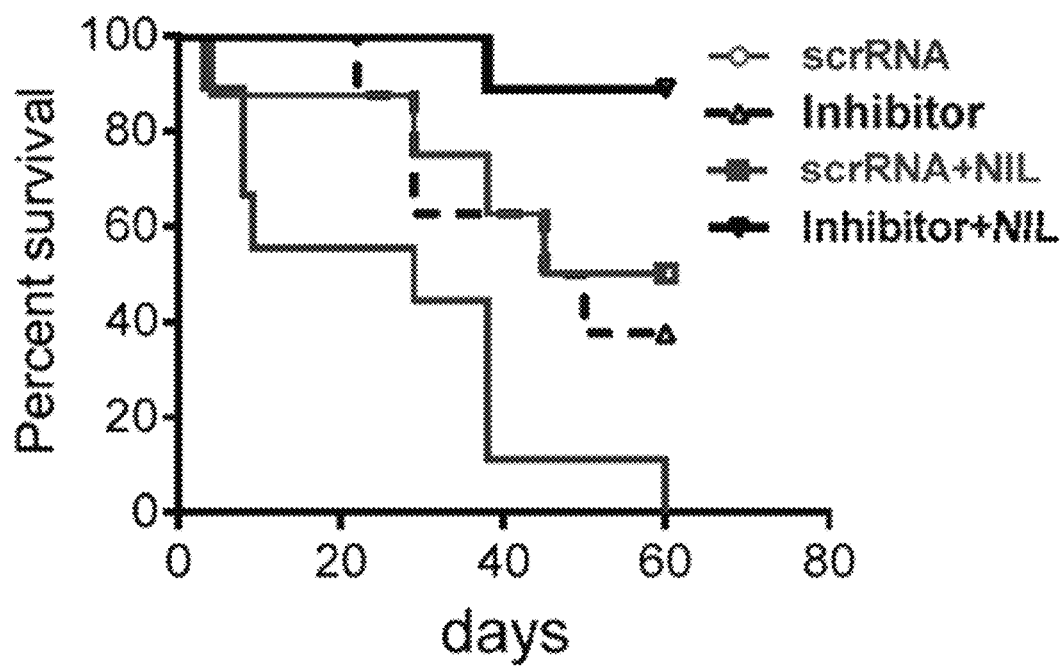
FIG. 6P shows survival of another cohort of CML mice treated with scrRNA (n=9), inhibitor (n=8), scrRNA+NIL (n=8), or inhibitor+NIL (n=9) for 3 weeks (total 34 mice). The line with the lowest value at day 60 represents data for scrRNA treated mice, the line with the second lowest value at day 60 represents data for Inhibitor treated mice, the line with the second highest value at day 60 represents data for scrRNA+NIL treated mice and the line with the highest value at day 60 represents data for Inhibitor+NIL treated mice. The log-rank test was used to assess significant differences between survival curves.
Figure 13L:
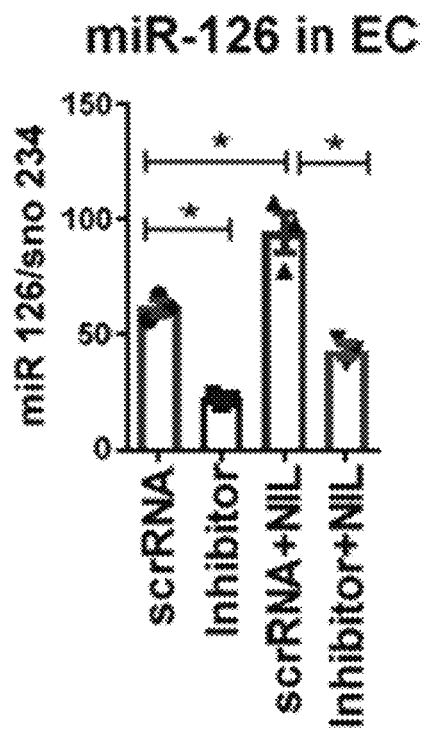
Figure 13M:
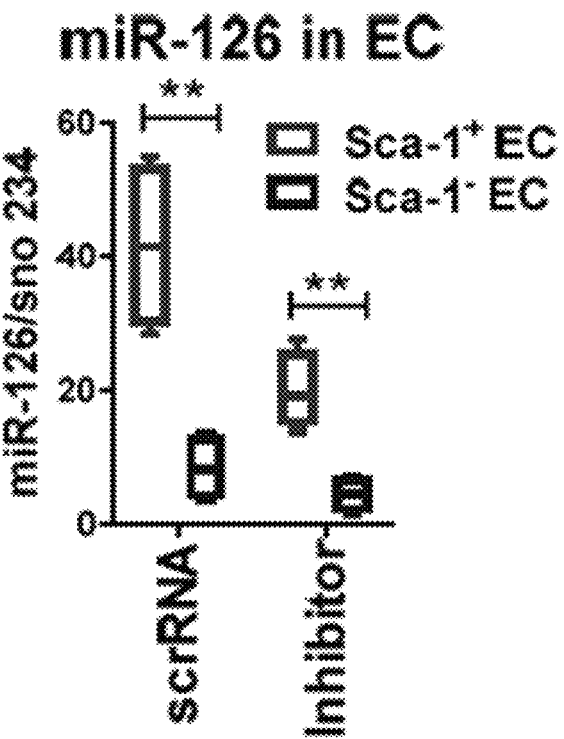

Next, we transplanted BM cells from SCLtTA/BCR-ABL mice (CD45.2) into congenic B6 mice (CD45.1). Following confirmation of CML development at 4 weeks after transplantation, mice were treated as above with scrRNA, inhibitor, scrRNA+NIL, or inhibitor+NIL for 3 weeks. As EC-derived miR-126 plays a key role in LSC maintenance, we sorted BM ECs from treated mice and confirmed significantly lower miR-126 levels in total ECs, Sca-1+ECs and Sca-1-ECs from inhibitor-treated mice, as compared with scrRNA-treated mice (FIG. 13L and FIG. 13M). Mice receiving the combination of inhibitor+NIL had a significant reduction in the percentage of CD45.2+CML cells in PB, spleen and BM (FIGS. 6I-6K), and a significant reduction in the numbers of CML LSK cells and LT-HSCs in spleen and BM, as compared with all other groups (FIGS. 6L-6O). We followed a cohort of mice for survival studies after 3 weeks of treatment, and found that all of the mice treated with scrRNA alone died of leukemia within 60 days after treatment discontinuation, whereas 50% of the mice treated with inhibitor alone or scrRNA+NIL and 90% of the mice treated with the combination of inhibitor+NIL survived (p=0.0012; FIG. 6P).

To quantify the frequency of leukemia-initiating cells (LICs) after treatment, BM cells from leukemic mice treated with scrRNA, inhibitor, scrRNA+NIL, or inhibitor+NIL for 3 weeks were transplanted in limiting dilution assays into secondary congenic CD45.1 recipient mice. Treatment with the combination of inhibitor+NIL resulted in a significantly higher levels of depletion of LICs, as assessed by leukemia development in secondary recipient mice after 16 weeks of follow-up, as compared with treatment with scrRNA alone, inhibitor alone or scrRNA+NIL (FIG. 6Q). None of the secondary recipients that received BM cells from the mice treated with the combination of inhibitor+NIL developed leukemia. These results indicate that, compared with NIL treatment, treatment with a combination of NIL and the CpG-miR-126 inhibitor enhances the eradication of CML LSCs capable of engraftment in secondary recipients.

Discussion.

We report here that miR-126 expression levels in both human and mouse CML cells follow the hierarchy of hematopoietic differentiation, with more primitive hematopoietic stem cells or progenitors expressing higher levels of miR-126 than mature cells. Moreover, quiescent CML LT-HSCs have higher levels of miR-126 and a higher leukemia engraftment capacity than proliferating CML LT-HSCs, in line with findings reported for normal hematopoiesis[4]. Unexpectedly, we found that miR-126 levels are significantly lower in CML LT-HSCs than their normal counterparts, consistent with previous findings that a lower frequency of long-term repopulating cells are observed within CML LT-HSCs as compared to normal LT-HSCs[2]. Indeed, we demonstrated that BCR-ABL expression lowers mature miR-126 levels and increases pri- and pre-miR-126 levels, whereas pharmacologic BCR-ABL inhibition by a TKI increases mature miR-126 levels and decreases pri- and pre-miR-126 levels. Altogether, these data support a role for BCR-ABL in altering the biogenesis of endogenous miR-126.

Figure 7J:
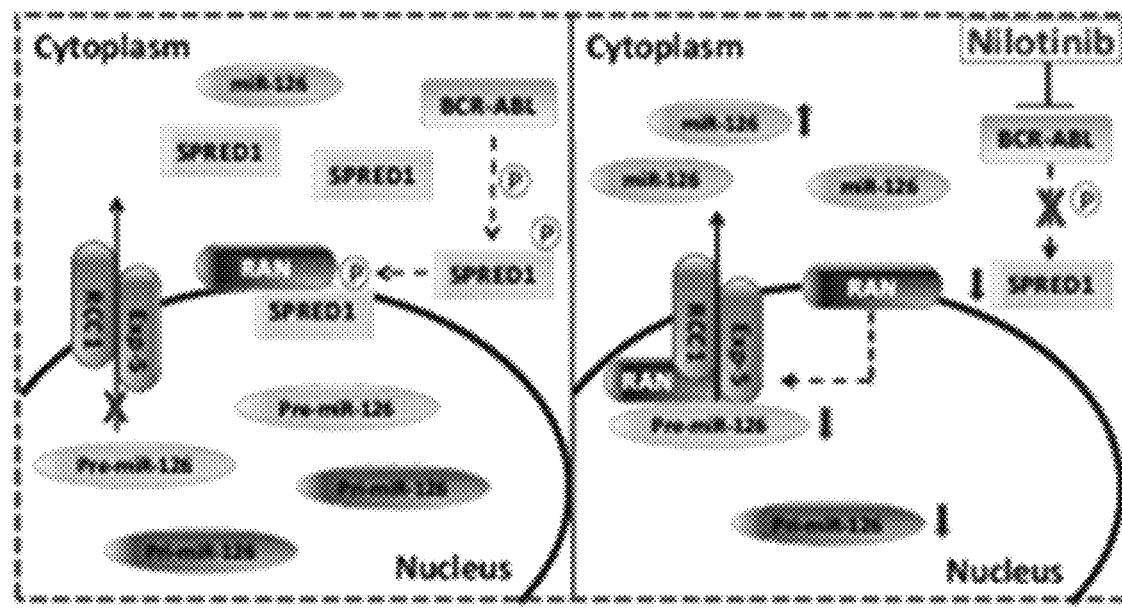
Figure 7K:
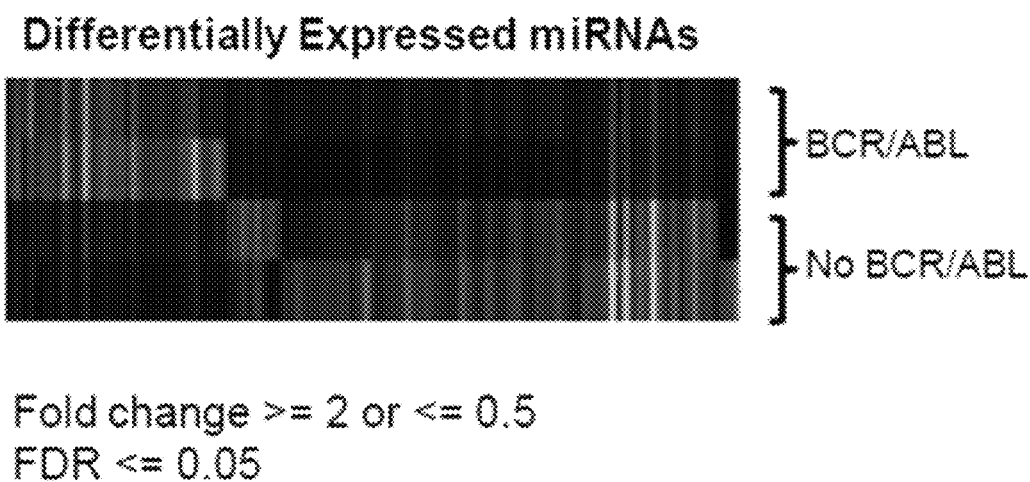

To our knowledge, BCR-ABL-dependent down-regulation of miR-126 in CML cells and its mechanistic basis has not been previously reported. SPRED1, a validated miR-126 target[4,7,9,14,15], is a tyrosine kinase substrate known to inhibit GF-mediated activation of RAS protein family members and, in turn, the RAS/MAPK/ERK pathway[16]. Tyrosine residue phosphorylation is required for SPRED1 inhibition of RAS/MAPK/ERK activation[17]. We show here that SPRED1 is a substrate for BCR-ABL and that BCR-ABL-induced SPRED1 phosphorylation is critical for miR-126 biogenesis in CML. We found that BCR-ABL-phosphorylated SPRED1 binds with RAN, a RAS family member, disrupts the RAN/Exp-5/RCC1 complex, which is involved in pre-miRNA nucleus-to-cytoplasm shuttling, increases nuclear levels of pri- and pre-miR-126 and decreases cytoplasmic levels of mature miR-126. Conversely, BCR-ABL inhibition disrupts the binding of SPRED1 with RAN, enhances formation of the RAN/Exp-5/RCC1 complex, increases mature miR-126 levels, and decreases pri- and pre-miR-126 levels (FIG. 7J).

Because miR-126 is necessary for normal and clonal HSC quiescence and continuous down-regulation of miR-126 can cause clonal exhaustion[4,8], we reasoned that this autoregulatory loop must be circumvented in order to maintain a reservoir of quiescent CML LSCs. Previous reports suggested that BM ECs participate in the regulation of normal hematopoiesis[10,26]. Here, we showed that among cell populations in the leukemic BM niche, ECs express the highest miR-126 levels and supply miR-126 to CML cells, likely through EV trafficking. Furthermore, consistent with previous reports showing that Sca-1+ECs are associated with quiescent normal HSCs and that Sca-1-ECs are associated with proliferating normal HSC in the marrow[10], we found that endosteal Sca-1+ECs express higher levels of miR-126 than central marrow Sca-1-ECs and are associated with a larger fraction of quiescent BCR-ABL+ LT-HSCs, which also express higher miR-126 levels than proliferating BCR-ABL+ LT-HSCs. Our data support a functional interplay between ECs and HSCs in CIVIL, resulting in a non-random BM distribution of the quiescent CML LSC fraction that is more likely to be found proximal to the high-level miR-126-expressing ECs from the endosteal marrow than to the low-level miR-126-expressing ECs from the central marrow. The functional relevance of the exchange of miR-126 between ECs and LT-HSCs to leukemia growth was demonstrated by showing a decreased engraftment of CML LSCs and improved survival observed in recipient mice with miR-126 KO in the endothelial compartment transplanted with BCR/ABL+ LT-HSCs.

Our results may be clinically relevant to CML patients treated with TKI. Persistence of CML LSCs during TKI treatment is an active area of investigation, as these agents are remarkably potent against cycling cells, but fail to eliminate quiescent CML LSCs[3,27]. Using primary human CML cells and CML mouse models, we showed that the resistance of CML LSCs to TKI treatment is likely mediated by decreased levels of phosphorylated SPRED1 due to BCR-ABL inhibition, leading to increased endogenous miR-126 levels, which pushes LSCs into a relatively treatment-refractory quiescent state. Furthermore, miR-126 up-regulation in TKI-treated CML CD34+ cells resulted in decreased SPRED1 levels, activation of the MAPK/ERK pathway and increased cell survival[25,28]. Accordingly, miR- 126 KD in CML cells and/or ECs enhances the anti-leukemic activity of TKI treatment by counteracting the undesired TKI-induced miR-126 up-regulation. In vivo, all NIL-treated CIVIL mice with genetic miR-126 KD in ECs survived, demonstrating the therapeutic potential of targeting miR-126 in CML.

For clinical translation of this concept, we designed a novel CpG-miR-126 ODN inhibitor that could be efficiently taken-up by both hematopoietic and non-hematopoietic cells in the BM niche. We have previously shown that the uptake of CpG-ODN conjugated molecules depends on endocytosis by scavenger family dextran sulfate-sensitive receptors (SRs)[29,30], which are expressed on the surface of normal and malignant myeloid cells[31,32]. Following SR-mediated internalization, CpG-conjugates bind to endosomal TLR9, triggering their cytoplasmic release[29]. SRs and TLR9 are both expressed on hematopoietic cells and ECs33-36, and likely facilitate the efficient intracellular delivery of CpG-miR-126 inhibitor and its subsequent endosomal release and pharmacologic activity. We found that the CpG-miR-126 inhibitor was efficiently taken up by both LT-HSCs and ECs in vitro and in vivo, down-regulated miR-126 expression and reduced LT-HSC quiescence and frequency. Combination treatment with the CpG-miR-126 inhibitor and a TKI in CML mice resulted in increased survival, compared to treatment with either agent alone; moreover, no leukemia development in secondary recipients transplanted with BM cells from combination-treated mice was observed, suggesting that combination treatment results in the elimination of CML LSCs. In support of the possibility of clinical translation of this treatment strategy, we observed no hematologic toxicity in normal mice treated with CpG-miR-126 inhibitor.

Figure 13N:
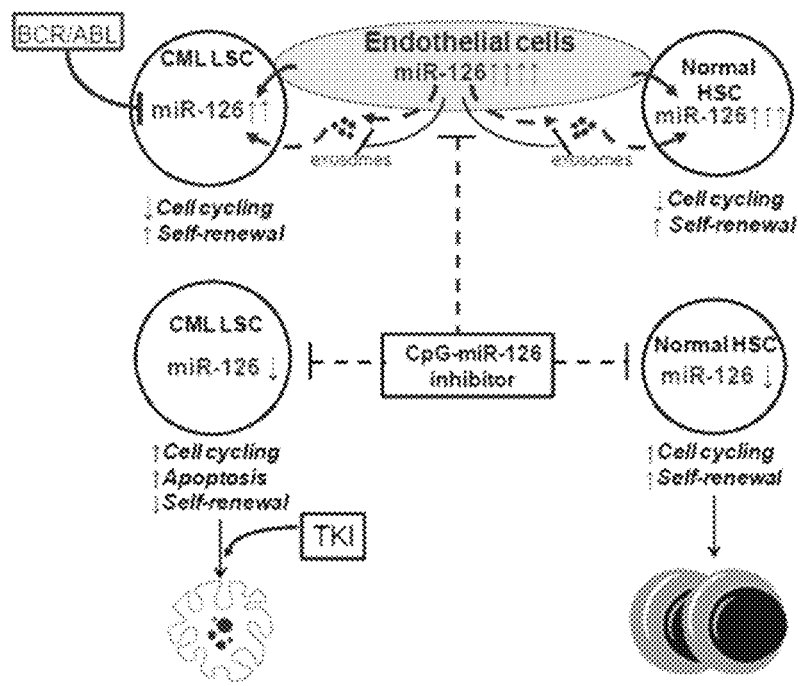

In summary, we report that BCR-ABL-mediated SPRED1 phosphorylation down regulates miR-126 biogenesis in CML LSCs, such that CIVIL LSC quiescence and leukemogenic capacity relies on trafficking of miR-126 from ECs to LSCs in the BM niche (FIG. 13N). Consistent with this model, TKI treatment inhibits BCR-ABL-induced SPRED1 phosphorylation, leading to the undesired increase in miR-126 levels. Based on the proof-of-concept findings reported here, which showed that in vivo treatment of CML mice with a newly-developed CpG-miR-126 inhibitor enhances TKI activity in vivo and results in LSC elimination; this CpG-miR-126 inhibitor is now being translated to the clinic for the treatment of CML patients.

Animal studies. Inducible transgenic SCLtTA/BCR-ABL mice in the FVB/N background[37,38] were backcrossed to the B6 background (CD45.2) for 10 generations. Transgenic BCR-ABL mice were maintained on tetracycline water at 0.5 g/L. Withdrawal of tetracycline results in expression of BCR-ABL and generation of a CML-like disease in these mice[37,38]. Unless otherwise indicated, BCR-ABL expression was induced for 2-3 weeks by tetracycline withdrawal in 6-8 weeks old male and female mice and then BM cells (from both tibias and femurs) were collected for experiments. SCLtTA/BCR-ABL mice (CD45.2, B6) were also bred with CD45.1 B6 mice to produce CD45.1/CD45.2 SCLtTA/BCR-ABL mice as donors. miR-126$^{flox/flox}$ mice (B6, from Dr. Kuo, Stanford) were crossed with Mx1-cre, Tie2-cre (both from The Jackson Laboratory) and SCLtTA/BCR-ABL mice (all B6) to obtain the following strains: miR-126$^{flox/flox}$/Mx1-cre, SCLtTA/BCR-ABL/miR-126$^{flox/flox}$/Mx1-cre, miR-126$^{flox/wt}$/Tie2-cre and miR-126$^{flox/flox}$/Tie2-cre. Recipient mice in the CD45.1 B6 background (from Charles River) were used to allow tracking of donor CD45.2 cells after transplantation. Recipients were 6 to 8 weeks old male and female mice and were irradiated at 900 cGy within 24 h before transplantation. The number of mice for each study group was chosen based on the expected endpoint variation (i.e., engraftment rate and latency period of leukemia) and on the availability of mice of different strains. Mice of the same gender and age were randomly divided into groups. Investigators were blinded to mouse genotype while performing treatment or monitoring engraftment or survival. Mouse care and experimental procedures were performed in accordance with federal guidelines and protocols and were approved by the Institutional Animal Care and Use Committee at the City of Hope.

Engraftment of human cells in immunodeficient mice. GFP+ cells ($2\times10^5$ cells/mouse) selected from CML Lin-CD34+CD38− cells transduced with miRZip anti-miR-126 (126 KD) or control (Ctrl) lentiviruses were cultured with or without NIL (5 µM) for 96 h. Cells were then harvested, washed and transplanted via tail vein injection into sublethally irradiated (300cGy) 6-8 week old NOD.Cg-Prkdc$^{scid}$ Il2rg$^{tm1Wjl}$Tg (CMV-IL3,CSF2,KITLG)1Eav/MloySzJ mice (NSG-SGM3, The Jackson Laboratory). Engraftment of human CD45+ cells in PB was monitored at 6 weeks. Mice were euthanized after 16 weeks and femur marrow contents, spleen cells and blood cells were obtained at necropsy. To assess human cell engraftment, cells were labeled with anti-mouse CD45 and anti-human CD45 and CD33 antibody and analyzed by flow cytometry. To assess engraftment of malignant BCR-ABL expressing cells, BM cells obtained were evaluated for BCR-ABL mRNA levels by QPCR39.

In Vivo Treatment of Normal and CML Mice.

BM cells (CD45.2) were obtained from SCLtTA/BCR-ABL mice at 4 weeks after induction of BCR-ABL expression by tetracycline withdrawal and were then transplanted by tail vein injection ($10^6$ cells/mouse) into irradiated (900 cGy) recipient mice (CD45.1). Blood samples were obtained 4 weeks after transplantation to confirm development of neutrophilic leukocytosis. Mice were treated with scrRNA (5 mg/kg, 4 times a week by vein injection), CpG-miR-126 inhibitor (inhibitor, 5 mg/kg, 4 times a week by vein injection), scrRNA+NIL (50 mg/kg, daily by oral gavage), or inhibitor+NIL for 21 days. After 3 weeks of treatment, mice were euthanized and BM cells from the right femur and spleen cells were analyzed for CML cell output. BM cells from the left femur of the treated mice were pooled and $4\times10^6$, $2\times10^6$, $1\times10^6$ and $5\times10^5$ cells/mouse (6 mice/dose×4 doses×4 conditions=96 mice) were transplanted into irradiated (900 cGy) recipient mice (CD45.1). WBC counts and CIVIL cell engraftment were monitored every 4 weeks. The mice were euthanized at 16 weeks, followed by assessment of donor CML cell engraftment in PB, BM and spleen. The fraction of mice showing evidence of CML development at 16 weeks after secondary transplantation was determined and the frequency of LICs was calculated using L-Calc software. Another cohort of mice was followed for survival up to 60 days after discontinuation of treatment. To determine the in vivo effect of the CpG-miR-126 inhibitor on normal hematopoiesis, normal mice were treated with scrRNA or inhibitor for 3 weeks, followed by assessment of WBC, RBC, PLT counts in PB and BM subpopulations in BM.

Isolation of Cells from Different Marrow Regions.

Tibias and femurs were excised from 8-12 week old mice. After removing the muscle and connective tissue, the bones were flushed 5 times using a 23-gauge needle and 3 ml of cold IMDM medium and collected as central marrow. The marrow-depleted bones were crushed gently with a mortar and pestle in cold IMDM medium and the bone fragments were incubated at 37° C. with 3 ml of 3 mg/ml collagenase I (Sigma) and gently agitated for 45 min. The digested bones were then filtered through a 40 μm strainer (BD Bioscience) and collected as endosteal marrow.

Flow Cytometry Analyses.

Human Lin-CD34+CD38+ committed progenitors, Lin-CD34+CD38− and Lin-CD34+CD38−CD90− primitive progenitors, and Lin-CD34+CD38−CD90+ stem cells were obtained by flow cytometry sorting. The following human antibodies were used: human biotinylated lineage antibodies against CD2 (clone RPA-2.10, cat 555325, BD), CD7(124-1D1, 13-0079-80, ebioscience), CD10(CB-CALLA, 15259439, Thermo Fisher), CD11b (C67F154, 13019682, Thermo Fisher), CD19 (eBioID3 (1D3), 13-0193-82, Thermo Fisher), CD33 (HIM3-4, MA1-19522, Thermo Fisher), CD235a (HIR2 (GA-R2), 13-9987-82, Thermo Fisher); human antibodies against CD34 (PE-Cy7, 581, 560710; FITC, 581, 555821; APC, 581, 555824; all from BD), CD38 (PE, HIT2, 560981; APC, HIT2, 555462, both from BD), CD90 (PerCP-Cy5.5, eBio5E10 (5E10), 45-0909-42, Thermo Fisher), CD33 (PE, P67.6, 347787, BD), CD45 (FITC, 2D1,11-9459-42; PerCP-Cy5.5, 2D1,45-9459-42, Thermo Fisher), CD31 (PE, 390, 50-103-20, Thermo Fisher), Ki-67 (PE, B56, 556027; FITC, B56, 556026, BD), CD63 (PE-Cy7, H5C6, 561982, BD), CD9 (FITC, H19a, 312104, Biolegend), and CD81 (APC, JS81, 561958, BD). Mouse cells were obtained from PB, BM (from both tibias and femurs), or spleen. For analysis of stem and progenitor cells, c-kit+ cells were selected using anti-mouse CD117 microbeads or Lin-cells were selected using Lineage depletion microbeads (both from Miltenyi Biotec, San Diego, Calif.). The following mouse antibodies were used: mouse biotinylated lineage antibodies (all from ebioscience) against: CD3 (clone 17A2, cat 13-0031-85), CD4 (GK1.5, 13-0041-85), CD8 (53-6.7, 13-0083-85), B220 (RA3-6B2, 13-0452-85), CD19 (eBioID3 (1D3), 13-0193-85), IgM (eB121-15F9, 13-5790-85), Gr-1 (RB6-8C5, 13-5931-85), CD11b (M1/70, 13-0112-85), NK1.1 (PK136, 13-5941-85), Ter119 (clone TER-119, cat 13-5921-85), Flt3 (A2F10, 13-1351-85); mouse antibodies against Flt3 (PE, A2F10, 12-1351-82, ebioscience), Sca-1 (PE-Cy7, D7, 25-5981-82, ebioscience), CD117 (APC-eflu780, ACK2, 47-1172-82, ebioscience), CD16/32 (PE-Cy7, 2.4G2, 560829, BD), CD34 (Alexa Fluor 647, RAM34, 560230, BD), CD150 (PerCP-Cy5.5, TC15-12F12.2, 115922, Biolegend), CD48 (APC, HM48-1,17-0481-82, ebioscience; Pacific blue, HM48-1, 103418, Biolegend), CD45.1(PE-Cy7, A20, 25-0453-82; PerCP-Cy5.5, A20, 45-0453-80, both from ebioscience), CD45.2 (FITC, 104, 11-0454-85; eFluor450, 104,48-0454-82, both from ebioscience), CD45 (PE-Cy7, 30-F11, 25-0451-82, ebioscience), Ter119 (APC-eflu780, TER-119, 50-162-15, ebioscience), CD31 (APC, 390, 17-0311-82; PE, 390, 12-0311-82, both from ebioscience), CD166 (PE, FAB1172P, R&D Systems). Other antibodies include anti-streptavidin (PE, 12-4317-87; FITC, 11-4317-87; PerCP-Cy5.5, 45-4317-80, ebioscience) and Annexin V (PE, 559763, BD). Myeloid progenitors were identified as Lin-Sca-1-c-Kit+CD34+FcγRII/III$^{lo}$ (CMP), Lin-Sca-1-c-Kit+CD34+FcγRII/III$^{hi}$ (GMP), or Lin-Sca-1-c-Kit+CD34−FcγRII/III$^{lo}$ (MEP)[38,40]. Stem and progenitor populations were identified as LSK cells (Lin-Sca-1hic-Kithi) and long-term hematopoietic stem cells (LT-HSCs; LSK Flt3-CD150+CD48−)38, 41. Endothelial cells were identified as CD45−Ter119-CD31+. All analyses were performed on a LSRII flow cytometer (BD Biosciences) and sorting was performed on ARIAIII or ARIA SORP instruments (BD Biosciences).

Cell Culture.

Human HPCs (Lin-CD34+) and HSCs (Lin-CD34+CD38−) were cultured in Stemspan serum-free medium II (SFEM II, StemCell Technologies), supplemented with low concentrations of growth factors (GFs) similar to those present in long-term BM culture stroma-conditioned medium [granulocyte-macrophage colony-stimulating factor (GM-CSF) 200 pg/mL, leukemia inhibitory factor (LIF) 50 pg/mL, granulocyte colony-stimulating factor (G-CSF) 1 ng/mL, stem cell factor (SCF) 200 pg/mL, macrophage-inflammatory protein-1α (MIP-1α) 200 pg/mL, and interleukin-6 (IL-6) 1 ng/mL]42. Mouse BM LT-HSCs were cultured in SFEM II supplemented with 10 ng/ml SCF and 10 ng/ml TPO. Human Umbilical Vein Endothelial Cells (HUVEC) and K562 cells were recently purchased from Lonza and ATCC respectively. We confirmed that HUVEC cells are human CD31 positive by flow cytometry and that K562 cells are BCR-ABL positive by QPCR. These two cell lines were tested for mycoplasma contamination and both were negative. HUVEC cells were cultured in complete EGM-2 medium (Lonza) and mouse BM ECs were cultured in complete mouse endothelial cell medium (Cell biologics). K562 cells were cultured in RPMI-1640 medium supplemented with 10% FBS (Life Technologies). All cells were cultured at 37° C. with 5% $CO_2$ and high humidity.

Differential Ultracentrifugation.

Conditioned medium was made by centrifuging the culture medium containing FBS for 8-10 h at 100,000×g, 4° C. to remove the FBS-derived EV contamination and the supernatant was collected (leaving the FBS-derived EVs/protein pellet). The cells were cultured with the conditioned medium for 2 days. EVs were isolated by differential ultracentrifugation[43-45]. Briefly, the supernatant was collected and centrifuged for 5 min at 500×g, 4° C.; the supernatant was then collected and centrifuged for 10 min at 2,000×g, 4° C.; and the supernatant was then collected and centrifuged for 15 min at 10,000×g, 4° C. It was important that none of the pellets consisting of cells and cell debris was collected. The supernatant was then transferred to a new tube and centrifuged for 60 min at 100,000×g, 4° C. The EV pellet was washed once with PBS and centrifuged again for 60 min at 100,000×g, 4° C. to obtain the final EV pellet. The EV pellet was dissolved in 50 ul of PBS and stored at 4° C. for up to one week.

Nanoparticle Tracking Analysis.

NanoSight measurements were carried out in 0.2 μm filtered PBS. The concentration and size distribution profile of the particles isolated by differential ultracentrifugation were evaluated using a NanoSight NS300 instrument (Malvern, Worcestershire, UK) and NTA 3.2 software. Videos were recorded at camera level 15. Samples were diluted 1:100 in PBS to achieve a measured particle concentration of 5-15×$10^8$/mL in accordance with the manufacturer's recommendations. For each sample, three 60 sec videos were recorded and analyzed in the batch processing mode.

Electron Microscopy (EM).

Specimens at an optimal concentration were placed onto a 300-mesh carbon/formvar coated grids and allowed to absorb to the formvar for a minimum of 1 min. Grids were rinsed with ddH2O and stained for contrast using 1% uranyl acetate. The samples were viewed with an FEI Tecnai T12 transmission electron microscope at 120 keV and images were taken with a Gatan Ultrascan 2K CCD camera.

Cytofluorimetric Analysis.

A fraction was isolated from HUVEC-derived EVs using magnetic beads coated with anti-CD63 antibody (10606D, ThermoFisher). Briefly, EVs isolated from HUVEC by differential ultracentrifugation were incubated with magnetic beads coated with anti-CD63 antibody overnight. The bead-bound CD63+ EVs were selected using a DynaMag-5 magnetic separator (12303D, ThermoFisher), stained with PE-Cy7-anti-human CD63, FITC-anti-human CD9 and APC-anti-human CD81 (BD) antibodies and then analyzed by flow cytometry.

Lentiviral or Retroviral Transduction of Human and Mouse Cells.

GFP-expressing miRZip anti-miR-126-3p (126 KD, CS940MZ-1, a custom order from System Biosciences, with EF1a promoter for anti-miR-126-3p), miR-126 precursor (126 OE, CS940MR-1, a custom order from System Biosciences, with EF1a promoter for miRNA and PGK promoter for GFP-T2A-Puro expression) and control [MZIP000-PA-1, miRZip negative control; CD813A-1, pCDH-EF1-MCS-(PGK-GFP-T2A-Puro); both from System Biosciences] lentiviruses were produced and used for transduction of human and/or mouse HSCs, HUVECs and mouse ECs. Briefly, human HPCs or HSCs were cultured overnight in SFEM II supplemented with IL-3 (25 ng/ml), IL-6 (10 ng/ml), SCF (50 ng/ml), TPO (100 ng/ml) and Flt-3 ligand (100 ng/ml). Mouse BM LT-HSCs were cultured overnight in SFEM II supplemented with mouse SCF (10 ng/ml) and mouse TPO (long/ml). The next day, cells were resuspended in SFEM II and lentiviral supernatant [multiplicity of infection (MOI)=10-20], supplemented with the above GFs and 1×TransDux virus transduction reagent (System Biosciences), and centrifuged at 1500 g for 90 minutes for transduction by spinoculation. We observed 30-60% of GFP+ cells in human HSCs and 90-100% in mouse LT-HSCs transduced with 126 KD lentivirus (MOI=20), and 10-30% of GFP+ cells in human HSCs and 30-50% in mouse LT-HSCs transduced with 126 OE lentivirus (MOI=10) at 48 h. HUVECs and mouse BM ECs were exposed to 126 KD or control lentiviral supernatant (MOI=10) with 1×TransDux virus transduction reagent, and 100% of GFP+ cells were detected at 48 h. Normal BM LSK cells were transduced with BCR-ABL or control retroviral supernatant (MOI=5) with polybrene (5 μg/ml, American Bioanalytical) by spinoculation, and 20-30% of GFP+ cells were detected at 48 h. GFP+ cells from the samples with low transduction efficiency (<80%) were selected by flow cytometry at 48 h for further studies.

Apoptosis, Cell Cycle, Cell Growth and Colony-Forming Cell Assays.

After transduction performed as above, GFP+ cells selected at 48 h were exposed to NIL (2 μM and 5 μM, Novartis) for another 72 h, and analyzed using assays for cell growth, apoptosis, cell cycle, CFC and CFC replating. Human HSCs and mouse LT-HSCs were also treated with CpG-miR-126 inhibitor or CpG-scrRNA (500 nM), with or without NIL (5 μM), for 72 h and analyzed for cell growth, apoptosis, cell cycle and CFC. Human CML HSCs co-cultured with control or miR-126 KD HUVECs and mouse CML LT-HSCs co-cultured with control or miR-126 KD ECs for 96 h, with or without NIL (5 μM), were also analyzed for cell growth, apoptosis, cell cycle and CFC. Cell growth was measured by Lumino Glo (Promega). Apoptosis was measured by labeling cells with Annexin V-PE or FITC or APC and 4, 6-diamidino-2-phenylindole (DAPI) (all from BD-PharMingen, San Diego, Calif.) and analyzed by flow cytometry. Cell cycle was analyzed by Ki-67-Alexa Fluor 647 (B56, BD) and DAPI labeling based on the manufacturer's protocol. Cells were also exposed to EdU (C10640, Invitrogen) for 2 h and EdU staining was analyzed according to the manufacturer's protocol. Cell proliferation was also measured by CFSE staining (Molecular probes) based on the manufacturer's protocol. For CFC, Lin-CD34+CD38− cells cultured with or without NIL (5 μM) were plated in methylcellulose progenitor culture, and burst-forming unit-erythroid and colony-forming unit-granulocyte and macrophage cells were counted after 14 days. Colony replating assays were performed by collecting and pooling colonies from primary CFC assays and plating 10,000 cells in secondary CFC assays.

QPCR Analysis.

To measure the miRNA and mRNA expression, total RNA was extracted using the miRNeasy Mini Kit (Qiagen, Valencia, Calif.). For miRNA expression, reverse transcription using MultiScribe™ Reverse Transcriptase and Q-PCR analysis using Taqman assays (Applied Biosystems) were performed according to the manufacturer's protocol. RNU44 and snoRNA234 was used as internal controls for human and mouse miRNA respectively. For mRNA expression, first-strand cDNA was synthesized using the Super-Script III First-Strand Kit and then QPCR was performed using TaqMan Gene Expression Assays (Thermo Fisher). BCR-ABL expression in human and mouse samples were measured with primer and probe sequences for BCR-ABL (B3A2 or B2A2), as previously described[46]. Results are presented as log 2-transformed ratio according to the 2−ΔCt method (ΔCt=Ct of target−Ct of reference).

TABLE 1

| Gene name | Assay ID |
| --- | --- |
| miR-126 | 2228 |
| RNU44 | 111094 |
| RNU48 | 1006 |
| snoRNA234 | 1234 |
| Pri-miR-126 | Hs03303230_pri |
| Pre-miR-126 | Hs04273250_s1 |
| PIK3R2 | Hs00178181_m1 |
| SPRED1 | Hs01084559_m1 |
| BCL-2 | Hs00608023_m1 |
| β2M | Hs00187842_m1 |
| Pik3r2 | Mm00435694_m1 |
| Spred1 | Mm01277511_m1 |
| β2m | Mm00437762_m1 | miRNA Labeling and Analysis.

K562, HUVEC, normal and CML CD34+CD38− cells were cultured and incubated with miR126 SmartFlare RNA probe (EMD Millipore) for 16 h. To ensure that the cell types, including K562, HUVEC and primary CML cells, were able to effectively endocytose the SmartFlare probes, we examined the uptake of probes in these cells using SmartFlare uptake control, scramble control and housekeeping 18S control (according to the manufacturer's guidelines). Cells were then washed in 1× phosphate buffered saline (PBS) and fixed in 4% paraformaldehyde for 3 min. Nuclei were counterstained with DAPI and the images were analyzed using a confocal microscope (Carl Zeiss).

Immunofluorescence.

K562 cells were collected and washed in PBS followed by spinning down onto slides using the CytoSpin4 Cytocentrifuge (600 rpm, 10 min). The cells were then fixed in 4% paraformaldehyde for 15 min and permeabilized in 0.5% Triton X-100 for 15 min. Non-specific epitopes were blocked with 5% bovine serum albumin (BSA) in PBS for 30 min. SPRED1 and RAN were visualized using anti-SPRED1 (ab64740, Abcam) and anti-RAN (ab4781, Abcam) antibodies and secondary anti-mouse/rabbit-Alexa 594/488 goat antibodies (Molecular Probes). 3D cell images were acquired using a Zeiss confocal Laser Scanning Microscope (Carl Zeiss). Nuclei were counterstained with DAPI.

Western Blotting and Immunoprecipitation Analysis.

Normal and CML CD34+ cells with or without miR-126 KD were lysed in buffer containing 0.5% Nonidet P-40, 0.5% sodium deoxycholate, 1 mM PMSF, 50 mM NaF, 1 mM Na3VO4, and a protease inhibitor cocktail (all from Sigma Diagnostics). Proteins were resolved on 10% sodium dodecyl sulfate-polyacrylamide gel electrophoresis (SDS-PAGE) gels and transferred to nitrocellulose membrane. Membranes were sequentially reprobed with primary and secondary antibodies. Primary antibodies included anti-SPRED1 antibody (M23-P2G3, #ab64740, Abcam), anti-RAN antibody (C-20, #SC-1156, Santa Cruz), anti-Exportin5 antibody (D7W6W, #12565, Cell Signaling), anti-PARP antibody (#9542, Cell Signaling), anti-RCC1 antibody (F-2, #SC-376049, Santa Cruz), anti-Actin antibody (C-4, #SC-47778, Santa Cruz), anti-phospho-Tyrosine antibody (4G10, #05-321, Millipore), anti-BCL-2 antibody (124, #15071, Cell Signaling), anti-phospho-ERK (#9101, Cell Signaling), anti-normal mouse IgG (#SC-2025, Santa Cruz), anti-normal rabbit IgG (#SC-2027, Santa Cruz), CD63 (10628D, ThermoFisher), TSG101(SAB2702167, Sigma), HSP90 (2D12, Enzo Life Sciences), Cytochrome C (sc-13156, Santa Cruz). Horseradish peroxidase-conjugated secondary antibodies were from Jackson ImmunoResearch Laboratories (Westgrove, Pa.). Antibody detection was performed using the Superfemto kit (Pierce Biotechnology, Rockford, Ill.). Protein levels were determined by densitometry using Image-Quant software (Amersham Pharmacia Biotech, Piscataway, N.J.).

For fractionation, the cells were collected and washed in PBS following fractionation into nuclear and cytoplasmic fractions using a subcellular fractionation kit (Thermo Fisher). Briefly, the cells were vigorously vortex in cytoplasmic extraction reagents and subsequently centrifuged to isolate the soluble cytoplasmic fraction. The remaining insoluble fraction, which contains nuclei, was suspended in nuclear extraction reagent and centrifuged to collect the nuclear fraction.

For IP, the cells were washed and harvested in ice-cold PBS and subsequently lysed in buffer containing 1 mM PMSF and 10 mM protease inhibitor cocktail. 500 µg of cell lysate was incubated with the indicated antibody overnight at 4° C. 30 µl of Protein A/G agarose beads (Calbiochem) were added and the mixture was inverted for 2 h at 4° C. For immunoblotting, immunoprecipitated complex or 30 µg of each cell lysate were separated on NuPAGE 4-12% gradient gels (Invitrogen) and immunocomplexes were visualized with enhanced chemiluminescence reagent (Thermo Scientific).

Kinase assay. One microgram of purified SPRED1 protein (Novus) was incubated with recombinant active c-Abl (Sigma) and 10 µCi of [γ-32P]ATP (PerkinElmer Life Sciences) in 50 µL of kinase buffer. Reactions were incubated at 30° C. for 1 h. Protein was separated on NuPAGE 4-12% gradient gels (Invitrogen). The gel was then dried and phosphorylated protein was visualized by autoradiography. SPRED1 phosphorylated by c-Abl kinase was visualized on the autoradiogram.

Northern Blot.

Northern blot was performed using a Northern blot-based protocol (LED) for micro-RNA detection using digoxigenin (DIG)-labeled miR-126 probes containing locked nucleic acids (LNA) and 1-ethyl-3-(3-dimethylaminopropyl) carbodiimide for cross-linking the RNA to the membrane. Briefly, total RNA was prepared using Trizol reagent (Life Technologies). 20 µg of total RNA was separated on a 15% TBE-Urea gel (Life Technologies) and transferred onto positively charged nylon membrane (Roche). The blots were hybridized with LNA miR-126 probes for 12 h. After washing twice with 2×SSC and 0.1×SSC (containing 0.1% SDS), the blots were immunoblotted with anti-DIG antibody (Roche) and exposed.

Small RNA Deep Sequencing Using Illumina HiSeq2500.

LSK cells from non-induced and induced CML mice were sorted and total RNA was extracted using the miRNeasy Mini Kit (Qiagen, Valencia, Calif.). Small RNA sequencing was performed using Illumina HiSeq2500 at the COH Integrative Genomics Core following the manufacturer's sample preparation protocol (TruSeq Small RNA Sample Prep kit, Illumina, Inc.) with some modifications. Briefly, 250ng of total RNA was used for smRNA sequencing library construction. Total RNA was ligated to the modified 3' Adapter (5' TCTGGAATTCTCGGGTGC-CAAGGAACTCC) (SEQ ID NO:1) with T4 RNA Ligase 2, truncated (NEB, M0242L) for 1 h at 22° C. The unligated free 3' adaptors were blocked by annealing with RT primer (5' GGAGTTCCTTGGCACCCGAGAATTCCA) (SEQ ID NO:2) at 75° C. for 5 min, 37° C. for 30 min and 25° C. for 15 min. The product subsequently was ligated to the modified 5' adaptor (5'GUUCAGAGUUCUACAGU-CCGACGAUCNNN) (SEQ ID NO:3) with T4 RNA ligase1 (NEB, M0204L) for 1 h at 20° C. The constructed smRNA library was reverse-transcribed, then subjected to a PCR amplification for 12 cycles, using barcoded index primers GX1 (CAAGCAGAAGACGGCATACGAGATNNNNN-NGTGACTGGAGTTCAGACGTGTGCTCTT CCGATC) (SEQ ID NO:4) and GX2 (AATGATACGGCGAC-CACCGAGATCTACACGTTCAGAGTTCTACAGTCC-GA) (SEQ ID NO:5); followed by 6% TBE PAGE gel purification with size selection (for targeted smRNAs of 17-35 nt). The final libraries were sequenced using the Illumina HiSeq2500 platform in the single read mode of 51 cycle of read1 and 7 cycles of index read. Real-time analysis (RTA) 2.2.38 software was used to process the image analysis and base calling.

Oligonucleotide Design and Synthesis.

The partially phosphothioated oligodeoxyribonucleotide (ODN) and miR-126 inhibitor or scrRNA was linked using 5 units of C3 carbon chain linker, (CH2)3 (indicated by x). The constructs were also conjugated with Cy3 to track the internalization in cells by flow cytometry. The sequences were as follows:

```
CpG-miR-126 inhibitor
                                          (SEQ ID NO: 6)
5' G*G*T GCA TCG ATG CAGG*G*G* G*G xxxxx mCmGmC mAmUmU mAmUmU mAmCmU mCmAmC mGmGmU mAmCmG mA-3'

CpG-scrRNA
                                          (SEQ ID NO: 7)
5' G*G*T GCA TCG ATG CAGG*G*G* G*G xxxxx mGmUmA mGmAmA mCmCmG mUmAmC mUmCmG mUmCmA mCmUmU mA 3'
'*'-phosphorothioation. One none bridging oxygen on
phosphate replaced with sulfur.
'm'-2'-O-methyl analogue of the nucleotide
```

Transferrin or Anti-CD45.2 Antibody Conjugated Nanoparticle Preparation.

Previously we developed a transferrin(TF)-targeted neutral NP delivery system[47,48]. Briefly, positively charged polyethylenimine and negatively charged miR-126 inhibitor-Cy3 or scrRNA-Cy3 form a polyplex core. This core was then loaded into pre-made anionic liposomal NPs to form lipopolyplex NPs. The formulation consisted of 1,2-dioleoyl-sn-glycero-3-phosphoethanolamine (DOPE), 1,2-dimyristoyl-sn-glycerol, methoxypolyethylene glycol (DMG-PEG) and linoleic acid. TF or anti-human CD45 antibody conjugated with 1,2-distearoyl-sn-glycero-3-phosphoethanolamine-N-[maleimide(polyethylene glycol)-2000] (DSPEPEG2000 maleimide) was then post-inserted to the surface of lipopolyplex nanoparticles (TF-NP and Ab-NP). The molar ratio of lipids to TF was 2000 as previously described[47,48] and the molar ratio of lipids to anti-CD45 antibody was optimized to 10,000.

Statistics.

Comparison between groups was performed by two-tailed, paired or unpaired Student's t-test. The log-rank test was used to assess significant differences between survival curves. All statistical analyses were performed using Prism version 6.0 software (GraphPad Software). Sample sizes chosen are indicated in the individual figure legends and were not based on formal power calculations to detect prespecified effect sizes. All of the in vitro experiments were performed 3-6 times using biologically independent samples; the in vivo experiments were performed using 6-16 mice in each group. P values <0.05 were considered significant. Results shown represent mean±SEM. *p<0.05, p<0.01, *p<0.001, ****p<0.0001.

Data Availability.

miRNA deep sequencing data produced in our laboratory and analysed in this study are available at the Gene Expression Omnibus (GEO) repository of the National Center for Biotechnology Information, under the accession number GSE107431.

REFERENCES

1. Sawyers, C. L. Chronic myeloid leukemia. *The New England journal of medicine* 340, 1330-1340 (1999).
2. Zhang, B., et al. Altered microenvironmental regulation of leukemic and normal stem cells in chronic myelogenous leukemia. *Cancer cell* 21, 577-592 (2012).
3. Chu, S., et al. Persistence of leukemia stem cells in chronic myelogenous leukemia patients in prolonged remission with imatinib treatment. *Blood* 118, 5565-5572 (2011).
4. Lechman, E. R., et al. Attenuation of miR-126 activity expands HSC in vivo without exhaustion. *Cell stem cell* 11, 799-811 (2012).
5. de Leeuw, D. C., et al. Attenuation of microRNA-126 expression that drives CD34+38-stem/progenitor cells in acute myeloid leukemia leads to tumor eradication. *Cancer research* 74, 2094-2105 (2014).
6. Dorrance, A. M., et al. Targeting leukemia stem cells in vivo with antagomiR-126 nanoparticles in acute myeloid leukemia. *Leukemia* 29, 2143-2153 (2015).
7. Li, Z., et al. Overexpression and knockout of miR-126 both promote leukemogenesis. *Blood* 126, 2005-2015 (2015).
8. Lechman, E. R., et al. miR-126 Regulates Distinct Self-Renewal Outcomes in Normal and Malignant Hematopoietic Stem Cells. *Cancer cell* 29, 602-606 (2016).
9. Kuhnert, F., et al. Attribution of vascular phenotypes of the murine Egfl7 locus to the microRNA miR-126. *Development* 135, 3989-3993 (2008).
10. Itkin, T., et al. Distinct bone marrow blood vessels differentially regulate haematopoiesis. *Nature* 532, 323-328 (2016).
11. Lechman, E. R., et al. miR-126 Regulates Distinct Self-Renewal Outcomes in Normal and Malignant Hematopoietic Stem Cells. *Cancer cell* 29, 602-606 (2016).
12. Nucera, S., et al. miRNA-126 Orchestrates an Oncogenic Program in B Cell Precursor Acute Lymphoblastic Leukemia. *Cancer cell* 29, 905-921 (2016).
13. Koschmieder, S., et al. Inducible chronic phase of myeloid leukemia with expansion of hematopoietic stem cells in a transgenic model of BCR-ABL leukemogenesis. *Blood* 105, 324-334 (2005).
14. Fish, J. E., et al. miR-126 regulates angiogenic signaling and vascular integrity. *Developmental cell* 15, 272-284 (2008).
15. Wang, S., et al. The endothelial-specific microRNA miR-126 governs vascular integrity and angiogenesis. *Developmental cell* 15, 261-271 (2008).
16. Bohnsack, M. T., Czaplinski, K. & Gorlich, D. Exportin 5 is a RanGTP-dependent dsRNA-binding protein that mediates nuclear export of pre-miRNAs. *Rna* 10, 185-191 (2004).
17. Quintanar-Audelo, M., Yusoff, P., Sinniah, S., Chandramouli, S. & Guy, G. R. Sprouty-related Ena/vasodilator-stimulated phosphoprotein homology 1-domain-containing protein (SPRED1), a tyrosine-protein phosphatase non-receptor type 11 (SHP2) substrate in the Ras/extracellular signal-regulated kinase (ERK) pathway. *The Journal of biological chemistry* 286, 23102-23112 (2011).
18. Kuehbacher, A., Urbich, C., Zeiher, A. M. & Dimmeler, S. Role of Dicer and Drosha for endothelial microRNA expression and angiogenesis. *Circulation research* 101, 59-68 (2007).
19. Welten, S. M., Goossens, E. A., Quax, P. H. & Nossent, A. Y. The multifactorial nature of microRNAs in vascular remodelling. *Cardiovascular research* 110, 6-22 (2016).
20. Chitteti, B. R., et al. CD166 regulates human and murine hematopoietic stem cells and the hematopoietic niche. *Blood* 124, 519-529 (2014).
21. Houlihan, D. D., et al. Isolation of mouse mesenchymal stem cells on the basis of expression of Sca-1 and PDGFR-alpha. *Nature protocols* 7, 2103-2111 (2012).
22. Van Deun, J., et al. The impact of disparate isolation methods for extracellular vesicles on downstream RNA profiling. *Journal of extracellular vesicles* 3(2014).
23. Witwer, K. W., et al. Standardization of sample collection, isolation and analysis methods in extracellular vesicle research. *Journal of extracellular vesicles* 2(2013).
24. Chu, S., Holtz, M., Gupta, M. & Bhatia, R. BCR/ABL kinase inhibition by imatinib mesylate enhances MAP kinase activity in chronic myelogenous leukemia CD34+ cells. *Blood* 103, 3167-3174 (2004).
25. Galante, J. M., Mortenson, M. M., Bowles, T. L., Virudachalam, S. & Bold, R. J. ERK/BCL-2 pathway in the resistance of pancreatic cancer to anoikis. *The Journal of surgical research* 152, 18-25 (2009).
26. Kunisaki, Y., et al. Arteriolar niches maintain haematopoietic stem cell quiescence. *Nature* 502, 637-643 (2013).
27. Holyoake, T. L. & Vetrie, D. The chronic myeloid leukemia stem cell: stemming the tide of persistence. *Blood* 129, 1595-1606 (2017).
28. Boucher, M. J., et al. MEK/ERK signaling pathway regulates the expression of Bcl-2, Bcl-X(L), and Mcl-1 and promotes survival of human pancreatic cancer cells. *Journal of cellular biochemistry* 79, 355-369 (2000).
29. Nechaev, S., et al. Intracellular processing of immunostimulatory CpG-siRNA: Toll-like receptor 9 facilitates siRNA dicing and endosomal escape. *Journal of controlled release: official journal of the Controlled Release Society* 170, 307-315 (2013).
30. Zhang, Q., et al. Serum-resistant CpG-STAT3 decoy for targeting survival and immune checkpoint signaling in acute myeloid leukemia. *Blood* 127, 1687-1700 (2016).
31. Ewald, S. E., et al. The ectodomain of Toll-like receptor 9 is cleaved to generate a functional receptor. *Nature* 456, 658-662 (2008).
32. Nakamura, N., et al. Endosomes are specialized platforms for bacterial sensing and NOD2 signalling. *Nature* 509, 240-244 (2014).
33. Martin-Armas, M., et al. Toll-like receptor 9 (TLR9) is present in murine liver sinusoidal endothelial cells (LSECs) and mediates the effect of CpG-oligonucleotides. *Journal of hepatology* 44, 939-946 (2006).
34. Tamura, Y., et al. Scavenger receptor expressed by endothelial cells I (SREC-I) mediates the uptake of acetylated low density lipoproteins by macrophages stimulated with lipopolysaccharide. *The Journal of biological chemistry* 279, 30938-30944 (2004).
35. Yeh, Y. C., Hwang, G. Y., Liu, I. P. & Yang, V. C. Identification and expression of scavenger receptor SR-BI in endothelial cells and smooth muscle cells of rat aorta in vitro and in vivo. *Atherosclerosis* 161, 95-103 (2002).
36. Iwasaki, A. & Medzhitov, R. Toll-like receptor control of the adaptive immune responses. *Nature immunology* 5, 987-995 (2004).
37. Koschmieder, S., et al. Inducible chronic phase of myeloid leukemia with expansion of hematopoietic stem cells in a transgenic model of BCR-ABL leukemogenesis. Blood 105, 324-334 (2005).
38. Zhang, B., et al. Altered microenvironmental regulation of leukemic and normal stem cells in chronic myelogenous leukemia. Cancer cell 21, 577-592 (2012).
39. Branford, S., Hughes, T. P. & Rudzki, Z. Monitoring chronic myeloid leukemia therapy by real-time quantitative PCR in blood is a reliable alternative to bone marrow cytogenetics. British journal of haematology 107, 587-599 (1999).
40. Akashi, K., Traver, D., Miyamoto, T. & Weissman, I. L. A clonogenic common myeloid progenitor that gives rise to all myeloid lineages. Nature 404, 193-197 (2000).
41. Kiel, M. J., et al. SLAM family receptors distinguish hematopoietic stem and progenitor cells and reveal endothelial niches for stem cells. Cell 121, 1109-1121 (2005).
42. Bhatia, R., McGlave, P. B., Dewald, G. W., Blazar, B. R. & Verfaillie, C. M. Abnormal function of the bone marrow microenvironment in chronic myelogenous leukemia: role of malignant stromal macrophages. Blood 85, 3636-3645 (1995).
43. Van Deun, J., et al. The impact of disparate isolation methods for extracellular vesicles on downstream RNA profiling. Journal of extracellular vesicles 3(2014).
44. Witwer, K. W., et al. Standardization of sample collection, isolation and analysis methods in extracellular vesicle research. Journal of extracellular vesicles 2(2013).
45. Lotvall, J., et al. Minimal experimental requirements for definition of extracellular vesicles and their functions: a position statement from the International Society for Extracellular Vesicles. Journal of extracellular vesicles 3, 26913 (2014).
46. Branford, S., et al. Real-time quantitative PCR analysis can be used as a primary screen to identify patients with CML treated with imatinib who have BCR-ABL kinase domain mutations. Blood 104, 2926-2932 (2004).
47. Dorrance, A. M., et al. Targeting leukemia stem cells in vivo with antagomiR-126 nanoparticles in acute myeloid leukemia. Leukemia 29, 2143-2153 (2015).
48. Huang, X., et al. Targeted delivery of microRNA-29b by transferrin-conjugated anionic lipopolyplex nanoparticles: a novel therapeutic strategy in acute myeloid leukemia. Clinical cancer research: an official journal of the American Association for Cancer Research 19, 2355-2367 (2013).

EMBODIMENTS

Embodiment 1

A method of treating anemia in a subject in need thereof, said method comprising administering to said subject an effective amount of an anti-microRNA126 (miR126) compound.

Embodiment 2

A method of treating or preventing anemia in a subject in need thereof, said method comprising:
  (i) isolating a hematopoietic stem cell (HSC) from a subject, thereby forming an isolated HSC;
  (ii) contacting said isolated HSC with an anti-microRNA126 (miR126) compound thereby forming a contacted HSC; and
administering said contacted HSC to said subject, thereby treating or preventing anemia in said subject.

Embodiment 3

The method of embodiment 2, wherein said contacted HSC is allowed to divide prior to said administering of step (iii).

Embodiment 4

The method of embodiment 2 or 3, wherein said isolating comprises obtaining a biological sample from said subject and isolating said HSC from said biological sample.

Embodiment 5

The method of embodiment 4, wherein said biological sample is a blood sample or a bone marrow sample.

Embodiment 6

A method of forming a red blood cell, said method comprising:
  (i) contacting a hematopoietic stem cell (HSC) with an anti-microRNA126 (miR126) compound, thereby forming a contacted HSC; and
allowing said contacted HSC to divide, thereby forming a red blood cell.

Embodiment 7

The method of embodiment 6, wherein said contacting occurs in a subject.

Embodiment 8

The method of embodiment 6 or 7, wherein said HSC is derived from a biological sample.

Embodiment 9

The method of embodiment 8, wherein said biological sample is a blood sample or a bone marrow sample.

Embodiment 10

The method of embodiment 6, wherein said contacting occurs in vitro.

Embodiment 11

The method of embodiment 6 or 10, wherein after said contacting said contacted HSC is administered to a subject.

Embodiment 12

The method of any one of embodiments 2-11, wherein said contacting step is free of viral transduction.

Embodiment 13

The method of any one of embodiments 2-12, wherein said contacting step is free of viral transduction and said HSC is contacted with said compound.

Embodiment 14

The method of any one of embodiments 2-13, wherein said HSC is contacted with about 1-100 nanomolar concentration of said compound.

Embodiment 15

The method of any one of embodiments 1-14, wherein said anti-miR126 compound comprises:
(i) a phosphorothioated CpG oligodeoxynucleotide (CpG-ODN) conjugated to an anti-miR126 nucleic acid sequence;
(ii) a CpG-ODN conjugated to a miRNA126 mimic nucleic acid sequence; or
(iii) an unconjugated anti-miR126 nucleic acid sequence, wherein said unconjugated anti-miR126 nucleic acid sequence comprises one or more phosphorothioate linkages and one or more chemically modified nucleotides.

Embodiment 16

The method of embodiment 15, further comprising a covalent linker between said CpG-ODN and said anti-miR126 nucleic acid sequence or between said CpG-ODN and said miRNA126 mimic nucleic acid sequence.

Embodiment 17

The method of embodiment 16, wherein said linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 18

The method of embodiment 17, wherein said linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 19

The method of embodiment 17 or 18, wherein said linker is an unsubstituted $C_1$-$C_{40}$ alkylene, unsubstituted 2 to 40 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene.

Embodiment 20

The method of any one of embodiments 17-19, wherein said linker is a substituted 2 to 40 membered heteroalkylene.

Embodiment 21

The method of any one of embodiments 15-20, wherein said anti-miR126 nucleic acid sequence, said miRNA126 mimic nucleic acid sequence or said unconjugated anti-miR126 nucleic acid sequence are independently chemically modified.

Embodiment 22

The method of embodiment 21, wherein said anti-miR126 nucleic acid sequence, said miRNA126 mimic nucleic acid sequence or said unconjugated anti-miR126 nucleic acid sequence independently comprise a chemical modification selected for the group consisting of a 2' O-Methyl, 2'-deoxy-2'fluoro, 2'-deoxy, a universal base, 5-C-methyl, an inverted deoxy abasic residue incorporation, and a locked nucleic acid.

Embodiment 23

The method of embodiment 22, wherein said modification is positioned at the terminal nucleobase of said anti-miR126 nucleic acid sequence, said miRNA126 mimic nucleic acid sequence or said unconjugated anti-miR126 nucleic acid sequence.

Embodiment 24

The method of embodiment 22, wherein the modification is not positioned at the terminal nucleobase of said anti-miR126 nucleic acid sequence, said miRNA126 mimic nucleic acid sequence or said unconjugated anti-miR126 nucleic acid sequence.

Embodiment 25

The method of embodiment 23, wherein said modification protects against serum-derived nucleases.

Embodiment 26

The method of any one of embodiments 1-5, wherein the compound is administered to the subject by intravenous, parenteral, subcutaneous, intramuscular, transdermal, intraperitoneal, intranasal, aerosol, oral, or topical administration.

Embodiment 27

The method of any one of embodiments 1-5 or 26, wherein said treatment is dose-dependent of said compound or composition.

Embodiment 28

The method of any one of embodiments 1-5, 26 or 27, wherein about 0.001 mg/kg to about 100 mg/kg of said compound are administered to said subject.

```
INFORMAL SEQUENCE LISTING
modified 3' Adapter
                                            (SEQ ID NO: 1)
5' TCTGGAATTCTCGGGTGCCAAGGAACTCC RT primer
                                            (SEQ ID NO: 2)
5' GGAGTTCCTTGGCACCCGAGAATTCCA modified 5' adaptor
                                            (SEQ ID NO: 3)
5' GUUCAGAGUUCUACAGUCCGACGAUCNNN
'N' can be any nucleotide index primer GX1
                                            (SEQ ID NO: 4)
CAAGCAGAAGACGGCATACGAGATNNNNNNGTGACTGGAGTTCAGACGTG
TGCTCTTCCGATC
'N' can be any nucleotide index primer GX2
                                            (SEQ ID NO: 5)
AATGATACGGCGACCACCGAGATCTACACGTTCAGAGTTCTACAGTCCGA CpG-miR-126 inhibitor
                                            (SEQ ID NO: 6)
5' G*G*T GCA TCG ATG CAGG*G*G* G*G xxxxx mCmGmC
mAmUmU mAmUmU mAmCmU mCmAmC mGmGmU mAmCmG mA-3'
'*'-phosphorothioation. One none bridging oxygen on
phosphate replaced with sulfur.
'm'-2'-O-methyl analogue of the nucleotide
'x'-(CH2)3. C3 carbon chain linker.

CpG-scrRNA
                                            (SEQ ID NO: 7)
5' G*G*T GCA TCG ATG CAGG*G*G* G*G xxxxx mGmUmA
mGmAmA mCmCmG mUmAmC mUmCmG mUmCmA mCmUmU mA 3'
'*'-phosphorothioation. One none bridging oxygen on
phosphate replaced with sulfur.
'm'-2'-O-methyl analogue of the nucleotide
'x'-(CH2)3. C3 carbon chain linker.
```

---

What is claimed is:

1. A method of treating anemia in a subject in need thereof, said method comprising administering to said subject an effective amount of an anti-microRNA126 (miR126) compound.

2. The method of claim 1, wherein said anti-miR126 compound comprises:
   (i) a phosphorothioated CpG oligodeoxynucleotide (CpG-ODN) conjugated to an anti-miR126 nucleic acid sequence;
   (ii) a CpG-ODN conjugated to a miRNA126 mimic nucleic acid sequence; or
   (iii) an unconjugated anti-miR126 nucleic acid sequence, wherein said unconjugated anti-miR126 nucleic acid sequence comprises one or more phosphorothioate linkages and one or more chemically modified nucleotides.

3. The method of claim 1, wherein the compound is administered to the subject by intravenous, parenteral, subcutaneous, intramuscular, transdermal, intraperitoneal, intranasal, aerosol, oral, or topical administration.

4. The method of claim 1, wherein said treatment is dose-dependent of said compound or composition.

5. The method of claim 1, wherein about 0.001 mg/kg to about 100 mg/kg of said compound are administered to said subject.

6. A method of forming a red blood cell, said method comprising:
   (i) contacting a hematopoietic stem cell (HSC) with an anti-microRNA126 (miR126) compound, thereby forming a contacted HSC; and
   (ii) allowing said contacted HSC to divide, thereby forming a red blood cell.

7. The method of claim 6, wherein said contacting occurs in a subject.

8. The method of claim 6, wherein said contacting occurs in vitro.

9. The method of claim 6, wherein said anti-miR126 compound comprises:
   (a) a phosphorothioated CpG oligodeoxynucleotide (CpG-ODN) conjugated to an anti-miR 126 nucleic acid sequence;
   (b) a CpG-ODN conjugated to a miRNA126 mimic nucleic acid sequence; or
   (c) an unconjugated anti-miR126 nucleic acid sequence, wherein said unconjugated anti-miR 126 nucleic acid sequence comprises one or more phosphorothioate linkages and one or more chemically modified nucleotides.

10. A method of treating cancer in a subject in need thereof, the method comprising administering to the subject a therapeutically effective amount of a tyrosine kinase inhibitor and a therapeutically effective amount of an anti-microRNA126 (miR126) compound.

11. The method of claim 10, wherein said subject is a subject undergoing cancer treatment.

12. The method of claim 10, wherein the tyrosine kinase inhibitor is dasatinib, bevacizumab, vatalanib, vemurafenib, vandetanib, cabozantinib, poatinib, axitinib, ruxolitinib, regorafenib, crizotinib, bosutinib, lapatinib, lenvatinib, mubritinib, nilotinib, panitumumab or pazopanib.

13. The method of claim 10, wherein said anti-microRNA126 (miR126) compound is an anti-miR126 nucleic acid.

14. The method of claim 13, wherein said anti-miR126 nucleic acid comprises the sequence of SEQ ID NO:6.

* * * * *